United States Patent
Grice et al.

(10) Patent No.: US 11,142,526 B2
(45) Date of Patent: Oct. 12, 2021

(54) SPIROCYCLE COMPOUNDS AND METHODS OF MAKING AND USING SAME

(71) Applicant: H. Lundbeck A/S, Valby (DK)

(72) Inventors: Cheryl A. Grice, Encinitas, CA (US); Olivia D. Weber, San Diego, CA (US); Daniel J. Buzard, San Diego, CA (US); Michael B. Shaghafi, San Diego, CA (US); Todd K. Jones, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 16/642,717

(22) PCT Filed: Aug. 28, 2018

(86) PCT No.: PCT/US2018/048372
§ 371 (c)(1),
(2) Date: Feb. 27, 2020

(87) PCT Pub. No.: WO2019/046318
PCT Pub. Date: Mar. 7, 2019

(65) Prior Publication Data
US 2020/0255427 A1    Aug. 13, 2020

Related U.S. Application Data

(60) Provisional application No. 62/551,721, filed on Aug. 29, 2017.

(51) Int. Cl.
| | |
|---|---|
| *C07D 471/10* | (2006.01) |
| *C07D 401/12* | (2006.01) |
| *C07D 409/12* | (2006.01) |
| *C07D 487/04* | (2006.01) |
| *C07D 519/00* | (2006.01) |
| *A61P 25/02* | (2006.01) |
| *A61P 1/00* | (2006.01) |
| *A61P 25/08* | (2006.01) |
| *A61P 25/06* | (2006.01) |

(52) U.S. Cl.
CPC .............. *C07D 471/10* (2013.01); *A61P 1/00* (2018.01); *A61P 25/02* (2018.01); *A61P 25/06* (2018.01); *A61P 25/08* (2018.01); *C07D 401/12* (2013.01); *C07D 409/12* (2013.01); *C07D 487/04* (2013.01); *C07D 519/00* (2013.01)

(58) Field of Classification Search
CPC .......... C07D 471/10; C07D 471/40112; C07D 409/12; C07D 487/04; C07D 519/00; A61P 25/02; A61P 1/00; A61P 25/08; A61P 25/06
See application file for complete search history.

(56) References Cited

U.S. PATENT DOCUMENTS

| | | | |
|---|---|---|---|
| 9,133,148 B2 | 9/2015 | Cisar et al. | |
| 9,487,495 B2 * | 11/2016 | Cisar .................... | C07D 231/56 |
| 9,828,379 B2 | 11/2017 | Jones et al. | |
| 10,030,020 B2 | 7/2018 | Cisar et al. | |
| 2005/0234090 A1 | 10/2005 | Colon-Cruz et al. | |
| 2011/0071180 A1 | 3/2011 | Akireddy et al. | |
| 2011/0172230 A1 | 7/2011 | Ishii et al. | |
| 2012/0165422 A1 | 6/2012 | Vernon et al. | |
| 2012/0208812 A1 | 8/2012 | Chai et al. | |
| 2013/0165422 A1 | 6/2013 | Bartsch et al. | |
| 2016/0137649 A1 | 5/2016 | Jones et al. | |
| 2016/0272602 A1 | 9/2016 | Cisar et al. | |
| 2017/0029390 A1 | 2/2017 | Butler et al. | |
| 2020/0022977 A1 | 1/2020 | Cisar et al. | |
| 2020/0291023 A1 | 9/2020 | Grice et al. | |

FOREIGN PATENT DOCUMENTS

| | | |
|---|---|---|
| CL | 2019000661 A | 7/2019 |
| CL | 2019000662 A1 | 7/2019 |
| CN | 110267962 A | 9/2019 |
| WO | WO-2010089510 A2 | 8/2010 |
| WO | WO-2010141817 A1 | 12/2010 |
| WO | WO-2011109277 A1 | 9/2011 |
| WO | WO-2011151808 A1 | 12/2011 |
| WO | WO-2012052730 A1 | 4/2012 |
| WO | WO-2013103973 A1 | 7/2013 |
| WO | WO-2014048865 A1 | 4/2014 |
| WO | WO-2015003002 A1 | 1/2015 |
| WO | WO-2016149401 A2 | 9/2016 |
| WO | WO-2017021805 A1 | 2/2017 |
| WO | WO-2017087858 A1 | 5/2017 |
| WO | WO-2017171100 A1 | 10/2017 |
| WO | WO-2017197192 A1 | 11/2017 |
| WO | WO-2018093946 A1 | 5/2018 |
| WO | WO-2018093947 A1 | 5/2018 |
| WO | WO-2018093949 A1 | 5/2018 |
| WO | WO-2018093950 A1 | 5/2018 |
| WO | WO-2018093953 A1 | 5/2018 |
| WO | WO-2019046318 A1 | 3/2019 |
| WO | WO-2019046330 A1 | 3/2019 |

OTHER PUBLICATIONS

Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Brun et al. Drug sensitivity of Chinese Trypanosoma evansi and Trypanosoma equiperdum isolates. Vet. Parasitol. 52:37-46 (1994).
Chang et al. Highly Selective Inhibitors of Monoacylglycerol Lipase Bearing a Reactive Group that is Bioisosteric with Endocannabinoid Substrates. ChemBiol 19(5):579-588 (2012).

(Continued)

*Primary Examiner* — Timothy R Rozof
(74) *Attorney, Agent, or Firm* — Wilson Sonsini Goodrich & Rosati

(57) ABSTRACT

Provided herein are compounds and compositions useful as modulators of MAGL. Furthermore, the subject compounds and compositions are useful for the treatment of pain.

16 Claims, No Drawings

(56) References Cited

OTHER PUBLICATIONS

Changsen et al. Improved green fluorescent protein reporter gene-based microplate screening for antituberculosis compounds by utilizing an acctamidasc promoter. Antimicrob AgentsChemother 47:3682-3687 (2003).

Chen et al. SAP102 mediates synaptic clearance of NMDA receptors. Cell Rep. 2(5):1120-1128 (2012).

Cho et al. Low-oxygen-recovery assay for high-throughput screening of compounds against nonreplicating *Mycobacterium tuberculosis*. Antimicrobl Agents Chemother 51:1380-1385 (2007).

Collins et al. Microplate alamar blue assay versus BACTEC 460 system for high-throughput screening of compounds against *Mycobacterium tuberculosis* and *Mycobacterium avium*. Antimicrobl Agents Chemother 41:1004-1009 (1997).

Fleisher et al. Improved oral drug delivery: solubility limitations overcome by the use of prodrugs. Advanced Drug Delivery Reviews 19:115-130 (1996).

Long et al. Selective blockade of 2-arachidonoylglycerol hydrolysis produces cannabinoid behavioral effects. Nat Chem Biol. 5(1):37-44 (2009).

Niphakis et al. Evaluation of NHS carbamates as a potent and selective class of endocannabinoid hydrolase inhibitors. ACS Chem Neurosci 4(9):1322-1332 (2013).

Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).

Nomura et al. Activation of the endocannabinoid system by organophosphorus nerve agents. Nat Chem Biol. 4(6):373-378 (2008).

Nomura et al. Endocannabinoid hydrolysis generates brain prostaglandins that promote neuroinflammation. Science 334(6057):809-813 (2011).

Nomura et al. Monoacylglycerol lipase regulates 2-arachidonoylglycerol action and arachidonic acid levels. Bioorg Med Chem Lett. 18(22):5875-5878 (2008).

PCT/US2014/045145 International Search Report and Written Opinion dated Dec. 10, 2014.

PCT/US2017/032276 International Search Report and Written Opinion dated Sep. 26, 2017.

PCT/US2017/061870 International Search Report and Written Opinion dated Mar. 26, 2018.

PCT/US2017/061870 Invitation to Pay Additional Fees dated Jan. 22, 2018.

PCT/US2018/048372 International Search Report and Written Opinion dated Dec. 4, 2018.

PCT/US2018/048372 Invitation to Pay Additional Fees dated Oct. 4, 2018.

PCT/US2018/048388 International Search Report and Written Opinion dated Dec. 4, 2018.

PCT/US2018/048388 Invitation to Pay Additional Fees dated Oct. 4, 2018.

Piro et al. A dysregulated endocannabinoid-eicosanoid network supports pathogenesis in a mouse model of Alzheimer's disease. Cell Rep. 1(6):617-623 (2012).

Pubchem, Substance Database, SID 239803465. Retrieved from Internet< URL: https://pubchem.ncbi.nlm.nih.gov/substance/239803465> ( 7pgs.) (Available Date Feb. 13, 2015) (retrieved Jun. 27, 2017).

Raz et al. The Alamar Blue® assay to determine drug sensitivity of African trypanosomes (T.b. rhodesiense and T.b. gambiense) in vitro. Acta Tropica 68:139-147 (1997).

Snewin et al. Assessment of immunity to mycobacterial infection with luciferase reporter constructs. Infection and Immunity 67:4586-4593 (1999).

U.S. Appl. No. 14/902,324 Office Action dated Dec. 30, 2016.

Keith et al. Heteroarylureas with spirocyclic diamine cores as inhibitors of fatty acid amide hydrolase. Bioorg Med Chem Lett 24(3)737-41 (2014).

U.S. Appl. No. 16/349,047 Office Action dated Nov. 27, 2020.

U.S. Appl. No. 16/642,713 Ex Parte Quayle Action dated Mar. 19, 2021.

\* cited by examiner

SPIROCYCLE COMPOUNDS AND METHODS OF MAKING AND USING SAME

CROSS-REFERENCE

This application is a U.S. National Stage entry of PCT application PCT/US2018/048372, filed Aug. 28, 2018, which claims the benefit of U.S. Provisional Application No. 62/551,721, filed on Aug. 29, 2017, which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound of Formula (III):

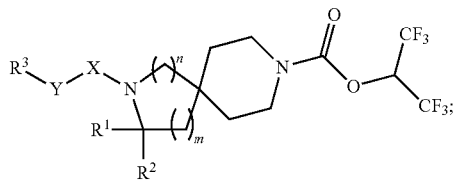

Formula (III)

wherein:
X is —$CH_2$— or —C(O)—;
Y is a bond, $C_{1-6}$alkyl, $C_{1-6}$haloalkyl, or $C_{3-8}$cycloalkyl;
$R^1$ is H or $C_{1-6}$alkyl;
$R^2$ is H or $C_{1-6}$alkyl;
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;
each $R^4$ is independently selected from $C_{1-6}$alkyl, halogen, —CN, $C_{3-8}$cycloalkyl, $C_{2-9}$heterocycloalkyl, —$C_{1-6}$alkyl-($C_{2-9}$heterocycloalkyl), phenyl, —$CH_2$—phenyl, $C_{1-9}$heteroaryl, —$CO_2R^6$, —$CH_2CO_2R^6$, and —$CH_2C(O)N(H)SO_2R^8$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;
each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl;
each $R^6$ is independently selected from H and $C_{1-6}$alkyl;
each $R^7$ is independently selected from H, $C_{1-6}$alkyl, $C_{1-6}$haloalkyl, and $C_{3-8}$cycloalkyl;
each $R^8$ is independently selected from $C_{1-6}$alkyl, $C_{1-6}$haloalkyl, and $C_{3-8}$cycloalkyl;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

In another embodiment is a compound of Formula (III), or a solvate, hydrate, tautomer, N-oxide, stereoisomer, or pharmaceutically acceptable salt thereof, wherein Y is a bond. In another embodiment is a compound of Formula (III), or a solvate, hydrate, tautomer, N-oxide, stereoisomer, or pharmaceutically acceptable salt thereof, wherein Y is $C_{1-6}$alkyl. In another embodiment is a compound of Formula (III), or a solvate, hydrate, tautomer, N-oxide, stereoisomer, or pharmaceutically acceptable salt thereof, wherein Y is —$CH_2$—. In another embodiment is a compound of Formula (III), or a solvate, hydrate, tautomer, N-oxide, stereoisomer, or pharmaceutically acceptable salt thereof, wherein Y is $C_{1-6}$haloalkyl. In another embodiment is a compound of Formula (III), or a solvate, hydrate, tautomer, N-oxide, stereoisomer, or pharmaceutically acceptable salt thereof, wherein Y is —$CH_2$—. In another embodiment is a compound of Formula (III), or a solvate, hydrate, tautomer, N-oxide, stereoisomer, or pharmaceutically acceptable salt thereof, wherein Y is $C_{3-8}$cycloalkyl. In another embodiment is a compound of Formula (III), or a solvate, hydrate, tautomer, N-oxide, stereoisomer, or pharmaceutically acceptable salt thereof, wherein Y is cyclopropyl.

In another aspect is a compound of Formula (I):

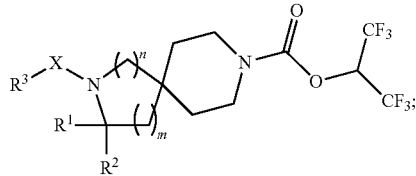

Formula (I)

wherein:
X is —$CH_2$— or —C(O)—;
$R^1$ is H or $C_{1-6}$alkyl;
$R^2$ is H or $C_{1-6}$alkyl;
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;
each $R^4$ is independently selected from $C_{1-6}$alkyl, halogen, —CN, $C_{3-8}$cycloalkyl, $C_{2-9}$heterocycloalkyl, $C_{1-6}$alkyl-($C_{2-9}$heterocycloalkyl), phenyl, —$CH_2$—phenyl, $C_{1-9}$heteroaryl, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;

each $R^5$ is independently selected from halogen, $C_{1-6}$alkyl, $C_{1-6}$heteroalkyl, $C_{1-6}$alkoxy, $C_{3-8}$cycloalkyl, $C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl;

each $R^6$ is independently selected from H and $C_{1-6}$alkyl;

each $R^7$ is independently selected from H, $C_{1-6}$haloalkyl, and $C_{3-8}$cycloalkyl;

n is 0 or 1; and m is 1 or 2; provided that when n is 0, then m is 2; and when n is 1, then m is 1;

or a solvate, hydrate, tautomer, N-oxide, stereoisomer, or pharmaceutically acceptable salt thereof.

In another embodiment is a compound of Formula (I) or (III), or a solvate, hydrate, tautomer, N-oxide, stereoisomer, or pharmaceutically acceptable salt thereof, wherein $R^1$ is H. In another embodiment is a compound of Formula (I) or (III), or a solvate, hydrate, tautomer, N-oxide, stereoisomer, or pharmaceutically acceptable salt thereof, wherein $R^2$ is H. In another embodiment is a compound of Formula (I) or (III), or a solvate, hydrate, tautomer, N-oxide, stereoisomer, or pharmaceutically acceptable salt thereof, wherein $R^1$ and $R^2$ are both H. In another embodiment is a compound of Formula (I) or (III), or a solvate, hydrate, tautomer, N-oxide, stereoisomer, or pharmaceutically acceptable salt thereof, wherein X is —$CH_2$—. In another embodiment is a compound of Formula (I) or (III), or a solvate, hydrate, tautomer, N-oxide, stereoisomer, or pharmaceutically acceptable salt thereof, wherein X is —C(O)—. In another embodiment is a compound of Formula (I) or (III), or a solvate, hydrate, tautomer, N-oxide, stereoisomer, or pharmaceutically acceptable salt thereof, wherein n is 0 and m is 2. In another embodiment is a compound of Formula (I) or (III), or a solvate, hydrate, tautomer, N-oxide, stereoisomer, or pharmaceutically acceptable salt thereof, wherein n is 1 and m is 1.

In another aspect is a compound of Formula (II):

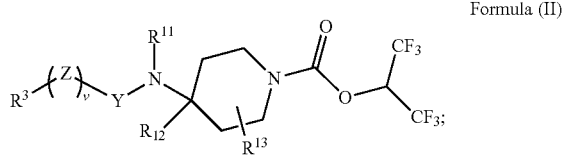

Formula (II)

wherein:

Y is —$CH_2$— or —C(O)—;

Z is $C_{3-6}$cycloalkyl;

$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;

each $R^4$ is independently selected from $C_{1-6}$alkyl, halogen, —CN, $C_{1-6}$haloalkyl, $C_{3-8}$cycloalkyl, $C_{2-9}$heterocycloalkyl, —$C_{1-6}$alkyl-($C_{2-9}$heterocycloalkyl), phenyl, —$CH_2$— phenyl, $C_{1-9}$heteroaryl, —$OR^7$, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;

each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl;

each $R^6$ is independently selected from H and $C_{1-6}$alkyl;

each $R^7$ is independently selected from H, $C_{1-6}$alkyl, $C_{1-6}$haloalkyl, and $C_{3-8}$cycloalkyl;

$R^{11}$ is H, $C_{1-6}$alkyl, or —$C_{1-6}$alkyl-O—$C_{1-6}$alkyl;

$R^{12}$ is $C_{1-6}$alkyl;

$R^{13}$ is H or $C_{1-6}$alkyl; and v is 0 or 1;

or a solvate, hydrate, tautomer, N-oxide, stereoisomer, or pharmaceutically acceptable salt thereof.

In another embodiment is a compound of Formula (II), or a solvate, hydrate, tautomer, N-oxide, stereoisomer, or pharmaceutically acceptable salt thereof, wherein $R^{13}$ is H. In another embodiment is a compound of Formula (II), or a solvate, hydrate, tautomer, N-oxide, stereoisomer, or pharmaceutically acceptable salt thereof, wherein v is 0. In another embodiment is a compound of Formula (II), or a solvate, hydrate, tautomer, N-oxide, stereoisomer, or pharmaceutically acceptable salt thereof, wherein v is 1. In another embodiment is a compound of Formula (II), or a solvate, hydrate, tautomer, N-oxide, stereoisomer, or pharmaceutically acceptable salt thereof, wherein Y is —C(O)—. In another embodiment is a compound of Formula (II), or a solvate, hydrate, tautomer, N-oxide, stereoisomer, or pharmaceutically acceptable salt thereof, wherein Y is —$CH_2$—. In another embodiment is a compound of Formula (II), or a solvate, hydrate, tautomer, N-oxide, stereoisomer, or pharmaceutically acceptable salt thereof, wherein Y is —C(O)—. In another embodiment is a compound of Formula (II), or a solvate, hydrate, tautomer, N-oxide, stereoisomer, or pharmaceutically acceptable salt thereof, wherein $R^{11}$ is $C_{1-6}$alkyl. In another embodiment is a compound of Formula (II), or a solvate, hydrate, tautomer, N-oxide, stereoisomer, or pharmaceutically acceptable salt thereof, wherein $R^{12}$ is —$CH_3$.

In another embodiment is a compound of Formula (I), (II), or (III), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (I), (II), or (III), or a solvate, hydrate, tautomer, N-oxide, stereoisomer, or pharmaceutically acceptable salt thereof, wherein $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (I), (II), or (III), or a solvate, hydrate, tautomer, N-oxide, stereoisomer, or pharmaceutically acceptable salt thereof, wherein $R^3$ is selected from:

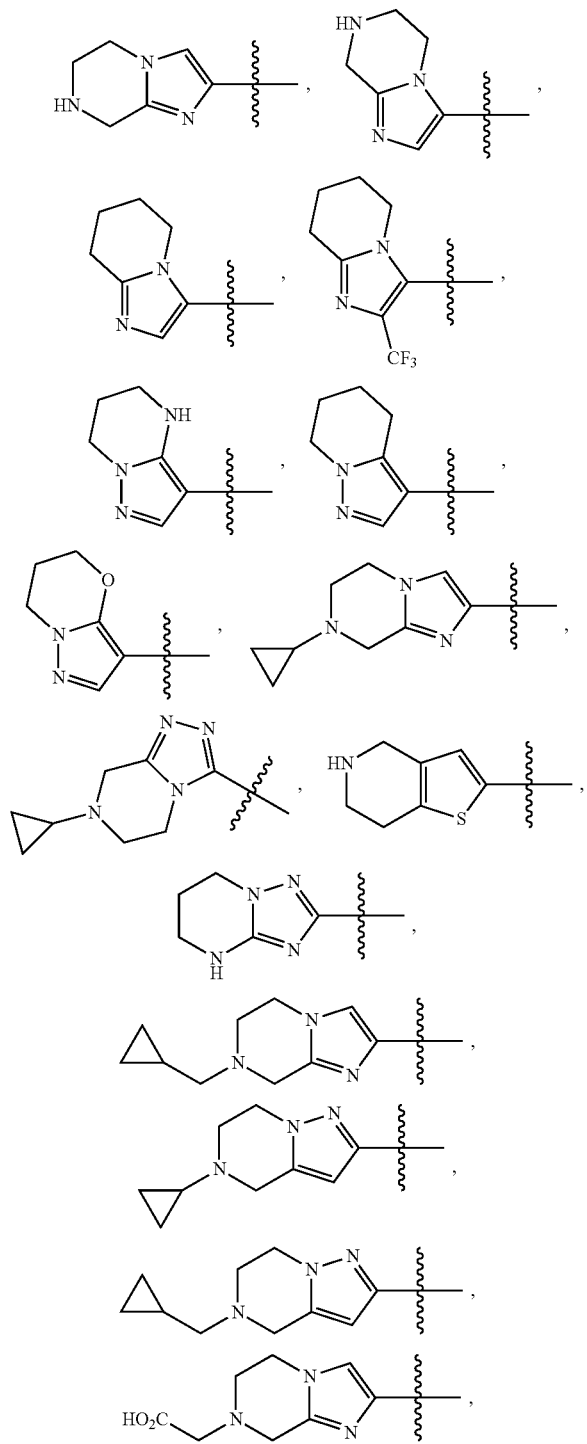

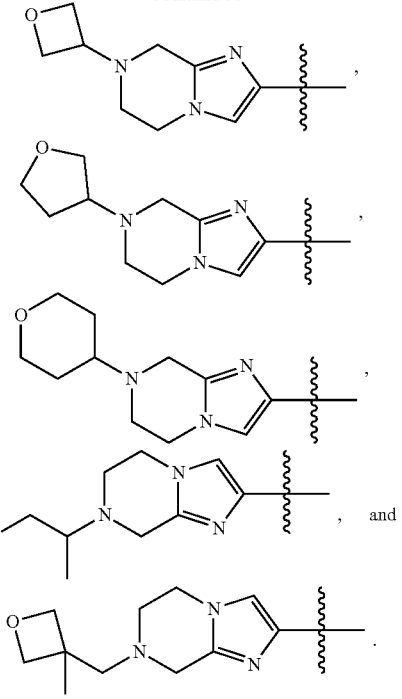

In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (I), (II), or (III), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (I), (II), or (III), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (I), (II), or (III), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —$C_{1-6}$alkyl, $C_{1-6}$haloalkyl, and $C_{2-9}$heterocycloalkyl, wherein $C_{2-9}$heterocycloalkyl is optionally substituted with one or two $R^5$. In another embodiment is a compound of Formula (I), (II), or (III), or a solvate, hydrate, tautomer, N-oxide, stereoisomer, or pharmaceutically acceptable salt thereof, wherein $R^3$ is a 6-membered heteroaryl ring substituted with one or two R⁴, wherein each R⁴ is independently selected from halogen, $C_{1-6}$alkyl, $C_{1-6}$haloalkyl, and $C_{2-9}$heterocycloalkyl, wherein $C_{2-9}$heterocycloalkyl is optionally substituted with one R⁵, and R⁵ is —CO₂H. In another embodiment is a compound of Formula (I), (II), or (III), or a solvate, hydrate, tautomer, N-oxide, stereoisomer, or pharmaceutically acceptable salt thereof, wherein R³ is an unsubstituted 6-membered heteroaryl ring. In another embodiment is a compound of Formula (I), (II), or (III), or a solvate, hydrate, tautomer, N-oxide, stereoisomer, or pharmaceutically acceptable salt thereof, wherein R³ is a 6-membered heteroaryl ring selected from a pyridine, pyrimidine, pyridazine, and pyrazine ring. In another embodiment is a compound of Formula (I), (II), or (III), or a solvate, hydrate, tautomer, N-oxide, stereoisomer, or pharmaceutically acceptable salt thereof, wherein R³ is a 9- to 10-membered bicyclic heteroaryl ring optionally substituted with one, two, or three R⁴. In another embodiment is a compound of Formula (I), (II), or (III), or a solvate, hydrate, tautomer, N-oxide, stereoisomer, or pharmaceutically acceptable salt thereof, wherein R³ is a 9-membered bicyclic heteroaryl ring substituted with one, two, or three R⁴. In another embodiment is a compound of Formula (I), (II), or (III), or a solvate, hydrate, tautomer, N-oxide, stereoisomer, or pharmaceutically acceptable salt thereof, wherein R³ is a 9-membered bicyclic heteroaryl ring substituted with one, two, or three R⁴, wherein each R⁴ is independently selected from halogen, —CN, $C_{1-6}$alkyl, $C_{1-6}$haloalkyl, $C_{3-8}$cycloalkyl, —OR⁷, and —CO₂R⁶. In another embodiment is a compound of Formula (I), (II), or (III), or a solvate, hydrate, tautomer, N-oxide, stereoisomer, or pharmaceutically acceptable salt thereof, wherein R³ is a 9-membered bicyclic heteroaryl ring substituted with one or two R⁴, wherein each R⁴ is independently selected from halogen, $C_{1-6}$alkyl, and $C_{1-6}$haloalkyl. In another embodiment is a compound of Formula (I), (II), or (III), or a solvate, hydrate, tautomer, N-oxide, stereoisomer, or pharmaceutically acceptable salt thereof, wherein R³ is an unsubstituted 9-membered bicyclic heteroaryl ring. In another embodiment is a compound of Formula (I), (II), or (III), or a solvate, hydrate, tautomer, N-oxide, stereoisomer, or pharmaceutically acceptable salt thereof, wherein R³ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (I), (II), or (III), or a solvate, hydrate, tautomer, N-oxide, stereoisomer, or pharmaceutically acceptable salt thereof, wherein R³ is selected from:

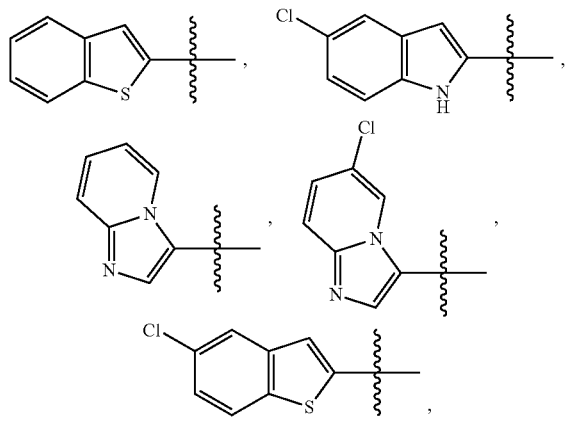

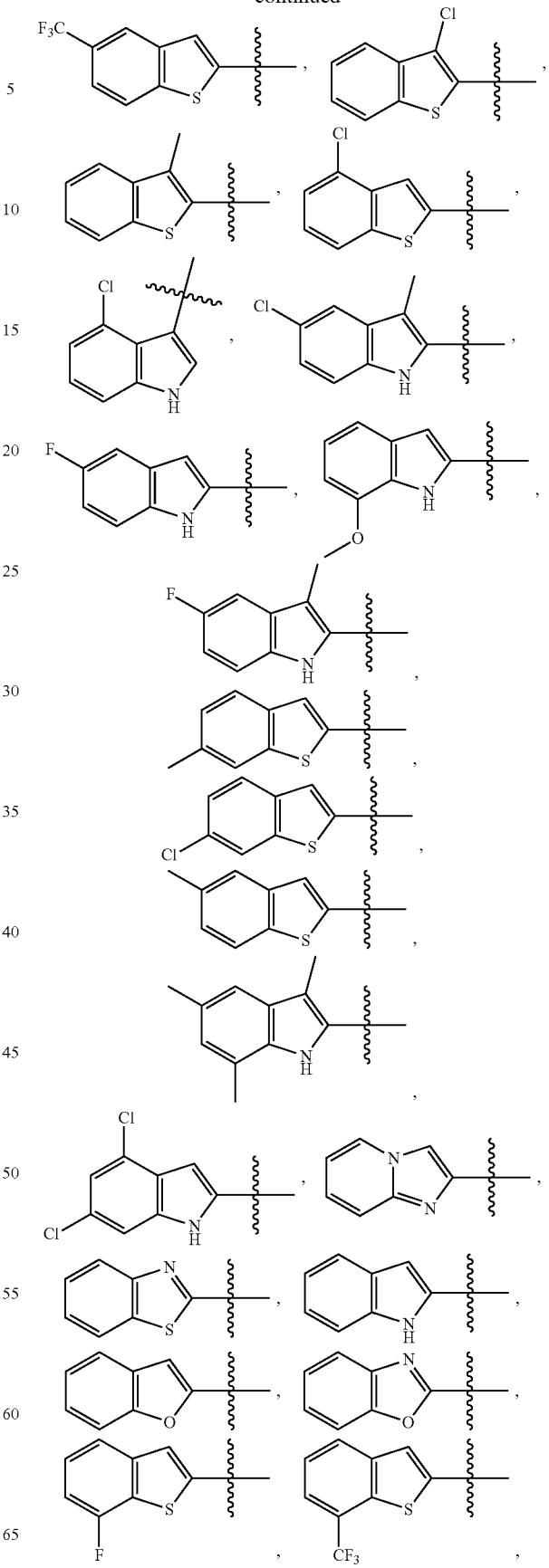

-continued
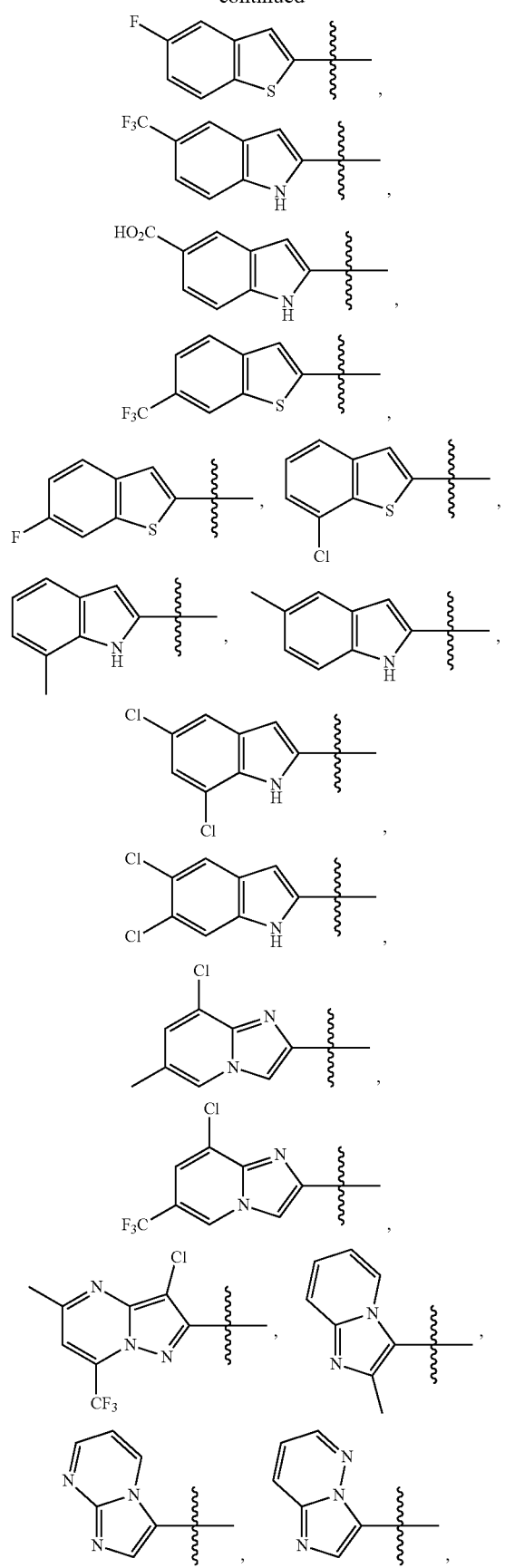
-continued
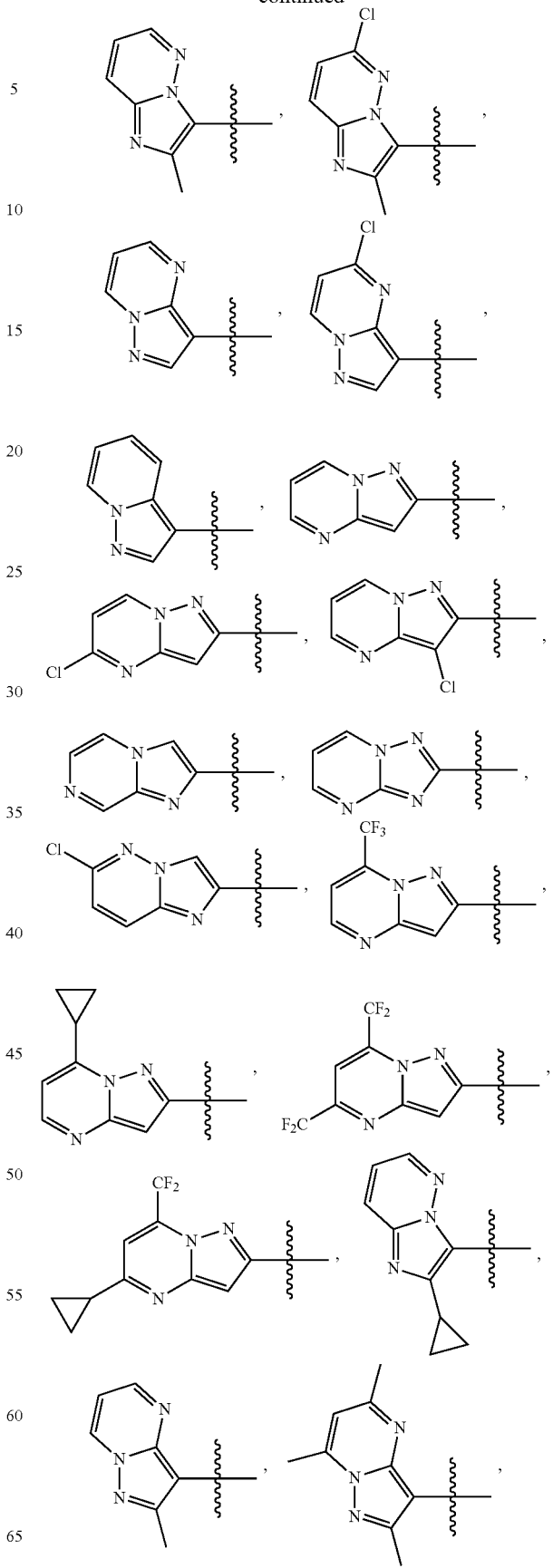

-continued

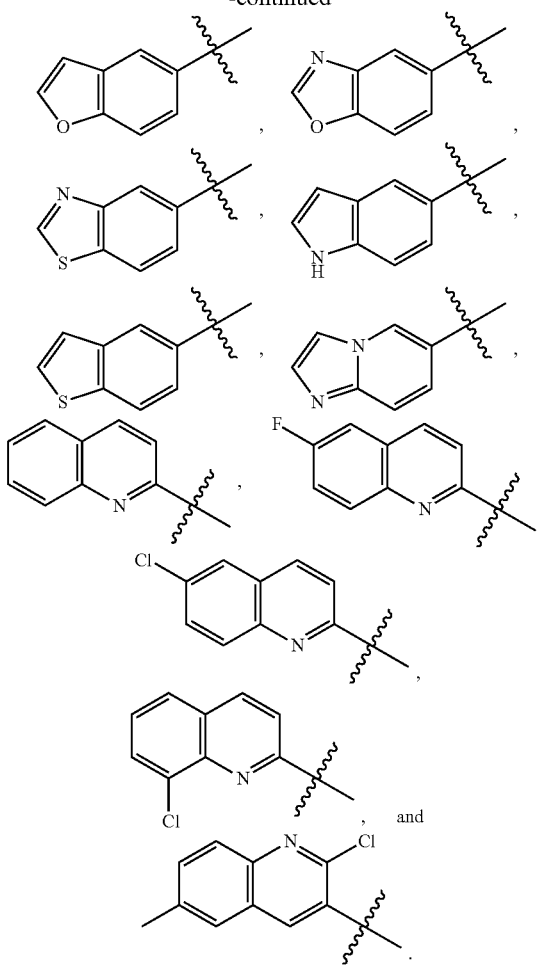

In another aspect is a compound of Formula (IV):

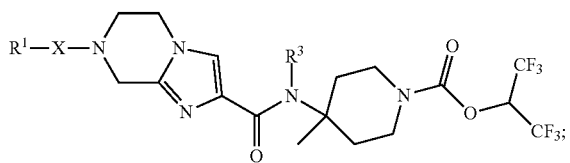

Formula (IV)

wherein:

X is a bond, —C(O)—, or —S(O)$_2$—;

R$^1$ is selected from C$_{1-6}$alkyl, C$_{1-6}$haloalkyl, C$_{3-8}$cycloalkyl, C$_{2-9}$heterocycloalkyl, phenyl, and C$_{1-9}$heteroaryl; wherein C$_{3-8}$cycloalkyl, C$_{2-9}$heterocycloalkyl, phenyl, and C$_{1-9}$heteroaryl are optionally substituted with one, two, or three R$^2$;

each R$^2$ is independently selected from halogen, C$_{1-6}$alkyl, and C$_{1-6}$haloalkyl; and R$^3$ is H, C$_{1-6}$alkyl, or —C$_{1-6}$alkyl-O—C$_{1-6}$alkyl;

or a solvate, hydrate, tautomer, N-oxide, stereoisomer, or pharmaceutically acceptable salt thereof.

In another embodiment is a compound of Formula (IV), or a solvate, hydrate, tautomer, N-oxide, stereoisomer, or pharmaceutically acceptable salt thereof, wherein X is a bond. In another embodiment is a compound of Formula (IV), or a solvate, hydrate, tautomer, N-oxide, stereoisomer, or pharmaceutically acceptable salt thereof, wherein X is —C(O)—. In another embodiment is a compound of Formula (IV), or a solvate, hydrate, tautomer, N-oxide, stereoisomer, or pharmaceutically acceptable salt thereof, wherein X is —S(O)$_2$—. In another embodiment is a compound of Formula (IV), or a solvate, hydrate, tautomer, N-oxide, stereoisomer, or pharmaceutically acceptable salt thereof, wherein R$^1$ is C$_{1-6}$alkyl. In another embodiment is a compound of Formula (IV), or a solvate, hydrate, tautomer, N-oxide, stereoisomer, or pharmaceutically acceptable salt thereof, wherein R$^1$ is C$_{1-6}$haloalkyl. In another embodiment is a compound of Formula (IV), or a solvate, hydrate, tautomer, N-oxide, stereoisomer, or pharmaceutically acceptable salt thereof, wherein R$^1$ is C$_{3-8}$cycloalkyl optionally substituted with one, two, or three R$^2$. In another embodiment is a compound of Formula (IV), or a solvate, hydrate, tautomer, N-oxide, stereoisomer, or pharmaceutically acceptable salt thereof, wherein R$^1$ is C$_{2-9}$heterocycloalkyl optionally substituted with one, two, or three R$^2$. In another embodiment is a compound of Formula (IV), or a solvate, hydrate, tautomer, N-oxide, stereoisomer, or pharmaceutically acceptable salt thereof, wherein R$^1$ is phenyl optionally substituted with one, two, or three R$^2$. In another embodiment is a compound of Formula (IV), or a solvate, hydrate, tautomer, N-oxide, stereoisomer, or pharmaceutically acceptable salt thereof, wherein R$^1$ is C$_{1-9}$heteroaryl optionally substituted with one, two, or three R$^2$. In another embodiment is a compound of Formula (IV), or a solvate, hydrate, tautomer, N-oxide, stereoisomer, or pharmaceutically acceptable salt thereof, wherein R$^3$ is H. In another embodiment is a compound of Formula (IV), or a solvate, hydrate, tautomer, N-oxide, stereoisomer, or pharmaceutically acceptable salt thereof, wherein R$^3$ is C$_{1-6}$alkyl.

In another embodiment is a pharmaceutical composition comprising a compound of Formula (I), (II), (III), or (IV) described herein, or a solvate, hydrate, tautomer, N-oxide, or a pharmaceutically acceptable salt thereof, and at least one pharmaceutically acceptable excipient.

In another embodiment is a method of treating pain in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating neuropathic pain in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating inflammatory pain in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof.

In another embodiment is a method of treating a disease or disorder in a patient comprising administering to the patient in need thereof a therapeutically effective amount of a compound of Formula (I), (II), (III), or (IV) described herein, or a solvate, hydrate, tautomer, N-oxide, or a pharmaceutically acceptable salt thereof, wherein the disease is selected from migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating epilepsy/seizure disorder in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating neuromyelitis optica (NMO) in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating Tourette syndrome in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating persistent motor tic disorder in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating persistent vocal tic disorder in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof. In another embodiment is a method of treating abdominal pain associated with irritable bowel syndrome in a patient in need thereof, comprising administering to the patient a therapeutically effective amount of a compound of Formula (I), (II), (III), or (IV) described herein, or a solvate, hydrate, tautomer, N-oxide, or a pharmaceutically acceptable salt thereof.

DETAILED DESCRIPTION OF THE INVENTION

This disclosure is directed, at least in part, to modulators or inhibitors of MAGL. For example, provided herein are compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^aR^f$, —N($R^a$)C(O)$R^f$, —N($R^a$)S(O)$_tR^f$ (where t is 1 or 2), —S(O)$_tOR^a$ (where t is 1 or 2), —S(O)$_tR^f$ (where t is 1 or 2) and —S(O)$_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—N$R^aR^f$, —N($R^a$)C(O)$R^f$, —N($R^a$)S(O)$_tR^f$ (where t is 1 or 2), —S(O)$_tOR^a$ (where t is 1 or 2), —S(O)$_tR^f$ (where t is 1 or 2), and —S(O)$_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_tR^a$ (where t is 1 or 2), —$R^b$—S(O)$_tOR^a$ (where t is 1 or 2), —$R^b$—S(O)$_tR^a$ (where t is 1 or 2), and —$R^b$—S(O)$_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl is saturated, (i.e., containing single C—C bonds only) or partially unsaturated (i.e., containing one or more double bonds). Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C (O)N(R$^a$)$_2$, —R$^b$—N(R$^a$)C(O)OR$^a$, —R$^b$—N(R$^a$)C(O)R$^a$, —R$^b$—N(R$^a$)S(O)R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_1$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heteroalkyl" refers to a straight or branched hydrocarbon chain alkyl radical containing no unsaturation, having from one to fifteen carbon atoms (e.g., C$_1$-C$_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl, or heteroarylalkyl, and each R$^f$ is independently alkyl, haloalkyl, cycloalkyl, aryl, aralkyl, heterocycloalkyl, heteroaryl, or heteroarylalkyl.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_1$R$^a$ (where t is 1 or 2), —R$^b$—S(O)$^t$OR$^a$ (where t is 1 or 2), —R$^b$—S(O)$_t$R$^a$ (where t is 1 or 2), and —R$^b$—S(O)$_1$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$ C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$-S(O)$_t$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as

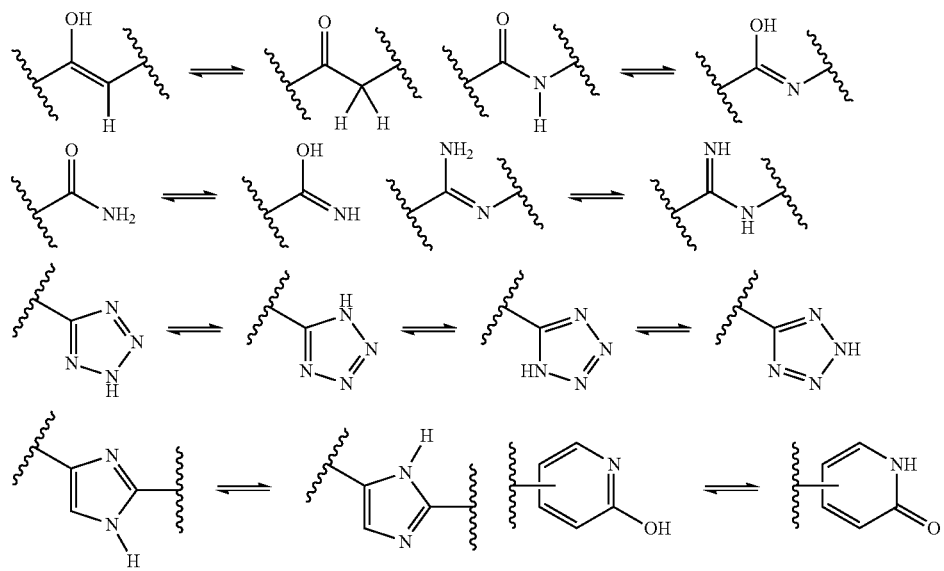

arginates, gluconates, and galacturonates (see, for example, Berge S. M et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Ib), (Ic), (Id), (II), (IIa), (IIb), (IIc), (III), or (IV) described herein are modulators of MAGL. In some embodiments, the compounds are inhibitors of MAGL. The compounds of Formula (I), (Ia), (Ib), (Ic), (Id), (II), (IIa), (IIb), (IIc), (III), or (IV) described herein, and compositions comprising these compounds, are useful for the treatment of pain.

In some embodiments is a compound of Formula (I):

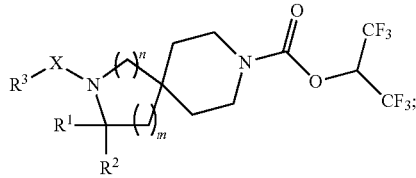

Formula (I)

wherein:
X is —CH$_2$— or —C(O)—;
R$^1$ is H or C$_{1-6}$alkyl;
R$^2$ is H or C$_{1-6}$alkyl;
R$^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R$^4$;
each R$^4$ is independently selected from C$_{1-6}$alkyl, halogen, —CN, C$_{1-6}$haloalkyl, C$_{3-8}$cycloalkyl, C$_{2-9}$heterocycloalkyl, —C$_{1-6}$alkyl-(C$_{2-9}$heterocycloalkyl), phenyl, —CH$_2$— phenyl, C$_{1-9}$heteroaryl, —OR$^7$, —CO$_2$R$^6$, and —CH$_2$CO$_2$R$^6$; wherein C$_{2-9}$heterocycloalkyl, —C$_{1-6}$alkyl(C$_{2-9}$heterocycloalkyl), phenyl, and C$_{1-9}$heteroaryl are optionally substituted with one or two R$^5$; or two adjacent R$^4$ form a 6-membered cycloalkyl or 6-membered heterocycloalkyl ring, wherein the cycloalkyl and heterocycloalkyl ring are optionally substituted with one or two R$^5$;
each R$^5$ is independently selected from halogen, C$_{1-6}$alkyl, C$_{1-6}$haloalkyl, C$_{1-6}$heteroalkyl, C$_{1-6}$alkoxy, C$_{3-8}$cycloalkyl, —C$_{1-6}$alkyl(C$_{3-8}$cycloalkyl), C$_{2-9}$heterocycloalkyl, —CO$_2$R$^6$, —CH$_2$CO$_2$R$^6$, and —C$_{1-6}$alkyl(C$_{2-9}$heterocycloalkyl) optionally substituted with C$_{1-6}$alkyl;
each R$^6$ is independently selected from H and C$_{1-6}$alkyl;
each R$^7$ is independently selected from H, C$_{1-6}$alkyl, C$_{1-6}$haloalkyl, and C$_{3-8}$cycloalkyl;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

In another embodiment is a compound of Formula (I), or a solvate, hydrate, tautomer, N-oxide, stereoisomer, or pharmaceutically acceptable salt thereof, wherein n is 0 and m is 2. In another embodiment is a compound of Formula (I), or a solvate, hydrate, tautomer, N-oxide, stereoisomer, or pharmaceutically acceptable salt thereof, wherein n is 1 and m is 1.

In another embodiment is a compound of Formula (I), or a solvate, hydrate, tautomer, N-oxide, stereoisomer, or pharmaceutically acceptable salt thereof, wherein R$^1$ is H. In another embodiment is a compound of Formula (I), or a solvate, hydrate, tautomer, N-oxide, stereoisomer, or pharmaceutically acceptable salt thereof, wherein R$^1$ is C$_{1-6}$alkyl. In another embodiment is a compound of Formula (I), or a solvate, hydrate, tautomer, N-oxide, stereoisomer, or pharmaceutically acceptable salt thereof, wherein R$^1$ is —CH$_3$. In another embodiment is a compound of Formula (I), or a solvate, hydrate, tautomer, N-oxide, stereoisomer, or pharmaceutically acceptable salt thereof, wherein R$^2$ is H. In another embodiment is a compound of Formula (I), or a solvate, hydrate, tautomer, N-oxide, stereoisomer, or pharmaceutically acceptable salt thereof, wherein R$^2$ is C$_{1-6}$alkyl. In another embodiment is a compound of Formula (I), or a solvate, hydrate, tautomer, N-oxide, stereoisomer, or pharmaceutically acceptable salt thereof, wherein R$^2$ is —CH$_3$. In another embodiment is a compound of Formula (I), or a solvate, hydrate, tautomer, N-oxide, stereoisomer, or pharmaceutically acceptable salt thereof, wherein R$^1$ is H and R$^2$ is H. In another embodiment is a compound of Formula (I), or a solvate, hydrate, tautomer, N-oxide, stereoisomer, or pharmaceutically acceptable salt thereof, wherein R$^1$ is H and R$^2$ is C$_{1-6}$alkyl. In another embodiment is a compound of Formula (I), or a solvate, hydrate, tautomer, N-oxide, stereoisomer, or pharmaceutically acceptable salt thereof, wherein R$^1$ is H and R$^2$ is —CH$_3$. In another embodiment is a compound of Formula (I), or a solvate, hydrate, tautomer, N-oxide, stereoisomer, or pharmaceutically acceptable salt thereof, wherein $R^1$ is $C_{1-6}$alkyl and $R^2$ is H.

In another embodiment is a compound of Formula (I), or a solvate, hydrate, tautomer, N-oxide, stereoisomer, or pharmaceutically acceptable salt thereof, wherein $R^1$ is —$CH_3$ and $R^2$ is H. In another embodiment is a compound of Formula (I), or a solvate, hydrate, tautomer, N-oxide, stereoisomer, or pharmaceutically acceptable salt thereof, wherein $R^1$ is $C_{1-6}$alkyl and $R^2$ is $C_{1-6}$alkyl. In another embodiment is a compound of Formula (I), or a solvate, hydrate, tautomer, N-oxide, stereoisomer, or pharmaceutically acceptable salt thereof, wherein $R^1$ is —$CH_3$ and $R^2$ is —$CH_3$.

In another embodiment is a compound of Formula (I), or a solvate, hydrate, tautomer, N-oxide, stereoisomer, or pharmaceutically acceptable salt thereof, wherein X is —$CH_2$—. In another embodiment is a compound of Formula (I), or a solvate, hydrate, tautomer, N-oxide, stereoisomer, or pharmaceutically acceptable salt thereof, wherein X is —C(O)—.

In another embodiment is a compound of Formula (I), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (I), or a solvate, hydrate, tautomer, N-oxide, stereoisomer, or pharmaceutically acceptable salt thereof, wherein $R^3$ is selected from:

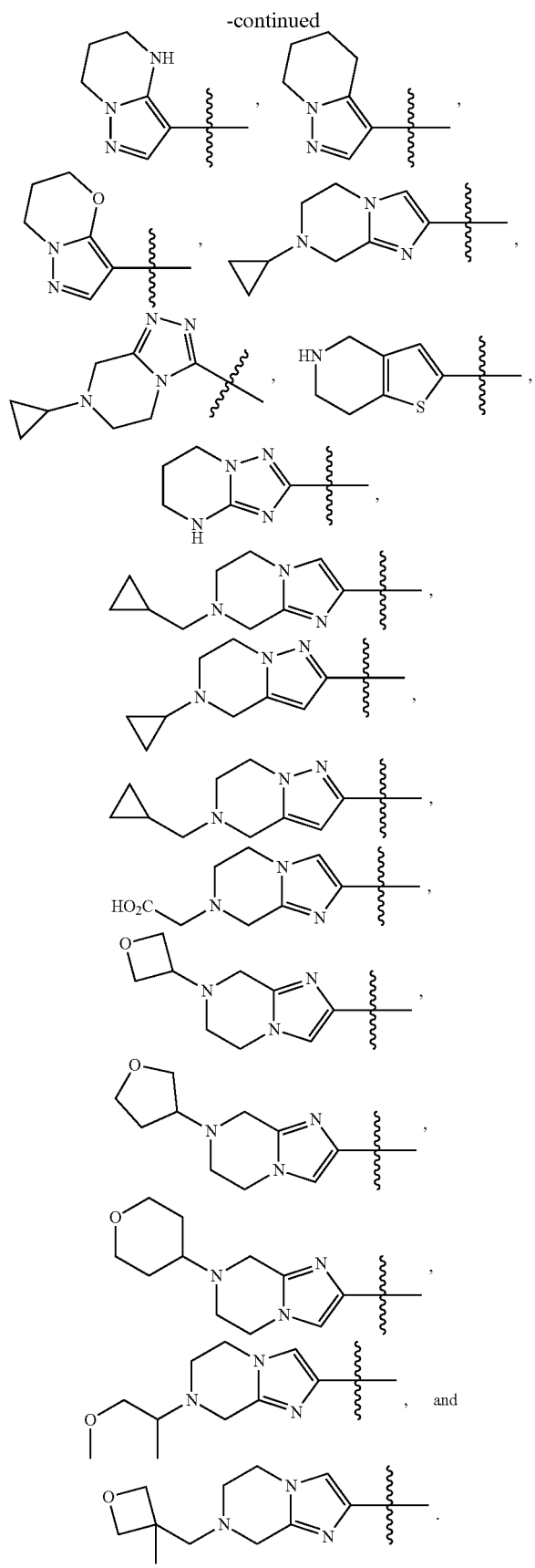

In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (I), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$ heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (I), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (I), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (I), or a solvate, hydrate, tautomer, N-oxide, stereoisomer, or pharmaceutically acceptable salt thereof, wherein $R^3$ is a pyrazole ring. In another embodiment is a compound of Formula (I), or a solvate, hydrate, tautomer, N-oxide, stereoisomer, or pharmaceutically acceptable salt thereof, wherein $R^3$ is a thiazole ring. In another embodiment is a compound of Formula (I), or a solvate, hydrate, tautomer, N-oxide, stereoisomer, or pharmaceutically acceptable salt thereof, wherein $R^3$ is an isoxazole ring. In another embodiment is a compound of Formula (I), or a solvate, hydrate, tautomer, N-oxide, stereoisomer, or pharmaceutically acceptable salt thereof, wherein $R^3$ is an oxazole ring. In another embodiment is a compound of Formula (I), or a solvate, hydrate, tautomer, N-oxide, stereoisomer, or pharmaceutically acceptable salt thereof, wherein $R^3$ is an imidazole ring. In another embodiment is a compound of Formula (I), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (I), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (I), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (I), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (I), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (I), or a solvate, hydrate, tautomer, N-oxide, stereoisomer, or pharmaceutically acceptable salt thereof, wherein $R^3$ is a pyridine ring. In another embodiment is a compound of Formula (I), or a solvate, hydrate, tautomer, N-oxide, stereoisomer, or pharmaceutically acceptable salt thereof, wherein $R^3$ is a pyrimidine ring. In another embodiment is a compound of Formula (I), or a solvate, hydrate, tautomer, N-oxide, stereoisomer, or pharmaceutically acceptable salt thereof, wherein $R^3$ is a pyridazine ring. In another embodiment is a compound of Formula (I), or a solvate, hydrate, tautomer, N-oxide, stereoisomer, or pharmaceutically acceptable salt thereof, wherein $R^3$ is a pyrazine ring.

In another embodiment is a compound of Formula (I), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_1$alkyl. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (I), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (I), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (I), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is $C_{1-6}$haloalkyl. In another embodiment is a compound of Formula (I), or a solvate, hydrate, tautomer, N-oxide, stereoisomer, or pharmaceutically acceptable salt thereof, wherein R³ is a 10-membered bicyclic heteroaryl ring selected from a quinolone, isoquinolone, quinazoline, quinoxaline, phthalazine, and a naphthyridine ring. In another embodiment is a compound of Formula (I), or a solvate, hydrate, tautomer, N-oxide, stereoisomer, or pharmaceutically acceptable salt thereof, wherein R³ is selected from:

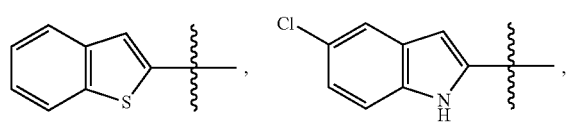

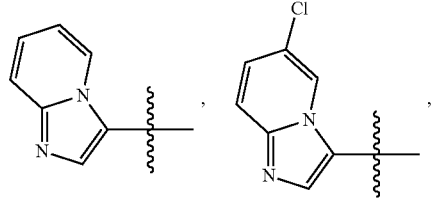

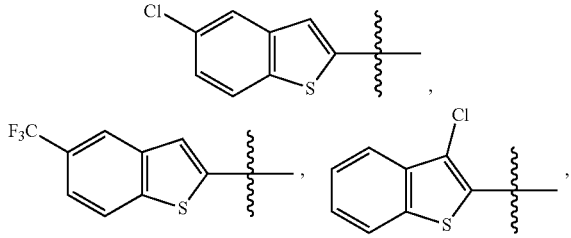

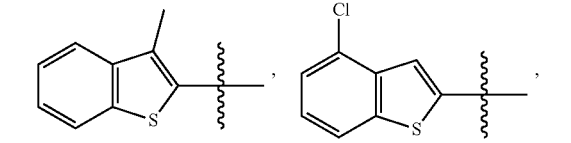

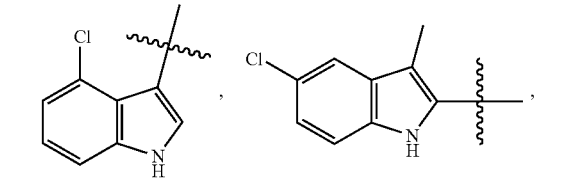

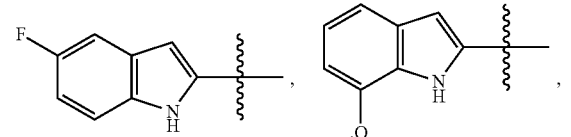

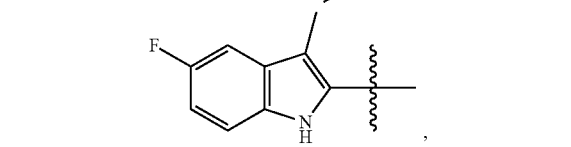

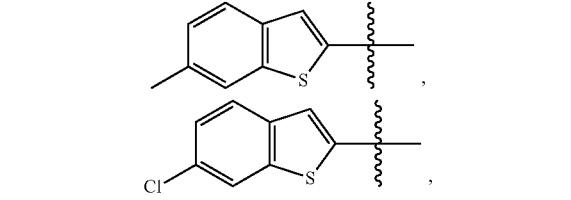

-continued

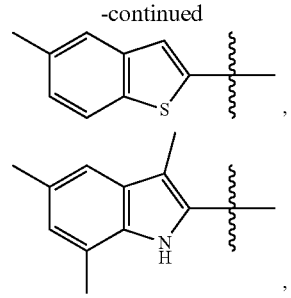

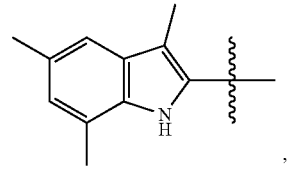

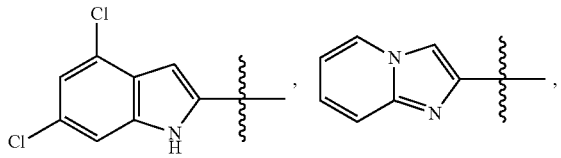

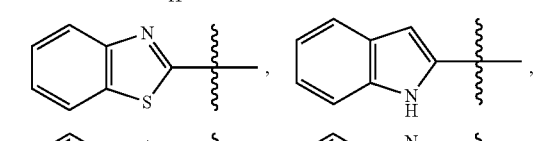

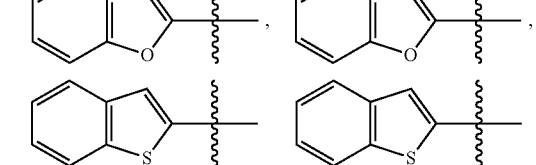

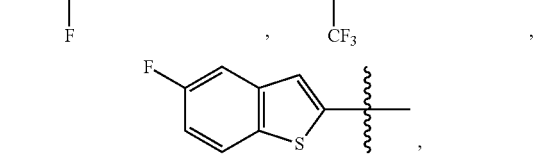

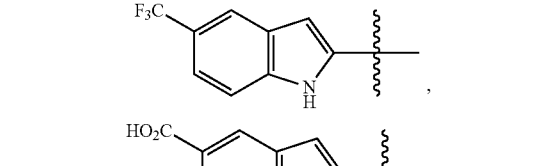

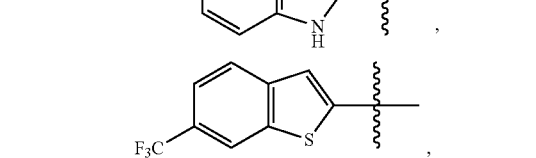

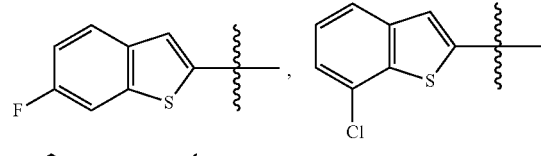

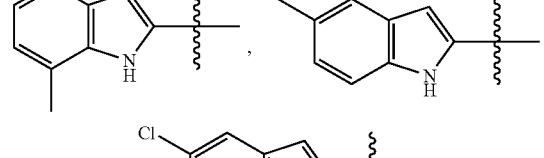

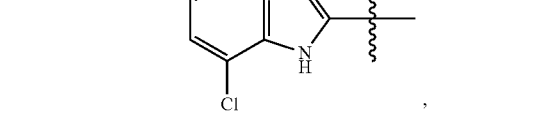

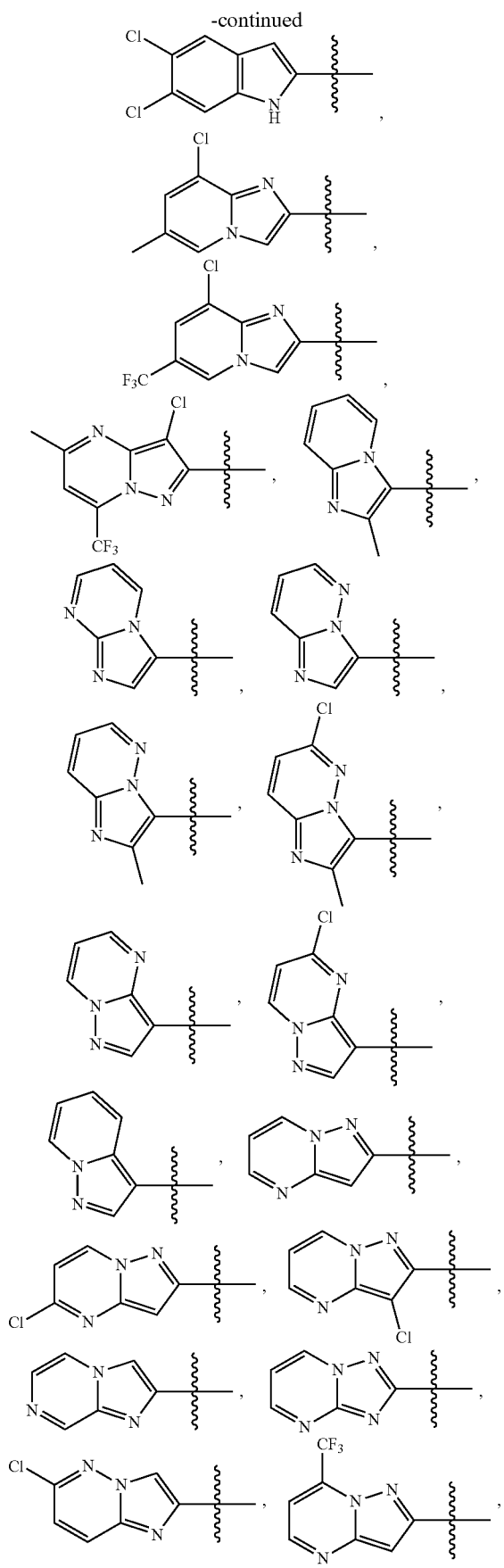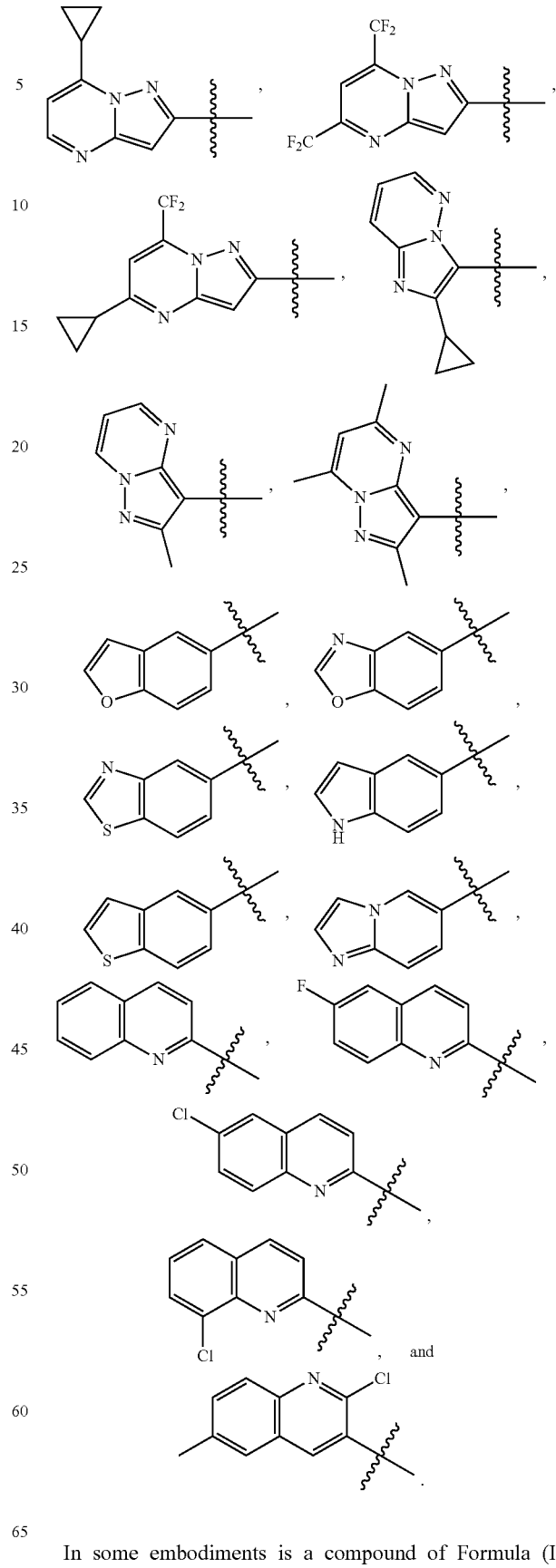
In some embodiments is a compound of Formula (I) having the structure of Formula (Ia):

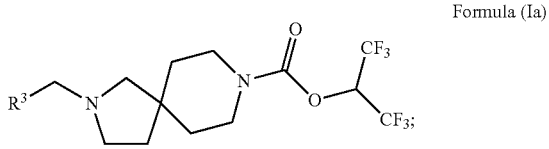

Formula (Ia)

wherein:
- $R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;
- each $R^4$ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —$CH_2$— phenyl, $C_{1-9}$heteroaryl, —$OR^7$, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;
- each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl; and
- each $R^6$ is independently selected from H and $C_{1-6}$alkyl;
- each $R^7$ is independently selected from H, $C_{1-6}$alkyl, $C_{1-6}$haloalkyl, and $C_{3-8}$cycloalkyl; or a solvate, hydrate, tautomer, N-oxide, stereoisomer, or pharmaceutically acceptable salt thereof.

In another embodiment is a compound of Formula (Ia), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (Ia), or a solvate, hydrate, tautomer, N-oxide, stereoisomer, or pharmaceutically acceptable salt thereof, wherein $R^3$ is selected from:

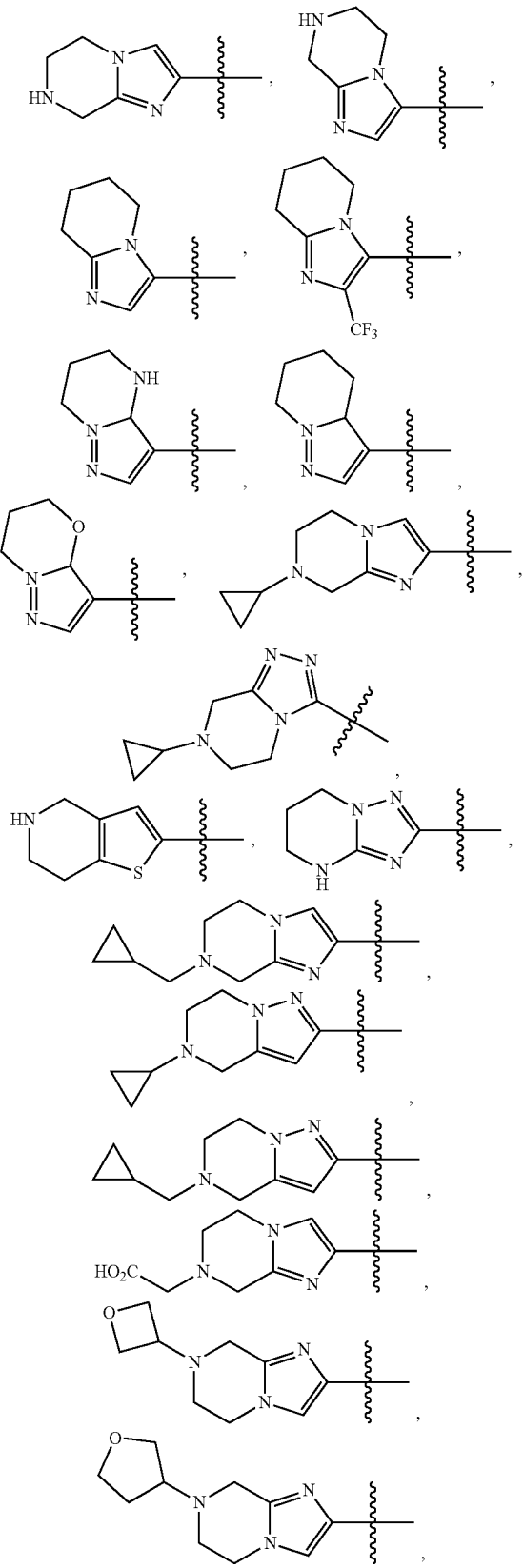

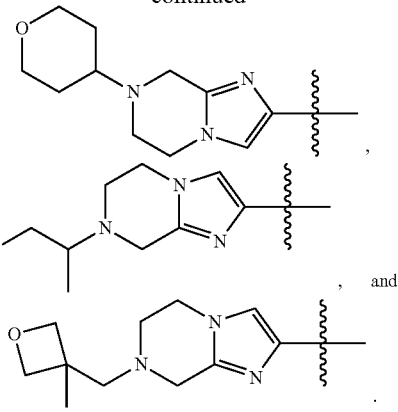

In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (Ia), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (Ia), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (Ia), or a solvate, hydrate, tautomer, N-oxide, stereoisomer, or pharmaceutically acceptable salt thereof, wherein $R^3$ is a pyrazole ring. In another embodiment is a compound of Formula (Ia), or a solvate, hydrate, tautomer, N-oxide, stereoisomer, or pharmaceutically acceptable salt thereof, wherein $R^3$ is a thiazole ring. In another embodiment is a compound of Formula (Ia), or a solvate, hydrate, tautomer, N-oxide, stereoisomer, or pharmaceutically acceptable salt thereof, wherein $R^3$ is an isoxazole ring. In another embodiment is a compound of Formula (Ia), or a solvate, hydrate, tautomer, N-oxide, stereoisomer, or pharmaceutically acceptable salt thereof, wherein $R^3$ is an oxazole ring. In another embodiment is a compound of Formula (Ia), or a solvate, hydrate, tautomer, N-oxide, stereoisomer, or pharmaceutically acceptable salt thereof, wherein $R^3$ is an imidazole ring. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (Ia), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (Ia), or a solvate, hydrate, tautomer, N-oxide, stereoisomer, or pharmaceutically acceptable salt thereof, wherein $R^3$ is a pyridine ring. In another embodiment is a compound of Formula (Ia), or a solvate, hydrate, tautomer, N-oxide, stereoisomer, or pharmaceutically acceptable salt thereof, wherein $R^3$ is a pyrimidine ring. In another embodiment is a compound of Formula (Ia), or a solvate, hydrate, tautomer, N-oxide, stereoisomer, or pharmaceutically acceptable salt thereof, wherein $R^3$ is a pyridazine ring. In another embodiment is a compound of Formula (Ia), or a solvate, hydrate, tautomer, N-oxide, stereoisomer, or pharmaceutically acceptable salt thereof, wherein $R^3$ is a pyrazine ring.

In another embodiment is a compound of Formula (Ia), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (Ia), or a solvate, hydrate, tautomer, N-oxide, stereoisomer, or pharmaceutically acceptable salt thereof, wherein $R^3$ is selected from:

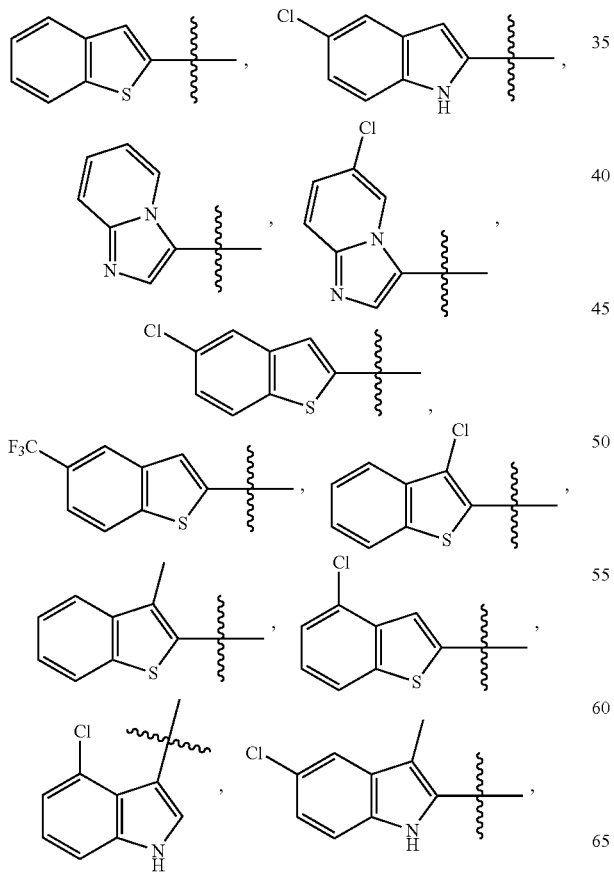

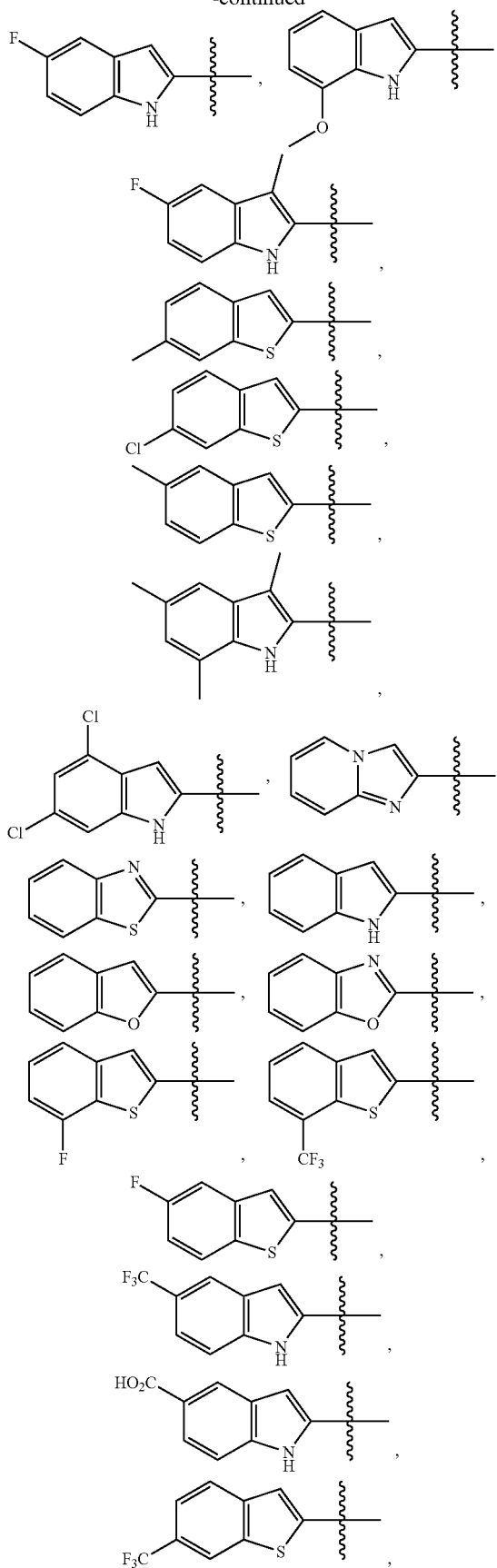

41
-continued
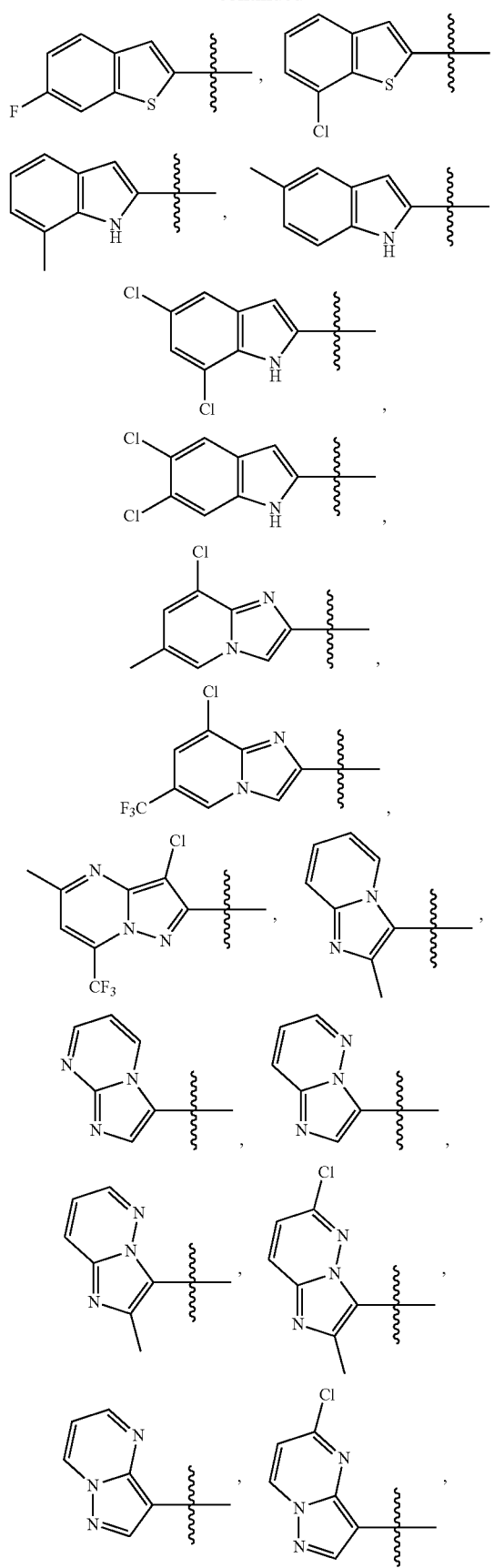
42
-continued
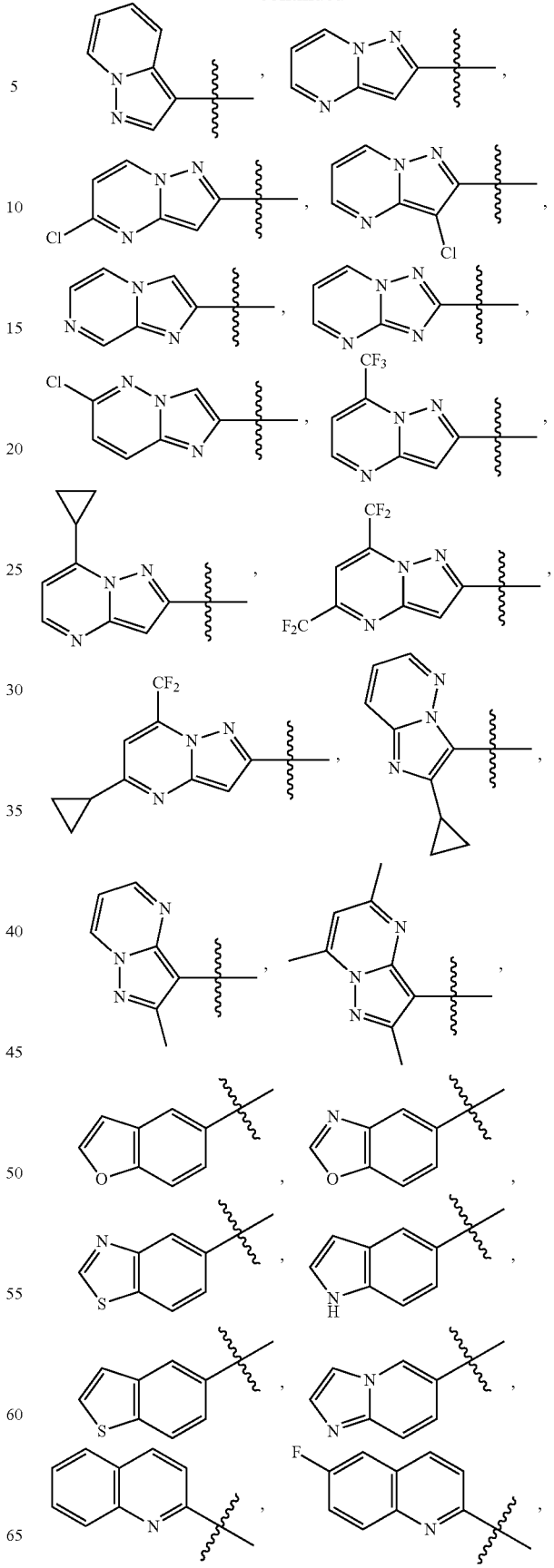

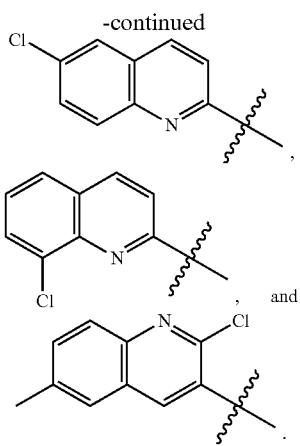

In some embodiments is a compound of Formula (I) having the structure of Formula (Ib):

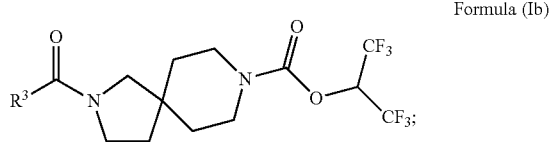

Formula (Ib)

wherein:
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;
each $R^4$ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —$CH_2$— phenyl, $C_{1-9}$heteroaryl, —$OR^7$, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;
each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl; and
each $R^6$ is independently selected from H and $C_{1-6}$alkyl;
each $R^7$ is independently selected from H, $C_{1-6}$alkyl, $C_{1-6}$haloalkyl, and $C_{3-8}$cycloalkyl;
or a solvate, hydrate, tautomer, N-oxide, stereoisomer, or pharmaceutically acceptable salt thereof.

In another embodiment is a compound of Formula (Ib), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent R⁴ form a 6-membered heterocycloalkyl ring substituted with one R⁵ and R⁵ is —CH₂CO₂H. In another embodiment is a compound of Formula (Ib), or a solvate, hydrate, tautomer, N-oxide, stereoisomer, or pharmaceutically acceptable salt thereof, wherein R³ is a 5-membered heteroaryl ring substituted with two or three R⁴, wherein two adjacent R⁴ form a 6-membered cycloalkyl ring optionally substituted with one or two R⁵. In another embodiment is a compound of Formula (Ib), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form an unsubstituted 6-membered cycloalkyl ring. In another embodiment is a compound of Formula (Ib), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered cycloalkyl ring substituted with one R⁵. In another embodiment is a compound of Formula (Ib), or a solvate, hydrate, tautomer, N-oxide, stereoisomer, or pharmaceutically acceptable salt thereof, wherein R³ is selected from:

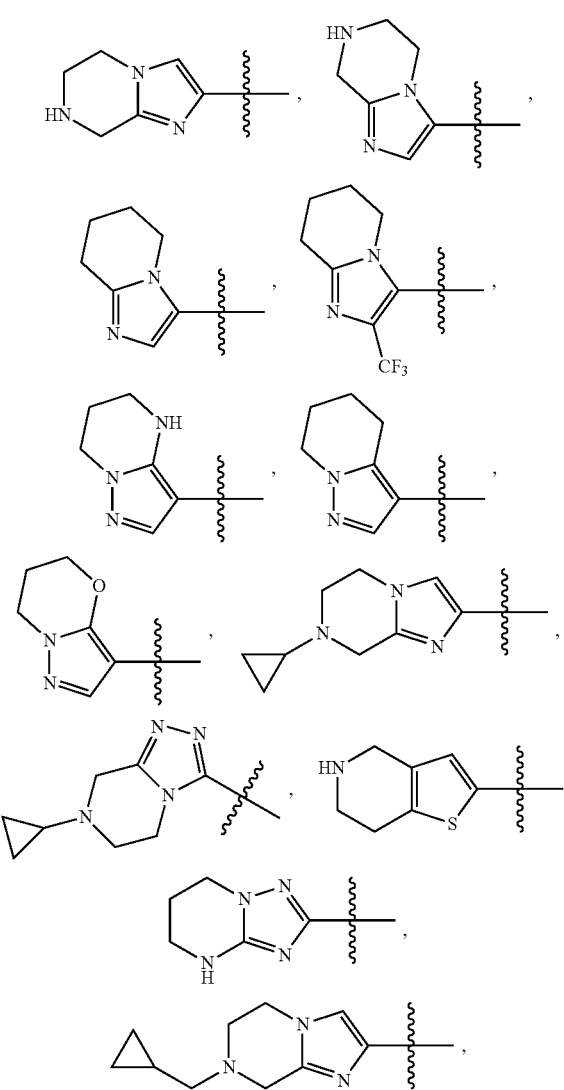

In another embodiment is a compound of Formula b), or a solvate, hydrate, tautomer, N-oxide, hydrate, tautomer, N-oxide, stereoisomer, or pharmaceutically acceptable salt thereof, wherein embodiment is a compound of Formula (Ib), or a solvate, hydrate tautomer, N-oxide, membered heteroaryl ring. In another embodiment is a compound of Formula (Ib), or a solvate, hydrate, tautomer, N-oxide, stereoisomer, or pharmaceutically acceptable salt thereof, wherein R³ is a 5-membered heteroaryl ring substituted with one, two, or three R⁴, wherein each R⁴ is independently selected from halogen, —CN, C₁₋₆alkyl, C₁₋₆haloalkyl, C₃₋₈cycloalkyl, C₂₋₉heterocycloalkyl, phenyl, —OR⁷, —CO₂H, and —CH₂CO₂H, and wherein C₂₋₉heterocycloalkyl and phenyl are optionally substituted with one or two R⁵. In another embodiment is a compound of Formula (Ib), or a solvate, hydrate, tautomer, N-oxide, stereoisomer, or pharmaceutically acceptable salt thereof, wherein R³ is a 5-membered heteroaryl ring substituted with one or two R⁴, wherein each R⁴ is independently selected from halogen, C₁₋₆alkyl, C₂₋₉heterocycloalkyl, and phenyl, and wherein C₂₋₉heterocycloalkyl and phenyl are optionally substituted with one or two R⁵, and each R⁵ is independently selected from halogen, C₁₋₆alkoxy, C₂₋₉heterocycloalkyl, or —CO₂H. In another embodiment is a compound of Formula (Ib), or a solvate, hydrate, tautomer, N-oxide, stereoisomer, or pharmaceutically acceptable salt thereof, wherein R³ is an unsubstituted 5-membered heteroaryl ring. In another embodiment is a compound of Formula (Ib), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (Ib), or a solvate, hydrate, tautomer, N-oxide, stereoisomer, or pharmaceutically acceptable salt thereof, wherein $R^3$ is a pyrazole ring. In another embodiment is a compound of Formula (Ib), or a solvate, hydrate, tautomer, N-oxide, stereoisomer, or pharmaceutically acceptable salt thereof, wherein $R^3$ is a thiazole ring. In another embodiment is a compound of Formula (Ib), or a solvate, hydrate, tautomer, N-oxide, stereoisomer, or pharmaceutically acceptable salt thereof, wherein $R^3$ is an isoxazole ring. In another embodiment is a compound of Formula (Ib), or a solvate, hydrate, tautomer, N-oxide, stereoisomer, or pharmaceutically acceptable salt thereof, wherein $R^3$ is an oxazole ring. In another embodiment is a compound of Formula (Ib), or a solvate, hydrate, tautomer, N-oxide, stereoisomer, or pharmaceutically acceptable salt thereof, wherein $R^3$ is an imidazole ring. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (Ib), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (Ib), or a solvate, hydrate, tautomer, N-oxide, stereoisomer, or pharmaceutically acceptable salt thereof, wherein $R^3$ is a pyridine ring. In another embodiment is a compound of Formula (Ib), or a solvate, hydrate, tautomer, N-oxide, stereoisomer, or pharmaceutically acceptable salt thereof, wherein $R^3$ is a pyrimidine ring. In another embodiment is a compound of Formula (Ib), or a solvate, hydrate, tautomer, N-oxide, stereoisomer, or pharmaceutically acceptable salt thereof, wherein $R^3$ is a pyridazine ring. In another embodiment is a compound of Formula (Ib), or a solvate, hydrate, tautomer, N-oxide, stereoisomer, or pharmaceutically acceptable salt thereof, wherein $R^3$ is a pyrazine ring.

In another embodiment is a compound of Formula (Ib), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (Ib), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (Ib), or a solvate, hydrate, tautomer, N-oxide, stereoisomer, or pharmaceutically acceptable salt thereof, wherein $R^3$ is selected from:

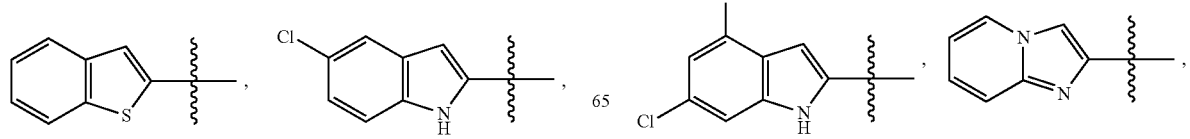

-continued

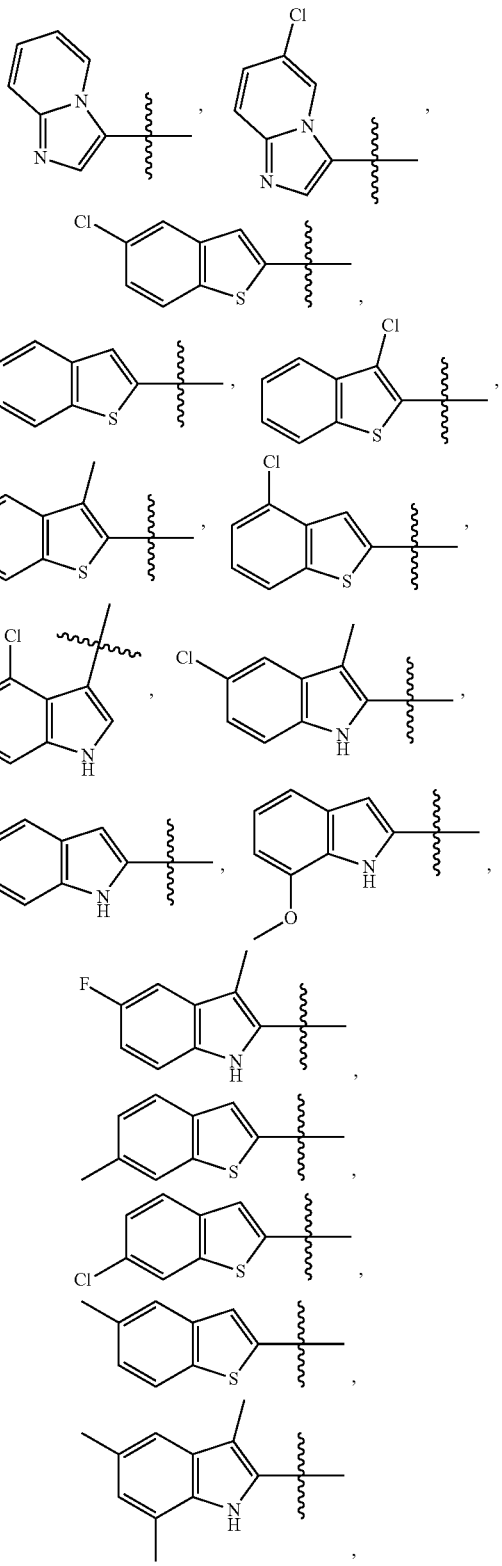

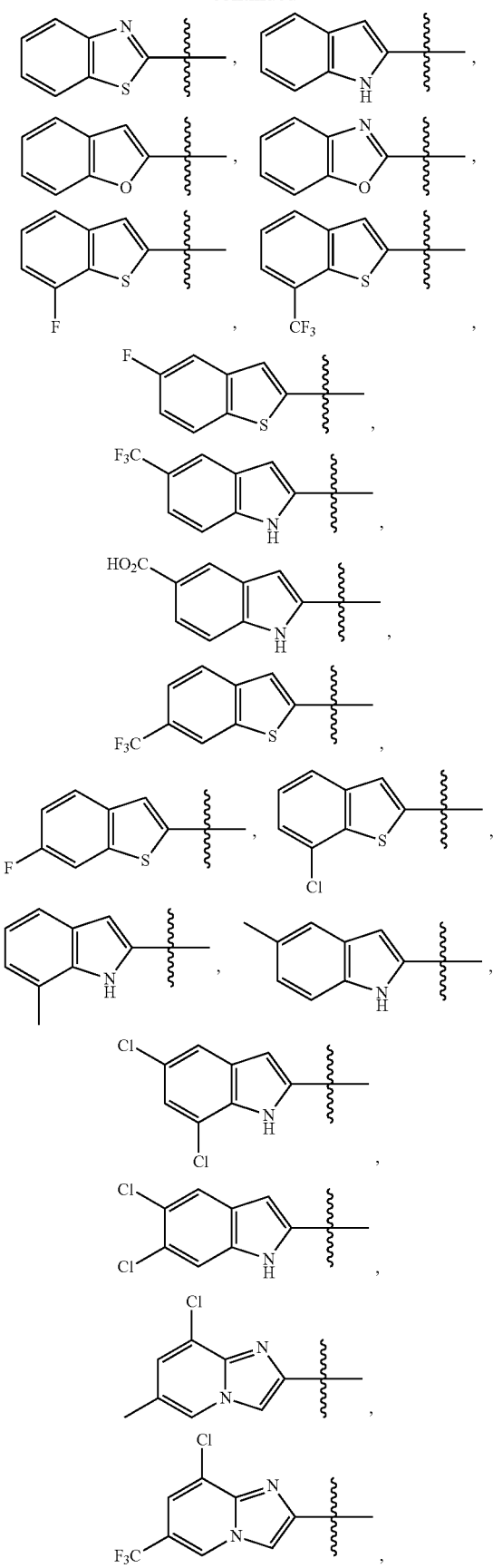
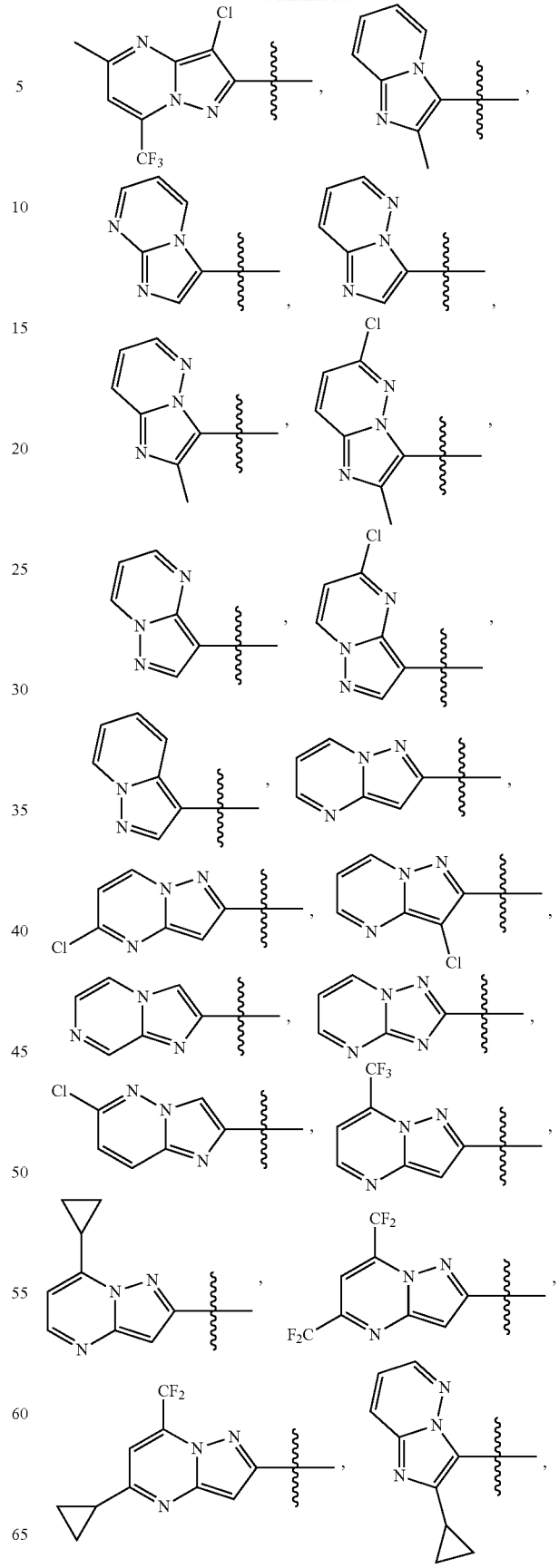

53

-continued

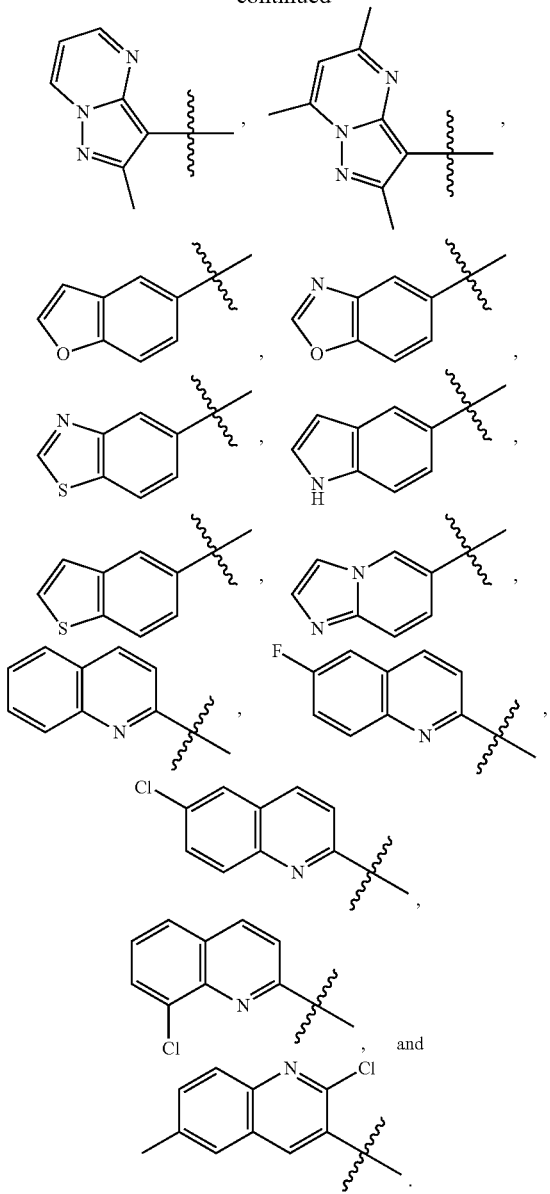

In some embodiments is a compound of Formula (I) having the structure of Formula (Ic):

Formula (Ic)

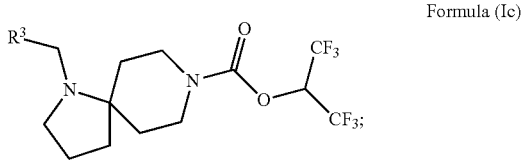

wherein:
R³ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R⁴;
each R⁴ is independently selected from $C_{1-6}$alkyl, halogen, —CN, $C_{1-6}$haloalkyl, $C_{3-8}$ cycloalkyl, $C_{2-9}$hetero-

54 cycloalkyl, —$C_{1-6}$alkyl-($C_{2-9}$heterocycloalkyl), phenyl, —$CH_2$— phenyl, $C_{1-9}$heteroaryl, —$OR^7$, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two R⁵; or two adjacent R⁴ form a 6-membered cycloalkyl or 6-membered heterocycloalkyl ring, wherein the cycloalkyl and heterocycloalkyl ring are optionally substituted with one or two R⁵;
each R⁵ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl; and
each R⁶ is independently selected from H and $C_{1-6}$alkyl;
each R⁷ is independently selected from H, $C_{1-6}$alkyl, $C_{1-6}$haloalkyl, and $C_{3-8}$cycloalkyl;
or a solvate, hydrate, tautomer, N-oxide, stereoisomer, or pharmaceutically acceptable salt thereof.

In another embodiment is a compound of Formula (Ic), or a solvate, hydrate, tautomer, N-oxide, stereoisomer, or pharmaceutically acceptable salt thereof, wherein R³ is a 5- to 6-membered heteroaryl ring optionally substituted with one, two, or three R⁴. In another embodiment is a compound of Formula (Ic), or a solvate, hydrate, tautomer, N-oxide, stereoisomer, or pharmaceutically acceptable salt thereof, wherein R³ is a 5-membered heteroaryl ring optionally substituted with one, two, or three R⁴. In another embodiment is a compound of Formula (Ic), or a solvate, hydrate, tautomer, N-oxide, stereoisomer, or pharmaceutically acceptable salt thereof, wherein R³ is an unsubstituted 5-membered heteroaryl ring. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with one, two, or three R⁴. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with two or three R⁴, wherein two adjacent R⁴ form a 6-membered heterocycloalkyl ring optionally substituted with one or two R⁵. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form an unsubstituted 6-membered heterocycloalkyl ring. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (Ic), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one $R^5$ and $R^5$ is $C_{1-6}$alkyl. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (Ic), or a solvate, hydrate, tautomer, N-oxide, stereoisomer, or pharmaceutically acceptable salt thereof, wherein $R^3$ is selected from:

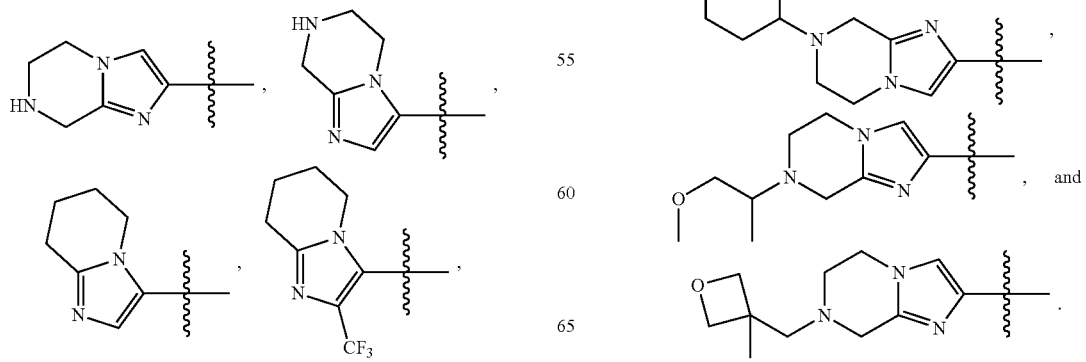

In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (Ic), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (Ic), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (Ic), or a solvate, hydrate, tautomer, N-oxide, stereoisomer, or pharmaceutically acceptable salt thereof, wherein $R^3$ is a pyrazole ring. In another embodiment is a compound of Formula (Ic), or a solvate, hydrate, tautomer, N-oxide, stereoisomer, or pharmaceutically acceptable salt thereof, wherein $R^3$ is a thiazole ring. In another embodiment is a compound of Formula (Ic), or a solvate, hydrate, tautomer, N-oxide, stereoisomer, or pharmaceutically acceptable salt thereof, wherein $R^3$ is an isoxazole ring. In another embodiment is a compound of Formula (Ic), or a solvate, hydrate, tautomer, N-oxide, stereoisomer, or pharmaceutically acceptable salt thereof, wherein $R^3$ is an oxazole ring. In another embodiment is a compound of Formula (Ic), or a solvate, hydrate, tautomer, N-oxide, stereoisomer, or pharmaceutically acceptable salt thereof, wherein $R^3$ is an imidazole ring. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (Ic), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (Ic), or a solvate, hydrate, tautomer, N-oxide, stereoisomer, or pharmaceutically acceptable salt thereof, wherein $R^3$ is a pyridine ring. In another embodiment is a compound of Formula (Ic), or a solvate, hydrate, tautomer, N-oxide, stereoisomer, or pharmaceutically acceptable salt thereof, wherein $R^3$ is a pyrimidine ring. In another embodiment is a compound of Formula (Ic), or a solvate, hydrate, tautomer, N-oxide, stereoisomer, or pharmaceutically acceptable salt thereof, wherein $R^3$ is a pyridazine ring. In another embodiment is a compound of Formula (Ic), or a solvate, hydrate, tautomer, N-oxide, stereoisomer, or pharmaceutically acceptable salt thereof, wherein $R^3$ is a pyrazine ring.

In another embodiment is a compound of Formula (Ic), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (Ic), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (Ic), or a solvate, hydrate, tautomer, N-oxide, stereoisomer, or pharmaceutically acceptable salt thereof, wherein $R^3$ is selected from:

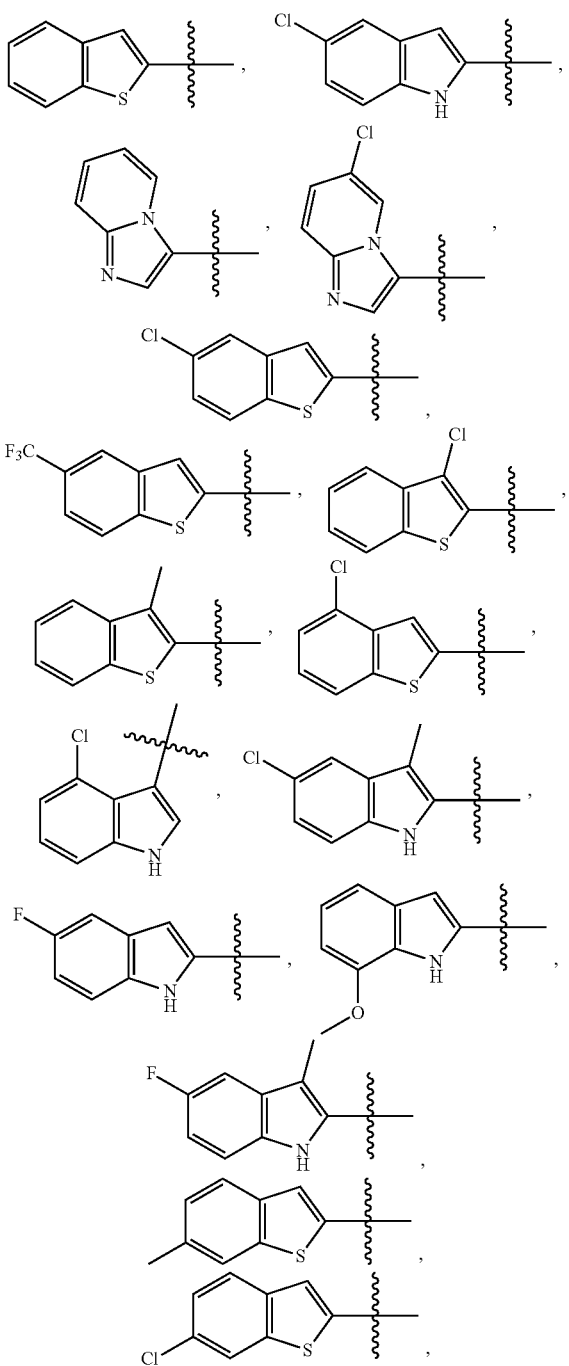

-continued
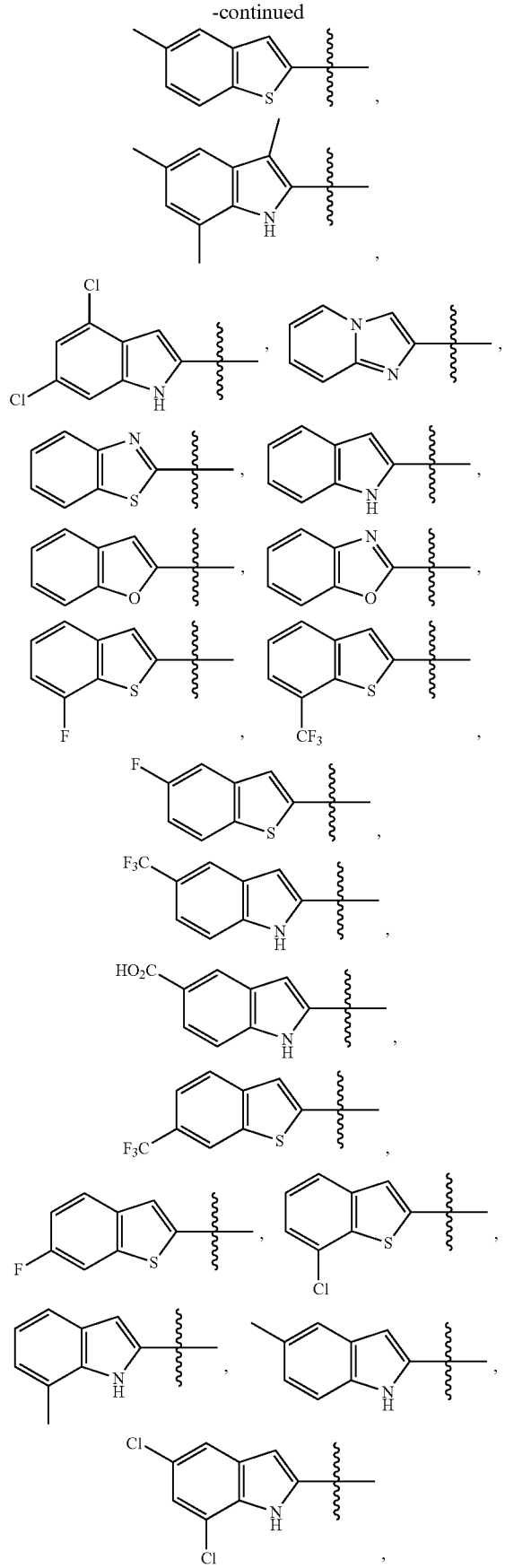
-continued
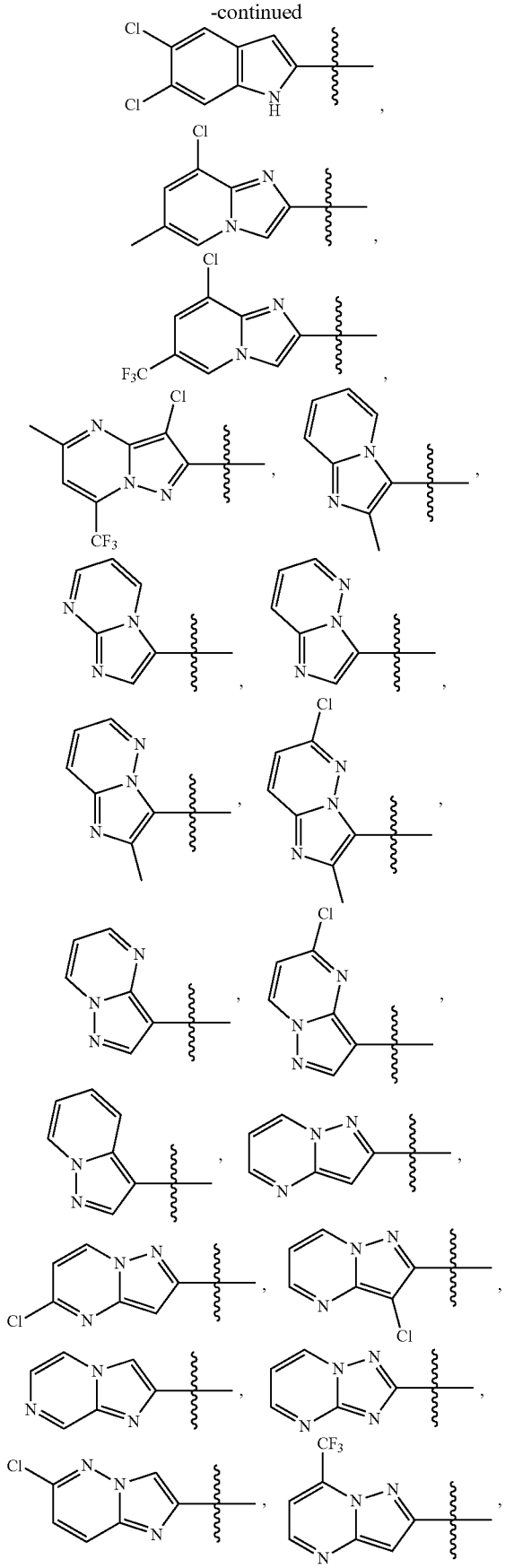

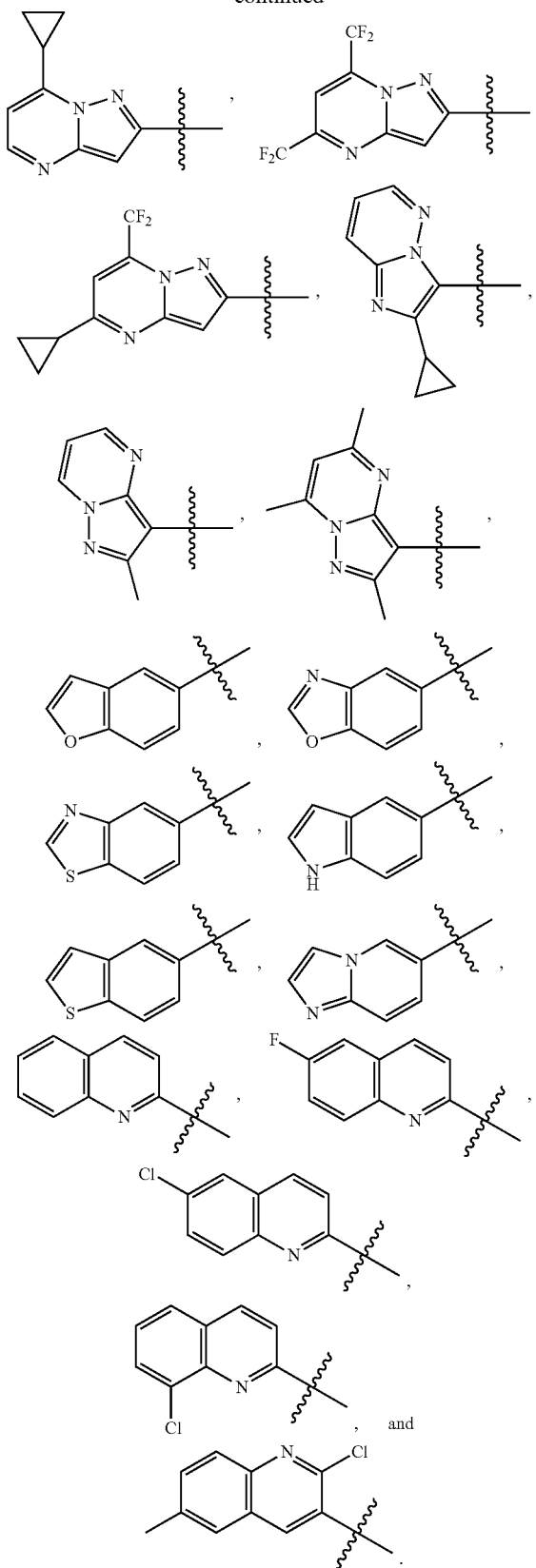

In some embodiments is a compound of Formula (I) having the structure of Formula (Id):

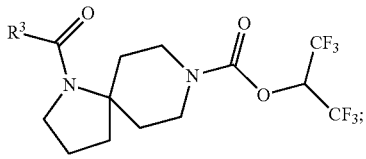

Formula (Id)

wherein:
R³ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R⁴;

each R⁴ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —$CH_2$— phenyl, $C_{1-9}$heteroaryl, —OR⁷, —$CO_2$R⁶, and —$CH_2CO_2$R⁶; wherein $C_{2-9}$heterocycloalkyl, —$C_{1-6}$alkyl($C_{2-9}$heterocycloalkyl), phenyl, and $C_{1-9}$heteroaryl are optionally substituted with one or two R⁵; or two adjacent R⁴ form a 6-membered cycloalkyl or 6-membered heterocycloalkyl ring, wherein the cycloalkyl and heterocycloalkyl ring are optionally substituted with one or two R⁵;

each R⁵ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2$R⁶, —$CH_2CO_2$R⁶, and —$C_{1-6}$alkyl($C_{2-9}$heterocycloalkyl) optionally substituted with $C_{1-6}$alkyl;

each R⁶ is independently selected from H and $C_{1-6}$alkyl; and each R⁷ is independently selected from H, $C_{1-6}$alkyl, $C_{1-6}$haloalkyl, and $C_{3-8}$cycloalkyl;

or a solvate, hydrate, tautomer, N-oxide, stereoisomer, or pharmaceutically acceptable salt thereof.

In another embodiment is a compound of Formula (Id), or a solvate, hydrate, tautomer, N-oxide, stereoisomer, or pharmaceutically acceptable salt thereof, wherein R³ is a 5- to 6-membered heteroaryl ring optionally substituted with one, two, or three R⁴. In another embodiment is a compound of Formula (Id), or a solvate, hydrate, tautomer, N-oxide, stereoisomer, or pharmaceutically acceptable salt thereof, wherein R³ is a 5-membered heteroaryl ring optionally substituted with one, two, or three R⁴. In another embodiment is a compound of Formula (Id), or a solvate, hydrate, tautomer, N-oxide, stereoisomer, or pharmaceutically acceptable salt thereof, wherein R³ is an unsubstituted 5-membered heteroaryl ring. In another embodiment is a compound of Formula (Id), or a solvate, hydrate, tautomer, N-oxide, stereoisomer, or pharmaceutically acceptable salt thereof, wherein R³ is a 5-membered heteroaryl ring substituted with one, two, or three R⁴. In another embodiment is a compound of Formula (Id), or a solvate, hydrate, tautomer, N-oxide, stereoisomer, or pharmaceutically acceptable salt thereof, wherein R³ is a 5-membered heteroaryl ring substituted with two or three R⁴, wherein two adjacent R⁴ form a 6-membered heterocycloalkyl ring optionally substituted with one or two R⁵. In another embodiment is a compound of Formula (Id), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form an unsubstituted 6-membered heterocycloalkyl ring. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (Id), or a solvate, hydrate, tautomer, N-oxide, stereoisomer, or pharmaceutically acceptable salt thereof, wherein $R^3$ is selected from:

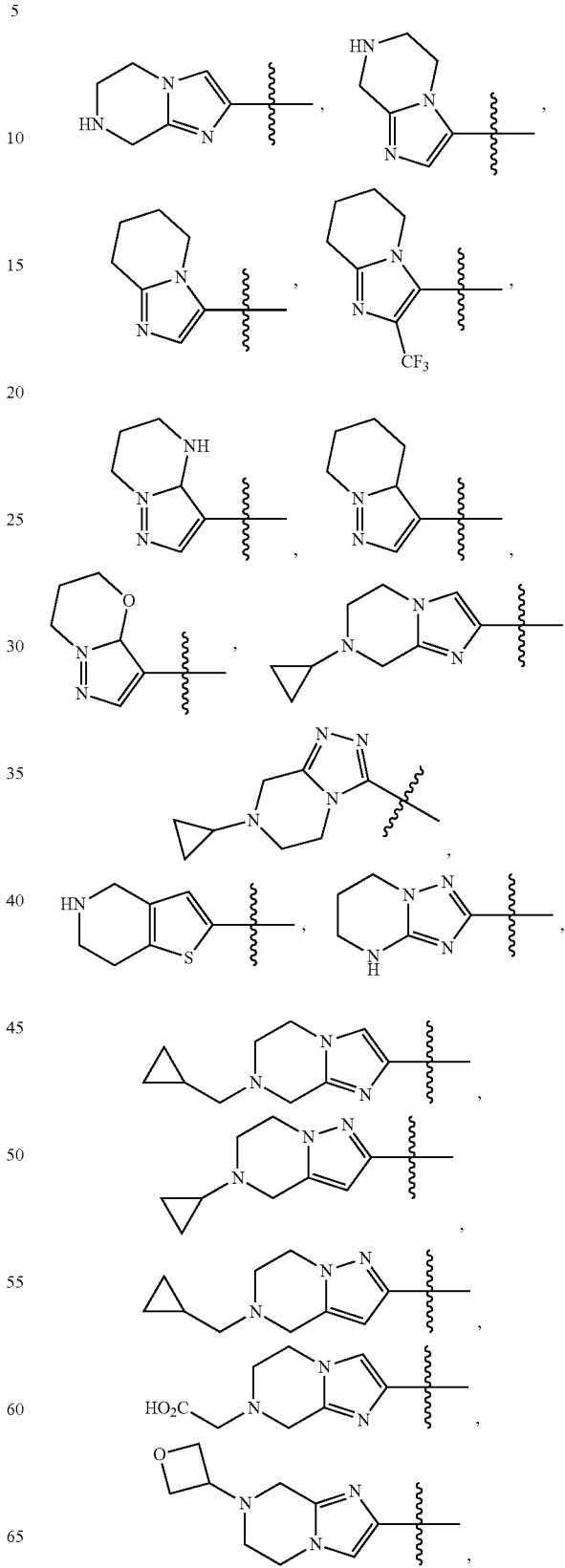

In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (Id), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (Id), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (Id), or a solvate, hydrate, tautomer, N-oxide, stereoisomer, or pharmaceutically acceptable salt thereof, wherein $R^3$ is a pyrazole ring. In another embodiment is a compound of Formula (Id), or a solvate, hydrate, tautomer, N-oxide, stereoisomer, or pharmaceutically acceptable salt thereof, wherein $R^3$ is a thiazole ring. In another embodiment is a compound of Formula (Id), or a solvate, hydrate, tautomer, N-oxide, stereoisomer, or pharmaceutically acceptable salt thereof, wherein $R^3$ is an isoxazole ring. In another embodiment is a compound of Formula (Id), or a solvate, hydrate, tautomer, N-oxide, stereoisomer, or pharmaceutically acceptable salt thereof, wherein $R^3$ is an oxazole ring. In another embodiment is a compound of Formula (Id), or a solvate, hydrate, tautomer, N-oxide, stereoisomer, or pharmaceutically acceptable salt thereof, wherein $R^3$ is an imidazole ring. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (Id), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (Id), or a solvate, hydrate, tautomer, N-oxide, stereoisomer, or pharmaceutically acceptable salt thereof, wherein $R^3$ is a pyridine ring. In another embodiment is a compound of Formula (Id), or a solvate, hydrate, tautomer, N-oxide, stereoisomer, or pharmaceutically acceptable salt thereof, wherein $R^3$ is a pyrimidine ring. In another embodiment is a compound of Formula (Id), or a solvate, hydrate, tautomer, N-oxide, stereoisomer, or pharmaceutically acceptable salt thereof, wherein $R^3$ is a pyridazine ring. In another embodiment is a compound of Formula (Id), or a solvate, hydrate, tautomer, N-oxide, stereoisomer, or pharmaceutically acceptable salt thereof, wherein $R^3$ is a pyrazine ring.

In another embodiment is a compound of Formula (Id), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (Id), or a solvate, hydrate, tautomer, N-oxide, stereoisomer, or pharmaceutically acceptable salt thereof, wherein $R^3$ is selected from:

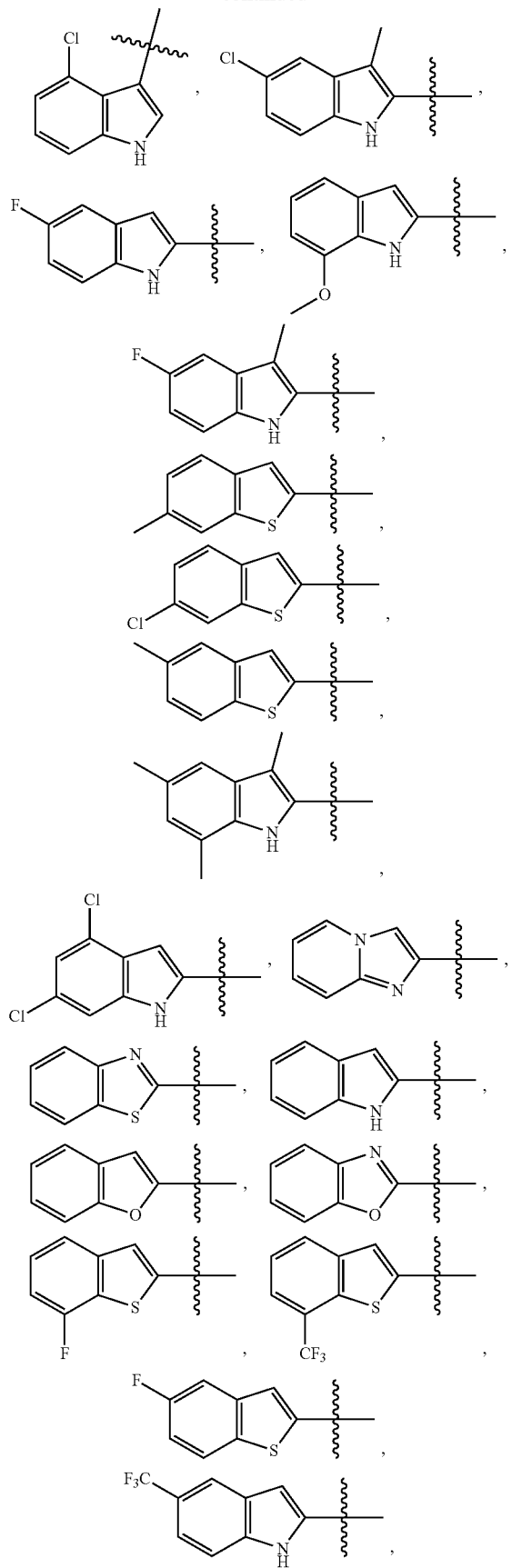
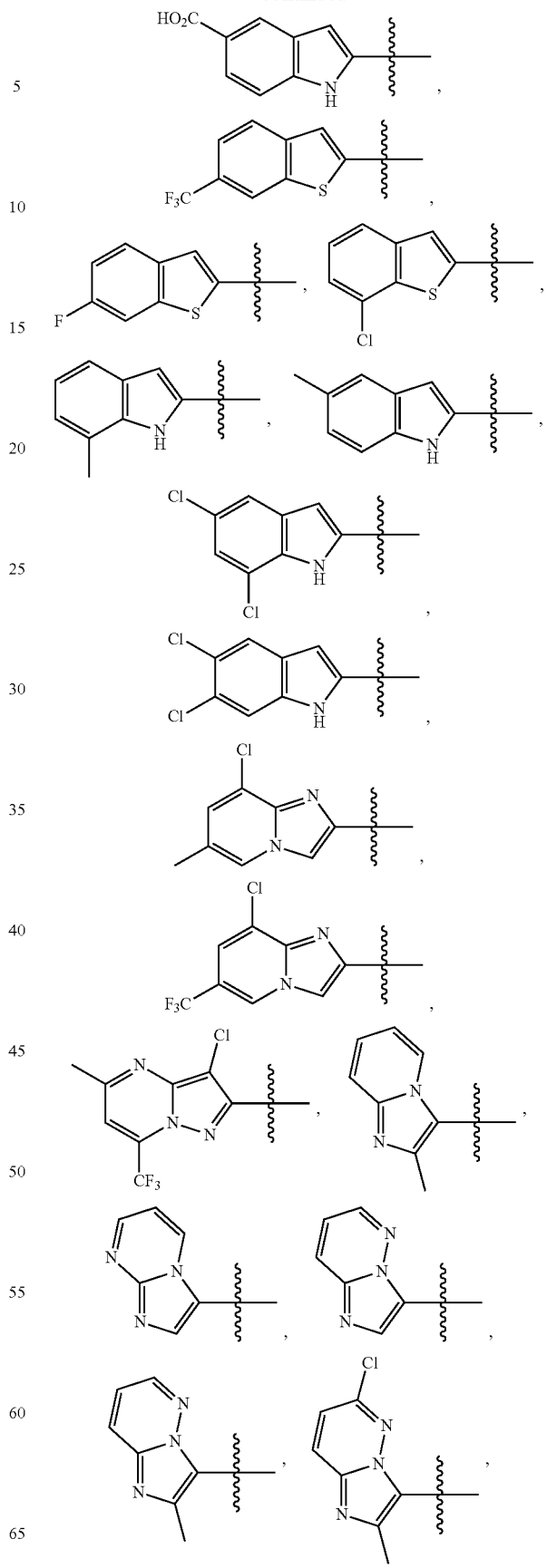

-continued

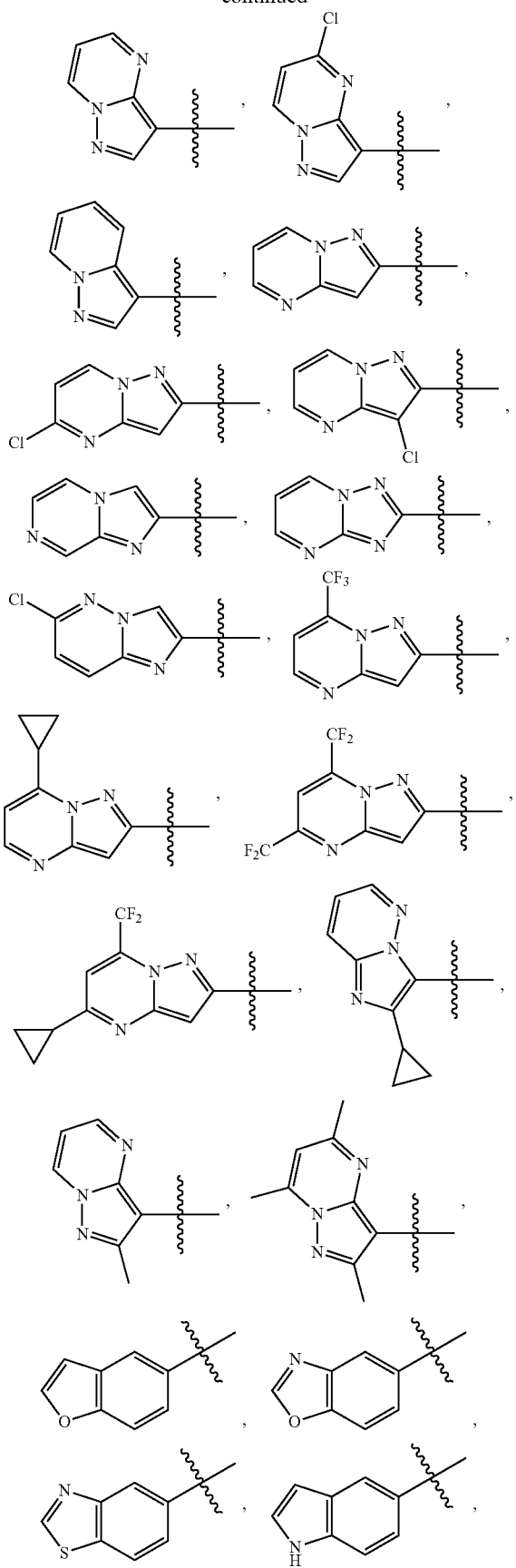

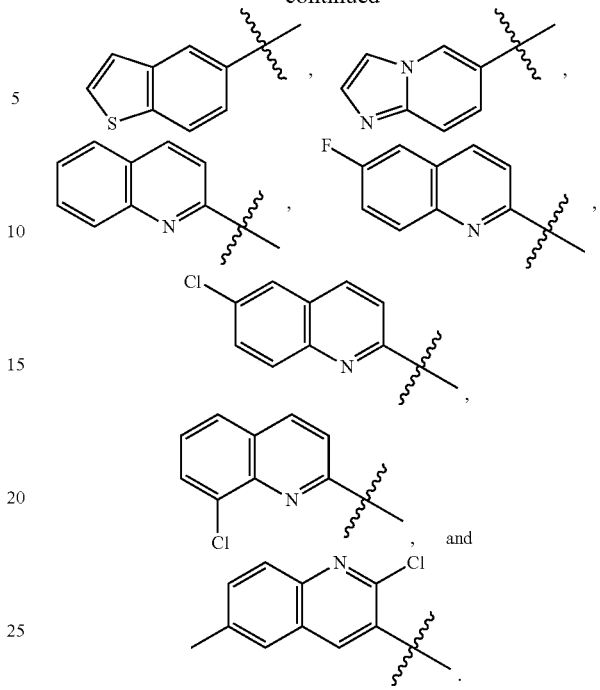

In another embodiment is a compound of Formula (II):

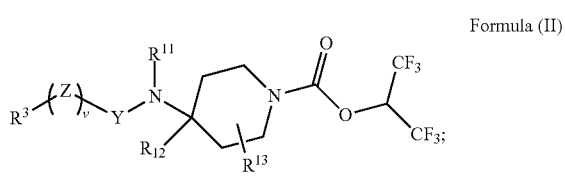

Formula (II)

wherein:
Y is —CH₂— or —C(O)—;
Z is $C_{3-6}$cycloalkyl;
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;
each $R^4$ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —CH₂— phenyl, $C_{1-9}$heteroaryl, —OR⁷, —CO₂R⁶, and —CH₂CO₂R⁶; wherein $C_{2-9}$heterocycloalkyl, —$C_{1-6}$alkyl($C_{2-9}$heterocycloalkyl), phenyl, and $C_{1-9}$heteroaryl are optionally substituted with one or two R⁵; or two adjacent R⁴ form a 6-membered cycloalkyl or 6-membered heterocycloalkyl ring, wherein the cycloalkyl and heterocycloalkyl ring are optionally substituted with one or two R⁵;
each R⁵ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —CO₂R⁶, —CH₂CO₂R⁶, and —$C_{1-6}$alkyl($C_{2-9}$heterocycloalkyl) optionally substituted with $C_{1-6}$alkyl;
each R⁶ is independently selected from H and $C_{1-6}$alkyl;
each R⁷ is independently selected from H, $C_{1-6}$alkyl, $C_{1-6}$haloalkyl, and $C_{3-8}$cycloalkyl;

$R^{11}$ is H, $C_{1-6}$alkyl, or —$C_{1-6}$alkyl-O—$C_{1-6}$alkyl;
$R^{12}$ is $C_{1-6}$alkyl;
$R^{13}$ is H or $C_{1-6}$alkyl; and
v is 0 or 1;
or a solvate, hydrate, tautomer, N-oxide, stereoisomer, or pharmaceutically acceptable salt thereof.

In another embodiment is a compound of Formula (II), or a solvate, hydrate, tautomer, N-oxide, stereoisomer, or pharmaceutically acceptable salt thereof, wherein $R^{13}$ is H. In another embodiment is a compound of Formula (II), or a solvate, hydrate, tautomer, N-oxide, stereoisomer, or pharmaceutically acceptable salt thereof, wherein $R^{13}$ is $C_{1-6}$alkyl. In another embodiment is a compound of Formula (II), or a solvate, hydrate, tautomer, N-oxide, stereoisomer, or pharmaceutically acceptable salt thereof, wherein $R^{13}$ is —$CH_3$. In another embodiment is a compound of Formula (II), or a solvate, hydrate, tautomer, N-oxide, stereoisomer, or pharmaceutically acceptable salt thereof, wherein $R^{13}$ is —$CH_2CH_3$. In another embodiment is a compound of Formula (II), or a solvate, hydrate, tautomer, N-oxide, stereoisomer, or pharmaceutically acceptable salt thereof, wherein $R^{12}$ is —$CH_3$. In another embodiment is a compound of Formula (II), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (II), or a solvate, hydrate, tautomer, N-oxide, stereoisomer, or pharmaceutically acceptable salt thereof, wherein $R^{12}$ is —$CH_3$ and $R^{13}$ is $C_{1-6}$alkyl. In another embodiment is a compound of Formula (II), or a solvate, hydrate, tautomer, N-oxide, stereoisomer, or pharmaceutically acceptable salt thereof, wherein $R^{12}$ is —$CH_3$ and $R^{13}$ is —$CH_3$. In another embodiment is a compound of Formula (II), or a solvate, hydrate, tautomer, N-oxide, stereoisomer, or pharmaceutically acceptable salt thereof, wherein $R^2$ is —$CH_3$ and $R^{13}$ is —$CH_2CH_3$.

In another embodiment is a compound of Formula (II), or a solvate, hydrate, tautomer, N-oxide, stereoisomer, or pharmaceutically acceptable salt thereof, wherein $R^{11}$ is H. In another embodiment is a compound of Formula (II), or a solvate, hydrate, tautomer, N-oxide, stereoisomer, or pharmaceutically acceptable salt thereof, wherein $R^{11}$ is $C_{1-6}$alkyl. In another embodiment is a compound of Formula (II), or a solvate, hydrate, tautomer, N-oxide, stereoisomer, or pharmaceutically acceptable salt thereof, wherein $R^{11}$ is —$CH_3$. In another embodiment is a compound of Formula (II), or a solvate, hydrate, tautomer, N-oxide, stereoisomer, or pharmaceutically acceptable salt thereof, wherein $R^{11}$ is —$CH_2CH_3$. In another embodiment is a compound of Formula (II), or a solvate, hydrate, tautomer, N-oxide, stereoisomer, or pharmaceutically acceptable salt thereof, wherein $R^{11}$ is —$C_{1-6}$alkyl-O—$C_{1-6}$alkyl. In another embodiment is a compound of Formula (II), or a solvate, hydrate, tautomer, N-oxide, stereoisomer, or pharmaceutically acceptable salt thereof, wherein $R^{11}$ is —$C_{1-6}$alkyl-$OCH_3$. In another embodiment is a compound of Formula (II), or a solvate, hydrate, tautomer, N-oxide, stereoisomer, or pharmaceutically acceptable salt thereof, wherein $R^{11}$ is —$CH_2CH_2OCH_3$.

In another embodiment is a compound of Formula (II), or a solvate, hydrate, tautomer, N-oxide, stereoisomer, or pharmaceutically acceptable salt thereof, wherein Y is —$CH_2$—. In another embodiment is a compound of Formula (II), or a solvate, hydrate, tautomer, N-oxide, stereoisomer, or pharmaceutically acceptable salt thereof, wherein Y is —C(O)—.

In another embodiment is a compound of Formula (II), or a solvate, hydrate, tautomer, N-oxide, stereoisomer, or pharmaceutically acceptable salt thereof, wherein v is 0. In another embodiment is a compound of Formula (II), or a solvate, hydrate, tautomer, N-oxide, stereoisomer, or pharmaceutically acceptable salt thereof, wherein v is 1. In another embodiment is a compound of Formula (II), or a solvate, hydrate, tautomer, N-oxide, stereoisomer, or pharmaceutically acceptable salt thereof, wherein v is 1 and Z is cyclopropyl. In another embodiment is a compound of Formula (II), or a solvate, hydrate, tautomer, N-oxide, stereoisomer, or pharmaceutically acceptable salt thereof, wherein v is 1 and Z is cyclobutyl. In another embodiment is a compound of Formula (II), or a solvate, hydrate, tautomer, N-oxide, stereoisomer, or pharmaceutically acceptable salt thereof, wherein v is 1 and Z is cyclopentyl. In another embodiment is a compound of Formula (II), or a solvate, hydrate, tautomer, N-oxide, stereoisomer, or pharmaceutically acceptable salt thereof, wherein v is 1 and Z is cyclohexyl.

In another embodiment is a compound of Formula (II), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is C₁₋₆heteroalkyl. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is C₃₋₈cycloalkyl. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is —C₁₋₆alkyl(C₃₋₈cycloalkyl). In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is C₂₋₉heterocycloalkyl. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered heterocycloalkyl ring substituted with one R⁵ and R⁵ is —CH₂CO₂H. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two or three R⁴, wherein two adjacent R⁴ form a 6-membered cycloalkyl ring optionally substituted with one or two R⁵. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form an unsubstituted 6-membered cycloalkyl ring. In another embodiment is a compound of Formula (II), or a solvate, hydrate, tautomer, N-oxide, stereoisomer, or pharmaceutically acceptable salt thereof, wherein R³ is a 5-membered heteroaryl ring substituted with two adjacent R⁴, wherein the two adjacent R⁴ form a 6-membered cycloalkyl ring substituted with one R⁵. In another embodiment is a compound of Formula (II), or a solvate, hydrate, tautomer, N-oxide, stereoisomer, or pharmaceutically acceptable salt thereof, wherein R³ is selected from:

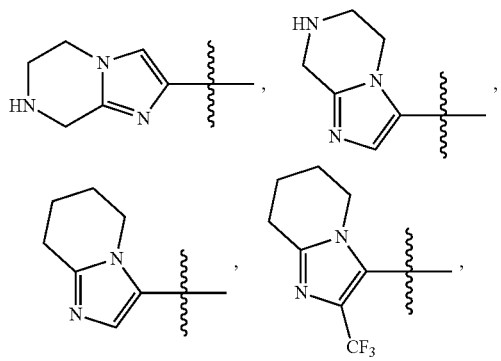

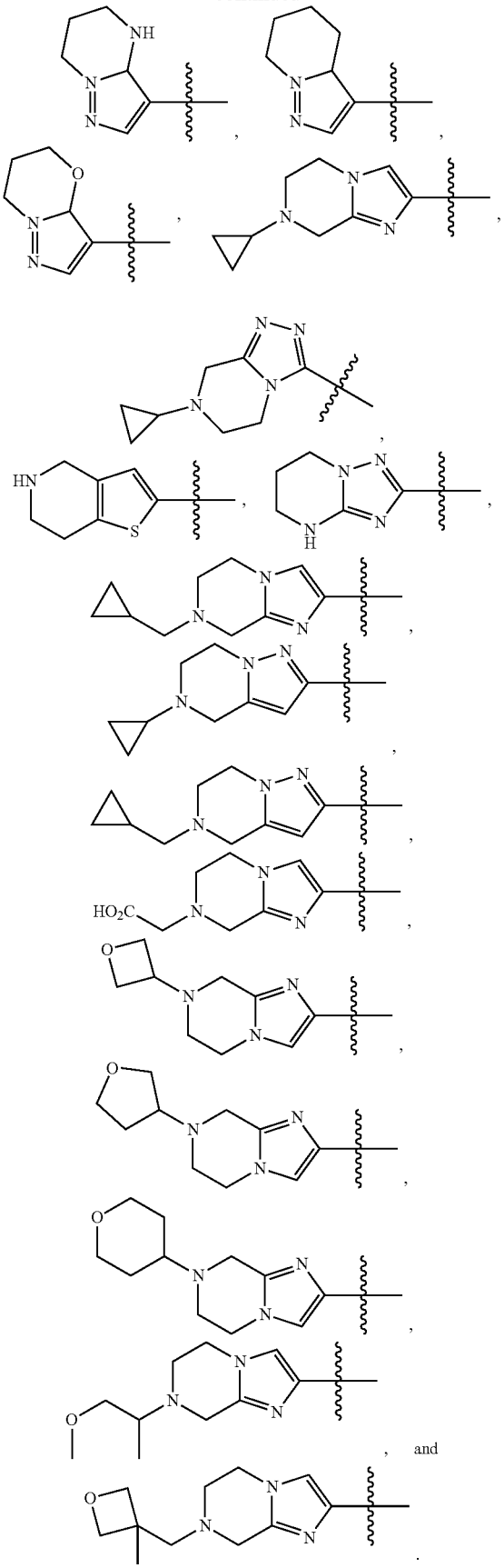

In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (II), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (II), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (II), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (II), or a solvate, hydrate, tautomer, N-oxide, stereoisomer, or pharmaceutically acceptable salt thereof, wherein $R^3$ is a pyrazole ring. In another embodiment is a compound of Formula (II), or a solvate, hydrate, tautomer, N-oxide, stereoisomer, or pharmaceutically acceptable salt thereof, wherein $R^3$ is a thiazole ring. In another embodiment is a compound of Formula (II), or a solvate, hydrate, tautomer, N-oxide, stereoisomer, or pharmaceutically acceptable salt thereof, wherein $R^3$ is an isoxazole ring. In another embodiment is a compound of Formula (II), or a solvate, hydrate, tautomer, N-oxide, stereoisomer, or pharmaceutically acceptable salt thereof, wherein $R^3$ is an oxazole ring. In another embodiment is a compound of Formula (II), or a solvate, hydrate, tautomer, N-oxide, stereoisomer, or pharmaceutically acceptable salt thereof, wherein $R^3$ is an imidazole ring. In another embodiment is a compound of Formula (II), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (II), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (II), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (II), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (II), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (II), or a solvate, hydrate, tautomer, N-oxide, stereoisomer, or pharmaceutically acceptable salt thereof, wherein $R^3$ is a pyridine ring. In another embodiment is a compound of Formula (II), or a solvate, hydrate, tautomer, N-oxide, stereoisomer, or pharmaceutically acceptable salt thereof, wherein $R^3$ is a pyrimidine ring. In another embodiment is a compound of Formula (II), or a solvate, hydrate, tautomer, N-oxide, stereoisomer, or pharmaceutically acceptable salt thereof, wherein $R^3$ is a pyridazine ring. In another embodiment is a compound of Formula (II), or a solvate, hydrate, tautomer, N-oxide, stereoisomer, or pharmaceutically acceptable salt thereof, wherein $R^3$ is a pyrazine ring.

In another embodiment is a compound of Formula (II), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (II), or a solvate, hydrate, tautomer, N-oxide, stereoisomer, or pharmaceutically acceptable salt thereof, wherein $R^3$ is a 9-membered bicyclic heteroaryl ring substituted with one R⁴, wherein R⁴ is selected from halogen, $C_{1-6}$alkyl, and $C_{1-6}$haloalkyl. In another embodiment is a compound of Formula (II), or a solvate, hydrate, tautomer, N-oxide, stereoisomer, or pharmaceutically acceptable salt thereof, wherein R³ is a 9-membered bicyclic heteroaryl ring substituted with one R⁴, wherein R⁴ is halogen. In another embodiment is a compound of Formula (II), or a solvate, hydrate, tautomer, N-oxide, stereoisomer, or pharmaceutically acceptable salt thereof, wherein R³ is a 9-membered bicyclic heteroaryl ring substituted with one R⁴, wherein R⁴ is $C_{1-6}$alkyl. In another embodiment is a compound of Formula (II), or a solvate, hydrate, tautomer, N-oxide, stereoisomer, or pharmaceutically acceptable salt thereof, wherein R³ is a 9-membered bicyclic heteroaryl ring substituted with one R⁴, wherein R⁴ is $C_{1-6}$haloalkyl. In another embodiment is a compound of Formula (II), or a solvate, hydrate, tautomer, N-oxide, stereoisomer, or pharmaceutically acceptable salt thereof, wherein R³ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring optionally substituted with one, two, or three R⁴. In another embodiment is a compound of Formula (II), or a solvate, hydrate, tautomer, N-oxide, stereoisomer, or pharmaceutically acceptable salt thereof, wherein R³ is an unsubstituted 10-membered bicyclic heteroaryl ring. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one, two, or three R⁴. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one, two, or three R⁴, wherein each R⁴ is independently selected from halogen, —CN, $C_{1-6}$alkyl, $C_{1-6}$haloalkyl, $C_{3-8}$cycloalkyl, —OR⁷, and —CO₂R⁶. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one or two R⁴, wherein each R⁴ is independently selected from halogen, $C_{1-6}$alkyl, $C_{1-6}$haloalkyl, $C_{3-8}$cycloalkyl, —OC$_{1-6}$alkyl, and —CO₂R⁶. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one or two R⁴, wherein each R⁴ is independently selected from halogen, $C_{1-6}$alkyl, and $C_{1-6}$haloalkyl. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is selected from halogen, $C_{1-6}$alkyl, and $C_{1-6}$haloalkyl. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is halogen. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is $C_{1-6}$alkyl. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is $C_{1-6}$haloalkyl. In another embodiment is a compound of Formula (II), or a solvate, hydrate, tautomer, N-oxide, stereoisomer, or pharmaceutically acceptable salt thereof, wherein R³ is a 10-membered bicyclic heteroaryl ring selected from a quinolone, isoquinolone, quinazoline, quinoxaline, phthalazine, and a naphthyridine ring. In another embodiment is a compound of Formula (II), or a solvate, hydrate, tautomer, N-oxide, stereoisomer, or pharmaceutically acceptable salt thereof, wherein R³ is selected from:

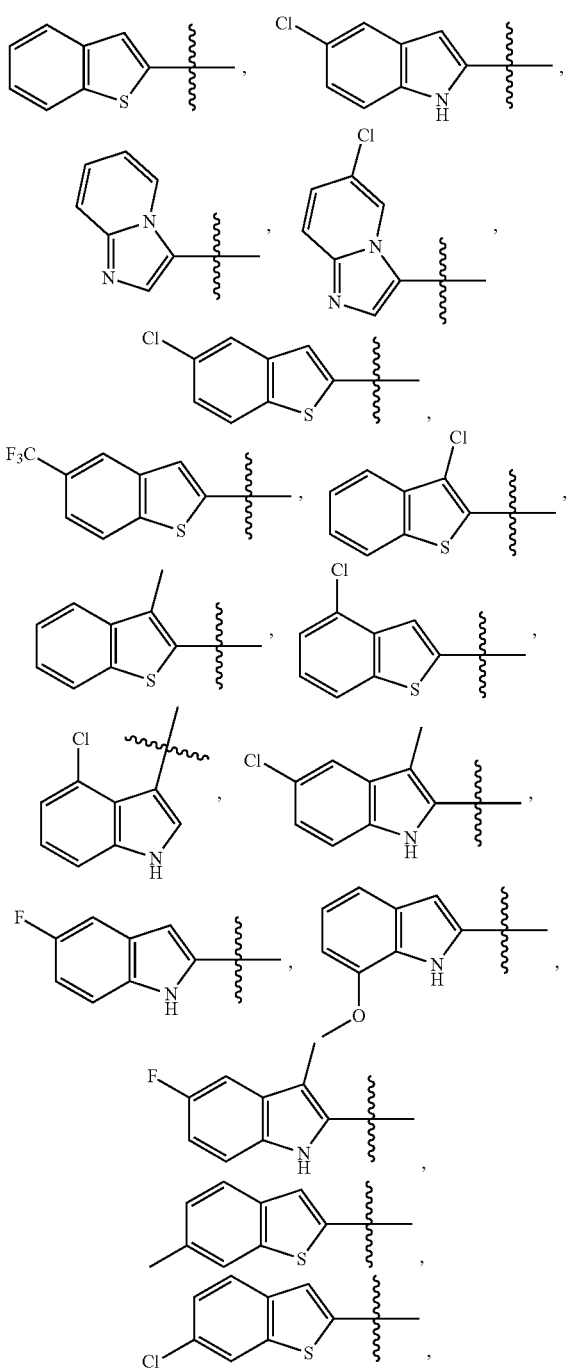

83
-continued
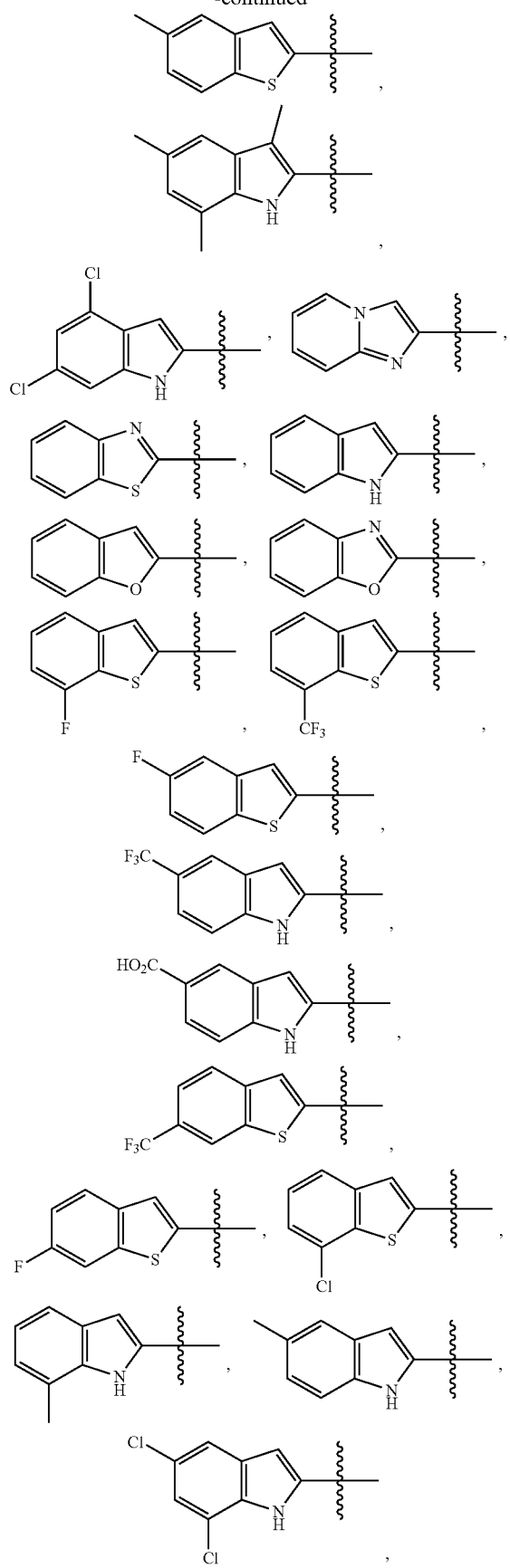
84
-continued
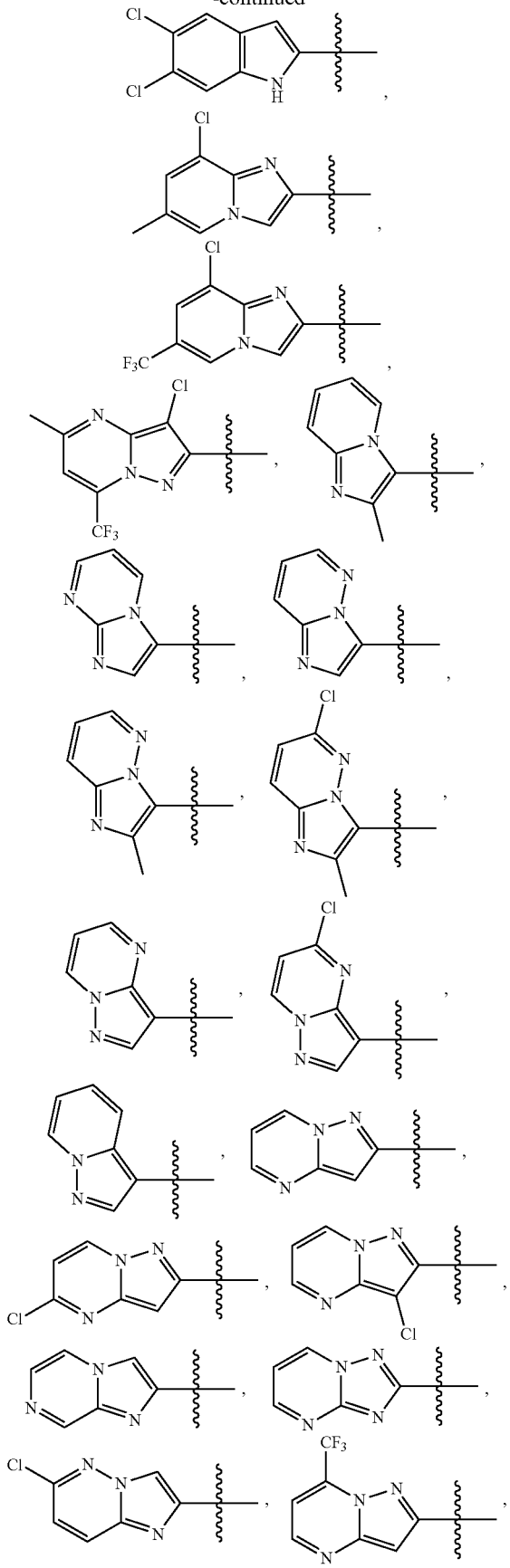

-continued

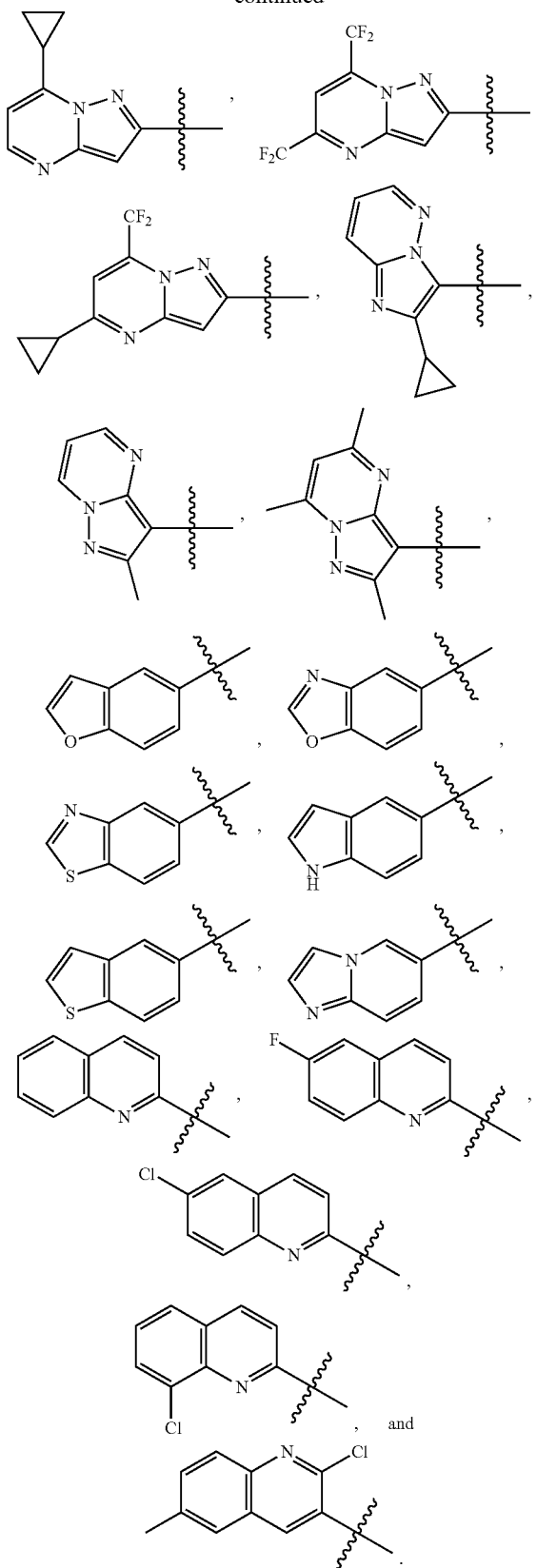

In another embodiment is a compound of Formula (II) having the structure of Formula (IIa):

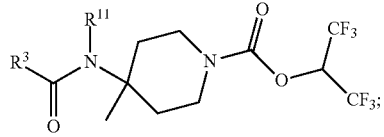

Formula (IIa)

wherein:
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;

each $R^4$ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —CH$_2$— phenyl, $C_{1-9}$heteroaryl, —OR$^7$, —CO$_2$R$^6$, and —CH$_2$CO$_2$R$^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;

each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —CO$_2$R$^6$, —CH$_2$CO$_2$R$^6$, and —$C_{1-6}$alkyl($C_{2-9}$heterocycloalkyl) optionally substituted with $C_{1-6}$alkyl;

each $R^6$ is independently selected from H and $C_{1-6}$alkyl;
each $R^7$ is independently selected from H, $C_{1-6}$alkyl, $C_{1-6}$haloalkyl, and $C_{3-8}$cycloalkyl; and $R^{11}$ is $C_{1-6}$alkyl;
or a solvate, hydrate, tautomer, N-oxide, stereoisomer, or pharmaceutically acceptable salt thereof.

In another embodiment is a compound of Formula (IIa), or a solvate, hydrate, tautomer, N-oxide, stereoisomer, or pharmaceutically acceptable salt thereof, wherein $R^{11}$ is —CH$_3$. In another embodiment is a compound of Formula (IIa), or a solvate, hydrate, tautomer, N-oxide, stereoisomer, or pharmaceutically acceptable salt thereof, wherein $R^{11}$ is —CH$_2$CH$_3$.

In another embodiment is a compound of Formula (IIa), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (IIa), or a solvate, hydrate, tautomer, N-oxide, stereoisomer, or pharmaceutically acceptable salt thereof, wherein $R^3$ is selected from:

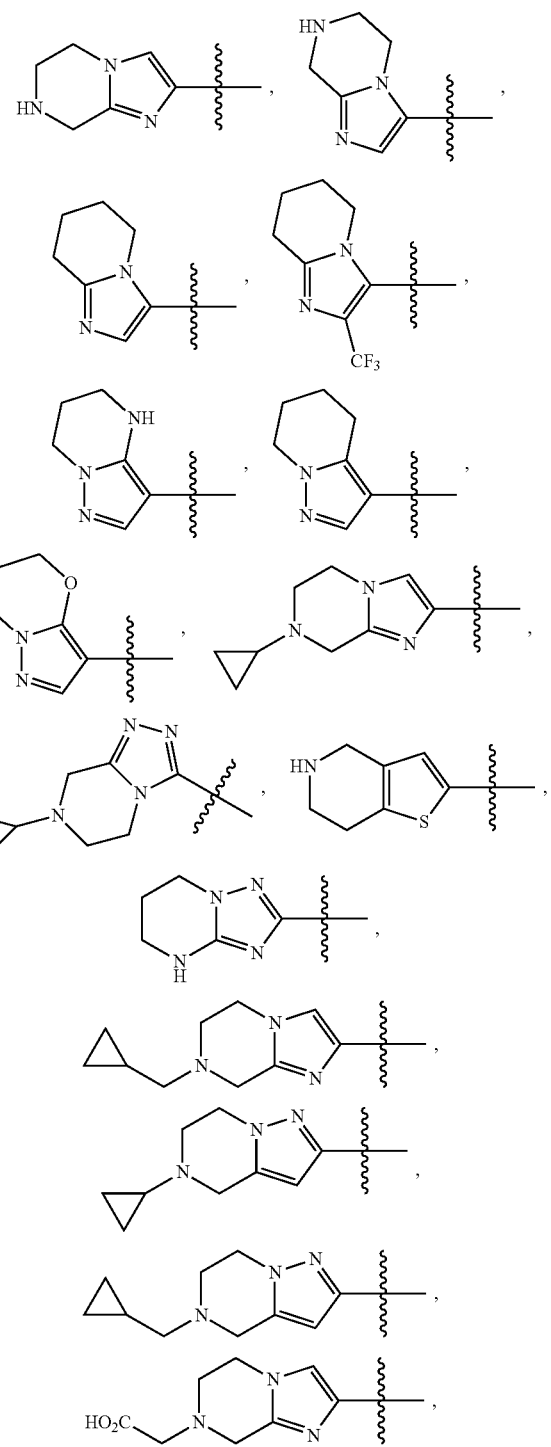

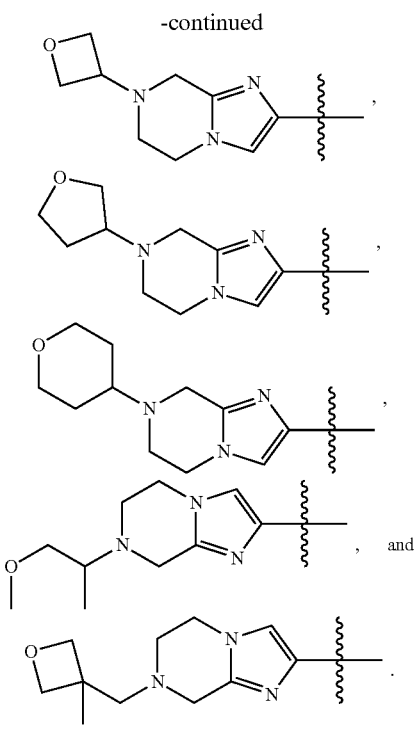

In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (IIa), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIa), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (IIa), or a solvate, hydrate, tautomer, N-oxide, stereoisomer, or pharmaceutically acceptable salt thereof, wherein $R^3$ is a pyrazole ring. In another embodiment is a compound of Formula (IIa), or a solvate, hydrate, tautomer, N-oxide, stereoisomer, or pharmaceutically acceptable salt thereof, wherein $R^3$ is a thiazole ring. In another embodiment is a compound of Formula (IIa), or a solvate, hydrate, tautomer, N-oxide, stereoisomer, or pharmaceutically acceptable salt thereof, wherein $R^3$ is an isoxazole ring. In another embodiment is a compound of Formula (IIa), or a solvate, hydrate, tautomer, N-oxide, stereoisomer, or pharmaceutically acceptable salt thereof, wherein $R^3$ is an oxazole ring. In another embodiment is a compound of Formula (IIa), or a solvate, hydrate, tautomer, N-oxide, stereoisomer, or pharmaceutically acceptable salt thereof, wherein $R^3$ is an imidazole ring. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (IIa), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (IIa), or a solvate, hydrate, tautomer, N-oxide, stereoisomer, or pharmaceutically acceptable salt thereof, wherein $R^3$ is a pyridine ring. In another embodiment is a compound of Formula (IIa), or a solvate, hydrate, tautomer, N-oxide, stereoisomer, or pharmaceutically acceptable salt thereof, wherein $R^3$ is a pyrimidine ring. In another embodiment is a compound of Formula (IIa), or a solvate, hydrate, tautomer, N-oxide, stereoisomer, or pharmaceutically acceptable salt thereof, wherein $R^3$ is a pyridazine ring. In another embodiment is a compound of Formula (IIa), or a solvate, hydrate, tautomer, N-oxide, stereoisomer, or pharmaceutically acceptable salt thereof, wherein $R^3$ is a pyrazine ring.

In another embodiment is a compound of Formula (IIa), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (IIa), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (IIa), or a solvate, hydrate, tautomer, N-oxide, stereoisomer, or pharmaceutically acceptable salt thereof, wherein $R^3$ is selected from:

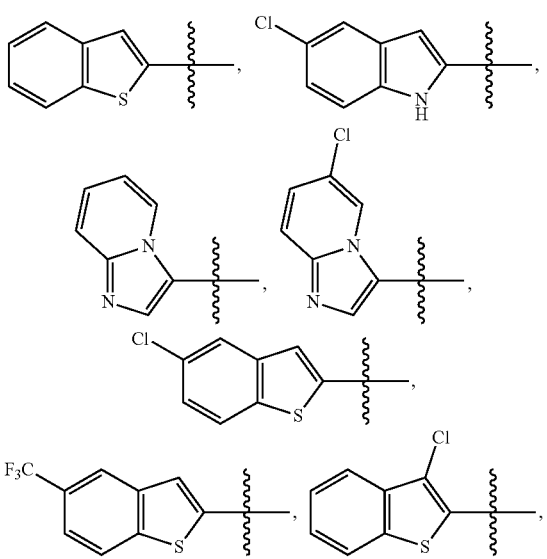

-continued
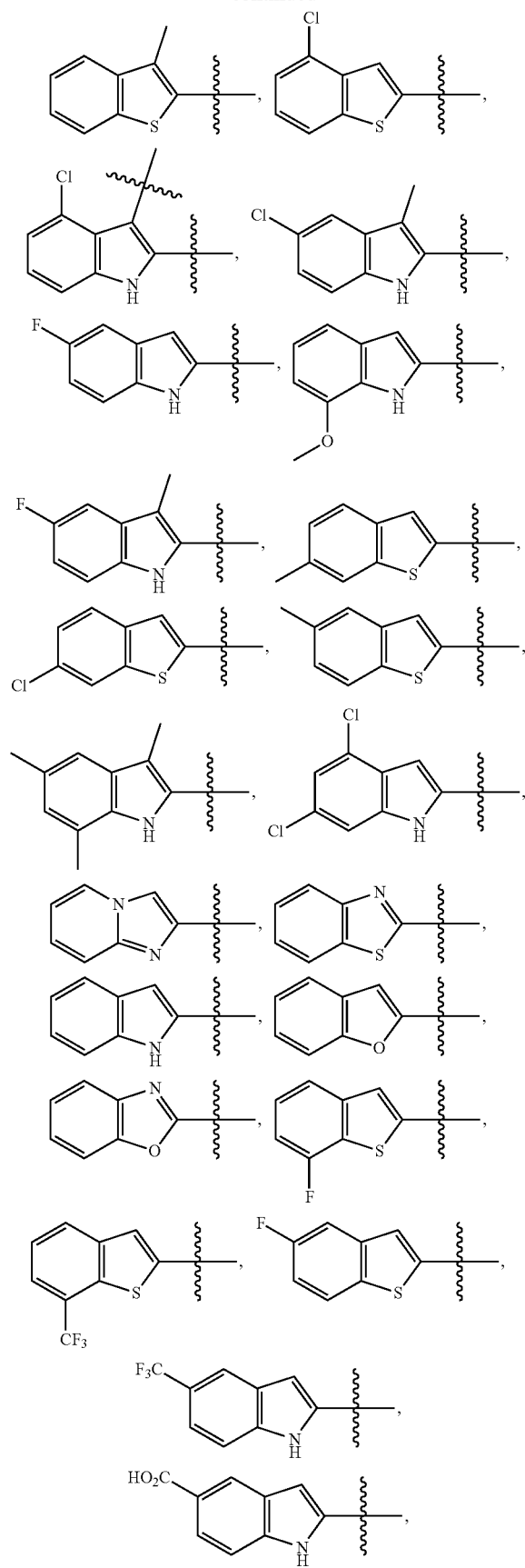
-continued
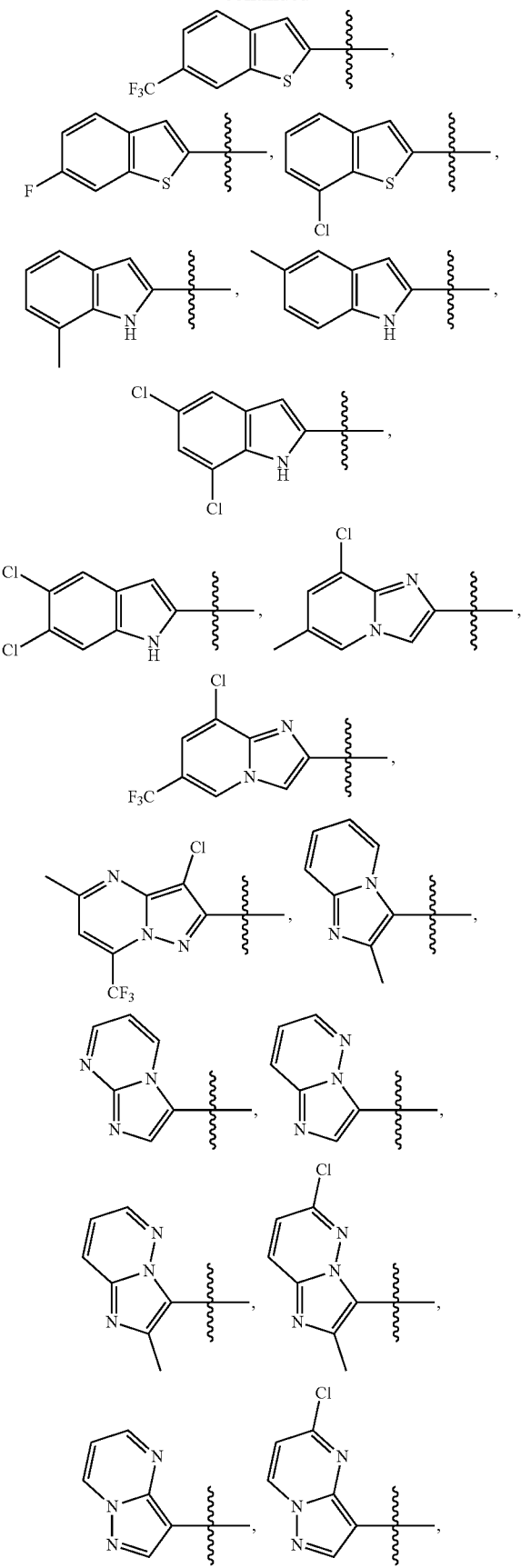

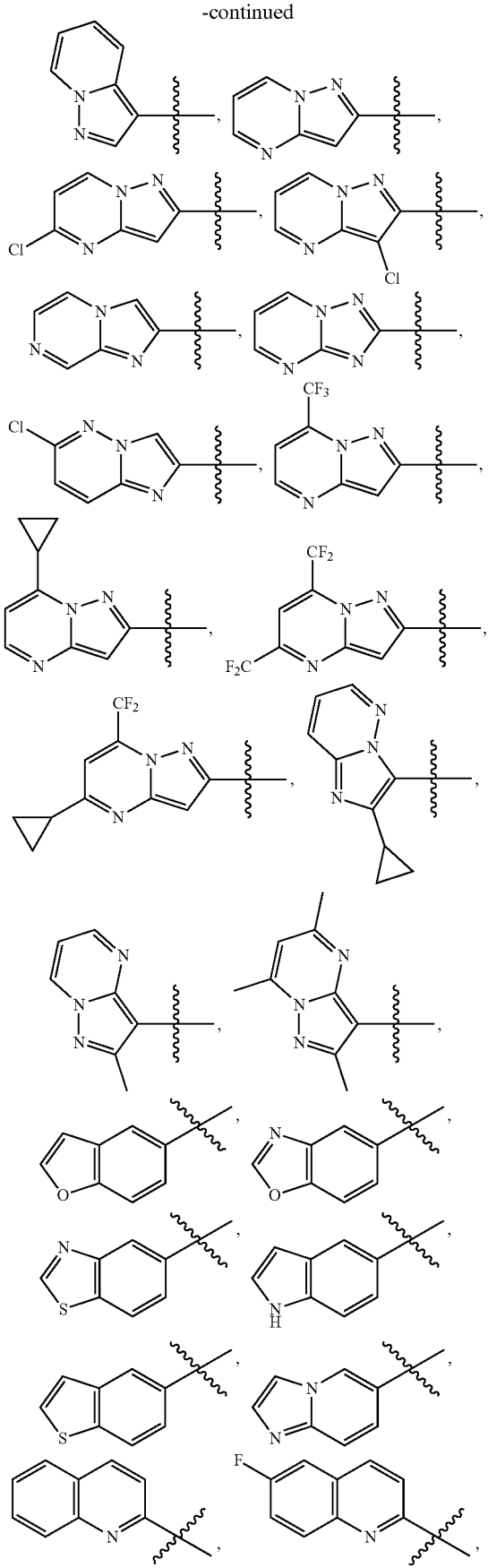

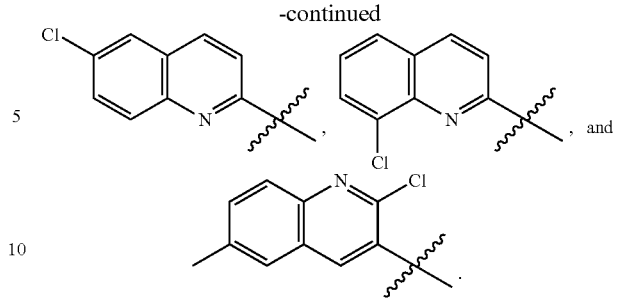

In another embodiment is a compound of Formula (II) having the structure of Formula (Ib):

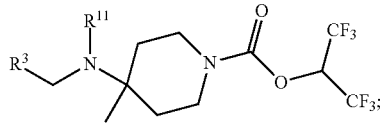

Formula (IIb)

wherein:
$R^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three $R^4$;

each $R^4$ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —$CH_2$— phenyl, $C_{1-9}$heteroaryl, —$OR^7$, —$CO_2R^6$, and —$CH_2CO_2R^6$; wherein $C_{2-9}$heterocycloalkyl, —$C_{1-6}$alkyl($C_{2-9}$heterocycloalkyl), phenyl, and $C_{1-9}$heteroaryl are optionally substituted with one or two $R^5$; or two adjacent $R^4$ form a 6-membered cycloalkyl or 6-membered heterocycloalkyl ring, wherein the cycloalkyl and heterocycloalkyl ring are optionally substituted with one or two $R^5$;

each $R^5$ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —$CO_2R^6$, —$CH_2CO_2R^6$, and —$C_{1-6}$alkyl($C_{2-9}$heterocycloalkyl) optionally substituted with $C_{1-6}$alkyl;

each $R^6$ is independently selected from H and $C_{1-6}$alkyl;
each $R^7$ is independently selected from H, $C_{1-6}$alkyl, $C_{1-6}$haloalkyl, and $C_{3-8}$cycloalkyl; and
$R^{11}$ is $C_{1-6}$alkyl;
or a solvate, hydrate, tautomer, N-oxide, stereoisomer, or pharmaceutically acceptable salt thereof.

In another embodiment is a compound of Formula (IIb), or a solvate, hydrate, tautomer, N-oxide, stereoisomer, or pharmaceutically acceptable salt thereof, wherein $R^{11}$ is —$CH_3$. In another embodiment is a compound of Formula (IIb), or a solvate, hydrate, tautomer, N-oxide, stereoisomer, or pharmaceutically acceptable salt thereof, wherein $R^{11}$ is —$CH_2CH_3$.

In another embodiment is a compound of Formula (IIb), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (IIb), or a solvate, hydrate, tautomer, N-oxide, stereoisomer, or pharmaceutically acceptable salt thereof, wherein $R^3$ is selected from:

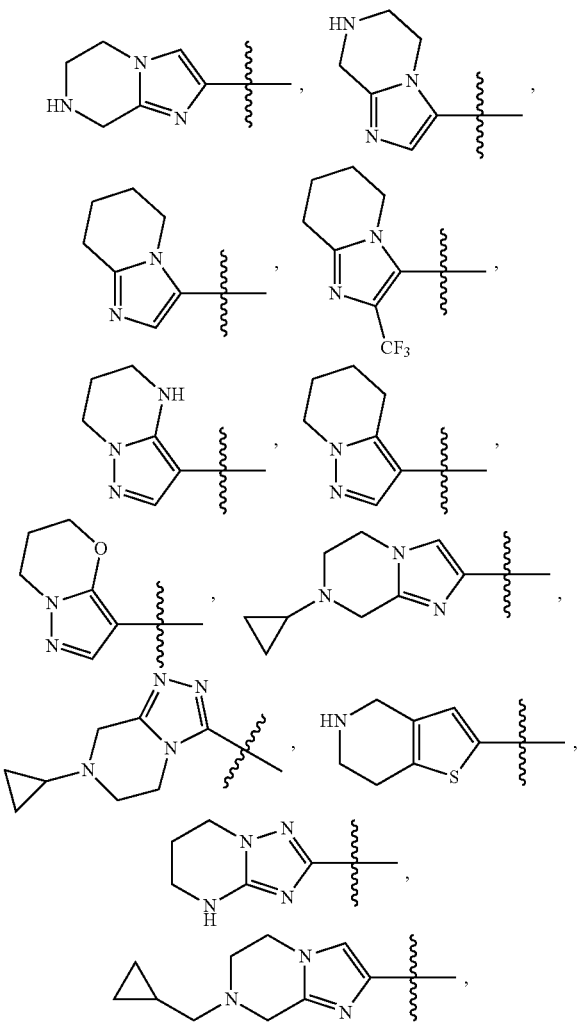

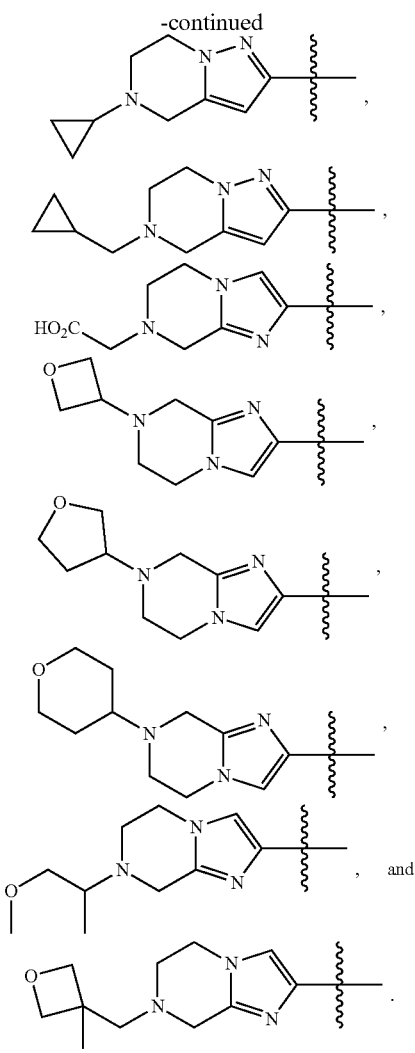

In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIb), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIb), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (IIb), or a solvate, hydrate, tautomer, N-oxide, stereoisomer, or pharmaceutically acceptable salt thereof, wherein $R^3$ is a pyrazole ring. In another embodiment is a compound of Formula (IIb), or a solvate, hydrate, tautomer, N-oxide, stereoisomer, or pharmaceutically acceptable salt thereof, wherein $R^3$ is a thiazole ring. In another embodiment is a compound of Formula (IIb), or a solvate, hydrate, tautomer, N-oxide, stereoisomer, or pharmaceutically acceptable salt thereof, wherein $R^3$ is an isoxazole ring. In another embodiment is a compound of Formula (IIb), or a solvate, hydrate, tautomer, N-oxide, stereoisomer, or pharmaceutically acceptable salt thereof, wherein $R^3$ is an oxazole ring. In another embodiment is a compound of Formula (IIb), or a solvate, hydrate, tautomer, N-oxide, stereoisomer, or pharmaceutically acceptable salt thereof, wherein $R^3$ is an imidazole ring. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (IIb), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (IIb), or a solvate, hydrate, tautomer, N-oxide, stereoisomer, or pharmaceutically acceptable salt thereof, wherein $R^3$ is a pyridine ring. In another embodiment is a compound of Formula (IIb), or a solvate, hydrate, tautomer, N-oxide, stereoisomer, or pharmaceutically acceptable salt thereof, wherein $R^3$ is a pyrimidine ring. In another embodiment is a compound of Formula (IIb), or a solvate, hydrate, tautomer, N-oxide, stereoisomer, or pharmaceutically acceptable salt thereof, wherein $R^3$ is a pyridazine ring. In another embodiment is a compound of Formula (IIb), or a solvate, hydrate, tautomer, N-oxide, stereoisomer, or pharmaceutically acceptable salt thereof, wherein $R^3$ is a pyrazine ring.

In another embodiment is a compound of Formula (IIb), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (IIb), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (IIb), or a solvate, hydrate, tautomer, N-oxide, stereoisomer, or pharmaceutically acceptable salt thereof, wherein $R^3$ is selected from:

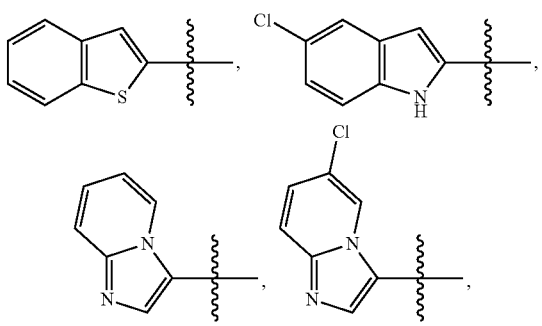

-continued
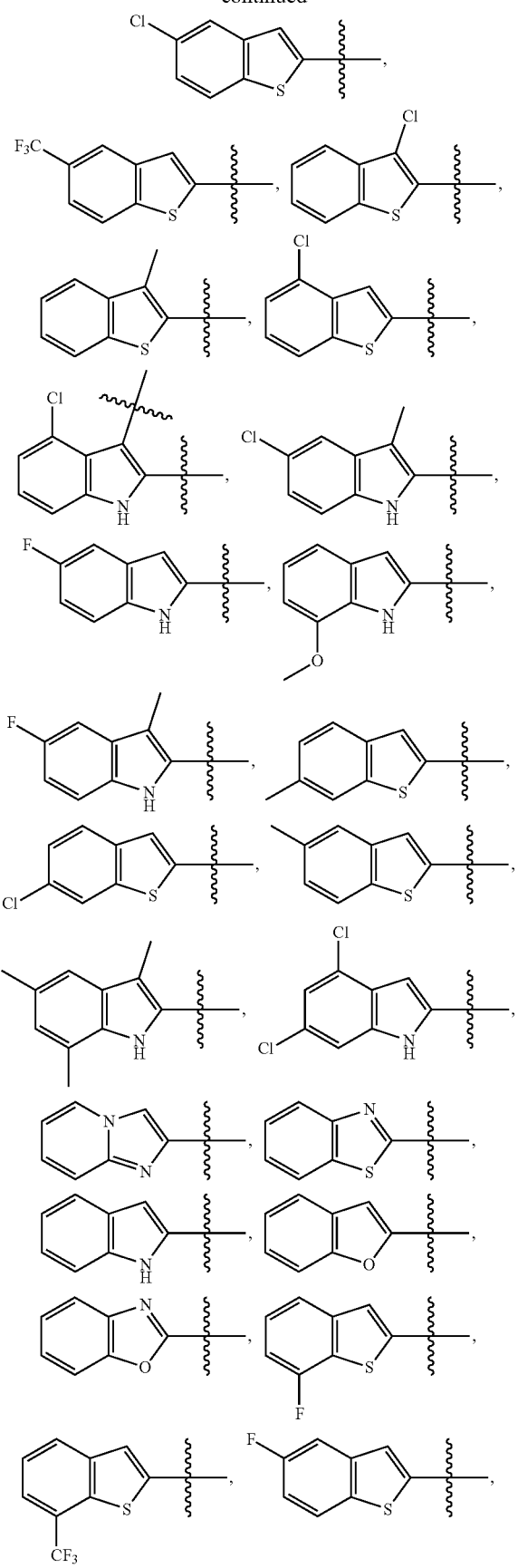
-continued
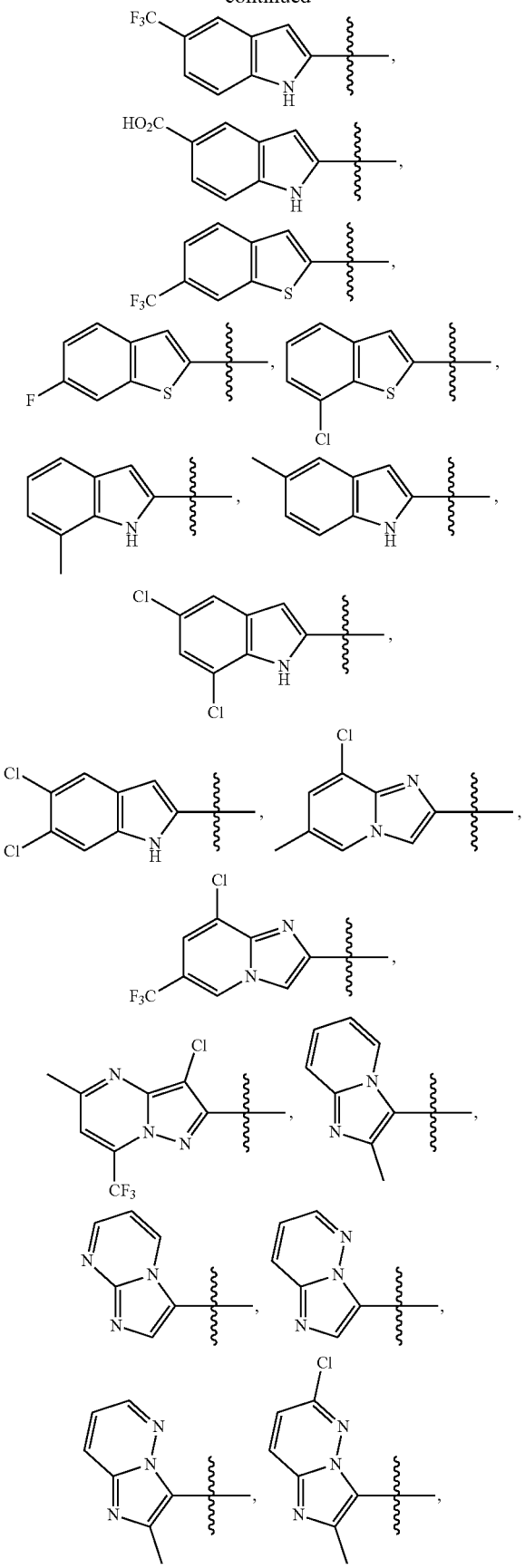

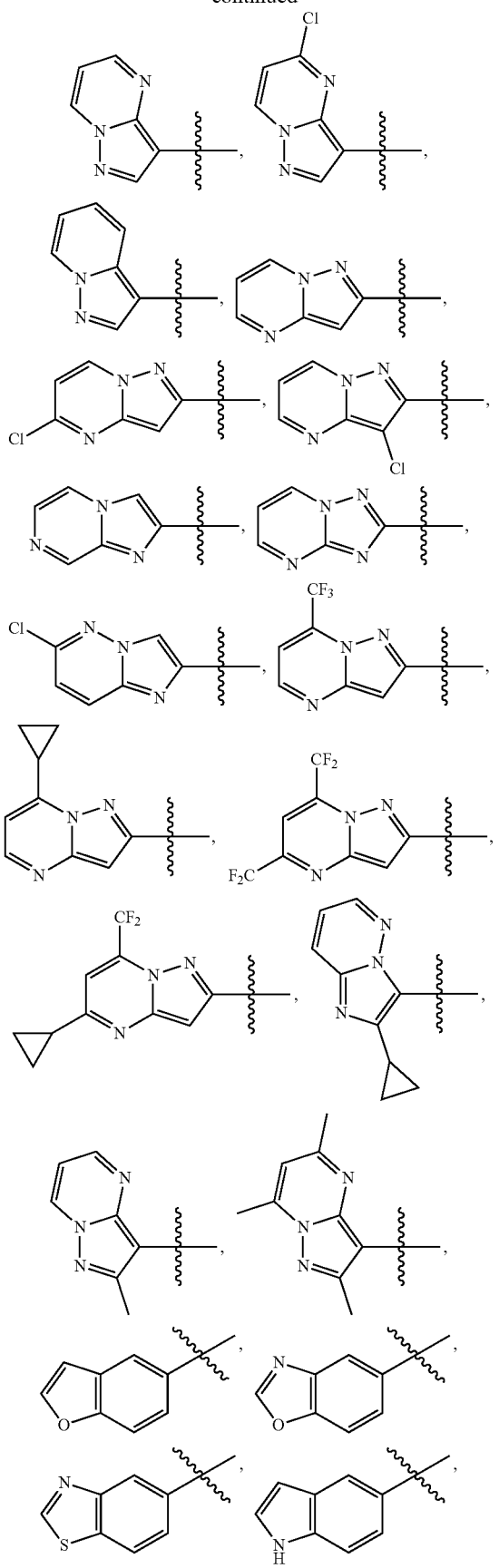

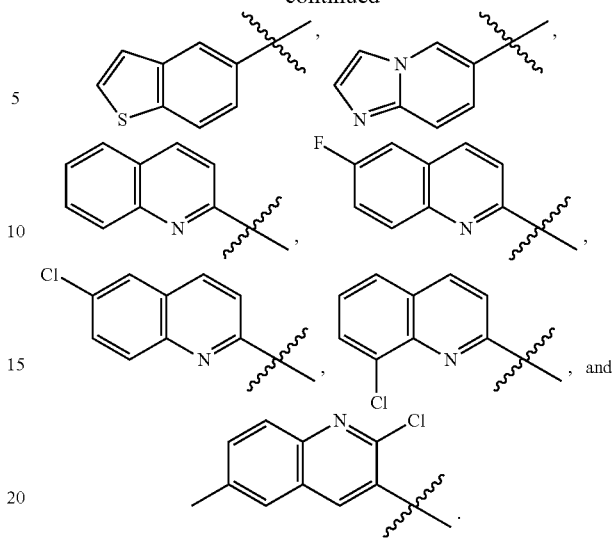

In another embodiment is a compound of Formula (II) having the structure of Formula (IIc):

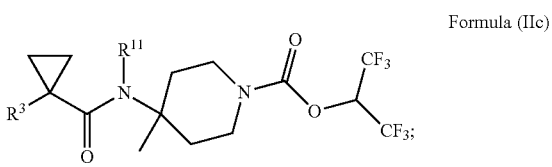

Formula (IIc)

wherein:
R³ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R⁴;

each R⁴ is independently selected from $C_{1-6}$alkyl, halogen, —CN, $C_{1-6}$haloalkyl, $C_{3-8}$cycloalkyl, $C_{2-9}$heterocycloalkyl, —$C_{1-6}$alkyl-($C_{2-9}$heterocycloalkyl), phenyl, —CH₂— phenyl, $C_{1-9}$heteroaryl, —OR⁷, —CO₂R⁶, and —CH₂CO₂R⁶; wherein $C_{2-9}$heterocycloalkyl, —$C_{1-6}$alkyl($C_{2-9}$heterocycloalkyl), phenyl, and $C_1$heteroaryl are optionally substituted with one or two R⁵; or two adjacent R⁴ form a 6-membered cycloalkyl or 6-membered heterocycloalkyl ring, wherein the cycloalkyl and heterocycloalkyl ring are optionally substituted with one or two R⁵;

each R⁵ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —CO₂R⁶, —CH₂CO₂R⁶, and —$C_{1-6}$alkyl($C_{2-9}$heterocycloalkyl) optionally substituted with $C_{1-6}$alkyl;

each R⁶ is independently selected from H and $C_{1-6}$alkyl;
each R⁷ is independently selected from H, $C_{1-6}$alkyl, $C_{1-6}$haloalkyl, and $C_{3-8}$cycloalkyl; and R¹¹ is $C_{1-6}$alkyl or —$C_{1-6}$alkyl-O—$C_{1-6}$alkyl; or a solvate, hydrate, tautomer, N-oxide, stereoisomer, or pharmaceutically acceptable salt thereof.

In another embodiment is a compound of Formula (IIc), or a solvate, hydrate, tautomer, N-oxide, stereoisomer, or pharmaceutically acceptable salt thereof, wherein R¹¹ is $C_{1-6}$alkyl. In another embodiment is a compound of Formula (IIc), or a solvate, hydrate, tautomer, N-oxide, stereoisomer, or pharmaceutically acceptable salt thereof, wherein $R^{11}$ is —$CH_3$. In another embodiment is a compound of Formula (IIc), or a solvate, hydrate, tautomer, N-oxide, stereoisomer, or pharmaceutically acceptable salt thereof, wherein $R^{11}$ is —$CH_2CH_3$. In another embodiment is a compound of Formula (IIc), or a solvate, hydrate, tautomer, N-oxide, stereoisomer, or pharmaceutically acceptable salt thereof, wherein $R^{11}$ is —$C_{1-6}$alkyl-O—$C_{1-6}$alkyl.

In another embodiment is a compound of Formula (IIc), or a solvate, hydrate, tautomer, N-oxide, stereoisomer, or pharmaceutically acceptable salt thereof, wherein $R^{11}$ is —$C_{1-6}$alkyl-$OCH_3$. In another embodiment is a compound of Formula (IIc), or a solvate, hydrate, tautomer, N-oxide, stereoisomer, or pharmaceutically acceptable salt thereof, wherein $R^{11}$ is —$CH_2CH_2OCH_3$.

In another embodiment is a compound of Formula (IIc), or a solvate, hydrate, tautomer, N-oxide, stereoisomer, or pharmaceutically acceptable salt thereof, wherein $R^3$ is a 5- to 6-membered heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered heterocycloalkyl ring optionally substituted with one or two $R^5$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$alkyl. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (IIc), or a solvate, hydrate, tautomer, N-oxide, stereoisomer, or pharmaceutically acceptable salt thereof, wherein $R^3$ is selected from:

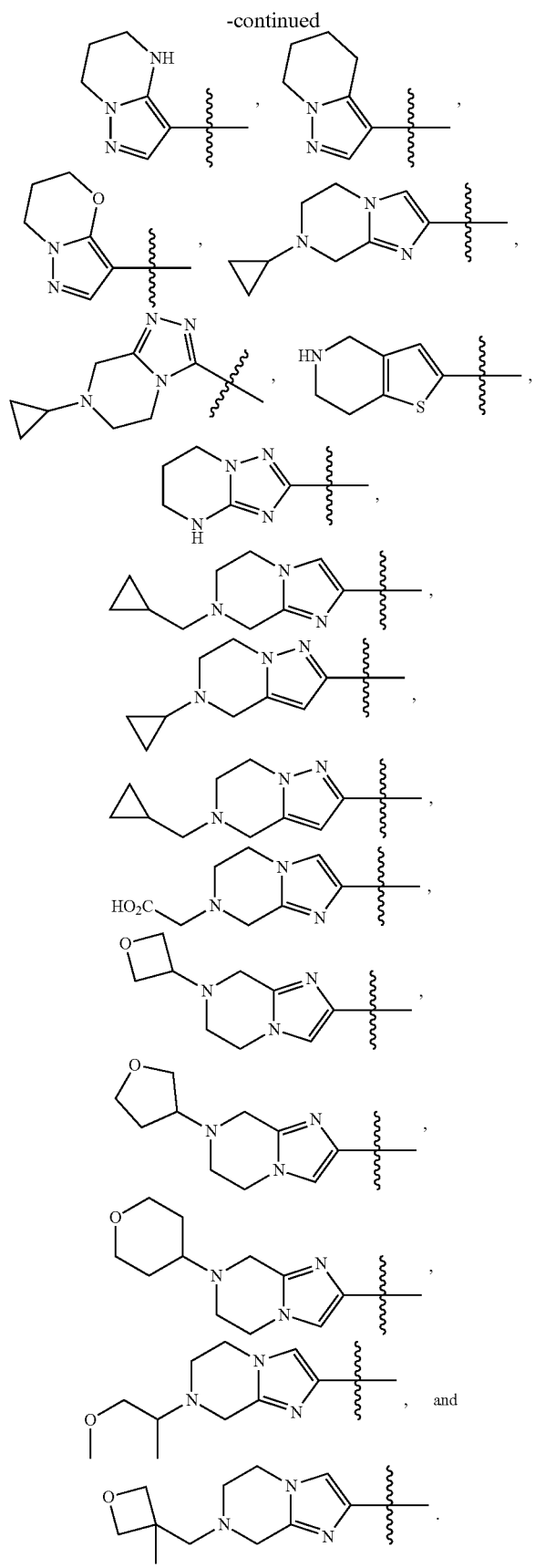

In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (IIc), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (IIc), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (IIc), or a solvate, hydrate, tautomer, N-oxide, stereoisomer, or pharmaceutically acceptable salt thereof, wherein $R^3$ is a pyrazole ring. In another embodiment is a compound of Formula (IIc), or a solvate, hydrate, tautomer, N-oxide, stereoisomer, or pharmaceutically acceptable salt thereof, wherein $R^3$ is a thiazole ring. In another embodiment is a compound of Formula (IIc), or a solvate, hydrate, tautomer, N-oxide, stereoisomer, or pharmaceutically acceptable salt thereof, wherein $R^3$ is an isoxazole ring. In another embodiment is a compound of Formula (IIc), or a solvate, hydrate, tautomer, N-oxide, stereoisomer, or pharmaceutically acceptable salt thereof, wherein $R^3$ is an oxazole ring. In another embodiment is a compound of Formula (IIc), or a solvate, hydrate, tautomer, N-oxide, stereoisomer, or pharmaceutically acceptable salt thereof, wherein $R^3$ is an imidazole ring. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (IIc), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (IIc), or a solvate, hydrate, tautomer, N-oxide, stereoisomer, or pharmaceutically acceptable salt thereof, wherein $R^3$ is a pyridine ring. In another embodiment is a compound of Formula (IIc), or a solvate, hydrate, tautomer, N-oxide, stereoisomer, or pharmaceutically acceptable salt thereof, wherein $R^3$ is a pyrimidine ring. In another embodiment is a compound of Formula (IIc), or a solvate, hydrate, tautomer, N-oxide, stereoisomer, or pharmaceutically acceptable salt thereof, wherein $R^3$ is a pyridazine ring. In another embodiment is a compound of Formula (IIc), or a solvate, hydrate, tautomer, N-oxide, stereoisomer, or pharmaceutically acceptable salt thereof, wherein $R^3$ is a pyrazine ring.

In another embodiment is a compound of Formula (IIc), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (IIc), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (IIc), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (IIc), or a solvate, hydrate, tautomer, N-oxide, stereoisomer, or pharmaceutically acceptable salt thereof, wherein R³ is a 10-membered bicyclic heteroaryl ring substituted with one R⁴, wherein R⁴ is $C_{1-6}$haloalkyl. In another embodiment is a compound of Formula (IIc), or a solvate, hydrate, tautomer, N-oxide, stereoisomer, or pharmaceutically acceptable salt thereof, wherein R³ is a 10-membered bicyclic heteroaryl ring selected from a quinolone, isoquinolone, quinazoline, quinoxaline, phthalazine, and a naphthyridine ring. In another embodiment is a compound of Formula (IIc), or a solvate, hydrate, tautomer, N-oxide, stereoisomer, or pharmaceutically acceptable salt thereof, wherein R³ is selected from:

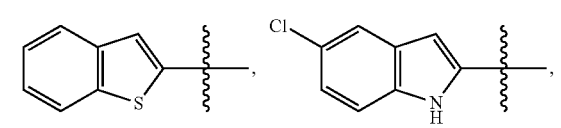

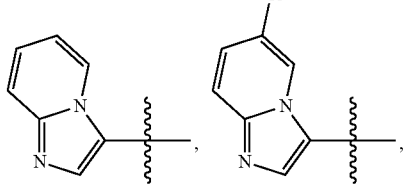

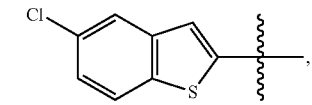

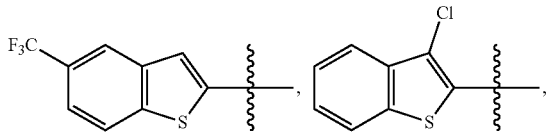

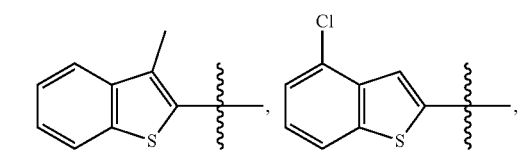

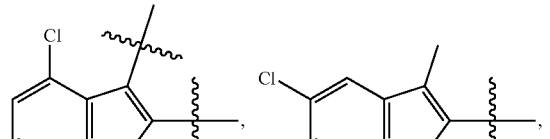

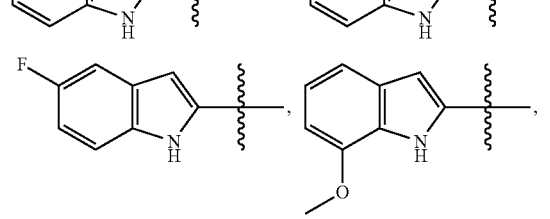

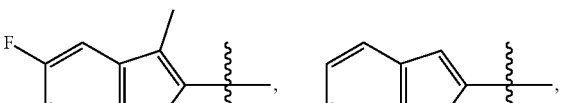

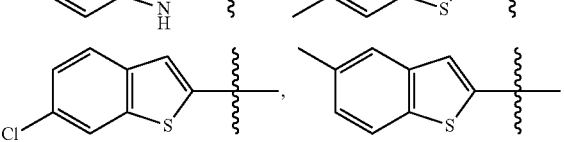

-continued

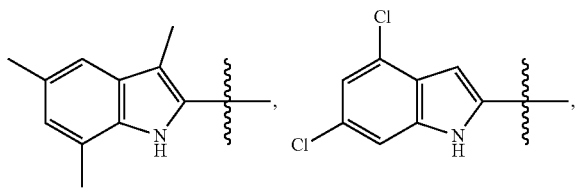

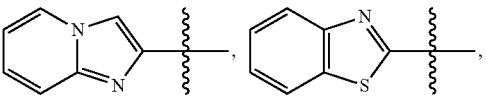

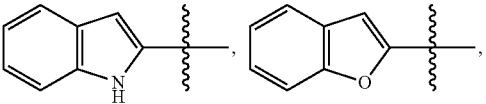

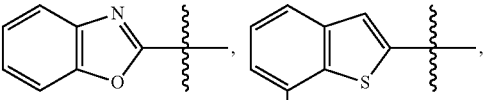

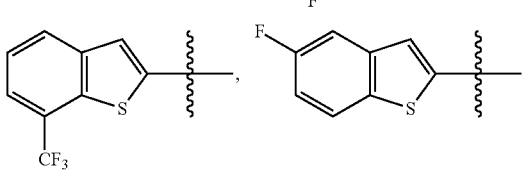

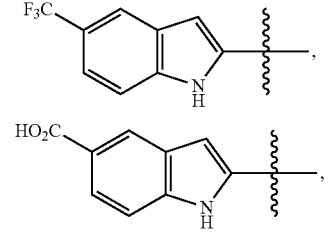

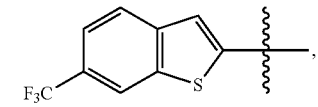

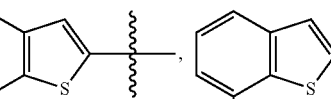

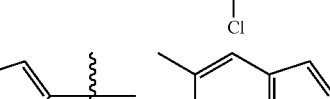

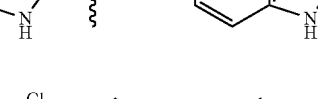

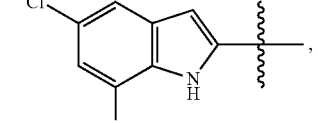

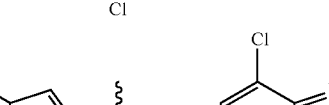

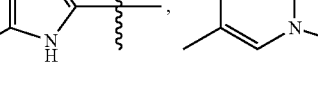

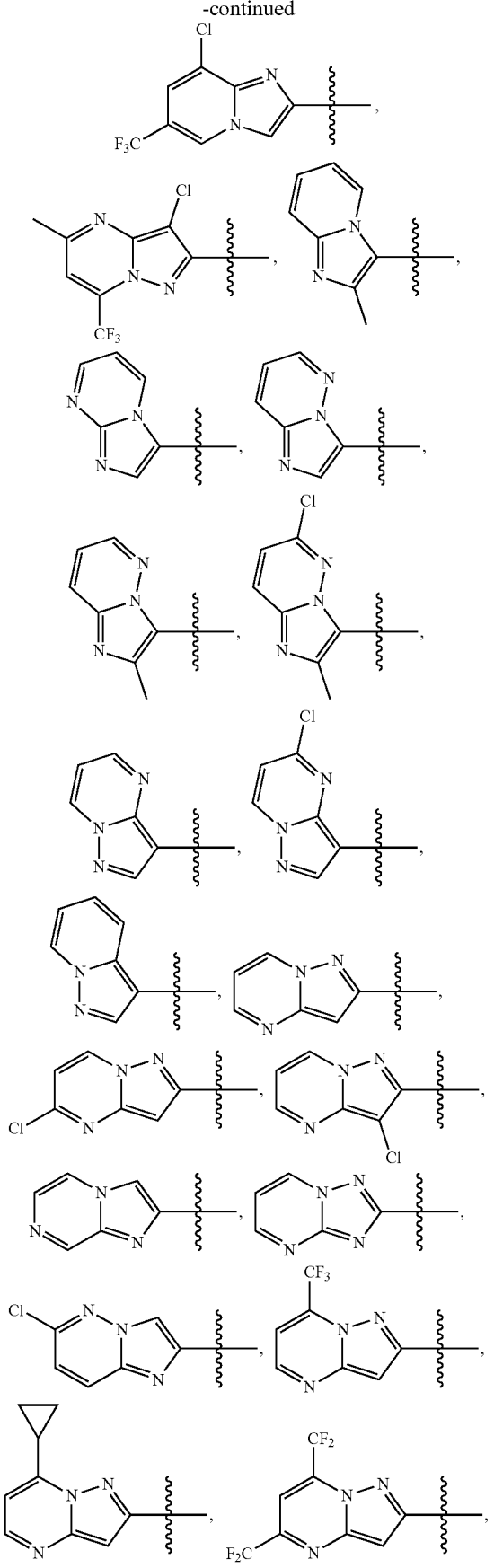
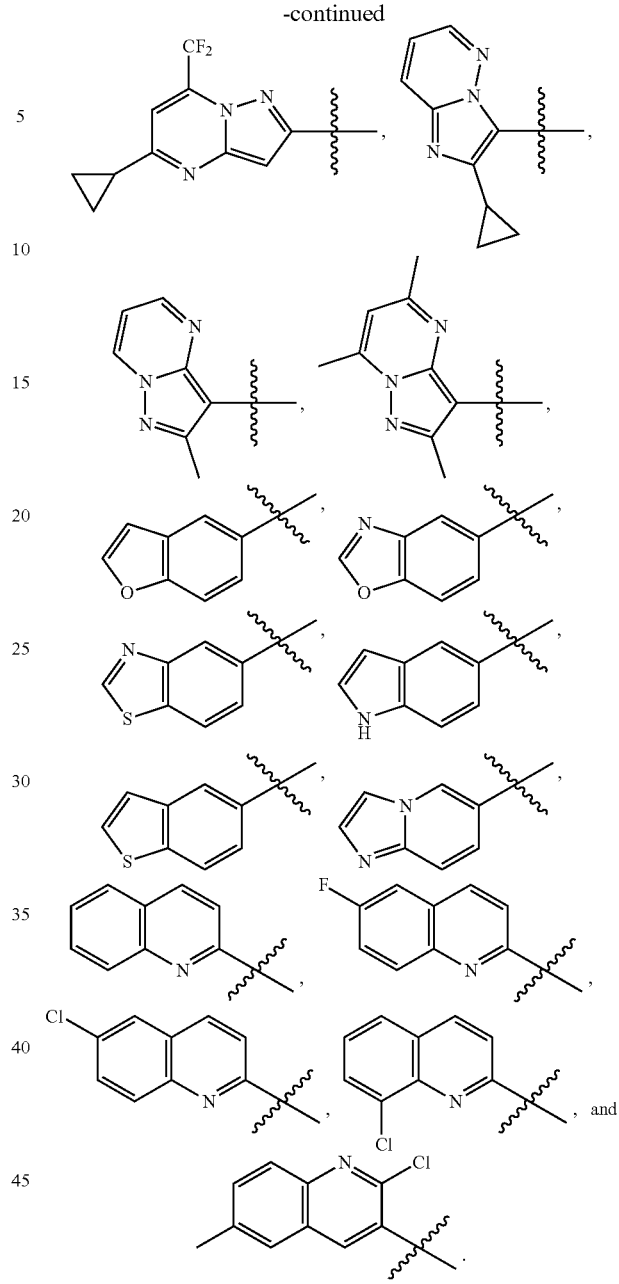
In some embodiments is a compound of Formula (III):
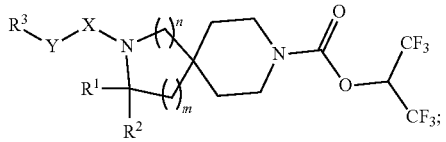
Formula (III)
wherein:
X is —CH$_2$— or —C(O)—;
Y is a bond, C$_{1-6}$alkyl, C$_{1-6}$haloalkyl, or C$_{3-9}$cycloalkyl;
R$^1$ is H or C$_{1-6}$alkyl;
R$^2$ is H or C$_{1-6}$alkyl;

R³ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R⁴;

each R⁴ is independently selected from $C_{1-6}$alkyl, halogen, —CN, $C_{1-6}$haloalkyl, $C_{3-8}$ cycloalkyl, $C_{2-9}$heterocycloalkyl, —$C_{1-6}$alkyl-($C_{2-9}$heterocycloalkyl), phenyl, —CH₂— phenyl, $C_{1-9}$heteroaryl, —OR⁷, —CO₂R⁶, —CH₂CO₂R⁶, and —CH₂C(O)N(H)SO₂R⁸; wherein $C_{2-9}$heterocycloalkyl, —$C_{1-6}$alkyl($C_{2-9}$heterocycloalkyl), phenyl, and $C_{1-9}$heteroaryl are optionally substituted with one or two R⁵; or two adjacent R⁴ form a 6-membered cycloalkyl or 6-membered heterocycloalkyl ring, wherein the cycloalkyl and heterocycloalkyl ring are optionally substituted with one or two R⁵;

each R⁵ is independently selected from halogen, $C_{1-6}$alkyl, $C_{1-6}$haloalkyl, $C_{1-6}$heteroalkyl, $C_{1-6}$alkoxy, $C_{3-8}$cycloalkyl, —$C_{1-6}$alkyl($C_{3-8}$cycloalkyl), $C_{2-9}$heterocycloalkyl, —CO₂R⁶, —CH₂CO₂R⁶, and —$C_{1-6}$alkyl($C_{2-9}$heterocycloalkyl) optionally substituted with $C_{1-6}$alkyl;

each R⁶ is independently selected from H and $C_{1-6}$alkyl;

each R⁷ is independently selected from H, $C_{1-6}$alkyl, $C_{1-6}$haloalkyl, and $C_{3-8}$cycloalkyl;

each R⁸ is independently selected from $C_{1-6}$alkyl, $C_{1-6}$haloalkyl, and $C_{3-8}$cycloalkyl;

n is 0 or 1; and m is 1 or 2; provided that when n is 0, then m is 2; and when n is 1, then m is 1;

or a solvate, hydrate, tautomer, N-oxide, stereoisomer, or pharmaceutically acceptable salt thereof.

In another embodiment is a compound of Formula (III), or a solvate, hydrate, tautomer, N-oxide, stereoisomer, or pharmaceutically acceptable salt thereof, wherein n is 0 and m is 2. In another embodiment is a compound of Formula (III), or a solvate, hydrate, tautomer, N-oxide, stereoisomer, or pharmaceutically acceptable salt thereof, wherein n is 1 and m is 1.

In another embodiment is a compound of Formula (III), or a solvate, hydrate, tautomer, N-oxide, stereoisomer, or pharmaceutically acceptable salt thereof, wherein R¹ is H. In another embodiment is a compound of Formula (III), or a solvate, hydrate, tautomer, N-oxide, stereoisomer, or pharmaceutically acceptable salt thereof, wherein R¹ is $C_{1-6}$alkyl. In another embodiment is a compound of Formula (III), or a solvate, hydrate, tautomer, N-oxide, stereoisomer, or pharmaceutically acceptable salt thereof, wherein R¹ is —CH₃. In another embodiment is a compound of Formula (III), or a solvate, hydrate, tautomer, N-oxide, stereoisomer, or pharmaceutically acceptable salt thereof, wherein R² is H. In another embodiment is a compound of Formula (III), or a solvate, hydrate, tautomer, N-oxide, stereoisomer, or pharmaceutically acceptable salt thereof, wherein R² is $C_{1-6}$alkyl. In another embodiment is a compound of Formula (III), or a solvate, hydrate, tautomer, N-oxide, stereoisomer, or pharmaceutically acceptable salt thereof, wherein R² is —CH₃. In another embodiment is a compound of Formula (III), or a solvate, hydrate, tautomer, N-oxide, stereoisomer, or pharmaceutically acceptable salt thereof, wherein R¹ is H and R² is H. In another embodiment is a compound of Formula (III), or a solvate, hydrate, tautomer, N-oxide, stereoisomer, or pharmaceutically acceptable salt thereof, wherein R¹ is H and R² is $C_{1-6}$alkyl. In another embodiment is a compound of Formula (III), or a solvate, hydrate, tautomer, N-oxide, stereoisomer, or pharmaceutically acceptable salt thereof, wherein R¹ is H and R² is —CH₃. In another embodiment is a compound of Formula (III), or a solvate, hydrate, tautomer, N-oxide, stereoisomer, or pharmaceutically acceptable salt thereof, wherein R¹ is $C_{1-6}$alkyl and R² is H. In another embodiment is a compound of Formula (III), or a solvate, hydrate, tautomer, N-oxide, stereoisomer, or pharmaceutically acceptable salt thereof, wherein R¹ is —CH₃ and R² is H. In another embodiment is a compound of Formula (III), or a solvate, hydrate, tautomer, N-oxide, stereoisomer, or pharmaceutically acceptable salt thereof, wherein R¹ is $C_{1-6}$alkyl and R² is $C_{1-6}$alkyl. In another embodiment is a compound of Formula (III), or a solvate, hydrate, tautomer, N-oxide, stereoisomer, or pharmaceutically acceptable salt thereof, wherein R¹ is —CH₃ and R² is —CH₃.

In another embodiment is a compound of Formula (III), or a solvate, hydrate, tautomer, N-oxide, stereoisomer, or pharmaceutically acceptable salt thereof, wherein X is —CH₂—. In another embodiment is a compound of Formula (III), or a solvate, hydrate, tautomer, N-oxide, stereoisomer, or pharmaceutically acceptable salt thereof, wherein X is —C(O)—.

In another embodiment is a compound of Formula (III), or a solvate, hydrate, tautomer, N-oxide, stereoisomer, or pharmaceutically acceptable salt thereof, wherein Y is a bond. In another embodiment is a compound of Formula (III), or a solvate, hydrate, tautomer, N-oxide, stereoisomer, or pharmaceutically acceptable salt thereof, wherein Y is $C_{1-6}$alkyl. In another embodiment is a compound of Formula (III), or a solvate, hydrate, tautomer, N-oxide, stereoisomer, or pharmaceutically acceptable salt thereof, wherein Y is —CH₂—. In another embodiment is a compound of Formula (III), or a solvate, hydrate, tautomer, N-oxide, stereoisomer, or pharmaceutically acceptable salt thereof, wherein Y is $C_{1-6}$haloalkyl. In another embodiment is a compound of Formula (III), or a solvate, hydrate, tautomer, N-oxide, stereoisomer, or pharmaceutically acceptable salt thereof, wherein Y is —CF₂—. In another embodiment is a compound of Formula (III), or a solvate, hydrate, tautomer, N-oxide, stereoisomer, or pharmaceutically acceptable salt thereof, wherein Y is $C_{3-8}$cycloalkyl. In another embodiment is a compound of Formula (III), or a solvate, hydrate, tautomer, N-oxide, stereoisomer, or pharmaceutically acceptable salt thereof, wherein Y is cyclopropyl.

In another embodiment is a compound of Formula (III), or a solvate, hydrate, tautomer, N-oxide, stereoisomer, or pharmaceutically acceptable salt thereof, wherein R³ is a 5- to 6-membered heteroaryl ring optionally substituted with one, two, or three R⁴. In another embodiment is a compound of Formula (III), or a solvate, hydrate, tautomer, N-oxide, stereoisomer, or pharmaceutically acceptable salt thereof, wherein R³ is a 5-membered heteroaryl ring optionally substituted with one, two, or three R⁴. In another embodiment is a compound of Formula (III), or a solvate, hydrate, tautomer, N-oxide, stereoisomer, or pharmaceutically acceptable salt thereof, wherein R³ is an unsubstituted 5-membered heteroaryl ring. In another embodiment is a compound of Formula (III), or a solvate, hydrate, tautomer, N-oxide, stereoisomer, or pharmaceutically acceptable salt thereof, wherein R³ is a 5-membered heteroaryl ring substituted with one, two, or three R⁴. In another embodiment is a compound of Formula (III), or a solvate, hydrate, tautomer, N-oxide, stereoisomer, or pharmaceutically acceptable salt thereof, wherein R³ is a 5-membered heteroaryl ring substituted with two or three R⁴, wherein two adjacent R⁴ form a 6-membered heterocycloalkyl ring optionally substituted with one or two R⁵. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered heterocycloalkyl ring. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is selected from $C_{1-6}$alkyl, $C_{1-6}$heteroalkyl, $C_{3-8}$cycloalkyl, —$C_{1-6}$alkyl($C_{3-8}$cycloalkyl), $C_{2-9}$heterocycloalkyl, and —$CH_2CO_2H$. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-4}$alkyl. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{1-6}$heteroalkyl. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{3-8}$cycloalkyl. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$C_{1-6}$alkyl($C_{3-8}$cycloalkyl). In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is $C_{2-9}$heterocycloalkyl. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered heterocycloalkyl ring substituted with one $R^5$ and $R^5$ is —$CH_2CO_2H$. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two or three $R^4$, wherein two adjacent $R^4$ form a 6-membered cycloalkyl ring optionally substituted with one or two $R^5$. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form an unsubstituted 6-membered cycloalkyl ring. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with two adjacent $R^4$, wherein the two adjacent $R^4$ form a 6-membered cycloalkyl ring substituted with one $R^5$. In another embodiment is a compound of Formula (III), or a solvate, hydrate, tautomer, N-oxide, stereoisomer, or pharmaceutically acceptable salt thereof, wherein $R^3$ is selected from:

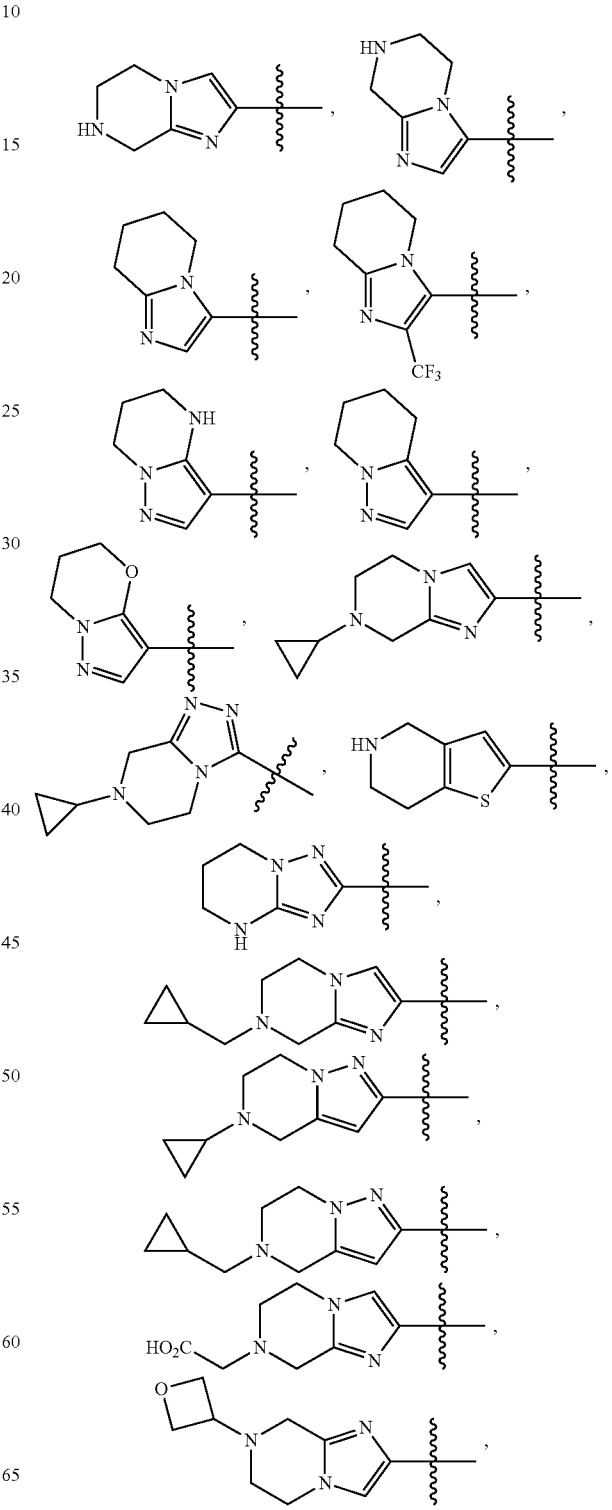

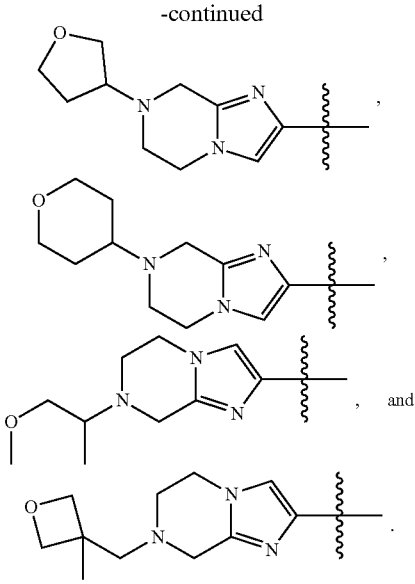

In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (III), or a solvate, hydrate, tautomer, N-oxide, stereoisomer, or pharmaceutically acceptable salt thereof, wherein $R^3$ is a 5-membered heteroaryl ring substituted with one or two $R^4$, wherein each $R^4$ is independently selected from halogen, $C_{1-6}$alkyl, $C_{2-9}$heterocycloalkyl, and phenyl, and wherein $C_{2-9}$heterocycloalkyl and phenyl are optionally substituted with one or two $R^5$, and each $R^5$ is independently selected from halogen, $C_{1-6}$alkoxy, $C_{2-9}$heterocycloalkyl, or —$CO_2H$. In another embodiment is a compound of Formula (III), or a solvate, hydrate, tautomer, N-oxide, stereoisomer, or pharmaceutically acceptable salt thereof, wherein $R^3$ is an unsubstituted 5-membered heteroaryl ring. In another embodiment is a compound of Formula (III), or a solvate, hydrate, tautomer, N-oxide, stereoisomer, or pharmaceutically acceptable salt thereof, wherein $R^3$ is a 5-membered heteroaryl ring selected from a pyrazole, thiazole, isoxazole, oxazole, and imidazole ring. In another embodiment is a compound of Formula (III), or a solvate, hydrate, tautomer, N-oxide, stereoisomer, or pharmaceutically acceptable salt thereof, wherein $R^3$ is a pyrazole ring. In another embodiment is a compound of Formula (III), or a solvate, hydrate, tautomer, N-oxide, stereoisomer, or pharmaceutically acceptable salt thereof, wherein $R^3$ is a thiazole ring. In another embodiment is a compound of Formula (III), or a solvate, hydrate, tautomer, N-oxide, stereoisomer, or pharmaceutically acceptable salt thereof, wherein $R^3$ is an isoxazole ring. In another embodiment is a compound of Formula (III), or a solvate, hydrate, tautomer, N-oxide, stereoisomer, or pharmaceutically acceptable salt thereof, wherein $R^3$ is an oxazole ring. In another embodiment is a compound of Formula (III), or a solvate, hydrate, tautomer, N-oxide, stereoisomer, or pharmaceutically acceptable salt thereof, wherein $R^3$ is an imidazole ring. In another embodiment is a compound of Formula (III), or a solvate, hydrate, tautomer, N-oxide, stereoisomer, or pharmaceutically acceptable salt thereof, wherein $R^3$ is a 6-membered heteroaryl ring optionally substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is an unsubstituted 6-membered heteroaryl ring. In another embodiment is a compound of Formula (III), or a solvate, hydrate, tautomer, N-oxide, stereoisomer, or pharmaceutically acceptable salt thereof, wherein $R^3$ is a 6-membered heteroaryl ring substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, $C_{2-9}$heterocycloalkyl, phenyl, —$OR^7$, —$CO_2H$, and —$CH_2CO_2H$, and wherein $C_{2-9}$heterocycloalkyl and phenyl are optionally substituted with one or two $R^5$. In another embodiment is a compound of Formula (III), or a solvate, hydrate, tautomer, N-oxide, stereoisomer, or pharmaceutically acceptable salt thereof, wherein $R^3$ is a 6-membered heteroaryl ring substituted with one, two, or three $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one or two $R^5$. In another embodiment is a compound of Formula (III), or a solvate, hydrate, tautomer, N-oxide, stereoisomer, or pharmaceutically acceptable salt thereof, wherein $R^3$ is a 6-membered heteroaryl ring substituted with one or two $R^4$, wherein each $R^4$ is independently selected from halogen, $C_{1-6}$alkyl, $C_{1-6}$haloalkyl, and $C_{2-9}$heterocycloalkyl, and wherein $C_{2-9}$heterocycloalkyl is optionally substituted with one $R^5$, and $R^5$ is —$CO_2H$. In another embodiment is a compound of Formula (III), or a solvate, hydrate, tautomer, N-oxide, stereoisomer, or pharmaceutically acceptable salt thereof, wherein $R^3$ is a 6-membered heteroaryl ring selected from a pyridine, pyrimidine, pyridazine, and pyrazine ring. In another embodiment is a compound of Formula (III), or a solvate, hydrate, tautomer, N-oxide, stereoisomer, or pharmaceutically acceptable salt thereof, wherein $R^3$ is a pyridine ring. In another embodiment is a compound of Formula (III), or a solvate, hydrate, tautomer, N-oxide, stereoisomer, or pharmaceutically acceptable salt thereof, wherein $R^3$ is a pyrimidine ring. In another embodiment is a compound of Formula (III), or a solvate, hydrate, tautomer, N-oxide, stereoisomer, or pharmaceutically acceptable salt thereof, wherein $R^3$ is a pyridazine ring. In another embodiment is a compound of Formula (III), or a solvate, hydrate, tautomer, N-oxide, stereoisomer, or pharmaceutically acceptable salt thereof, wherein $R^3$ is a pyrazine ring.

In another embodiment is a compound of Formula (III), or a solvate, hydrate, tautomer, N-oxide, stereoisomer, or pharmaceutically acceptable salt thereof, wherein $R^3$ is a 9- or 10-membered bicyclic heteroaryl ring optionally substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring optionally substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is an unsubstituted 9-membered bicyclic heteroaryl ring. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is halogen. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$alkyl. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring substituted with one $R^4$, wherein $R^4$ is $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 9-membered bicyclic heteroaryl ring selected from a benzothiophene, indole, benzimidazole, benzothiazole, benzofuran, benzoxazole, pyrazolpyridine, imidazopyridine, and pyrrolopyridine ring. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring optionally substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is an unsubstituted 10-membered bicyclic heteroaryl ring. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one, two, or three $R^4$, wherein each $R^4$ is independently selected from halogen, —CN, $C_{1-6}$alkyl, $C_{1-6}$haloalkyl, $C_{3-8}$cycloalkyl, —$OR^7$, and —$CO_2R^6$. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, $C_{1-6}$haloalkyl, $C_{3-8}$cycloalkyl, —$OC_{1-6}$alkyl, and —$CO_2R^6$. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one or two $R^4$, wherein each $R^4$ is independently selected from halogen, $C_{1-6}$alkyl, and $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is selected from halogen, $C_{1-6}$alkyl, and $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is halogen. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$alkyl. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring substituted with one $R^4$, wherein $R^4$ is $C_{1-6}$haloalkyl. In another embodiment is a compound of Formula (III), or a solvate, hydrate, tautomer, N-oxide, stereoisomer, or pharmaceutically acceptable salt thereof, wherein $R^3$ is a 10-membered bicyclic heteroaryl ring selected from a quinolone, isoquinolone, quinazoline, quinoxaline, phthalazine, and a naphthyridine ring. In another embodiment is a compound of Formula (III), or a solvate, hydrate, tautomer, N-oxide, stereoisomer, or pharmaceutically acceptable salt thereof, wherein $R^3$ is selected from:

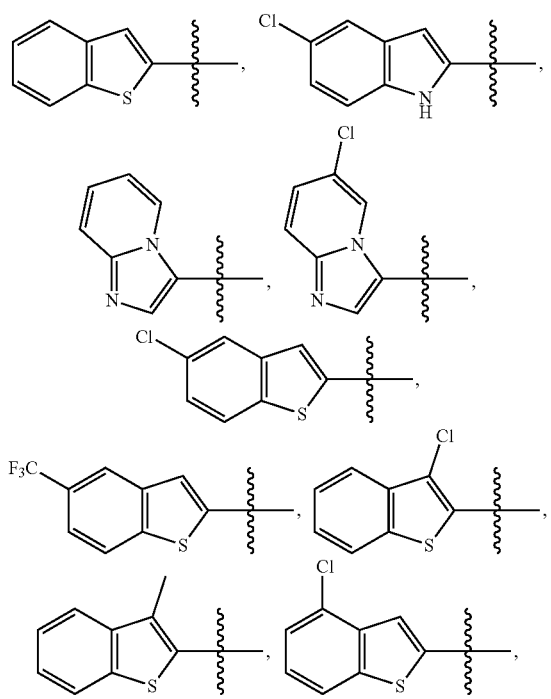

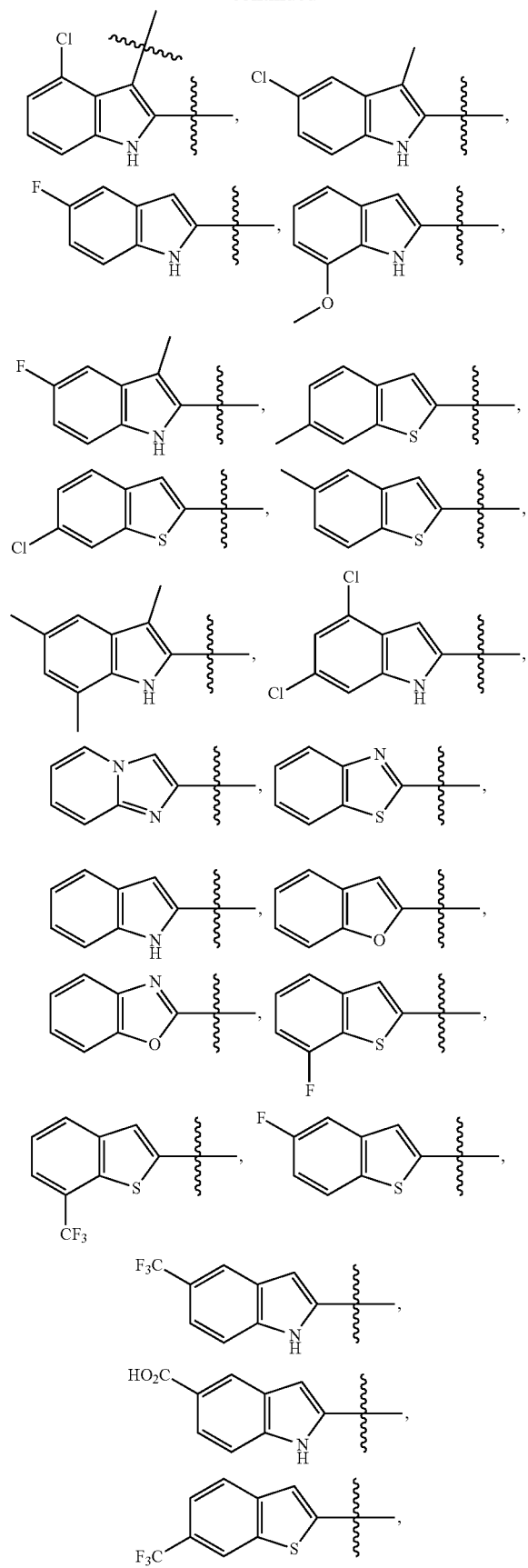
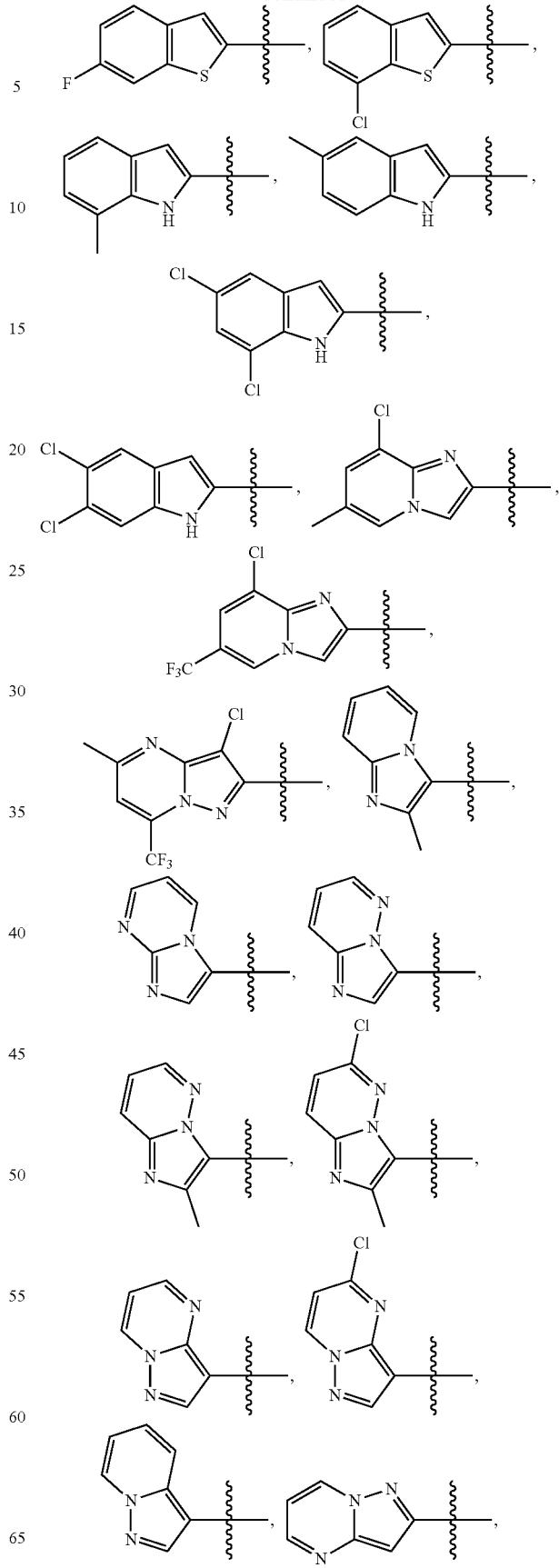

-continued

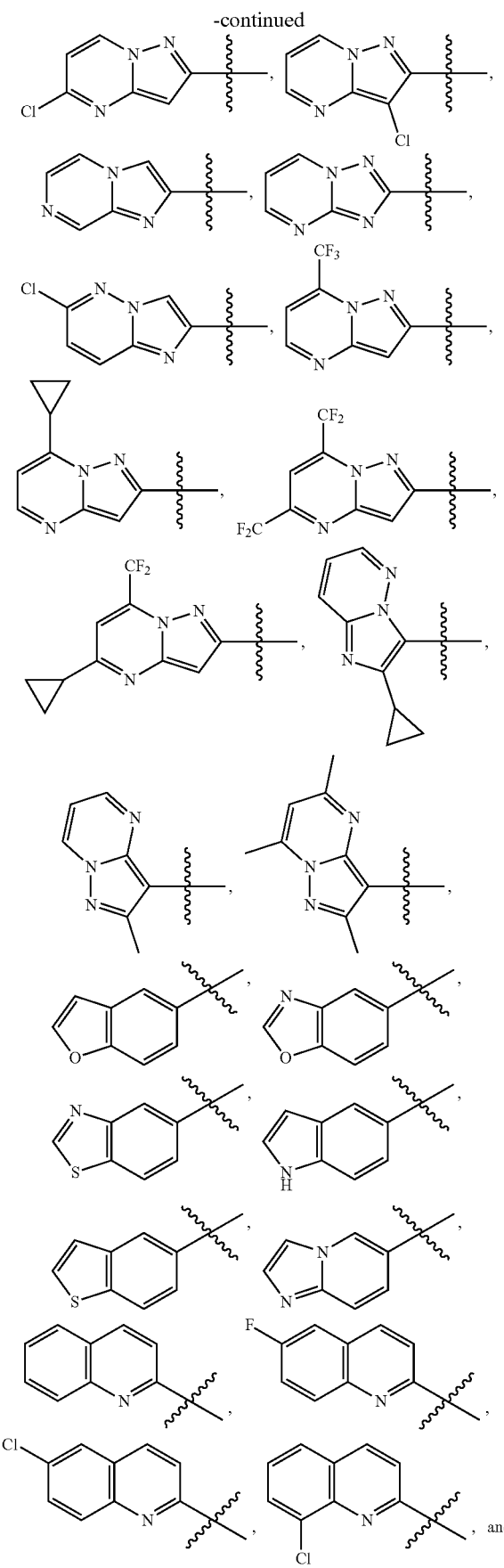

, and

-continued

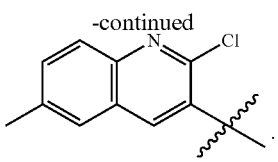

In another embodiment is a compound of Formula (IV):

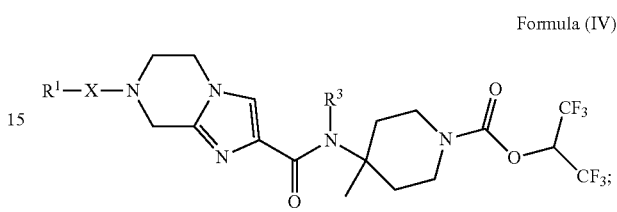

Formula (IV)

wherein:
X is a bond, —C(O)—, or —S(O)$_2$—;
R$^1$ is selected from C$_{1-6}$alkyl, C$_{1-6}$haloalkyl, C$_{3-8}$cycloalkyl, C$_{2-9}$heterocycloalkyl, phenyl, and C$_{1-9}$heteroaryl; wherein C$_{3-8}$cycloalkyl, C$_{2-9}$heterocycloalkyl, phenyl, and C$_{1-9}$heteroaryl are optionally substituted with one, two, or three R$^2$;
each R$^2$ is independently selected from halogen, C$_{1-6}$alkyl, and C$_{1-6}$haloalkyl; and R$^3$ is H, C$_{1-6}$alkyl, or —C$_{1-6}$alkyl-O—C$_{1-6}$alkyl;
or a solvate, hydrate, tautomer, N-oxide, stereoisomer, or pharmaceutically acceptable salt thereof.

In another embodiment is a compound of Formula (IV), or a solvate, hydrate, tautomer, N-oxide, stereoisomer, or pharmaceutically acceptable salt thereof, wherein R$^3$ is H. In another embodiment is a compound of Formula (IV), or a solvate, hydrate, tautomer, N-oxide, stereoisomer, or pharmaceutically acceptable salt thereof, wherein R$^3$ is C$_{1-6}$alkyl. In another embodiment is a compound of Formula (IV), or a solvate, hydrate, tautomer, N-oxide, stereoisomer, or pharmaceutically acceptable salt thereof, wherein R$^3$ is —CH$_3$. In another embodiment is a compound of Formula (IV), or a solvate, hydrate, tautomer, N-oxide, stereoisomer, or pharmaceutically acceptable salt thereof, wherein R$^3$ is —CH$_2$CH$_3$. In another embodiment is a compound of Formula (IV), or a solvate, hydrate, tautomer, N-oxide, stereoisomer, or pharmaceutically acceptable salt thereof, wherein R$^3$ is —C$_{1-6}$alkyl-O—C$_{1-6}$alkyl.

In another embodiment is a compound of Formula (IV), or a solvate, hydrate, tautomer, N-oxide, stereoisomer, or pharmaceutically acceptable salt thereof, wherein X is a bond. In another embodiment is a compound of Formula (IV), or a solvate, hydrate, tautomer, N-oxide, stereoisomer, or pharmaceutically acceptable salt thereof, wherein X is —C(O)—. In another embodiment is a compound of Formula (IV), or a solvate, hydrate, tautomer, N-oxide, stereoisomer, or pharmaceutically acceptable salt thereof, wherein X is —S(O)$_2$—.

In another embodiment is a compound of Formula (IV), or a solvate, hydrate, tautomer, N-oxide, stereoisomer, or pharmaceutically acceptable salt thereof, wherein R$^1$ is C$_{1-6}$alkyl. In another embodiment is a compound of Formula (IV), or a solvate, hydrate, tautomer, N-oxide, stereoisomer, or pharmaceutically acceptable salt thereof, wherein R$^1$ is C$_{1-6}$haloalkyl. In another embodiment is a compound of Formula (IV), or a solvate, hydrate, tautomer, N-oxide, stereoisomer, or pharmaceutically acceptable salt thereof, wherein R¹ is $C_{3-8}$cycloalkyl optionally substituted with one, two, or three R². In another embodiment is a compound of Formula (IV), or a solvate, hydrate, tautomer, N-oxide, stereoisomer, or pharmaceutically acceptable salt thereof, wherein R¹ is $C_{3-8}$cycloalkyl optionally substituted with one halogen. In another embodiment is a compound of Formula (IV), or a solvate, hydrate, tautomer, N-oxide, stereoisomer, or pharmaceutically acceptable salt thereof, wherein R¹ is $C_{3-8}$cycloalkyl optionally substituted with one $C_{1-6}$alkyl. In another embodiment is a compound of Formula (IV), or a solvate, hydrate, tautomer, N-oxide, stereoisomer, or pharmaceutically acceptable salt thereof, wherein R¹ is $C_{2-9}$heterocycloalkyl optionally substituted with one, two, or three R². In another embodiment is a compound of Formula (IV), or a solvate, hydrate, tautomer, N-oxide, stereoisomer, or pharmaceutically acceptable salt thereof, wherein R¹ is phenyl optionally substituted with one, two, or three R². In another embodiment is a compound of Formula (IV), or a solvate, hydrate, tautomer, N-oxide, stereoisomer, or pharmaceutically acceptable salt thereof, wherein R¹ is $C_{1-9}$heteroaryl optionally substituted with one, two, or three R². In another embodiment is a compound of Formula (IV), or a solvate, hydrate, tautomer, N-oxide, stereoisomer, or pharmaceutically acceptable salt thereof, wherein R¹ is $C_{1-9}$heteroaryl selected from oxazole and pyrazine; wherein the oxazole and pyrazine are optionally substituted with one, two, or three R². In another embodiment is a compound of Formula (IV), or a solvate, hydrate, tautomer, N-oxide, stereoisomer, or pharmaceutically acceptable salt thereof, wherein R¹ is $C_{1-9}$heteroaryl selected from oxazole and pyrazine; wherein the oxazole and pyrazine are unsubstituted.

Further embodiments provided herein include combinations of one or more of the particular embodiments set forth above.

In some embodiments, the compound disclosed herein is selected from examples 1-229.

In another embodiment is a compound having the structure:

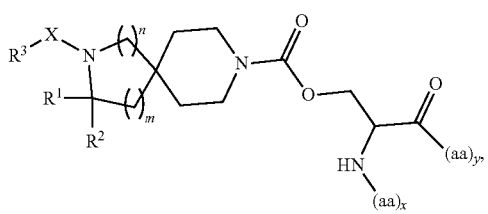

wherein R¹, R², R³, X, m, and n are defined as in Formula (I) described herein, and x and y are at least one amino acid (aa). In another embodiment is a compound having the structure:

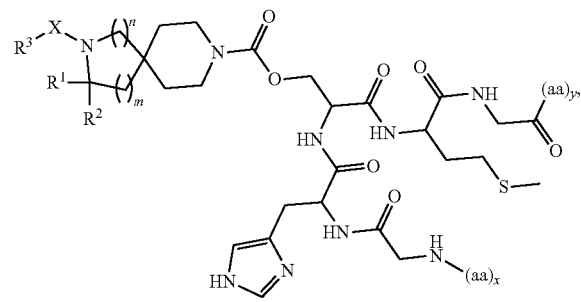

wherein R¹, R², R³, X, m, and n are defined as in Formula (I) described herein, and x and y are at least one amino acid (aa).

In another embodiment is a compound having the structure:

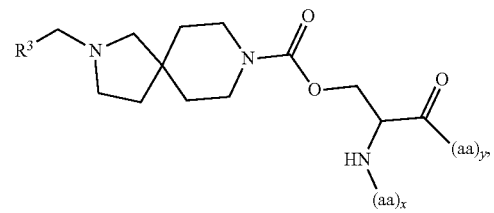

wherein R³ is defined as in Formula (Ia) described herein, and x and y are at least one amino acid (aa). In another embodiment is a compound having the structure:

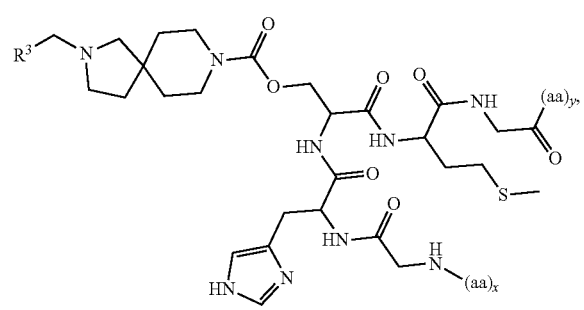

wherein R³ is defined as in Formula (Ia) described herein, and x and y are at least one amino acid (aa).

In another embodiment is a compound having the structure:

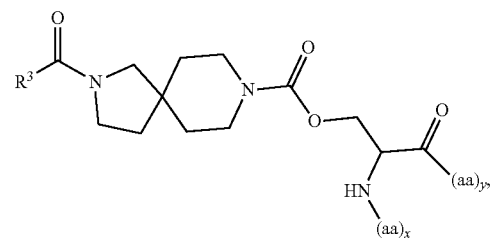

wherein R³ is defined as in Formula (Ib) described herein, and x and y are at least one amino acid (aa). In another embodiment is a compound having the structure:

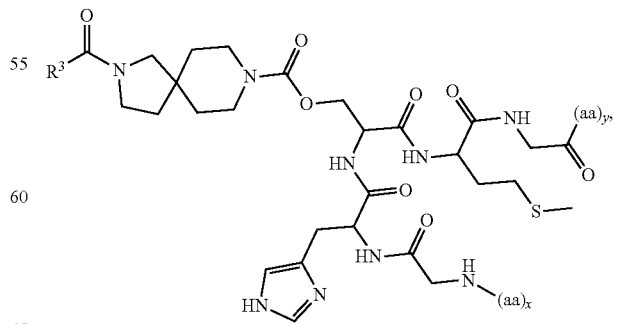

wherein R³ is defined as in Formula (Ib) described herein, and x and y are at least one amino acid (aa).

In another embodiment is a compound having the structure:

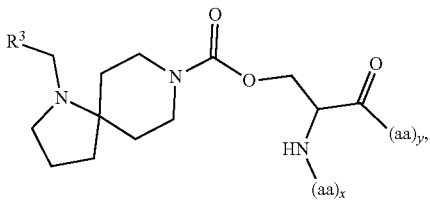

wherein $R^3$ is defined as in Formula (Ic) described herein, and x and y are at least one amino acid (aa). In another embodiment is a compound having the structure:

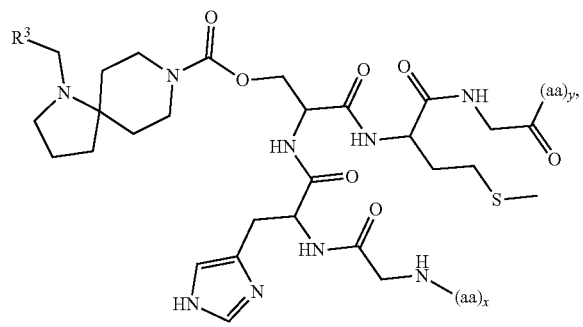

wherein $R^3$ is defined as in Formula (Ic) described herein, and x and y are at least one amino acid (aa).

In another embodiment is a compound having the structure:

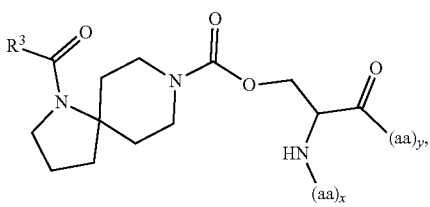

wherein $R^3$ is defined as in Formula (Id) described herein, and x and y are at least one amino acid (aa). In another embodiment is a compound having the structure:

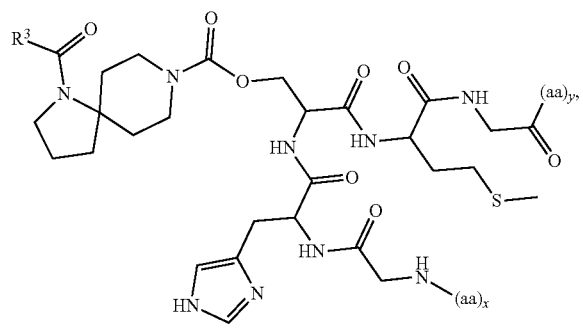

wherein $R^3$ is defined as in Formula (Id) described herein, and x and y are at least one amino acid (aa).

In another embodiment is a compound having the structure:

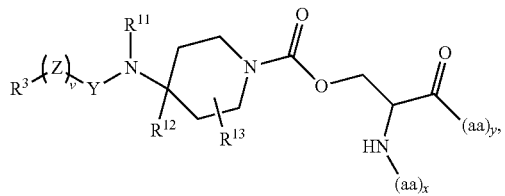

wherein $R^3$, $R^{11}$, $R^{12}$, $R^{13}$, Y, Z, and v are defined as in Formula (II) described herein, and x and y are at least one amino acid (aa). In another embodiment is a compound having the structure:

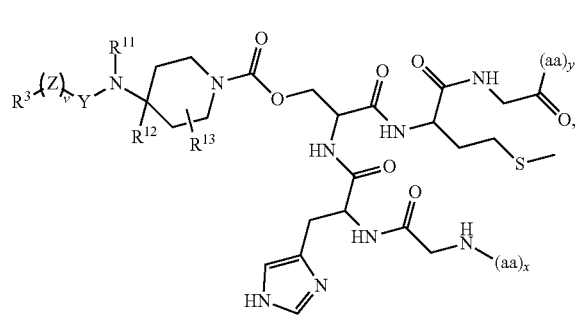

wherein $R^3$, $R^{11}$, $R^{12}$, $R^{13}$, Y, Z, and v are defined as in Formula (II) described herein, and x and y are at least one amino acid (aa).

In another embodiment is a compound having the structure:

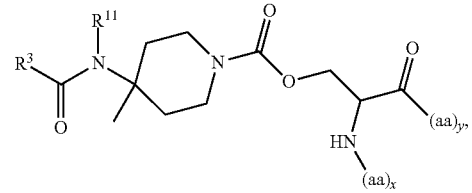

wherein $R^3$ and $R^{11}$ are defined as in Formula (IIa) described herein, and x and y are at least one amino acid (aa). In another embodiment is a compound having the structure:

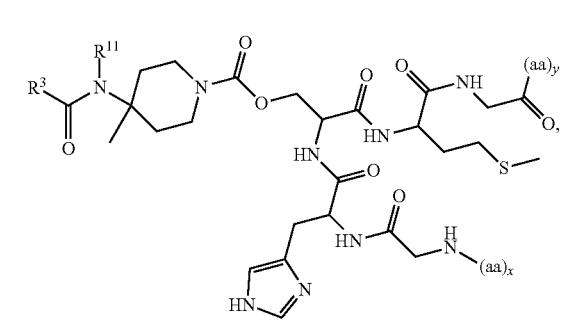

wherein $R^3$ and $R^{11}$ are defined as in Formula (IIa) described herein, and x and y are at least one amino acid (aa).

In another embodiment is a compound having the structure:

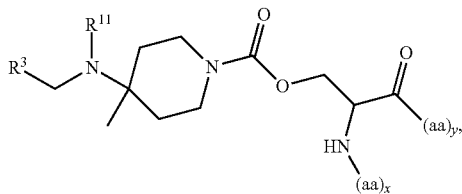

wherein $R^3$ and $R^{11}$ are defined as in Formula (IIb) described herein, and x and y are at least one amino acid (aa). In another embodiment is a compound having the structure:

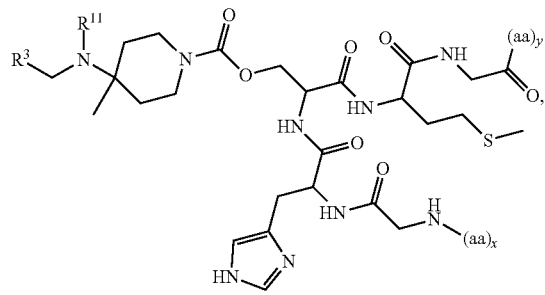

wherein $R^3$ and $R^{11}$ are defined as in Formula (IIb) described herein, and x and y are at least one amino acid (aa).

In another embodiment is a compound having the structure:

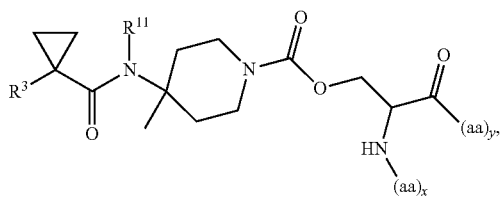

wherein $R^3$ and $R^{11}$ are defined as in Formula (IIc) described herein, and x and y are at least one amino acid (aa). In another embodiment is a compound having the structure:

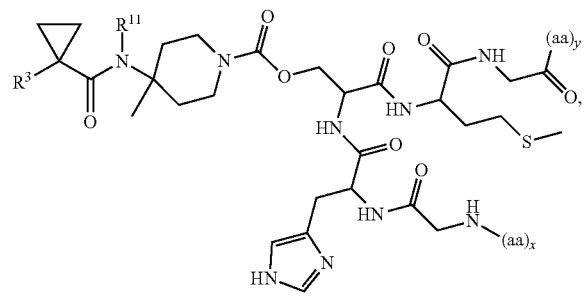

wherein $R^3$ and $R^{11}$ are defined as in Formula (IIc) described herein, and x and y are at least one amino acid (aa).

Described herein are inhibitors of monoacylglycerol lipase (MAGL) having the structure of Formula (I), (Ia), (Ib), (Ic), (Id), (II), (IIa), (IIb), (IIc), (III), or (IV). In one embodiment, the inhibitors of MAGL are covalent inhibitors of MAGL, that is, the compounds of Formula (I), (Ia), (Ib), (Ic), (Id), (II), (IIa), (IIb), (IIc), (III), or (IV) react with a serine residue of MAGL to form a modified serine residue, comprising the staying group of Formula (I), (Ia), (Ib), (Ic), (Id), (II), (IIa), (IIb), (IIc), (III), or (IV); in such an embodiment, the leaving group of Formula (I), (Ia), (Ib), (Ic), (Id), (II), (IIa), (IIb), (IIc), (III), or (IV) is removed from the compound of Formula (I), (Ia), (Ib), (Ic), (Id), (II), (IIa), (IIb), (IIc), (III), or (IV). In a further embodiment, the covalent inhibitors of MAGL react irreversibly with a serine residue of MAGL to form the modified serine residue.

The staying group portion of the compounds of Formula (I) is

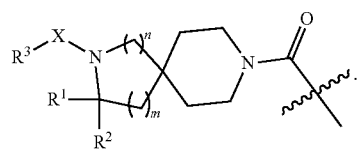

The staying group portion of the compounds of Formula (Ia) is

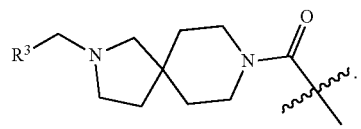

The staying group portion of the compounds of Formula (Ib) is

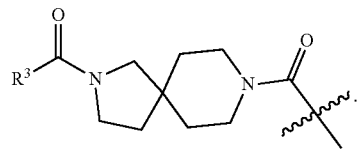

The staying group portion of the compounds of Formula (Ic) is

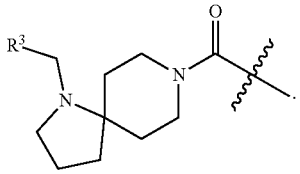

The staying group portion of the compounds of Formula (Id) is

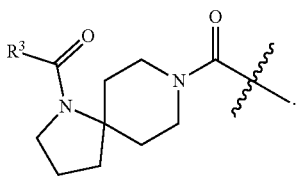

The staying group portion of the compounds of Formula (II) is

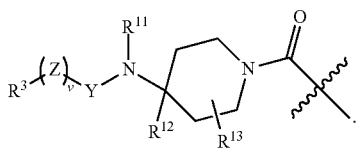

The staying group portion of the compounds of Formula (IIa) is

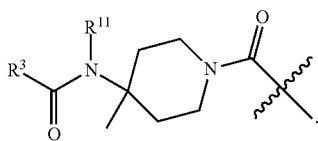

The staying group portion of the compounds of Formula (IIb) is

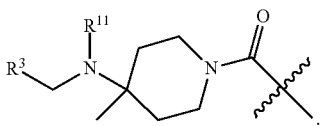

The staying group portion of the compounds of Formula (IIc) is

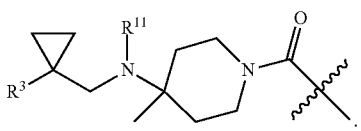

The leaving group portion of the compounds of Formula (I), (Ia), (Ib), (Ic), (Id), (II), (IIa), (IIb), (IIc), (III), or (IV) is:

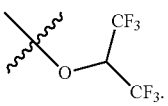

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2H$, $^3$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy, or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine, and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters, disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to the following groups and combinations of groups:

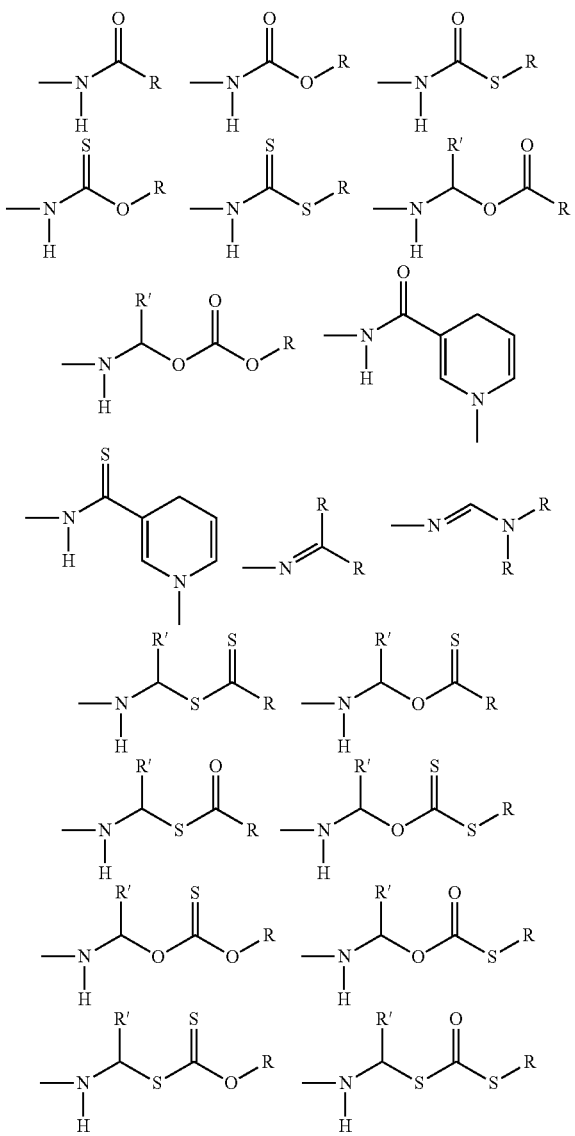

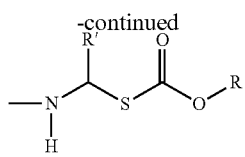

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), (Ib), (Ic), (Id), (II), (IIa), (IIb), (IIc), (III), or (IV) as described herein is administered as a pure chemical. In some embodiments, the compound of Formula (I), (Ia), (Ib), (Ic), (Id), (II), (IIa), (IIb), (IIc), (III), or (IV) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), (Ib), (Ic), (Id), (II), (IIa), (IIb), (IIc), (III), or (IV) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. Another embodiment provides a pharmaceutical composition comprising a pharmaceutically acceptable excipient and a compound of Formula (Ia), or a pharmaceutically acceptable salt thereof. Another embodiment provides a pharmaceutical composition comprising a pharmaceutically acceptable excipient and a compound of Formula (Ib), or a pharmaceutically acceptable salt thereof. Another embodiment provides a pharmaceutical composition comprising a pharmaceutically acceptable excipient and a compound of Formula (Ic), or a pharmaceutically acceptable salt thereof. Another embodiment provides a pharmaceutical composition comprising a pharmaceutically acceptable excipient and a compound of Formula (Id), or a pharmaceutically acceptable salt thereof. Another embodiment provides a pharmaceutical composition comprising a pharmaceutically acceptable excipient and a compound of Formula (II), or a pharmaceutically acceptable salt thereof. Another embodiment provides a pharmaceutical composition comprising a pharmaceutically acceptable excipient and a compound of Formula (IIa), or a pharmaceutically acceptable salt thereof. Another embodiment provides a pharmaceutical composition comprising a pharmaceutically acceptable excipient and a compound of Formula (IIb), or a pharmaceutically acceptable salt thereof. Another embodiment provides a pharmaceutical composition comprising a pharmaceutically acceptable excipient and a compound of Formula (IIc), or a pharmaceutically acceptable salt thereof.

Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (Id), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (IIa), or a pharmaceutically acceptable salt thereof. Another embodiment provides a pharmaceutical composition consisting essentially of a pharmaceutically acceptable excipient and a compound of Formula (IIb), or a pharmaceutically acceptable salt thereof. Another embodiment provides a pharmaceutical composition consisting essentially of a pharmaceutically acceptable excipient and a compound of Formula (IIc), or a pharmaceutically acceptable salt thereof.

In certain embodiments, the compound of Formula (I), (Ia), (Ib), (Ic), (Id), (II), (IIa), (IIb), (IIc), (III), or (IV) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches, and inhalants. In some embodiments, the active component is mixed under sterile conditions with a pharmaceutically acceptable carrier, and with any preservatives, buffers, or propellants as required.

In some embodiments, the ointments, pastes, creams, and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, and amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5, and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Ib), (Ic), (Id), (II), (IIa), (IIb), (IIc), (III), or (IV) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (Ib), (Ic), (Id), (II), (IIa), (IIb), (IIc), (III), or (IV). In some embodiments, provided herein is a compound of Formula (I), (Ia), (Ib), (Ic), (Id), (II), (IIa), (IIb), (IIc), (III), or (IV) wherein the compound is a MAGL inhibitor. In some embodiments, provided herein is a compound of Formula (I), (Ia), (Ib), (Ic), (Id), (II), (IIa), (IIb), (IIc), (III), or (IV) wherein the compound is a selective MAGL inhibitor. The ability of compounds described herein to modulate or inhibit MAGL is evaluated by procedures known in the art and/or described herein. Another aspect of this disclosure provides methods of treating a disease associated with expression or activity of MAGL in a patient. In some embodiments, provided herein is a compound of Formula (I), (Ia), (Ib), (Ic), (Id), (II), (IIa), (IIb), (IIc), (III), or (IV) wherein the compound is selective in inhibiting MAGL as compared to inhibition of other serine hydrolases. In some embodiments, provided herein is a compound of Formula (I), (Ia), (Ib), (Ic), (Id), (II), (IIa), (IIb), (IIc), (III), or (IV) wherein the compound is 10, 100, or 1000 fold selective in inhibiting MAGL as compared to inhibition of other serine hydrolases.

In another embodiment is a method of treating pain in a patient, comprising administering a therapeutically effective amount of a compound of Formula (I), (Ia), (Ib), (Ic), (Id), (II), (IIa), (IIb), (IIc), (III), or (IV) described herein, or a solvate, hydrate, tautomer, N-oxide, or a pharmaceutically acceptable salt thereof, to a patient in need thereof to treat said pain. In another embodiment is a method of treating neuropathic pain in a patient, comprising administering a therapeutically effective amount of a compound of Formula (I), (Ia), (Ib), (Ic), (Id), (II), (IIa), (IIb), (IIc), (III), or (IV) described herein, or a solvate, hydrate, tautomer, N-oxide, or a pharmaceutically acceptable salt thereof, to a patient in need thereof to treat said neuropathic pain. In another embodiment is a method of treating inflammatory pain in a patient, comprising administering a therapeutically effective amount of a compound of Formula (I), (Ia), (Ib), (Ic), (Id), (II), (IIa), (IIb), (IIc), (III), or (IV) described herein, or a solvate, hydrate, tautomer, N-oxide, or a pharmaceutically acceptable salt thereof, to a patient in need thereof to treat said inflammatory pain.

Also contemplated herein in some embodiments are methods of treating and/or preventing in a patient in need thereof a disorder such as one or more of acute or chronic pain, bone cancer pain, rheumatoid arthritis pain, pruritus, vomiting or nausea, Down's syndrome, Parkinson's disease, epilepsy, NSAID-induced ulcers, opioid withdrawal, cannabis withdrawal, nicotine withdrawal, traumatic brain injury, ischemia, renal ischemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), liver injury, lung injury, skeletal muscle contusions, inflammatory disorders, and/or anxiety disorders. Contemplated methods include administering a pharmaceutically effective amount of a disclosed compound.

In some embodiments, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that result in liver damage, in a patient in need thereof.

In some embodiments, provide herein is a method for treating chronic pain such as inflammatory pain, visceral pain, back pain, post operative pain, and pain related to migraine, osteoarthritis, or rheumatoid arthritis.

In some embodiments, provide herein are methods for ameliorating cognitive function in a patient suffering from Down's syndrome or Alzheimer's disease, comprising administering an effective amount of a disclosed compound. Exemplary patients suffering from Down's syndrome are a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). In some embodiments, such patients also suffer from further cognitive impairment and/or dementia, and/or seizures which, in some embodiments are due to production of prostaglandins and/or amyloid beta. For example, such patients also are suffering from, or have one or more of the following symptoms associated with early-mid or late stage cognitive impairment: loss of language, impairment of social skills, progressive loss of activities of daily living, and include psychotic behavior. Provided herein, for example, is a method for treating a patient having Down's syndrome or Alzheimer's disease with cognitive impairment, comprising administering an effective amount of a disclosed compound. Such disclosed methods result in cognitive improvement, for example, measured by IQ or the Arizona Cognitive Test Battery (e.g., measured with a cognitive test battery designed for use in individuals with Down's syndrome). For example, a treated patient using a disclosed method has at least one of: increased memory, improved memory or improved speech. In some embodiments, such disclosed methods result in a patient having an increased quality of life as measured by an adaptive behavior scale after said administration.

In other embodiments, a method for at least partially providing a Down's syndrome patient a neuroprotective (such as a disclosed compounds), that results in delayed onset of neurodegeneration or substantially prevents neurodegeneration, is provided. Administration to a patient is initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In another embodiment is a method of treating a disease or disorder in a patient in need thereof, comprising administering to the patient in need thereof a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof, wherein the disease or disorder is selected from the group consisting of migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating epilepsy/seizure disorder in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating neuromyelitis optica (NMO) in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating Tourette syndrome in a patient in need thereof, comprising administering to the patient a therapeutically effective amount of a compound of Formula (I), (Ia), (Ib), (Ic), (Id), (II), (Ia), (IIb), (IIc), (III), or (IV) described herein, or a pharmaceutically acceptable salt or solvate thereof. In another embodiment is a method of treating persistent motor tic disorder in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating persistent vocal tic disorder in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating abdominal pain associated with irritable bowel syndrome in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating pain associated with irritable bowel disease in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating pain associated with Crohn's disease in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In another embodiment is a method of treating cancer pain, pain caused by peripheral neuropathy, central pain, fibromyalgia, migraine, vasoocclussive painful crises in sickle cell disease, functional chest pain, rheumatoid arthritis, osteoarthritis, functional dyspepsia, or spasticity, pain, sleep disturbance, or bladder dysfunction associated with multiple sclerosis, in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating central pain in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating migraine in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating spasticity, pain, sleep disturbance, or bladder dysfunction associated with multiple sclerosis in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (Ib), (Ic), (Id), (II), (IIa), (IIb), (IIc), (III), or (IV) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (Ib), (Ic), (Id), (II), (IIa), (IIb), (IIc), (III), or (IV).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration includes subcutaneous injections, intravenous, or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($ClCH_2CH_2Cl$)
DCM dichloromethane ($CH_2Cl_2$)
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 1,1,1,3,3,3-Hexafluoropropan-2-yl 1-(5,6,7,8-tetrahydroimidazo[1,2-a]pyrazine-2-carbonyl)-1,8-diazaspiro[4.5]decane-8-carboxylate

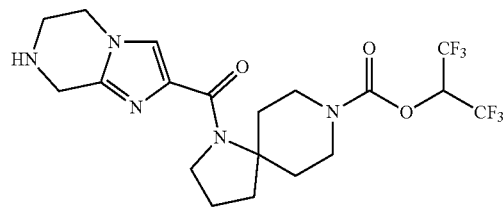 [SMILES: O=C(OC(C(F)(F)F)C(F)(F)F)N1CCC2(CCCN2C(=O)c2cn3c(n2)CNCC3)CC1]

Step 1: Synthesis of 1-(tert-butyl) 8-(1,1,1,3,3,3-hexafluoropropan-2-yl) 1,8-diazaspiro[4.5]decane-1,8-dicarboxylate

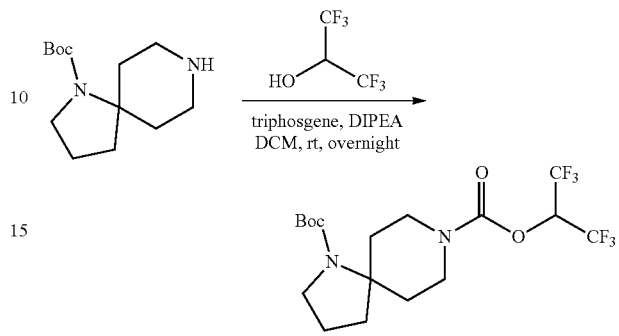

A flask was charged with 1,1,1,3,3,3-hexafluoropropan-2-ol (2.00 g, 11.9 mmol, 1.50 equiv), DCM (20 mL), and triphosgene (1.18 g, 3.97 mmol, 0.50 equiv). N,N-diisopropylethylamine (2.55 g, 19.7 mmol, 2.50 equiv) was added dropwise at 0° C., and the solution was stirred for 3 h at room temperature prior to the addition of tert-butyl 1,8-diazaspiro[4.5]decane-1-carboxylate (1.90 g, 7.91 mmol, 1.00 equiv). The reaction mixture was stirred overnight at room temperature and quenched with water (20 mL). The mixture was extracted with DCM (3×20 mL) and the organic layers were combined, washed with water (3×10 mL), dried over anhydrous sodium sulfate, filtered and concentrated under reduced pressure. The residue was chromatographed on a silica gel column to provide 1.58 g (46% yield) of 1-(tert-butyl) 8-(1,1,1,3,3,3-hexafluoropropan-2-yl) 1,8-diazaspiro[4.5]decane-1,8-dicarboxylate. LCMS (ESI, m/z): 435 [M+H]$^+$.

Step 2: Synthesis of 1,1,1,3,3,3-hexafluoropropan-2-yl 1,8-diazaspiro[4.5]decane-8-carboxylate

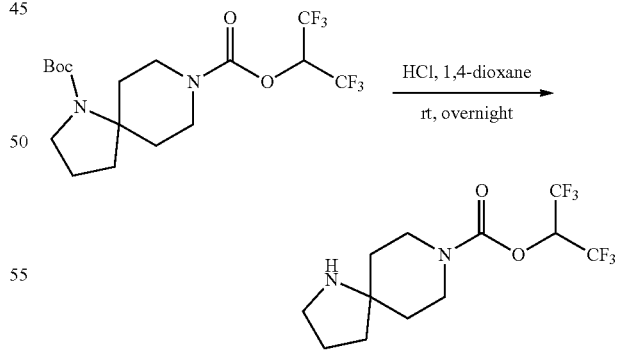

A flask was charged with 1-(tert-butyl) 8-(1,1,1,3,3,3-hexafluoropropan-2-yl) 1,8-diazaspiro[4.5]decane-1,8-dicarboxylate (1.58 g, 3.64 mmol, 1.00 equiv), 1,4-dioxane (15 mL), and concentrated hydrochloric acid (5 mL). The resulting solution was stirred overnight at room temperature and concentrated under reduced pressure to provide 1.15 g (crude) of 1,1,1,3,3,3-hexafluoropropan-2-yl 1,8-diazaspiro[4.5]decane-8-carboxylate. LCMS (ESI, m/z): 335 [M+H]$^+$.

Step 3: Synthesis of 1,1,1,3,3,3-hexafluoropropan-2-yl 1-(7-(tert-butoxycarbonyl)-5,6,7,8-tetrahydroimidazo[1,2-a]pyrazine-2-carbonyl)-1,8-diazaspiro[4.5]decane-8-carboxylate

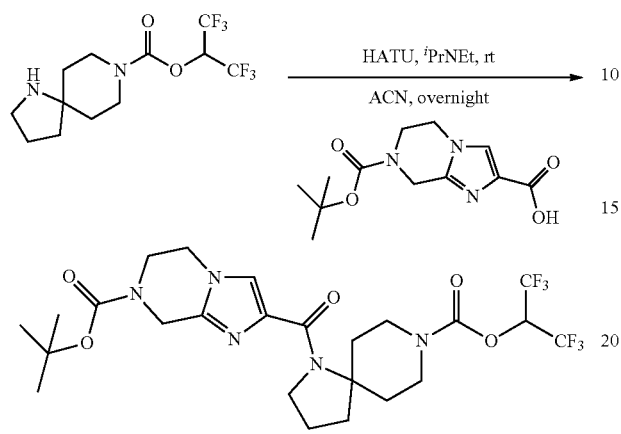

A 40-mL glass scintillation vial was charged with 1,1,1,3,3,3-hexafluoropropan-2-yl 1,8-diazaspiro[4.5]decane-8-carboxylate (500 mg, 1.50 mmol, 1.00 equiv) and ACN (7.5 mL). To the resulting solution was then added 7-(tert-butoxycarbonyl)-5,6,7,8-tetrahydroimidazo[1,2-a]pyrazine-2-carboxylic acid (440 mg, 1.65 mmol, 1.10 equiv), HATU (597 mg, 1.57 mmol, 1.05 equiv), and N,N-diisopropylethylamine (483 mg, 3.74 mmol, 2.50 equiv). The vial was closed with a screw-top septum cap and stirred at ambient temperature overnight. The reaction mixture was concentrated in vacuo to half of the original volume, then purified using silica gel chromatography, providing 1,1,1,3,3,3-hexafluoropropan-2-yl 1-(7-(tert-butoxycarbonyl)-5,6,7,8-tetrahydroimidazo[1,2-a]pyrazine-2-carbonyl)-1,8-diazaspiro[4.5]decane-8-carboxylate as a white solid (804 mg, 92%). LCMS (ESI, m/z): 584 [M+H]+.

Step 4: Synthesis of 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate

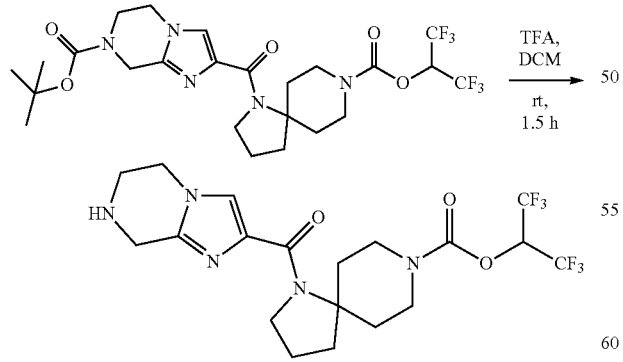

An 8-mL scintillation vial was charged with the 1,1,1,3,3,3-hexafluoropropan-2-yl 1-(7-(tert-butoxycarbonyl)-5,6,7,8-tetrahydroimidazo[1,2-a]pyrazine-2-carbonyl)-1,8-diazaspiro[4.5]decane-8-carboxylate (400 mg, 0.6900 mmol, 1.00 equiv), DCM (2.25 mL) and TFA (0.75 mL, 9.79 mmol, 14.29 equiv). The solution was stirred at room temperature for 1.5 h, diluted with DCM (30 mL), and quenched with 1 N NaOH (15 mL). The organics were separated, washed with sodium hydroxide (2×15 mL 1 N NaOH), dried over Na$_2$SO$_4$, and filtered through celite. The filtrate was concentrated to provide 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate as a white solid (280 mg, 84%). $^1$H NMR (400 MHz, Chloroform-d) δ 7.38 (s, 1H), 5.81-5.69 (m, 1H), 4.23-4.08 (m, 4H), 4.06-3.98 (m, 4H), 3.31-3.24 (m, 2H), 3.21-2.92 (m, 4H), 2.04 (s, 1H), 2.05-1.82 (m, 4H), 1.49-1.39 (m, 2H). LCMS (ESI, m/z): 484 [M+H]+.

Example 2: 1,1,1,3,3,3-Hexafluoropropan-2-yl 1-(7-cyclopropyl-5,6,7,8-tetrahydroimidazo[1,2-a]pyrazine-2-carbonyl)-1,8-diazaspiro[4.5]decane-8-carboxylate

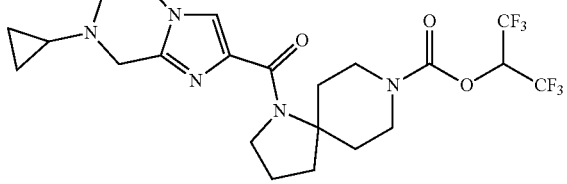

Step 1: Synthesis of 1,1,1,3,3,3-hexafluoropropan-2-yl 1-(7-cyclopropyl-5,6,7,8-tetrahydroimidazo[1,2-a]pyrazine-2-carbonyl)-1,8-diazaspiro[4.5]decane-8-carboxylate

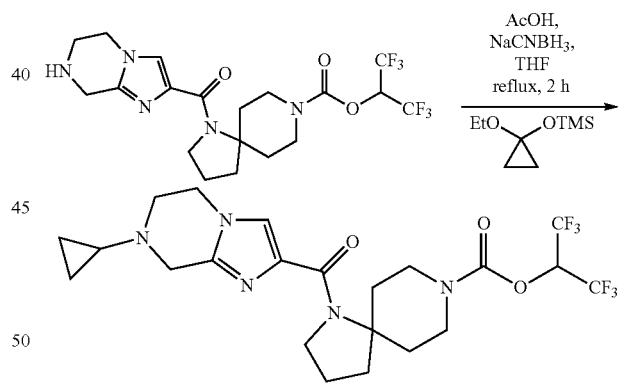

To a solution of 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate (Example 1, 75.0 mg, 0.16 mmol, 1.00 equiv) in THF (0.60 mL) was added AcOH (88.1 mg, 1.55 mmol, 10.00 equiv), (1-ethoxycyclopropoxy)trimethylsilane (94.7 mg, 0.54 mmol, 3.50 equiv), and sodium cyanoborohydride (29.2 mg, 0.47 mmol, 3.00 equiv) in sequence. The reaction was stirred at reflux for 2 h and allowed to cool to room temperature. After diluting with 1 N NaOH (5 mL) the resulting solution was extracted with DCM (2×10 mL), dried over Na$_2$SO$_4$, filtered and concentrated under reduced pressure. The residue was purified by reverse phase HPLC and lyophilized to provide 1,1,1,3,3,3-hexafluoropropan-2-yl 1-(7-cyclopropyl-5,6,7,8-tetrahydroimidazo[1,2-a]pyrazine-2-carbonyl)-1,8-diazaspiro[4.5]

decane-8-carboxylate (33.6 mg, 41%). ¹H NMR (400 MHz, Chloroform-d) δ 7.37 (s, 1H), 5.80-5.70 (m, 1H), 4.23-4.10 (m, 2H), 4.09-4.03 (m, 2H), 4.01-3.95 (m, 2H), 3.84 (s, 2H), 3.23-3.11 (m, 2H), 3.09-2.93 (m, 4H), 2.05-1.80 (m, 5H), 1.50-1.39 (m, 2H), 0.62-0.47 (m, 4H). LCMS (ESI, m/z): 524 [M+H]⁺.

Example 3: 1,1,1,3,3,3-Hexafluoropropan-2-yl 1-(2-cyclopropylimidazo[1,2-b]pyridazine-3-carbonyl)-1,8-diazaspiro[4.5]decane-8-carboxylate

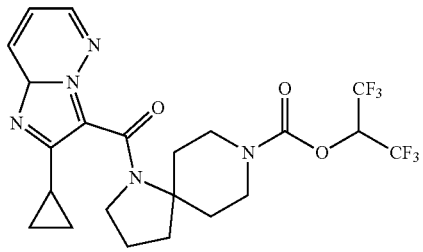

Step 1: Synthesis of methyl 2-cyclopropylimidazo[1,2-b]pyridazine-3-carboxylate

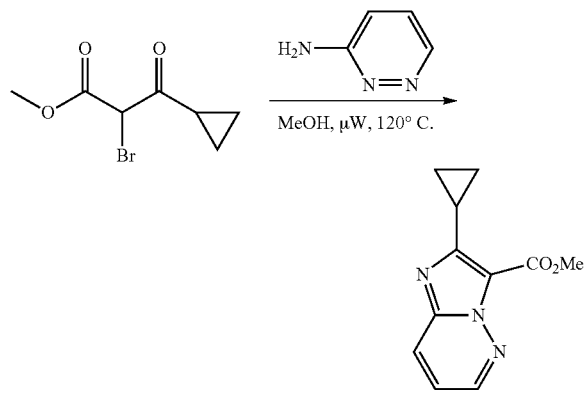

To a 20 mL microwave vial was added methyl 2-bromo-3-cyclopropyl-3-oxopropanoate (1.29 g, 5.26 mmol, 1.00 equiv), pyridazin-3-amine (500.0 mg, 5.26 mmol, 1.00 equiv), and methanol (10 mL). The vial was sealed with a septum cap and microwave heated to 120° C. for 20 min. After cooling, the volatiles were removed on a rotary evaporator and purified via silica gel chromatography to provide methyl 2-cyclopropylimidazo[1,2-b]pyridazine-3-carboxylate (187 mg, 16%). LCMS (ESI, m/z): 218 [M+H]⁺.

Step 2: Synthesis of 2-cyclopropylimidazo[1,2-b]pyridazine-3-carboxylic acid

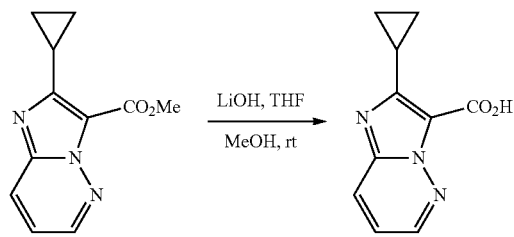 [SMILES: COC(=O)c1c(C2CC2)nc2cccnn12 ; O=C(O)c1c(C2CC2)nc2cccnn12]

To an 8 mL scintillation vial was added methyl 2-cyclopropylimidazo[1,2-b]pyridazine-3-carboxylate (187.0 mg, 0.86 mmol, 1.00 equiv), THF (3.5 mL) and methanol (2.0 mL), followed by LiOH (2.0 mL, 10 mmol, 11.63 equiv). The reaction mixture was stirred at room temperature for 18 h, then acidified to pH 4-5 using 2N HCl. The mixture was diluted with DCM (20 mL), extracted with DCM (3×20 mL), dried over Na₂SO₄, filtered through celite and concentrated to provide the 2-cyclopropylimidazo[1,2-b]pyridazine-3-carboxylic acid (55 mg, 31%). LCMS (ESI, m/z): 203 [M+H]⁺.

Step 3: Synthesis of 1,1,1,3,3,3-hexafluoropropan-2-yl 1-(2-cyclopropylimidazo[1,2-b]pyridazine-3-carbonyl)-1,8-diazaspiro[4.5]decane-8-carboxylate

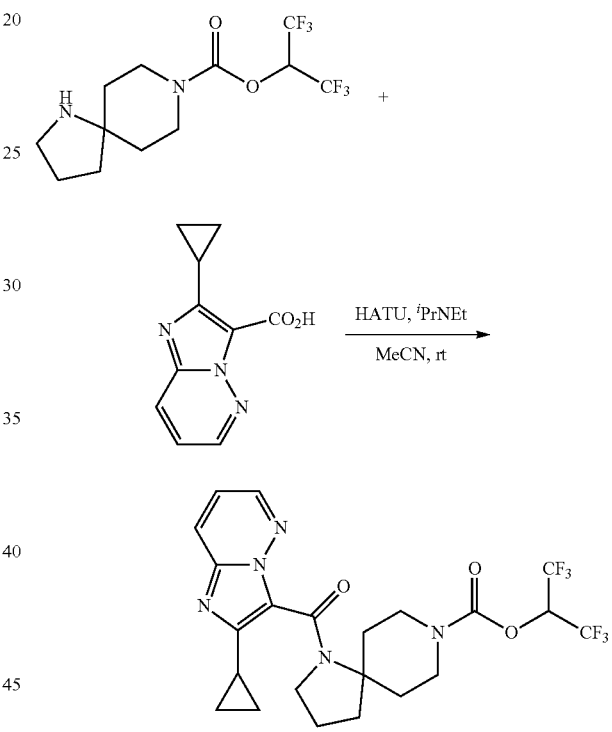

A 4 mL scintillation vial was charged with 1,1,1,3,3,3-hexafluoropropan-2-yl 1,8-diazaspiro[4.5]decane-8-carboxylate (78 .mg, 0.23 mmol, 1.00 equiv) and DMF (1 mL), followed by HATU (111 mg, 0.29 mmol, 1.25 equiv), 2-cyclopropylimidazo[1,2-b]pyridazine-3-carboxylic acid (55 mg, 0.27 mmol, 1.16 equiv), and N,N-diisopropylethylamine (75 mg, 0.58 mmol, 2.50 equiv). The reaction mixture stirred at room temperature for 5 h before diluting with DMF (2 mL). The crude mixture was purified by reverse phase HPLC and lyophilized to afford 1,1,1,3,3,3-hexafluoropropan-2-yl 1-(2-cyclopropylimidazo[1,2-b]pyridazine-3-carbonyl)-1,8-diazaspiro[4.5]decane-8-carboxylate (70 mg, 57%). ¹H NMR (400 MHz, Chloroform-d) δ 8.35-8.29 (m, 1H), 7.91-7.82 (m, 1H), 7.09-7.00 (m, 1H), 5.83-5.70 (m, 1H), 4.34-4.16 (m, 2H), 3.60-3.44 (m, 2H), 3.33-3.18 (m, 2H), 3.16-2.94 (m, 2H), 2.21-2.02 (m, 3H), 1.94-1.82 (m, 2H), 1.70-1.50 (m, 2H), 1.25-0.97 (m, 4H). LCMS (ESI, m/z): 520 [M+H]⁺.

Example 4: 1,1,1,3,3,3-hexafluoropropan-2-yl 1-((2-(piperazin-1-yl)thiazol-5-yl)methyl)-1,8-diazaspiro[4.5]decane-8-carboxylate

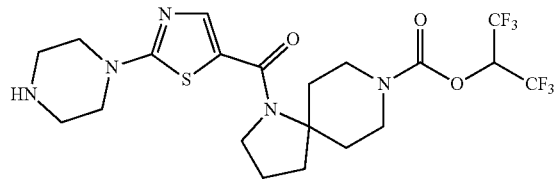 [SMILES: O=C(OC(C(F)(F)F)C(F)(F)F)N1CCC2(CCCN2C(=O)c2cnc(N3CCNCC3)s2)CC1]

Step 1: Synthesis of tert-butyl 4-(5-formylthiazole-2-yl)piperazine-1-carboxylate

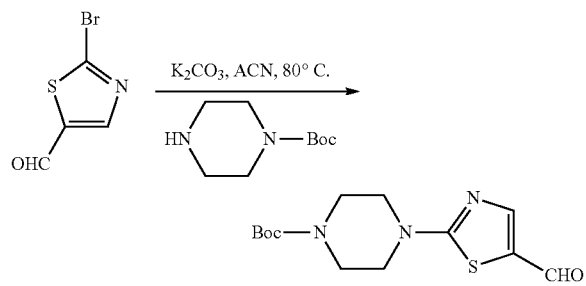

A flask was charged with 2-bromo-5-formylthiazole (150 mg, 0.78 mmol, 1.00 equiv), ACN (40 ml), K$_2$CO$_3$ (269 mg, 1.95 mmol, 2.50 equiv), and tert-butyl piperazine-1-carboxylate (174 mg, 0.94 mmol, 1.20 equiv). The reaction mixture was stirred at 80° C. for 16 h. The resulting solution was cooled to room temperature and ACN was removed in vacuo. The crude mixture was dissolved in EtOAc (20 mL) and diluted with brine (10 mL satd. aq. NaCl). The solution was extracted with EtOAc (3×20 mL), dried over Na$_2$SO$_4$, filtered through celite and concentrated to tert-butyl 4-(5-formylthiazole-2-yl)piperazine-1-carboxylate (83 mg, 36% crude) $^1$H NMR (400 MHz, Chloroform-d) δ 9.71 (s, 1H), 7.86 (s, 1H), 3.82-3.42 (m, 8H), 1.48 (s, 9H).

Step 2: Synthesis of 1,1,1,3,3,3-hexafluoropropan-2-yl 1-((2-(piperazin-1-yl)thiazol-5-yl)methyl)-1,8-diazaspiro[4.5]decane-8-carboxylate

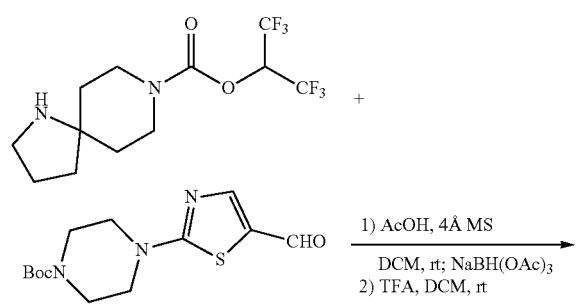

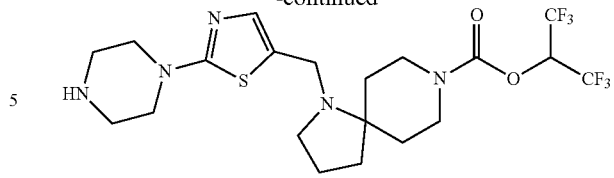

A 4 mL scintillation vial was charged with 1,1,1,3,3,3-hexafluoropropan-2-yl 1,8-diazaspiro[4.5]decane-8-carboxylate (75.0 mg, 0.22 mmol), tert-butyl 4-(5-formylthiazole-2-yl)piperazine-1-carboxylate (83.4 mg, 0.28 mmol, 1.27 equiv), DCM (1 mL), and 4 Å molecular sieves. Acetic acid (19.2 uL, 0.34 mmol, 1.55 equiv) was added and the solution was stirred at room temperature for 1.5 h, prior to addition of NaBH(OAc)$_3$ (59.4 mg, 0.28 mmol, 1.27 equiv). The reaction mixture was stirred for 16 h before diluting with additional DCM (20 mL) and satd. aq. NaHCO$_3$ (10 mL). The organics were extracted (2×10 mL DCM), dried over Na$_2$SO$_4$, filtered and concentrated under reduced pressure. The crude product was purified by reverse phase HPLC to provide a pale-yellow solid. This material was dissolved in DCM (1 mL) to which TFA (0.20 mL, 2.61 mmol, 11.64 equiv) was added, and the reaction mixture was stirred at room temperature for 4 h. The reaction mixture was purified by reverse phase HPLC to afford 1,1,1,3,3,3-hexafluoropropan-2-yl 1-((2-(piperazin-1-yl)thiazol-5-yl)methyl)-1,8-diazaspiro[4.5]decane-8-carboxylate (9.1 mg, 8%). $^1$H NMR (400 MHz, Chloroform-d) δ 6.94 (s, 1H), 5.82-5.68 (m, 1H), 4.26-4.10 (m, 2H), 3.63 (s, 2H), 3.48-3.36 (m, 4H), 3.07-2.87 (m, 5H), 2.80-2.70 (m, 2H), 2.09-1.88 (m, 2H), 1.86-1.58 (m, 6H), 1.52-1.35 (m, 2H). LCMS (ESI, m/z): 516 [M+H]$^+$.

Example 5: 1,1,1,3,3,3-Hexafluoropropan-2-yl 1-(4-(pyrrolidin-1-yl)pyrimidine-5-carbonyl)-1,8-diazaspiro[4.5]decane-8-carboxylate

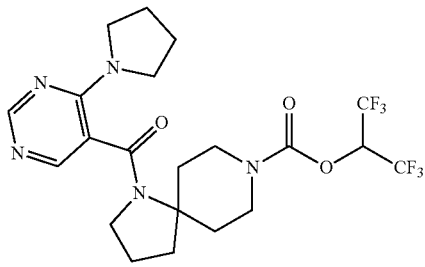 [SMILES: O=C(OC(C(F)(F)F)C(F)(F)F)N1CCC2(CCCN2C(=O)c2cncnc2N2CCCC2)CC1]

Step 1: Synthesis of methyl 2-chloro-4-(pyrrolidin-1-yl)pyrimidine-5-carboxylate

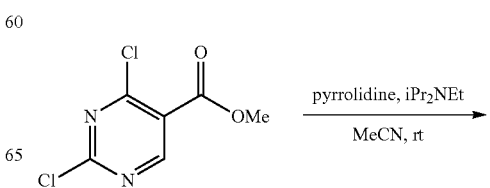

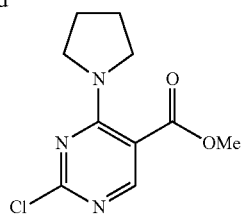

To a 16 mL vial was added methyl 2,4-dichloropyrimidine-5-carboxylate (2.00 g, 9.66 mmol, 1.00 equiv), ACN (30 mL), N,N-diisopropylethylamine (2.50 g, 19.32 mmol, 3.37 equiv) and pyrrolidine (0.69 g, 9.66 mmol, 1.00 equiv). The solution was stirred for 4.5 h at room temperature and concentrated under reduced pressure. The residue was purified by silica gel chromatography to provide methyl 2-chloro-4-(pyrrolidin-1-yl)pyrimidine-5-carboxylate (1.60 g, 69%). LCMS (ESI, m/z): 242 [M+H]$^+$.

Step 2: Synthesis of 2-chloro-4-(pyrrolidin-1-yl)pyrimidine-5-carboxylic acid

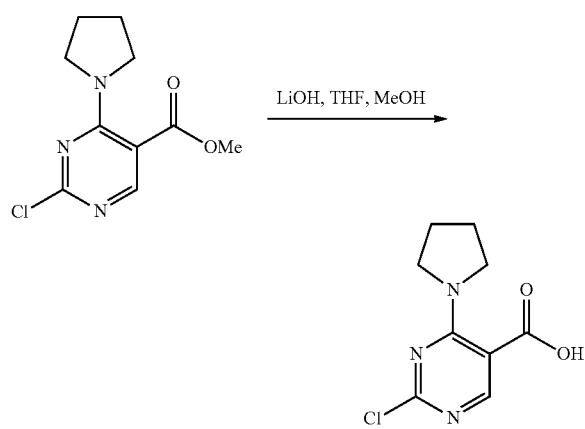

To a 40 mL scintillation vial was added methyl 2-chloro-4-(pyrrolidin-1-yl)pyrimidine-5-carboxylate (1.00 g, 4.14 mmol, 1.00 equiv), THF (20.0 mL), and MeOH (4.0 mL), followed by LiOH (5 N, 4.0 mL, 20.00 mmol, 4.83 equiv). The reaction mixture was stirred at room temperature for 15 min and acidified to pH 4-5 using 2 N HCl. The resulting solution was extracted with DCM (3×30 mL). The combined organics were dried over Na$_2$SO$_4$, filtered through celite, and concentrated under reduced pressure to provide 2-chloro-4-(pyrrolidin-1-yl)pyrimidine-5-carboxylic acid (630 mg, crude). LCMS (ESI, m/z): 228 [M+H]$^+$.

Step 3: Synthesis of 1,1,1,3,3,3-hexafluoropropan-2-yl 1-(2-chloro-4-(pyrrolidin-1-yl)pyrimidine-5-carbonyl)-1,8-diazaspiro[4.5]decane-8-carboxylate

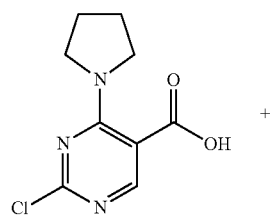

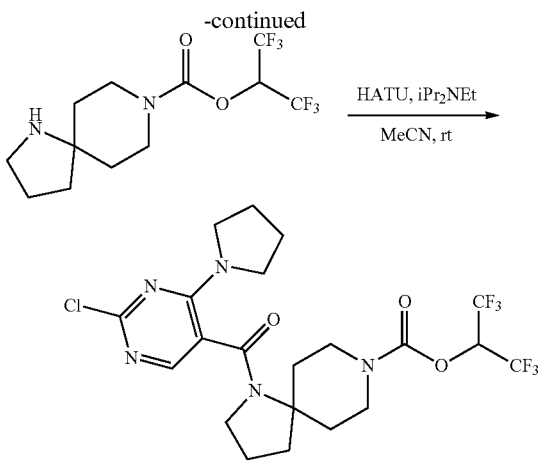

To an 8 mL scintillation vial was added 1,1,1,3,3,3-hexafluoropropan-2-yl 1,8-diazaspiro[4.5]decane-8-carboxylate (295 mg, 0.88 mmol, 1.00 equiv), 2-chloro-4-(pyrrolidin-1-yl)pyrimidine-5-carboxylic acid (221 mg, 0.97 mmol, 1.10 equiv), HATU (352 mg, 0.93 mmol, 1.05 equiv), and ACN (3.5 mL). The solution was stirred briefly prior to cooling to 0° C. N,N-diisopropylethylamine (285.2 mg, 2.21 mmol, 2.50 equiv) was added, and the reaction was stirred at 0-5° C. for 1 h, followed by 26.5 h at room temperature. The resulting solution was diluted with DCM (20 mL) and water (10 mL), extracted with DCM (3×20 mL), dried over Na$_2$SO$_4$, filtered and concentrated under reduced pressure. The residue was chromatographed on a silica gel column to provide 1,1,1,3,3,3-hexafluoropropan-2-yl 1-(2-chloro-4-(pyrrolidin-1-yl)pyrimidine-5-carbonyl)-1,8-diazaspiro[4.5]decane-8-carboxylate (348 mg, 73%). LCMS (ESI, m/z): 544 [M+H]$^+$.

Step 4: Synthesis of 1,1,1,3,3,3-hexafluoropropan-2-yl 1-(4-(pyrrolidin-1-yl)pyrimidine-5-carbonyl)-1,8-diazaspiro[4.5]decane-8-carboxylate

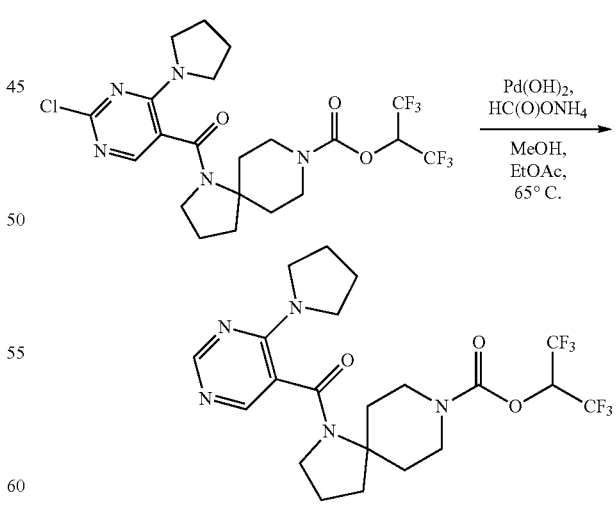

A 4 mL scintillation was charged with [2,2,2-trifluoro-1-(trifluoromethyl)ethyl] 1-(2-chloro-4-pyrrolidin-1-yl-pyrimidine-5-carbonyl)-1,8-diazaspiro[4.5]decane-8-carboxylate (75.0 mg, 0.14 mmol, 1.00 equiv), palladium hydroxide (36.0 mg, 0.05 mmol, 0.35 equiv), ammonium formate (70 mg, 1.11 mmol, 7.93 equiv), methanol (0.50 mL) and ethyl acetate (1.00 mL). The vial was closed with a septum cap affixed with a needle outlet to atmosphere, then the vial was placed in a heating block at 65° C. for 2 h. The reaction mixture was then cooled to room temperature and filtered through celite. The filtrate was concentrated, purified by preparative REVERSE PHASE HPLC, and lyophilized to provide the title compound (27.8 mg, 40% yield). $^1$H NMR (400 MHz, Chloroform-d) δ 8.55-8.52 (m, 1H), 6.55-6.48 (m, 1H), 5.81-5.69 (m, 1H), 4.26-4.13 (m, 2H), 3.71-3.56 (m, 4H), 3.42-3.28 (m, 2H), 3.18-2.90 (m, 4H), 2.11-2.92 (m, 6H), 1.89-1.78 (m, 2H), 1.57-1.45 (m, 2H). LCMS (ESI, m/z): 510 [M+H]$^+$.

Example 6: 1,1,1,3,3,3-Hexafluoropropan-2-yl 2-((1-isopropyl-3-phenyl-1H-pyrazol-4-yl)methyl)-2,8-diazaspiro[4.5]decane-8-carboxylate

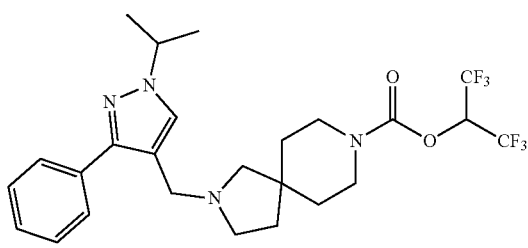 [SMILES: CC(C)n1cc(CN2CCC3(CCN(C(=O)OC(C(F)(F)F)C(F)(F)F)CC3)C2)c(-c2ccccc2)n1]

Step 1: Synthesis of (E)-1-isopropyl-2-(1-phenylethylidene)hydrazine

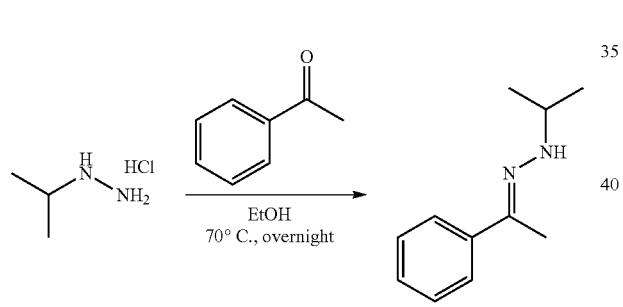

A 250-mL round-bottom flask was charged with 1-phenylethan-1-one (5.94 g, 49.5 mmol, 1.00 equiv), propan-2-ylhydrazine hydrochloride (10.9 g, 99.0 mmol, 2.00 equiv), and ethanol (80 mL). The resulting solution was stirred overnight at 70° C. and concentrated under reduced pressure to provide 16.0 g (crude) of (E)-1-isopropyl-2-(1-phenylethylidene)hydrazine. LCMS (ESI, m/z): 177 [M+H]$^+$.

Step 2: Synthesis of 1-isopropyl-3-phenyl-1H-pyrazole-4-carbaldehyde

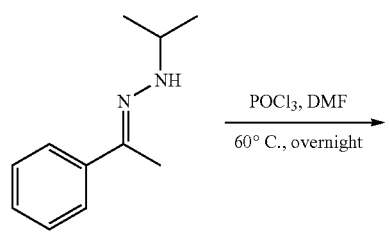

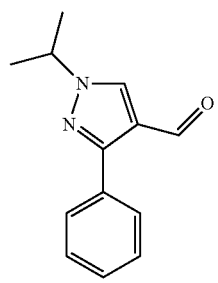

A 100-mL round-bottom flask was charged with (E)-1-(1-phenylethylidene)-2-(propan-2-yl)hydrazine (1.00 g, 5.68 mmol, 1.00 equiv), and N,N-dimethylformamide (20 mL). Phosphoryl trichloride (6.91 g, 45.4 mmol, 8.00 equiv) was added at 0° C. The reaction mixture was stirred overnight at 60° C. and quenched with water (150 mL). The resulting solution was extracted with ethyl acetate (2×200 mL) and the organic layers were combined, washed with brine (2×150 mL), dried over anhydrous sodium sulfate, filtered and concentrated under reduced pressure. The residue was chromatographed on a silica gel column to provide 370 mg (30% yield) of 1-isopropyl-3-phenyl-1H-pyrazole-4-carbaldehyde. LCMS (ESI, m/z): 215 [M+H]$^+$.

Step 3: Synthesis of tert-butyl 2-((1-isopropyl-3-phenyl-1H-pyrazol-4-yl)methyl)-2,8-diazaspiro[4.5]decane-8-carboxylate

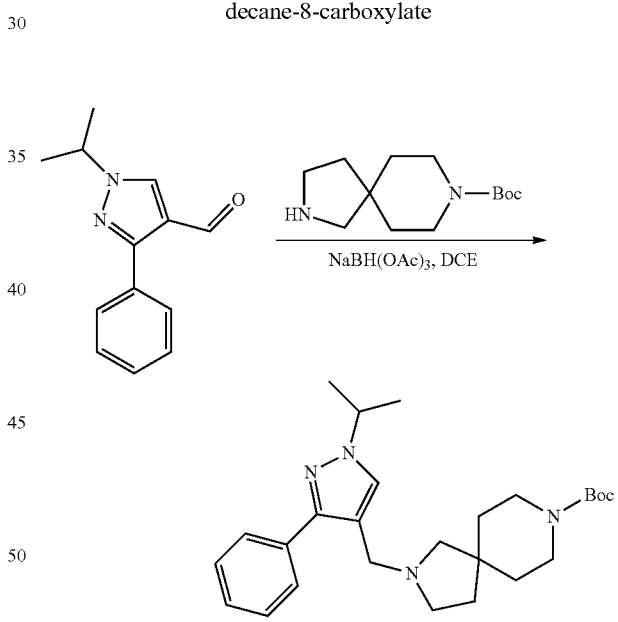

A 50-mL round-bottom flask was charged with 1-isopropyl-3-phenyl-1H-pyrazole-4-carbaldehyde (300 mg, 1.40 mmol, 1.00 equiv), 1,2-dichloroethane (10 mL), and tert-butyl 2,8-diazaspiro[4.5]decane-8-carboxylate (336 mg, 1.40 mmol, 1.00 equiv). The mixture was stirred for 1 h at room temperature prior to addition of sodium triacetoxyborohydride (890 mg, 4.20 mmol, 3.00 equiv). The reaction mixture was stirred overnight at room temperature and quenched with water (30 mL). The resulting solution was extracted with dichloromethane (2×50 mL) and the organic layers were combined, washed with brine (2×30 mL), dried over anhydrous sodium sulfate, filtered and concentrated under reduced pressure. The residue was chromatographed on a silica gel column to provide 760 mg (93% yield) of tert-butyl 2-((1-isopropyl-3-phenyl-1H-pyrazol-4-yl)methyl)-2,8-diazaspiro[4.5]decane-8-carboxylate. LCMS (ESI, m/z): 439 [M+H]+.

Step 4: Synthesis of 2-((1-isopropyl-3-phenyl-1H-pyrazol-4-yl)methyl)-2,8-diazaspiro[4.5]decane

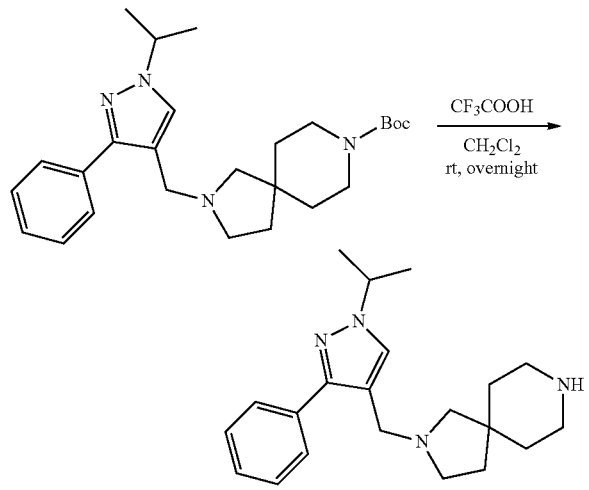

A 100-mL round-bottom flask was charged with tert-butyl 2-((1-isopropyl-3-phenyl-1H-pyrazol-4-yl)methyl)-2,8-diazaspiro[4.5]decane-8-carboxylate (760 mg, 1.74 mmol, 1.00 equiv), dichloromethane (15 mL), and trifluoroacetic acid (3 mL). The resulting solution was stirred overnight at room temperature and concentrated under reduced pressure to provide 900 mg (crude) of 2-((1-isopropyl-3-phenyl-1H-pyrazol-4-yl)methyl)-2,8-diazaspiro[4.5]decane. LCMS (ESI, m/z): 339 [M+H]+.

Step 5: Synthesis of 1,1,1,3,3,3-hexafluoropropan-2-yl 2-((1-isopropyl-3-phenyl-1H-pyrazol-4-yl)methyl)-2,8-diazaspiro[4.5]decane-8-carboxylate

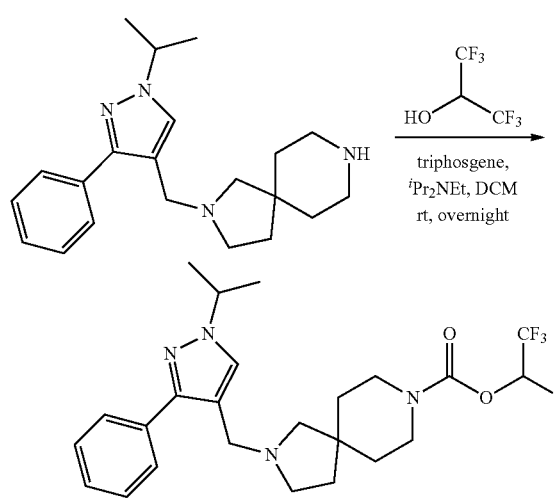

A 50-mL round-bottom flask was charged with triphosgene (181 mg, 0.610 mmol, 0.70 equiv), dichloromethane (15 mL), and 1,1,1,3,3,3-hexafluoropropan-2-ol (292 mg, 1.74 mmol, 2.00 equiv). N,N-diisopropylethylamine (337 mg, 2.61 mmol, 3.00 equiv) was added at 0° C. The mixture was stirred for 2 h at room temperature prior to addition of 2-((1-isopropyl-3-phenyl-1H-pyrazol-4-yl)methyl)-2,8-diazaspiro[4.5]decane (294 mg, 0.870 mmol, 1.00 equiv). The reaction mixture was stirred overnight at room temperature and quenched with water (30 mL). The resulting solution was extracted with dichloromethane (2×50 mL) and the organic layers were combined, washed with brine (2×30 mL), dried over anhydrous sodium sulfate, filtered and concentrated under reduced pressure. The crude product (300 mg) was purified by reverse phase HPLC to yield 71.4 mg (15% yield) of 1,1,1,3,3,3-hexafluoropropan-2-yl 2-((1-isopropyl-3-phenyl-1H-pyrazol-4-yl)methyl)-2,8-diazaspiro[4.5]decane-8-carboxylate. $^1$H NMR (300 MHz, Chloroform-d) δ 7.80 (d, J=7.2 Hz, 2H), 7.39-7.44 (m, 3H), 7.28-7.32 (m, 1H), 5.70-5.79 (m, 1H), 4.47-4.56 (m, 1H), 3.38-3.55 (m, 6H), 2.62 (br, 2H), 2.41 (s, 2H), 1.66 (t, J=7.0 Hz, 2H), 1.54-1.61 (m, 10H). LCMS (ESI, m/z): 533 [M+H]+.

Example 7: 1,1,1,3,3,3-Hexafluoropropan-2-yl 2-((3-ethyl-1-(tetrahydro-2H-pyran-4-yl)-1H-pyrazol-5-yl)methyl)-2,8-diazaspiro[4.5]decane-8-carboxylate

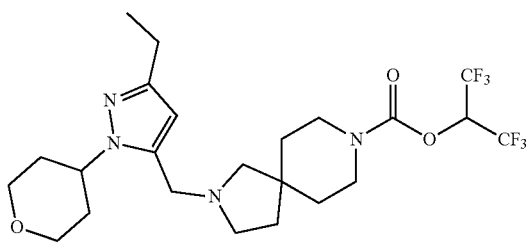 [SMILES: CCc1cc(CN2CCC3(CCN(C(=O)OC(C(F)(F)F)C(F)(F)F)CC3)C2)n(C2CCOCC2)n1]

Step 1: Synthesis of ethyl (E)-2-(methoxyimino)-4-oxohexanoate

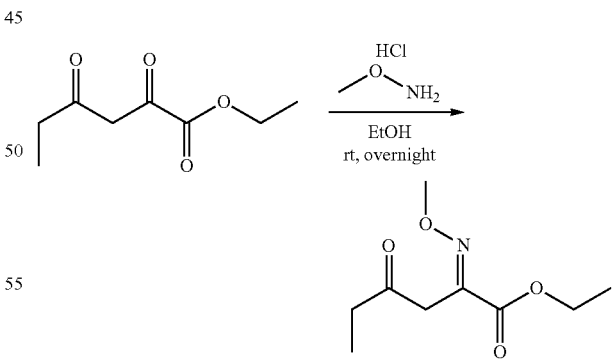

A 100-mL round-bottom flask was charged with ethyl 2,4-dioxohexanoate (3.00 g, 17.4 mmol, 1.00 equiv) in ethanol (30 mL), and O-methylhydroxylamine hydrochloride (1.59 g, 19.0 mmol, 1.10 equiv) under nitrogen. The resulting solution was stirred overnight at room temperature and concentrated under reduced pressure to yield 3.40 g (97% crude yield) of ethyl (E)-2-(methoxyimino)-4-oxohexanoate. LCMS (ESI, m/z): 202 [M+H]+.

Step 2: Synthesis of ethyl 3-ethyl-1-(tetrahydro-2H-pyran-4-yl)-1H-pyrazole-5-carboxylate

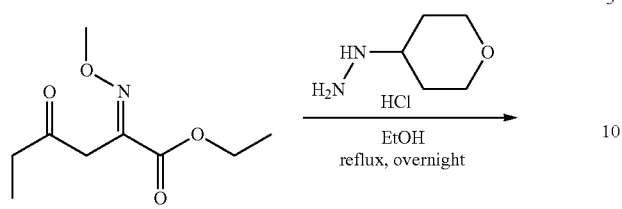

A 100-mL round-bottom flask was charged with ethyl (E)-2-(methoxyimino)-4-oxohexanoate (3.40 g, 16.9 mmol, 1.00 equiv) in ethanol (40 mL), and oxan-4-ylhydrazine hydrochloride (3.10 g, 20.3 mmol, 1.20 equiv) under nitrogen. The resulting solution was heated to reflux overnight and concentrated under reduced pressure. The residue was chromatographed on a silica gel column to yield 4.00 g (94% yield) of ethyl 3-ethyl-1-(tetrahydro-2H-pyran-4-yl)-1H-pyrazole-5-carboxylate. LCMS (ESI, m/z): 253 [M+H]$^+$.

Step 3: Synthesis of (3-ethyl-1-(tetrahydro-2H-pyran-4-yl)-1H-pyrazol-5-yl)methanol

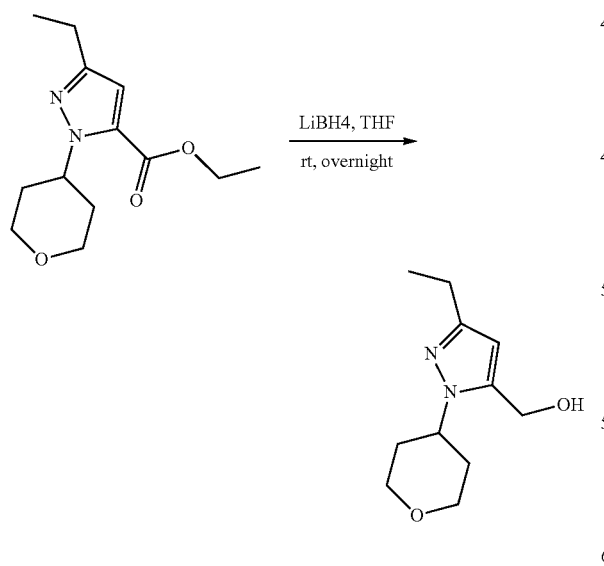

A 100-mL round-bottom flask was charged with ethyl 3-ethyl-1-(tetrahydro-2H-pyran-4-yl)-1H-pyrazole-5-carboxylate (4.00 g, 15.8 mmol, 1.00 equiv) in tetrahydrofuran (40 mL), and lithiumborohydride (1.70 g, 77.3 mmol, 5.00 equiv) under nitrogen. The reaction mixture was stirred overnight at room temperature and quenched with water (30 mL). The resulting solution was extracted with ethyl acetate (3×30 mL) and the organic layers were combined, washed with brine (2×30 mL), dried over anhydrous sodium sulfate, filtered and concentrated under reduced pressure to provide 3.00 g (90% yield) of (3-ethyl-1-(tetrahydro-2H-pyran-4-yl)-1H-pyrazol-5-yl)methanol. LCMS (ESI, m/z): 211 [M+H]$^+$.

Step 4: Synthesis of 3-ethyl-1-(tetrahydro-2H-pyran-4-yl)-1H-pyrazole-5-carbaldehyde

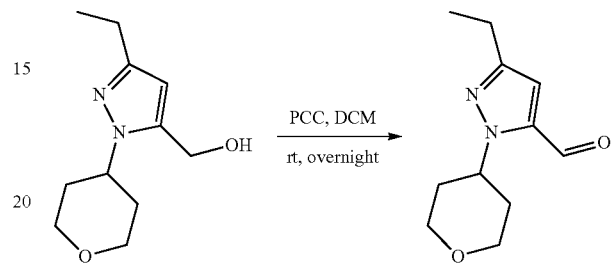

A 100-mL round-bottom flask was charged with (3-ethyl-1-(tetrahydro-2H-pyran-4-yl)-1H-pyrazol-5-yl)methanol (3.00 g, 14.3 mmol, 1.00 equiv) in dichloromethane (30 mL), and pyridinium chlorochromate (6.20 g, 28.8 mmol, 2.00 equiv). The reaction mixture was stirred overnight at room temperature and quenched with water (30 mL). The resulting solution was extracted with dichloromethane (3×30 mL) and the organic layers were combined, washed with brine (2×30 mL), dried over anhydrous sodium sulfate, filtered and concentrated under reduced pressure. The residue was chromatographed on a silica gel column to yield 3.00 g (100% yield) of 3-ethyl-1-(tetrahydro-2H-pyran-4-yl)-1H-pyrazole-5-carbaldehyde. LCMS (ESI, m/z): 209 [M+H]$^+$.

Step 5: Synthesis of tert-butyl 2-((3-ethyl-1-(tetrahydro-2H-pyran-4-yl)-1H-pyrazol-5-yl)methyl)-2,8-diazaspiro[4.5]decane-8-carboxylate

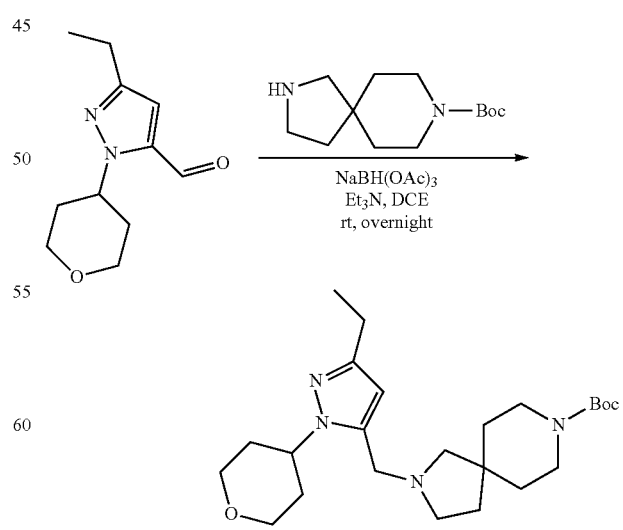

A 100-mL round-bottom flask was charged with 3-ethyl-1-(tetrahydro-2H-pyran-4-yl)-1H-pyrazole-5-carbaldehyde (208 mg, 1.00 mmol, 1.00 equiv) in DCE (10 mL), I-butyl 2,8-diazaspiro[4.5]decane-8-carboxylate (360 mg, 1.50 mmol, 1.50 equiv), and triethylamine (202 mg, 2.00 mmol, 2.00 equiv). The resulting solution was stirred for 30 min at room temperature prior to addition of sodium triacetoxyborohydride (636 mg, 3.00 mmol, 3.00 equiv). The reaction mixture was stirred overnight at room temperature and quenched with water (10 mL). The resulting solution was extracted with dichloromethane (3×10 mL) and the organic layers were combined, washed with brine (2×10 mL), dried over anhydrous sodium sulfate, filtered and concentrated under reduced pressure. The residue was chromatographed on a silica gel column to yield 400 mg (93% yield) of tert-butyl 2-((3-ethyl-1-(tetrahydro-2H-pyran-4-yl)-1H-pyrazol-5-yl)methyl)-2,8-diazaspiro[4.5]decane-8-carboxylate. LCMS (ESI, m/z): 433 [M+H]+.

Step 6: Synthesis of 2-((3-ethyl-1-(tetrahydro-2H-pyran-4-yl)-1H-pyrazol-5-yl)methyl)-2,8-diazaspiro[4.5]decane

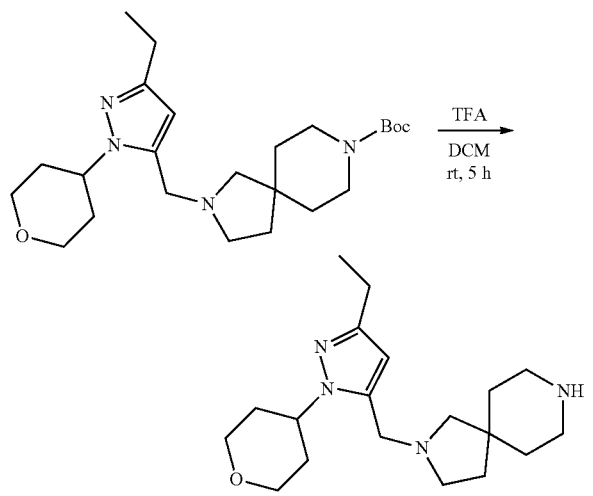

A 100-mL round-bottom flask was charged with tert-butyl 2-((3-ethyl-1-(tetrahydro-2H-pyran-4-yl)-1H-pyrazol-5-yl)methyl)-2,8-diazaspiro[4.5]decane-8-carboxylate (400 mg, 0.920 mmol, 1.00 equiv) in dichloromethane (10 mL), and trifluoroacetic acid (2.5 mL). The resulting solution was stirred for 5 h at room temperature and concentrated under reduced pressure to provide 300 mg (crude) of 2-((3-ethyl-1-(tetrahydro-2H-pyran-4-yl)-1H-pyrazol-5-yl)methyl)-2,8-diazaspiro[4.5]decane. LCMS (ESI, m/z): 333 [M+H]+.

Step 7: Synthesis of 1,1,1,3,3,3-hexafluoropropan-2-yl 2-((3-ethyl-1-(tetrahydro-2H-pyran-4-yl)-1H-pyrazol-5-yl)methyl)-2,8-diazaspiro[4.5]decane-8-carboxylate

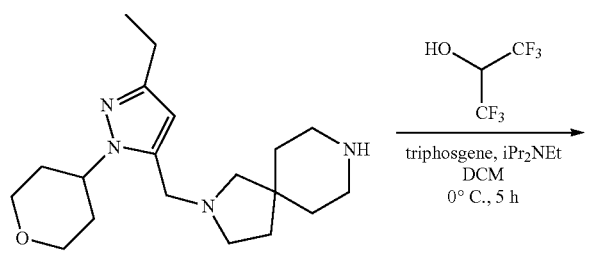

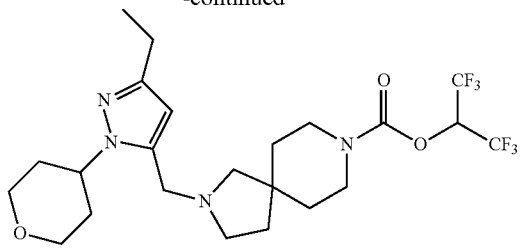

A 50-mL round-bottom flask was charged with triphosgene (94.0 mg, 0.320 mmol, 0.35 equiv) in dichloromethane (5 mL), and 1,1,1,3,3,3-hexafluoropropan-2-ol (228 mg, 1.36 mmol, 1.50 equiv) under nitrogen. N-ethyl-N-isopropylpropan-2-amine (350 mg, 2.71 mmol, 3.00 equiv) was added dropwise at 0° C., after which the mixture stirred for 2 h at 0° C. prior to dropwise addition of a solution of 2-[[3-ethyl-1-(oxan-4-yl)-1H-pyrazol-5-yl]methyl]-2,8-diazaspiro[4.5]decane (300 mg, 0.900 mmol, 1.00 equiv) in dichloromethane (5 mL). The reaction mixture was stirred for 3 h at 0° C. and quenched with water (20 mL). The mixture was extracted with dichloromethane (3×20 mL) and the organic layers were combined, washed with brine (2×20 mL), dried over anhydrous sodium sulfate, filtered and concentrated under reduced pressure. The crude product (360 mg) was purified by reverse phase HPLC to provide 123.5 mg (26% yield) of 1,1,1,3,3,3-hexafluoropropan-2-yl 2-((3-ethyl-1-(tetrahydro-2H-pyran-4-yl)-1H-pyrazol-5-yl)methyl)-2,8-diazaspiro[4.5]decane-8-carboxylate. 1H NMR (300 MHz, Chloroform-d) δ 5.89 (s, 1H), 5.70-5.79 (m, 1H), 4.34-4.45 (m, 1H), 4.08-4.13 (m, 2H), 3.37-3.60 (m, 8H), 2.55-2.66 (m, 4H), 2.26-2.39 (m, 4H), 1.75-1.79 (m, 2H), 1.52-1.69 (m, 6H), 1.19-1.24 (m, 3H). LCMS (ESI, m/z): 527 [M+H]+.

Example 8: 1,1,1,3,3,3-Hexafluoropropan-2-yl 1-((1-isopropyl-3-(3-(pyrrolidin-1-yl)phenyl)-1H-pyrazol-4-yl)methyl)-1,8-diazaspiro[4.5]decane-8-carboxylate

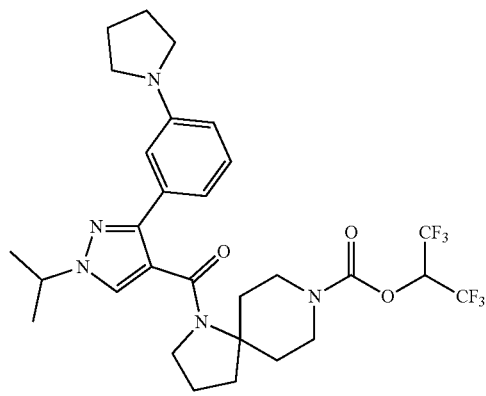 [SMILES: CC(C)n1cc(C(=O)N2CCCC23CCN(C(=O)OC(C(F)(F)F)C(F)(F)F)CC3)c(-c2cccc(N3CCCC3)c2)n1]

Step 1: Synthesis of (E)-1-(1-(3-bromophenyl)ethylidene)-2-isopropylhydrazine

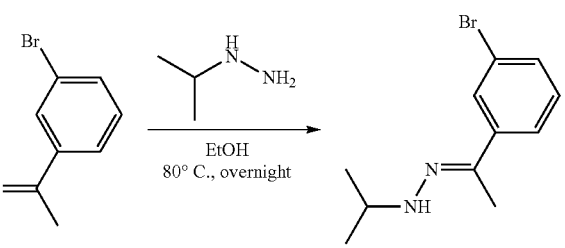

A 100-mL round-bottom flask was charged with 1-(3-bromophenyl)ethan-1-one (2.00 g, 10.1 mmol, 1.00 equiv), propan-2-ylhydrazine (0.747 g, 10.1 mmol, 1.00 equiv), and ethanol (20 mL) under nitrogen. The resulting solution was stirred overnight at 80° C. and concentrated under reduced pressure to provide 3.00 g (crude) of (E)-1-(1-(3-bromophenyl)ethylidene)-2-isopropylhydrazine. LCMS (ESI, m/z): 255 [M+H]⁺.

Step 2: Synthesis of 3-bromophenyl)-1-isopropyl-1H-pyrazole-4-carbaldehyde

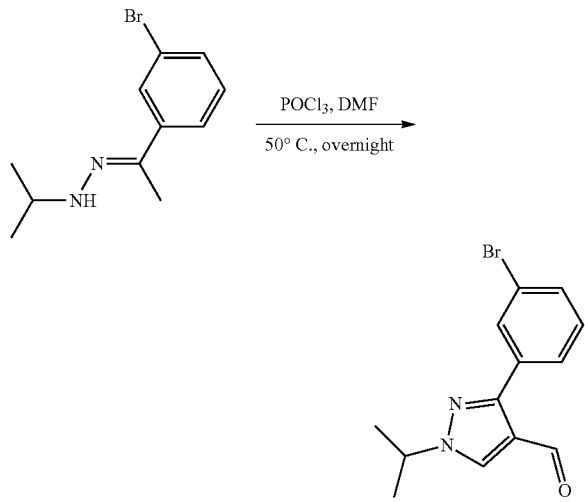

A 250-mL round-bottom flask was charged with N,N-dimethylformamide (100 mL) under nitrogen. Phosphoryl trichloride (18.0 g, 118 mmol, 10.0 equiv) was added dropwise at 0° C. The resulting solution was stirred for 1 h at room temperature prior to addition of (E)-1-(1-(3-bromophenyl)ethylidene)-2-isopropylhydrazine (3.00 g, 11.8 mmol, 1.00 equiv). The reaction mixture was stirred overnight at 50° C. and quenched with water (30 mL). The pH value of the solution was adjusted to 8 with saturated NaHCO₃. The mixture was extracted with ethyl acetate (3×50 mL) and the organic layers were combined, washed with brine (1×50 mL), dried over anhydrous sodium sulfate, filtered and concentrated under reduced pressure. The residue was chromatographed on a silica gel column to provide 2.13 g (62% yield) of 3-(3-bromophenyl)-1-isopropyl-1H-pyrazole-4-carbaldehyde. LCMS (ESI, m/z): 293 [M+H]⁺.

Step 3: Synthesis of tert-butyl 1-((3-(3-bromophenyl)-1-isopropyl-1H-pyrazol-4-yl)methyl)-1,8-diazaspiro[4.5]decane-8-carboxylate

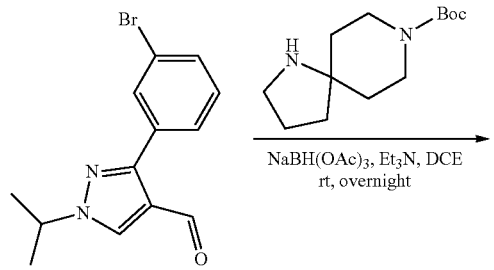

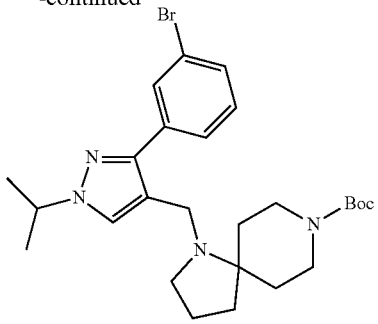

A 100-mL round-bottom flask was charged with tert-butyl 1,8-diazaspiro[4.5]decane-8-carboxylate (500 mg, 2.08 mmol, 1.00 equiv), 1,2-dichloroethane (10 mL), triethylamine (630 mg, 6.23 mmol, 3.00 equiv), and 3-(3-bromophenyl)-1-isopropyl-1H-pyrazole-4-carbaldehyde (609 mg, 2.08 mmol, 1.00 equiv). The mixture was stirred for 1 h at room temperature prior to addition of sodium triacetoxyborohydride (1.32 g, 6.24 mmol, 3.00 equiv). The reaction mixture was stirred overnight at room temperature and quenched with water (20 mL). The resulting solution was extracted with dichloromethane (3×30 mL) and the organic layers were combined, washed with brine (1×30 mL), dried over anhydrous sodium sulfate, filtered and concentrated under reduced pressure. The residue was chromatographed on a silica gel column to provide 520 mg (48% yield) of tert-butyl 1-((3-(3-bromophenyl)-1-isopropyl-1H-pyrazol-4-yl)methyl)-1,8-diazaspiro[4.5]decane-8-carboxylate as light yellow oil. LCMS (ESI, m/z): 517 [M+H]⁺.

Step 4: Synthesis of tert-butyl 1-((1-isopropyl-3-(3-(pyrrolidin-1-yl)phenyl)-1H-pyrazol-4-yl)methyl)-1,8-diazaspiro[4.5]decane-8-carboxylate

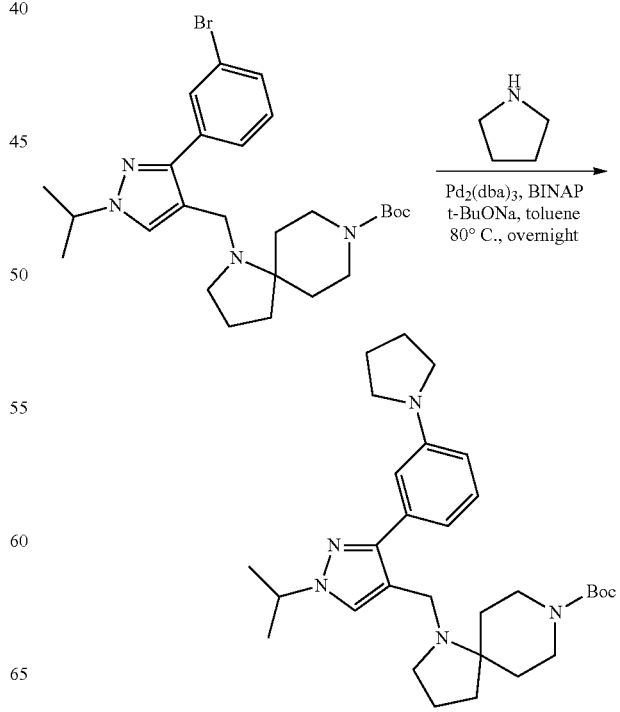

A 100-mL round-bottom flask was charged with tert-butyl 1-((3-(3-bromophenyl)-1-isopropyl-1H-pyrazol-4-yl)methyl)-1,8-diazaspiro[4.5]decane-8-carboxylate (1.08 g, 2.09 mmol, 1.00 equiv), pyrrolidine (223 mg, 3.14 mmol, 1.50 equiv), tris(dibenzylideneacetone)dipalladium (96.2 mg, 0.105 mmol, 0.05 equiv), 2,2'-bis(diphenylphosphino)-1,1'-binaphthyl (195 mg, 0.314 mmol, 0.15 equiv), sodium tert-butoxide (301 mg, 3.14 mmol, 1.50 equiv), and toluene (20 mL) under nitrogen. The reaction mixture was stirred overnight at 80° C. and quenched with water (20 mL). The resulting solution was extracted with dichloromethane (3×30 mL) and the organic layers were combined, washed with brine (1×30 mL), dried over anhydrous sodium sulfate, filtered and concentrated under reduced pressure. The residue was chromatographed on a silica gel column to provide 578 mg (55% yield) of tert-butyl 1-((1-isopropyl-3-(3-(pyrrolidin-1-yl)phenyl)-1H-pyrazol-4-yl)methyl)-1,8-diazaspiro[4.5]decane-8-carboxylate. LCMS (ESI, m/z): 508 [M+H]$^+$.

Step 5: Synthesis of 1-((1-isopropyl-3-(3-(pyrrolidin-1-yl)phenyl)-1H-pyrazol-4-yl)methyl)-1,8-diazaspiro[4.5]decane

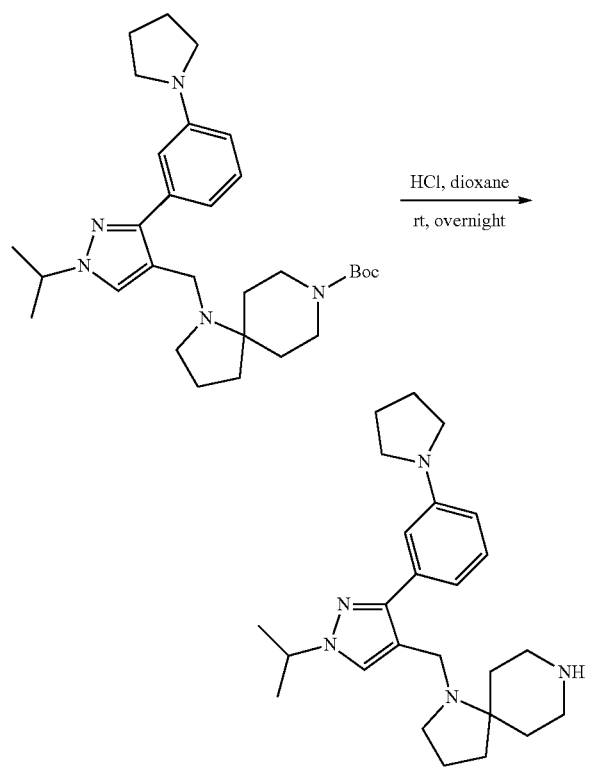

A 100-mL round-bottom flask was charged with tert-butyl 1-((1-isopropyl-3-(3-(pyrrolidin-1-yl)phenyl)-1H-pyrazol-4-yl)methyl)-1,8-diazaspiro[4.5]decane-8-carboxylate (578 mg, 1.14 mmol, 1.00 equiv), 1,4-dioxane (15 mL), and concentrated aqueous hydrochloric acid (3 mL). The resulting solution was stirred overnight at room temperature and concentrated under reduced pressure to provide 461 mg (crude) of 1-((1-isopropyl-3-(3-(pyrrolidin-1-yl)phenyl)-1H-pyrazol-4-yl)methyl)-1,8-diazaspiro[4.5]decane. LCMS (ESI, m/z): 408 [M+H]$^+$.

Step 6: Synthesis of 1,1,1,3,3,3-hexafluoropropan-2-yl 1-((1-isopropyl-3-(3-(pyrrolidin-1-yl)phenyl)-1H-pyrazol-4-yl)methyl)-1,8-diazaspiro[4.5]decane-8-carboxylate

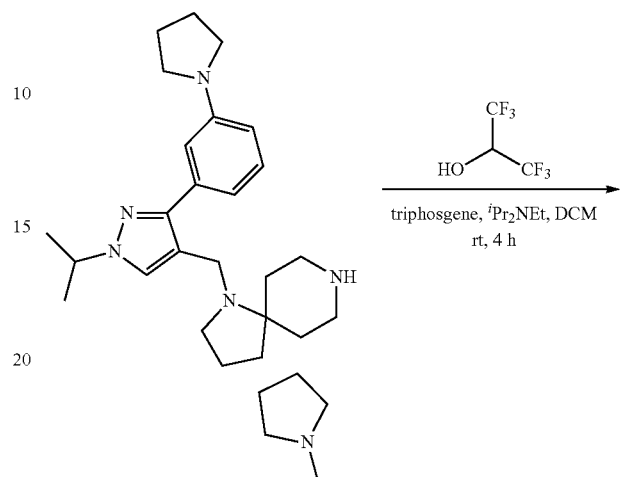

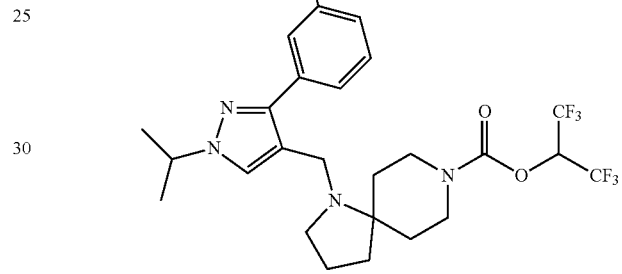

A 40-mL round-bottom flask was charged with triphosgene (77.0 mg, 0.259 mmol, 0.70 equiv) and dichloromethane (10 mL). 1,1,1,3,3,3-hexafluoropropan-2-ol (124 mg, 0.740 mmol, 2.00 equiv) and N,N-diisopropylethylamine (239 mg, 1.85 mmol, 5.15 equiv) were added at 0° C. The mixture was stirred for 2 h at room temperature prior to addition of 1-((1-isopropyl-3-(3-(pyrrolidin-1-yl)phenyl)-1H-pyrazol-4-yl)methyl)-1,8-diazaspiro[4.5]decane (150 mg, 0.370 mmol, 1.00 equiv). The reaction mixture was stirred for 2 h at room temperature and concentrated under reduced pressure. The crude product (530 mg) was purified by reverse phase HPLC to provide 26.0 mg (12% yield) of 1,1,1,3,3,3-hexafluoropropan-2-yl 1-((1-isopropyl-3-(3-(pyrrolidin-1-yl)phenyl)-1H-pyrazol-4-yl)methyl)-1,8-diazaspiro[4.5]decane-8-carboxylate. $^1$H NMR (300 MHz, Chloroform-d) δ 7.65 (s, 1H), 7.21 (t, J=8.0 Hz, 1H), 6.85 (d, J=7.5 Hz, 1H), 6.78 (s, 1H), 6.58-6.60 (m, 1H), 6.07-6.16 (m, 1H), 4.47-4.85 (m, 1H), 4.08-4.12 (m, 2H), 3.61 (s, 2H), 3.29-3.33 (m, 4H), 2.98-3.06 (m, 2H), 2.71-2.76 (m, 2H), 2.01-2.06 (m, 4H), 1.66-1.87 (m, 6H), 1.52 (d, J=6.6 Hz, 6H), 1.40-1.44 (m, 2H). LCMS (ESI, m/z): 602 [M+H]$^+$.

Example 9: 1,1,1,3,3,3-Hexafluoropropan-2-yl 2-(pyridazin-3-ylmethyl)-2,8-diazaspiro[4.5]decane-8-carboxylate

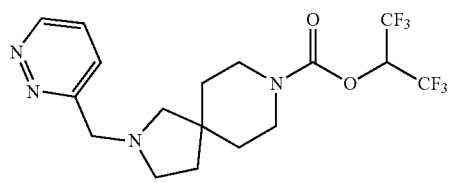 [SMILES: O=C(OC(C(F)(F)F)C(F)(F)F)N1CCC2(CCN(Cc3cccnn3)C2)CC1]

Step 1: Synthesis of pyridazine-3-carbaldehyde

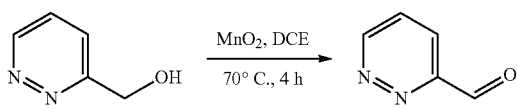

A 50-mL round-bottom flask was charged with pyridazin-3-ylmethanol (220 mg, 2.00 mmol, 1.00 equiv), DCE (10 mL), and manganese dioxide (870 mg, 10.0 mmol, 5.00 equiv). The resulting solution was stirred for 4 h at 70° C. and the solids were filtered. The filtrate was concentrated under reduced pressure to provide 250 mg (crude) of pyridazine-3-carbaldehyde. LCMS (ESI, m/z): 109 [M+H]$^+$.

Step 2: Synthesis of 1,1,1,3,3,3-hexafluoropropan-2-yl 2-(pyridazin-3-ylmethyl)-2,8-diazaspiro[4.5]decane-8-carboxylate

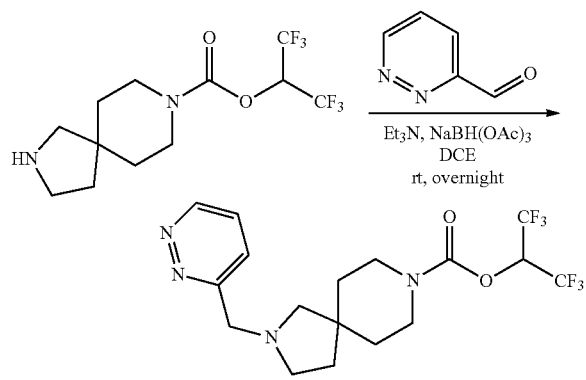

A 50-mL round-bottom flask was charged with 1,1,1,3,3,3-hexafluoropropan-2-yl 2,8-diazaspiro[4.5]decane-8-carboxylate (150 mg, 0.450 mmol, 1.00 equiv), DCM (10 mL), triethylamine (189 mg, 1.87 mmol, 3.00 equiv), and pyridazine-3-carbaldehyde (48.0 mg, 0.440 mmol, 1.00 equiv). The mixture was stirred for 1 h at room temperature prior to addition of sodium triacetoxyborohydride (285 mg, 1.34 mmol, 3.00 equiv). The reaction mixture was stirred overnight at room temperature and quenched with water (40 mL). The resulting solution was extracted with dichloromethane (3×80 mL) and the organic layers were combined, washed with water (3×20 mL), dried over anhydrous sodium sulfate, filtered and concentrated under reduced pressure. The crude product was purified by reverse phase HPLC to provide 144.7 mg (76% yield) of 1,1,1,3,3,3-hexafluoropropan-2-yl 2-(pyridazin-3-ylmethyl)-2,8-diazaspiro[4.5]decane-8-carboxylate. $^1$H NMR (400 MHz, Chloroform-d) δ 9.09-9.11 (m, 1H), 7.62-7.65 (m, 1H), 7.44-7.48 (m, 1H), 5.72-5.78 (m, 1H), 3.98 (s, 2H), 3.41-3.55 (m, 4H), 2.69-2.73 (m, 2H), 2.49 (s, 2H), 1.68-1.72 (m, 2H), 1.58-1.64 (m, 4H). LCMS (ESI, m/z): 427 [M+H]$^+$.

Example 10: 1,1,1,3,3,3-Hexafluoropropan-2-yl 1-(7-(tetrahydrofuran-3-yl)-5,6,7,8-tetrahydroimidazo[1,2-a]pyrazine-2-carbonyl)-1,8-diazaspiro[4.5]decane-8-carboxylate

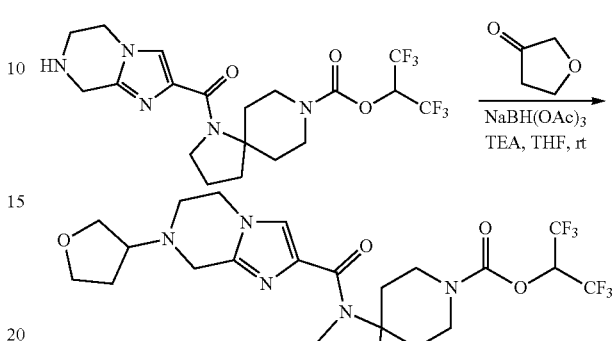

To a 4 mL scintillation vial was added 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate (Example 1, 75 mg, 0.16 mmol), DCE (1 mL), dihydrofuran-3(2H)-one (60 mg, 0.70 mmol, 4.50 equiv), and TEA (47 mg, 0.47 mmol, 3.00 equiv). The reaction mixture was stirred for 1.5 h at room temperature prior to the addition of sodium triacetoxyborohydride (99 mg, 0.47 mmol, 3.00 equiv). The resulting solution was stirred for 4 h at room temperature, and diluted with DCM (10 mL) and 1 N NaOH (5 mL). The mixture was extracted with 1 N NaOH (3×5 mL), and the organic layer was dried over Na$_2$SO$_4$, filtered and concentrated under reduced pressure. The crude product was purified by preparative HPLC and lyophilized to provide 1,1,1,3,3,3-hexafluoropropan-2-yl 1-(7-(tetrahydrofuran-3-yl)-5,6,7,8-tetrahydroimidazo[1,2-a]pyrazine-2-carbonyl)-1,8-diazaspiro[4.5]decane-8-carboxylate (71 mg, 86%). $^1$H NMR (400 MHz, Chloroform-d) δ 7.39 (s, 1H), 5.81-5.69 (m, 1H), 4.24-4.09 (m, 2H), 4.09-3.88 (m, 5H), 3.87-3.63 (m, 5H), 3.31-3.09 (m, 3H), 3.08-2.90 (m, 3H), 2.90-2.78 (m, 1H), 2.21-2.08 (m, 1H), 2.07-1.79 (m, 5H), 1.52-1.35 (m, 2H). LCMS (ESI, m/z): 554 [M+H]$^+$.

Example 11: 1,1,1,3,3,3-Hexafluoropropan-2-yl 1-((4,6-dichloro-1H-indol-2-yl)methyl)-1,8-diazaspiro[4.5]decane-8-carboxylate

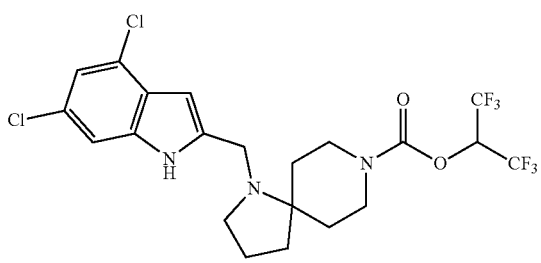 [SMILES: O=C(OC(C(F)(F)F)C(F)(F)F)N1CCC2(CCCN2Cc2cc3c(Cl)cc(Cl)cc3[nH]2)CC1]

Step 1: Preparation of ethyl 4,6-dichloro-1H-indole-2-carboxylate

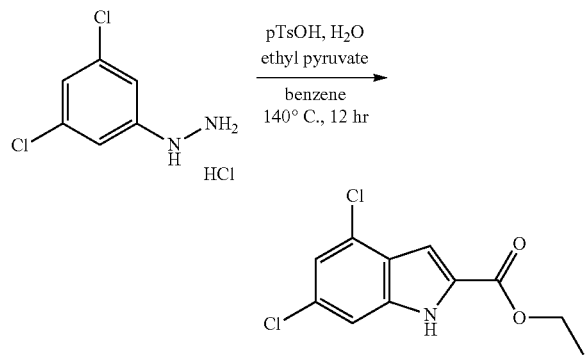

A flask was charged with 3,5 dichlorophenyl hydrazine hydrochloride (2 g, 9.4 mmol, 1.00 equiv), p-toluenesulfonic acid monohydrate (20 mg, 0.11 mmol, 0.01 equiv), and benzene (30 mL). Ethyl pyruvate (1.1 g, 9.4 mmol. 1.00 equiv) was added, and the mixture was fitted with a Dean-Stark trap, heated to reflux for 2 hr, and cooled to room temperature. The resulting solution was concentrated under reduced pressure and set aside. A separate flask containing p-toluenesulfonic acid monohydrate (3.1 g, 16.3 mmol, 1.73 equiv) in benzene (30 mL) was fitted with a Dean-Stark trap and heated to reflux for 2 hr. Both mixtures were combined and transferred to a sealed tube, purged with $N_2$, and heated to 140° C. overnight. The mixture was cooled, diluted with DCM (3 mL), and washed with sat. $NaHCO_3$ (5 mL) and brine (5 mL). The organic layer was dried over $Na_2SO_4$ and concentrated under reduced pressure to yield ethyl 4,6-dichloro-1H-indole-2-carboxylate (700 mg, 28% yield). LCMS (ESI, m/z): 229.0 [M+H]$^+$.

Step 2: Preparation of 4,6-dichloro-1H-indole-2-carboxylic acid

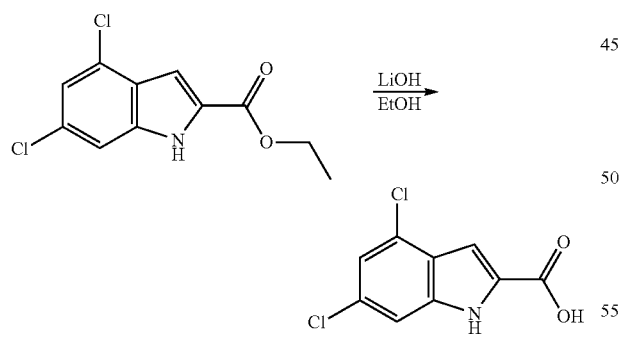

A flask was charged with ethyl 4,6-dichloro-1H-indole-2-carboxylate (700 mg, 2.7 mmol, 1 equiv) and ethanol (20 mL). Lithium hydroxide (162 mg, 6.76 mmol, 2.5 equiv) was dissolved in water (3 mL) and transferred to the reaction mixture at 0° C. The mixture stirred at reflux for 3 hr prior to acidification to pH 4 with 1 N HCl. The mixture was poured into EtOAc (5 mL), washed with brine (2×5 mL), dried over $Na_2SO_4$ and concentrated under reduced pressure to yield 4,6-dichloro-1H-indole-2-carboxylic acid (451 mg, 72% yield). LCMS (ESI, m/z): 229.9 [M+H]$^+$.

Step 3: Preparation of tert-butyl 1-(4,6-dichloro-1H-indole-2-carbonyl)-1,8-diazaspiro[4.5]decane-8-carboxylate

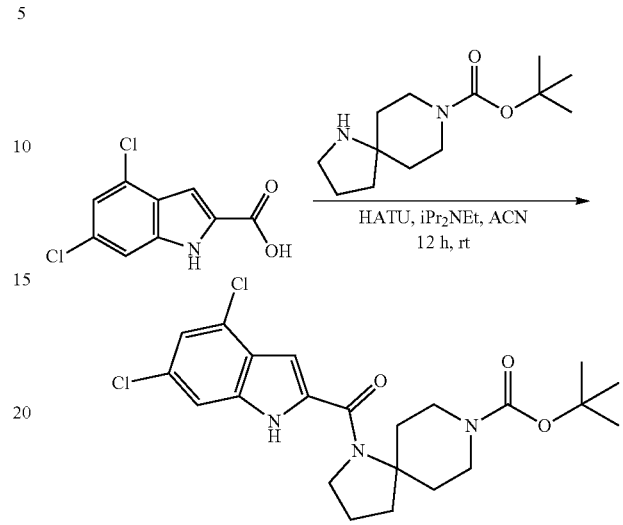

A flask was charged with tert-butyl 1,8-diazaspiro[4.5]decane-8-carboxylate (165 mg, 0.69 mmol, 1 equiv), 4,6-dichloro-1H-indole-2-carboxylic acid (219 mg, 0.95 mmol, 1.39 equiv) and DMF (5 mL). The mixture was stirred until all reagents were solubilized prior to the addition of HATU (339 mg, 0.89 mmol, 1.29 equiv) and TEA (383 µL, 2.75 mmol, 3.99 equiv). The reaction mixture was stirred overnight at room temperature, poured into EtOAc (5 mL), washed with sat. $NaHCO_3$ (5 mL) and brine (5 mL), dried over $Na_2SO_4$, concentrated under reduced pressure, and purified over silica to afford tert-butyl 1-(4,6-dichloro-1H-indole-2-carbonyl)-1,8-diazaspiro[4.5]decane-8-carboxylate (247 mg, 79% yield). LCMS (ESI, m/z): 452.1 [M+H]$^+$.

Step 4: Preparation of (4,6-dichloro-1H-indol-2-yl) (1,8-diazaspiro[4.5]decan-1-yl)methanone

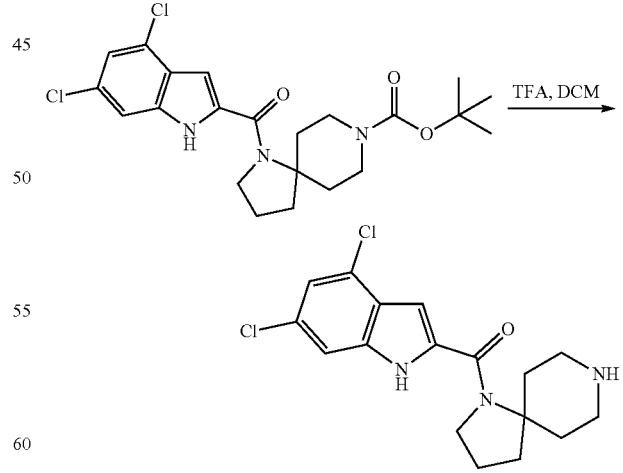

To a scintillation vial was added tert-butyl 1-(4,6-dichloro-1H-indole-2-carbonyl)-1,8-diazaspiro[4.5]decane-8-carboxylate (156 mg, 0.34 mmol, 1.00 equiv) and dissolved DCM (3 mL). The mixture was cooled to 0° C., and TFA (0.9 mL, 11.7 mmol, 21.5 equiv) was added dropwise. The resulting solution was stirred for 3 h at room temperature.

The mixture was diluted with DCM (5 mL), and washed sat. NaHCO₃ (3×5 mL). The aqueous layer had a pH ~10 and was extracted with DCM (3×10 mL), and combined organic layers were dried over Na₂SO₄, and concentrated under reduced pressure to yield (4,6-dichloro-1H-indol-2-yl)(1,8-diazaspiro[4.5]decan-1-yl)methanone (222, 87% yield). LCMS (ESI, m/z): 353.1 [M+H]⁺.

Step 5: Preparation of 1-((4,6-dichloro-1H-indol-2-yl)methyl)-1,8-diazaspiro[4.5]decane

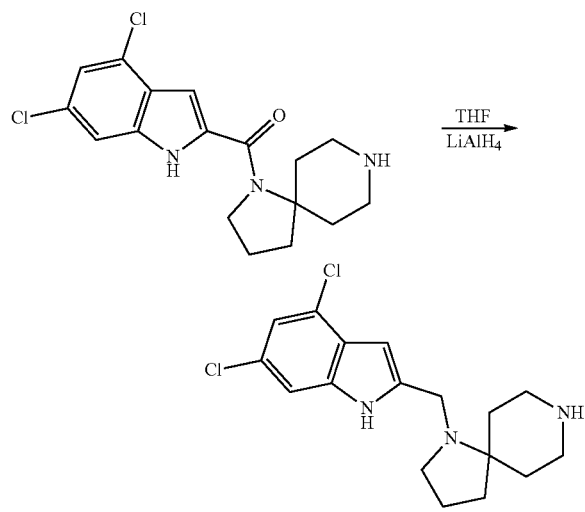

A flask was charged with (4,6-dichloro-1H-indol-2-yl)(1,8-diazaspiro[4.5]decan-1-yl)methanone (222 mg, 0.63 mmol, 1 equiv) and placed under vacuum. Stir bar and septum cap were added and the flask was flushed with N₂. Dry THF was added via syringe (~5 mL) and the mixture was cooled to 0° C. LiAlH₄ solution (0.79 mL, 1.8 mmol, 3 equiv) was transferred via syringe and added dropwise. The mixture was stirred at room temperature for 2 hr. LCMS analysis lacked desired product, so the solution was heated to 60° C. for 1 h, after which the temperature was increased to 70° C. overnight for 16 h. The mixture was cooled to 0° C. prior to the addition of water (47 µL), 15% by weight aqueous NaOH solution (47 µL), and additional water (141 µL). The mixture stirred at room temperature for 10 min, filtered through a pad of Celite, and washed thoroughly with THF. The solution was dried over Na₂SO₄, decanted and concentrated under reduced pressure to yield 1-((4,6-dichloro-1H-indol-2-yl)methyl)-1,8-diazaspiro[4.5]decane (199 mg, 93% yield). LCMS (ESI, m/z): 339.9 [M+H]⁺.

Step 6: Preparation of 1,1,1,3,3,3-hexafluoropropan-2-yl 1-((4,6-dichloro-1H-indol-2-yl)methyl 1,8-diazaspiro[4.5]decane-8-carboxylate

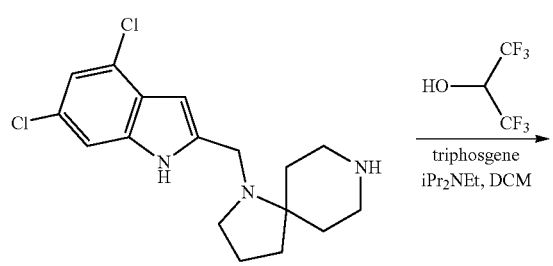

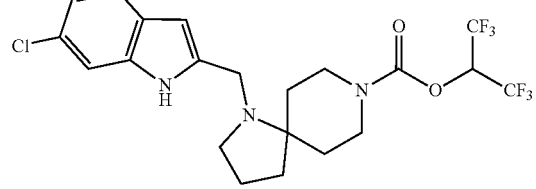

To a vial was added triphosgene (350 mg, 1.18 mmol, 2 equiv) and DCM (5 mL). Once solids were solubilized, the solution was cooled to 0° C. and purged with N₂. Hexafluoroisopropanol (470 µL, 3.8 mmol, 6.5 equiv) and N,N-diisopropylethylamine (1028 µL, 5.9 mmol, 10 equiv) were added. The mixture stirred for 2 h at room temperature and set aside. A separate vial was charged with 1-[(4,6-dichloro-1H-indol-2-yl)methyl-1,8-diazaspiro[4.5]decane (199 mg, 0.59 mmol, 1 equiv), DCM (2 mL), and N,N-diisopropylethylamine (0.2 mL, 1.15 mmol, 10 equiv). The vial was purged with N₂, after which the contents were transferred to the HFIP chloroformate solution via syringe. The resulting solution was allowed to stir overnight at room temperature. The mixture was diluted with DCM (5 mL), washed with sat. NaHCO₃ (3×5 mL), dried over Na₂SO₄, concentrated under reduced pressure, and purified on silica gel by flash column chromatography to afford 1,1,1,3,3,3-hexafluoropropan-2-yl 1-((4,6-dichloro-1H-indol-2-yl)methyl)-1,8-diazaspiro[4.5]decane-8-carboxylate (35 mg, 11% yield). ¹H NMR (400 MHz, Chloroform-d) δ 8.60 (s, 1H), 7.24 (s, 1H), 7.11 (s, 1H), 6.42 (s, 1H), 5.85-5.71 (m, 1H), 4.33-4.16 (m, 2H), 3.79 (s, 2H), 3.12-2.89 (m, 2H), 2.82-2.64 (m, 2H), 1.98-1.63 (m, 6H), 1.59-1.44 (m, 2H). LCMS (ESI, m/z): 533.1 [M+H]⁺.

Example 12: 1,1,1,3,3,3-Hexafluoropropan-2-yl 1-(pyrimidine-2-carbonyl)-1,8-diazaspiro[4.5]decane-8-carboxylate

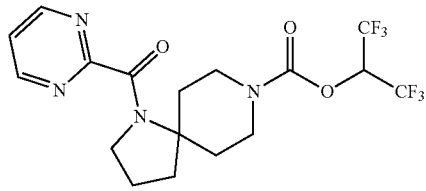 [SMILES: O=C(OC(C(F)(F)F)C(F)(F)F)N1CCC2(CCCN2C(=O)c2ncccn2)CC1]

Step 1: Synthesis of pyrimidine-2-carbonyl chloride

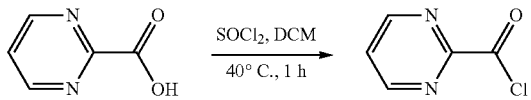

A flask was charged with pyrimidine-2-carboxylic acid (63.2 mg, 0.509 mmol, 1.00 equiv), DCM (5 mL), and thionyl chloride (121 mg, 1.02 mmol, 2.00 equiv). The resulting solution was stirred for 1 h at 40° C. The resulting mixture was concentrated under reduced pressure to provide 72.0 mg (99% yield) of pyrimidine-2-carbonyl chloride.

Step 2: Synthesis of 1,1,1,3,3,3-hexafluoropropan-2-yl 1-(pyrimidine-2-carbonyl)-1,8-diazaspiro 4.5 decane-8-carboxylate

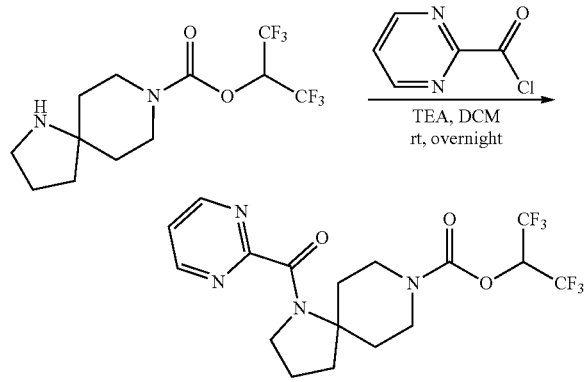

A flask was charged with 1,1,1,3,3,3-hexafluoropropan-2-yl 1,8-diazaspiro[4.5]decane-8-carboxylate (113 mg, 0.341 mmol, 1.00 equiv), pyrimidine-2-carbonyl chloride (72.0 mg, 0.515 mmol, 1.50 equiv), DCM (5 mL), and TEA (103 mg, 1.02 mmol, 3.00 equiv). The resulting solution was stirred overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (101 mg) was purified by reverse phase HPLC to provide 75.2 mg (51% yield) of 1,1,1,3,3,3-hexafluoropropan-2-yl 1-(pyrimidine-2-carbonyl)-1,8-diazaspiro[4.5]decane-8-carboxylate. $^1$H NMR (400 MHz, Chloroform-d) δ 8.81 (d, J=5.2 Hz, 2H), 7.34 (t, J=7.2 Hz, 1H), 5.72-5.80 (m, 1H), 4.18-4.27 (m, 2H), 3.47 (t, J=6.4 Hz, 2H), 3.15-3.24 (m, 2H), 2.96-3.08 (m, 2H), 2.01-2.11 (m, 2H), 1.86-1.90 (m, 2H), 1.48-1.62 (m, 2H). LCMS (ESI, m/z): 441 [M+H]$^+$.

Example 13: 1,1,1,3,3,3-Hexafluoropropan-2-yl 1-nicotinoyl-1,8-diazaspiro[4.5]decane-8-carboxylate

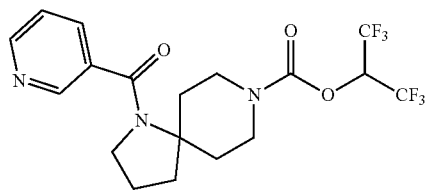 [SMILES: O=C(OC(C(F)(F)F)C(F)(F)F)N1CCC2(CCCN2C(=O)c2cccnc2)CC1]

Step 1: Synthesis of 1-(tert-butyl) 8-(1,1,1,3,3,3-hexafluoropropan-2-yl) 1,8-diazaspiro[4.5]decane-1,8-dicarboxylate

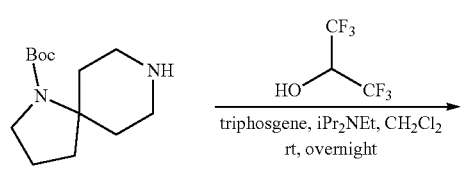

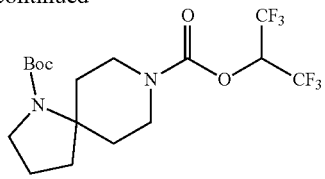

A flask was charged with triphosgene (4.75 g, 16.0 mmol, 0.80 equiv) and DCM (50 mL). 1,1,1,3,3,3-Hexafluoropropan-2-ol (6.72 g, 40.0 mmol, 2.00 equiv) and N,N-diisopropylethylamine (7.74 g, 59.9 mmol, 3.00 equiv) were added sequentially at 0° C. The mixture was stirred for 2 h at room temperature prior to addition of tert-butyl 1,8-diazaspiro [4.5]decane-1-carboxylate (4.80 g, 20.0 mmol, 1.00 equiv). The resulting solution was stirred overnight at room temperature and quenched with water (50 mL). The mixture was extracted with DCM (3×100 mL) and the organic layers were combined, washed with brine (3×100 mL), dried over anhydrous sodium sulfate, filtered and concentrated under reduced pressure. The residue was chromatographed on a silica gel column to provide 3.96 g (46% yield) of 1-(tert-butyl) 8-(1,1,1,3,3,3-hexafluoropropan-2-yl) 1,8-diazaspiro [4.5]decane-1,8-dicarboxylate. LCMS (ESI, m/z): 435 [M+H]$^+$.

Step 2: Synthesis of 1,1,1,3,3,3-hexafluoropropan-2-yl 1,8-diazaspiro[4.5]decane-8-carboxylate

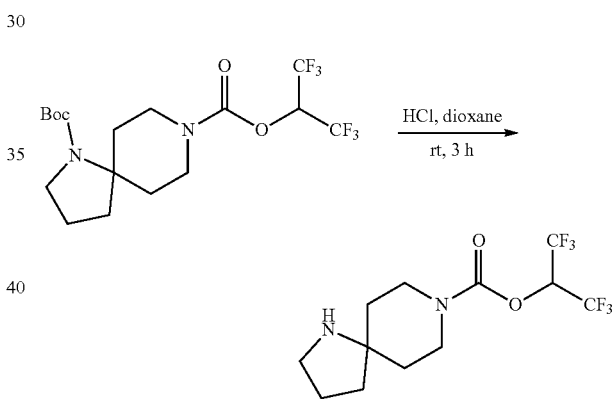

A flask was charged with 1-(tert-butyl) 8-(1,1,1,3,3,3-hexafluoropropan-2-yl) 1,8-diazaspiro[4.5]decane-1,8-dicarboxylate (1.50 g, 3.45 mmol, 1.00 equiv), dioxane (15 mL), and hydrochloric acid (3 mL). The resulting solution was stirred for 3 h at room temperature and concentrated under reduced pressure to provide 1.15 g (99% yield) of 1,1,1,3,3,3-hexafluoropropan-2-yl 1,8-diazaspiro[4.5]decane-8-carboxylate. LCMS (ESI, m/z): 335 [M+H]$^+$.

Step 3: Synthesis of 1,1,1,3,3,3-hexafluoropropan-2-yl 1-nicotinoyl-1,8-diazaspiro[4.5]decane-8-carboxylate

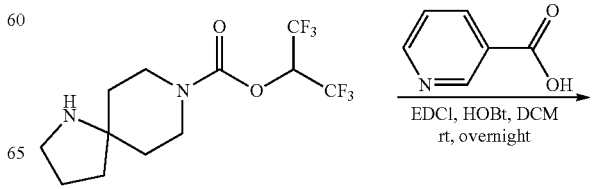

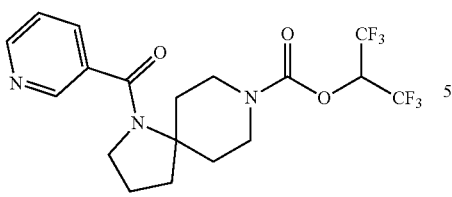

A flask was charged with pyridine-3-carboxylic acid (62.6 mg, 0.503 mmol, 1.50 equiv), N-(3-dimethylaminopropyl)-N'-ethylcarbodiimide hydrochloride (126 mg, 0.670 mmol, 2.00 equiv), 1-hydroxybenzotrizole (89.0 mg, 0.670 mmol, 2.00 equiv), and DCM (5 mL). The resulting solution was stirred for 1 h at room temperature prior to addition of 1,1,1,3,3,3-hexafluoropropan-2-yl 1,8-diazaspiro[4.5]decane-8-carboxylate (115 mg, 0.335 mmol, 1.00 equiv). The reaction mixture was stirred overnight at room temperature and quenched with water (20 mL). The mixture was extracted with DCM (3×30 mL) and the organic layers were combined, washed with brine (3×30 mL), dried over anhydrous sodium sulfate, filtered and concentrated under reduced pressure. The crude product (106 mg) was purified by reverse phase HPLC to provide 71.5 mg (47% yield) of 1,1,1,3,3,3-hexafluoropropan-2-yl 1-nicotinoyl-1,8-diazaspiro[4.5]decane-8-carboxylate. $^1$H NMR (400 MHz, Chloroform-d) δ 8.63-8.69 (m, 2H), 7.75 (d, J=7.6 Hz, 1H), 7.32-7.36 (m, 1H), 5.72-5.82 (m, 1H), 4.19-4.27 (m, 2H), 3.47 (t, J=6.4 Hz, 2H), 3.13-3.19 (m, 2H), 2.95-3.08 (m, 2H), 2.01-2.14 (m, 2H), 1.83-1.90 (m, 2H), 1.45-1.55 (m, 2H). LCMS (ESI, m/z): 440 [M+H]$^+$.

Example 14: 1,1,1,3,3,3-Hexafluoropropan-2-yl 1-(5-methyl-1H-indole-2-carbonyl)-1,8-diazaspiro[4.5]decane-8-carboxylate

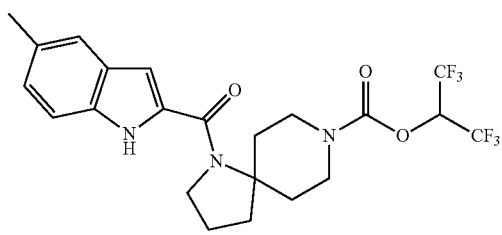 [SMILES: Cc1ccc2[nH]c(C(=O)N3CCCC34CCN(C(=O)OC(C(F)(F)F)C(F)(F)F)CC4)cc2c1]

Step 1: Synthesis of 5-methyl-1H-indole-2-carbonyl chloride

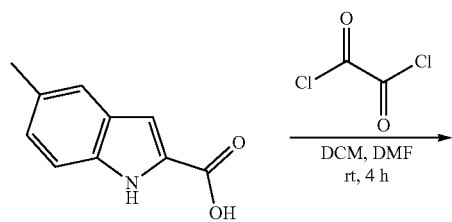

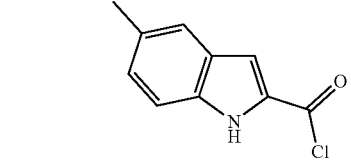

A vial was charged with 5-methyl-1H-indole-2-carboxylic acid (175 mg, 1.00 mmol, 1.00 equiv), DCM (10 mL) and oxalyl chloride (381 mg, 3.00 mmol, 3.00 equiv). N,N-Dimethylformamide (0.05 mL) was added at 0° C. The resulting solution was stirred for 4 h at room temperature and concentrated under reduced pressure to provide 194 mg (crude) of 5-methyl-1H-indole-2-carbonyl chloride.

Step 2: Synthesis of 1,1,1,3,3,3-hexafluoropropan-2-yl 1-(5-methyl-1H-indole-2-carbonyl)-1,8-diazaspiro[4.5]decane-8-carboxylate

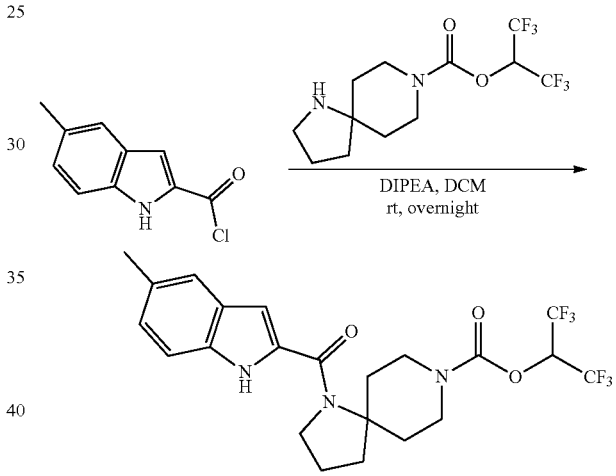

A vial was charged with 1,1,1,3,3,3-hexafluoropropan-2-yl 1,8-diazaspiro[4.5]decane-8-carboxylate (334 mg, 1.00 mmol, 1.00 equiv), DCM (10 mL), and N,N-diisopropylethylamine (258 mg, 2.00 mmol, 2.00 equiv). 5-Methyl-1H-indole-2-carbonyl chloride (194 mg, 1.00 mmol, 1.00 equiv) was added at 0° C. The resulting solution was stirred overnight at room temperature before quenching by water (10 mL). The mixture was extracted with DCM (3×10 mL) and the organic layers were combined, washed with water (3×10 mL), dried over anhydrous sodium sulfate and concentrated under reduced pressure. The crude product was purified by reverse phase HPLC to provide 22.5 mg (5% yield) of 1,1,1,3,3,3-hexafluoropropan-2-yl 1-(5-methyl-1H-indole-2-carbonyl)-1,8-diazaspiro[4.5]decane-8-carboxylate. $^1$H NMR (300 MHz, Chloroform-d) δ 8.85-9.40 (s, 1H), 7.40-7.50 (s, 1H), 7.30-7.39 (m, 1H), 7.05-7.20 (m, 1H), 5.60-6.00 (m, 1H), 4.10-4.40 (m, 3H), 3.60-4.10 (m, 2H), 2.82-3.40 (m, 4H), 2.40-2.50 (s, 3H), 1.90-2.30 (m, 4H), 1.40-1.55 (m, 2H). LCMS (ESI, m/z): 492 [M+H]$^+$.

Example 15: 2-((8-(((1,1,1,3,3,3-Hexafluoropropan-2-yl)oxy)carbonyl)-1,8-diazaspiro[4.5]decan-1-yl)methyl)-1H-indole-5-carboxylic acid

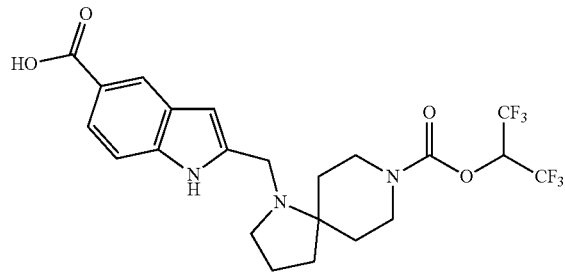 [SMILES: O=C(O)c1ccc2[nH]c(CN3CCCC34CCN(C(=O)OC(C(F)(F)F)C(F)(F)F)CC4)cc2c1]

Step 1: Synthesis of methyl 4-amino-3-iodobenzoate

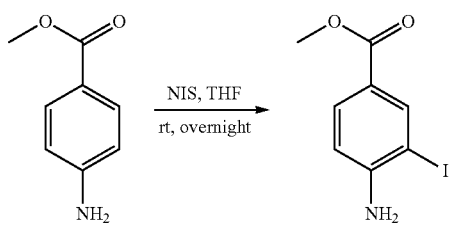

A flask was charged with methyl 4-aminobenzoate (9.00 g, 59.5 mmol, 1.00 equiv), THF (100 mL) and 1-iodo-5-pyrrolidinedione (16.2 g, 72.0 mmol, 1.20 equiv). The resulting solution was stirred overnight at room temperature and concentrated under reduced pressure. The residue was diluted with water (50 mL) and extracted with DCM (3×50 mL), the organic layers were combined, washed with water (3×50 mL), dried over anhydrous sodium sulfate, filtered and concentrated under reduced pressure. The residue was chromatographed on a silica gel column to provide 7.60 g (46% yield) of methyl 4-amino-3-iodobenzoate as a yellow solid. LCMS (ESI, m/z): 278 [M+H]$^+$.

Step 2: Synthesis of methyl 3-iodo-4-(2,2,2-trifluoroacetamido)benzoate

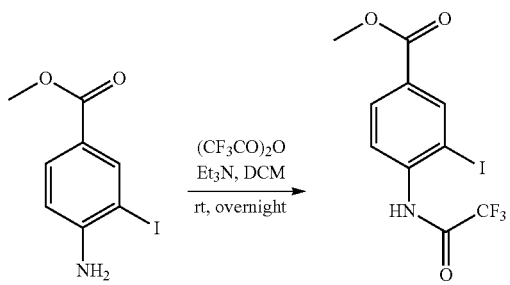 [SMILES: COC(=O)c1ccc(N)c(I)c1 ; COC(=O)c1ccc(NC(=O)C(F)(F)F)c(I)c1]

A flask was charged with methyl 4-amino-3-iodobenzoate (7.50 g, 27.1 mmol, 1.00 equiv), DCM (50 mL), triethylamine (7.20 g, 71.3 mmol, 2.63 equiv) and trifluoroacetic anhydride (8.90 g, 42.4 mmol, 1.57 equiv), as described in Example 1, Step 1. The residue was chromatographed on a silica gel column to provide 8.00 g (79% yield) of methyl 3-iodo-4-(2,2,2-trifluoroacetamido)benzoate as a yellow solid.

Step 3: Synthesis of methyl 2-(hydroxymethyl)-1H-indole-5-carboxylate

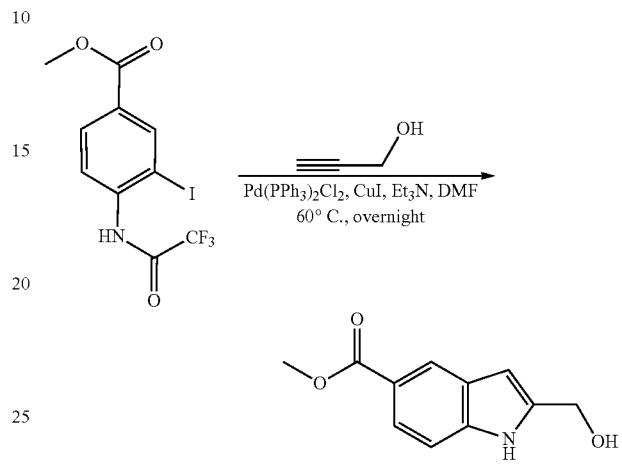

A flask was charged with methyl 3-iodo-4-(2,2,2-trifluoroacetamido)benzoate (3.73 g, 10.0 mmol, 1.00 equiv), N,N-dimethylformamide (50 mL), prop-2-yn-1-ol (0.840 g, 15.0 mmol, 1.50 equiv), triethylamine (5.05 g, 50.0 mmol, 5.00 equiv), cuprous iodide (0.190 g, 1.00 mmol, 0.10 equiv) and bis(triphenylphosphine)palladium(II) chloride (0.350 g, 0.500 mmol, 0.05 equiv) under nitrogen. The resulting solution was stirred overnight at 60° C. and diluted with water (500 mL). The mixture was extracted with EtOAc (3×500 mL) and the organic layers were combined, washed with water (3×100 mL), dried over anhydrous sodium sulfate, filtered and concentrated under reduced pressure. The residue was chromatographed on a silica gel column to provide in 1.80 g (85% yield) of methyl 2-(hydroxymethyl)-1H-indole-5-carboxylate as a brown oil. LCMS (ESI, m/z): 206 [M+H]$^+$.

Step 4: Synthesis of 2-(hydroxymethyl)-1H-indole-5-carboxylic acid

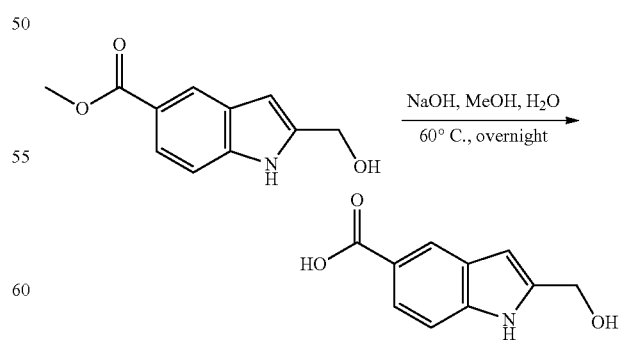

A vial was charged with methyl 2-(hydroxymethyl)-1H-indole-5-carboxylate (800 mg, 3.90 mmol, 1.00 equiv), MeOH (5 mL), water (5 mL) and sodium hydroxide (234 mg, 5.85 mmol, 1.50 equiv). The resulting solution was stirred overnight at 60° C. and concentrated under reduced pressure. The residue was diluted with water (25 mL) and the pH value was adjusted to 4~5 with 1 N hydrochloric acid solution. The solid was filtered, washed with water (3×10 mL) and dried to provide 620 mg (83% yield) of 2-(hydroxymethyl)-1H-indole-5-carboxylic acid as a light brown solid. LCMS (ESI, m/z): 192 [M+H]+.

Step 5: Synthesis of 2-formyl-1H-indole-5-carboxylic acid

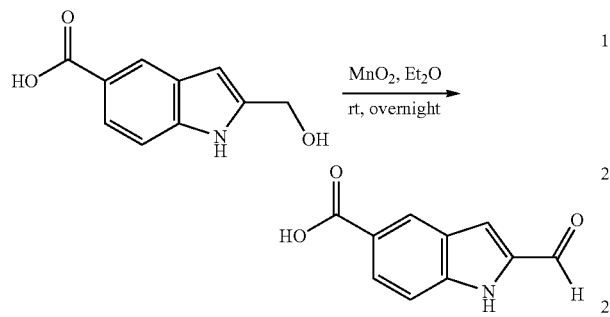

A vial was charged with 2-(hydroxymethyl)-1H-indole-5-carboxylic acid (0.300 g, 1.57 mmol, 1.00 equiv), ether (10 mL) and manganese dioxide (1.37 g, 15.7 mmol, 10.0 equiv). The resulting solution was stirred overnight at room temperature, as described in Example 10, Step 1. The solid was filtered out and washed with ACN (3×10 mL). The filtrate was combined and concentrated under reduced pressure to provide 0.189 g (64% yield) of 2-formyl-1H-indole-5-carboxylic acid as a yellow oil. LCMS (ESI, m/z): 190 [M+H]+.

Step 6: Synthesis of 1-(t-butyl) 8-(1,1,1,3,3,3-hexafluoropropan-2-yl) 1,8-diazaspiro[4.5]decane-1,8-dicarboxylate

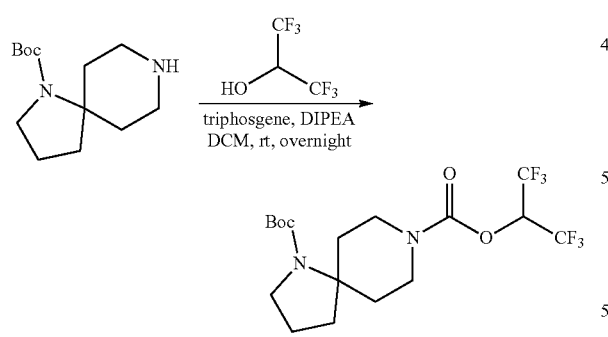

A flask was charged with 1,1,1,3,3,3-hexafluoropropan-2-ol (2.00 g, 11.9 mmol, 1.50 equiv), DCM (20 mL) and triphosgene (1.18 g, 3.97 mmol, 0.50 equiv). N,N-diisopropylethylamine (2.55 g, 19.7 mmol, 2.50 equiv) was added dropwise at 0° C. The solution was stirred for 3 h at room temperature. Then t-butyl 1,8-diazaspiro[4.5]decane-1-carboxylate (1.90 g, 7.91 mmol, 1.00 equiv) was added. The resulting solution was stirred overnight at room temperature and quenched by water (20 mL), as described in Example 6, Step 4. The residue was chromatographed on a silica gel column to provide 1.58 g (46% yield) of 1-t-butyl 8-(1,1,1,3,3,3-hexafluoropropan-2-yl) 1,8-diazaspiro[4.5]decane-1,8-dicarboxylate as a yellow oil. LCMS (ESI, m/z): 435 [M+H]+.

Step 7: Synthesis of 1,1,1,3,3,3-hexafluoropropan-2-yl 1,8-diazaspiro[4.5]decane-8-carboxylate

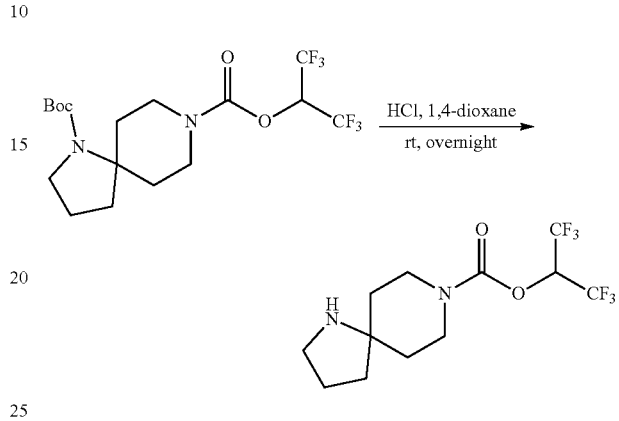

A flask was charged with 1-t-butyl 8-(1,1,1,3,3,3-hexafluoropropan-2-yl) 1,8-diazaspiro[4.5]decane-1,8-dicarboxylate (1.58 g, 3.64 mmol, 1.00 equiv), 1,4-dioxane (15 mL) and concentrated hydrochloric acid (5 mL), as described in Example 9, Step 5. The resulting solution was stirred overnight at room temperature and concentrated under reduced pressure to provide 1.15 g (crude) of 1,1,1,3,3,3-hexafluoropropan-2-yl 1,8-diazaspiro[4.5]decane-8-carboxylate as an off-white solid. LCMS (ESI, m/z): 335 [M+H]+.

Step 8: Synthesis of 2-((8-(((1,1,1,3,3,3-hexafluoropropan-2-yl)oxy)carbonyl)-1,8-diazaspiro[4.5]decan-1-yl)methyl)-1H-indole-5-carboxylic acid

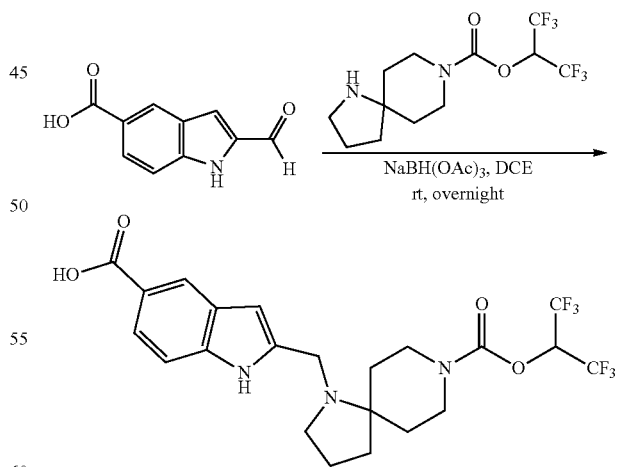

A vial was charged with 2-formyl-1H-indole-5-carboxylic acid (132 mg, 0.700 mmol, 1.00 equiv), DCE (10 mL), 1,1,1,3,3,3-hexafluoropropan-2-yl 1,8-diazaspiro[4.5]decane-8-carboxylate (234 mg, 0.700 mmol, 1.00 equiv) and sodium triacetoxyborohydride (445 mg, 2.10 mmol, 3.00 equiv). The resulting solution was stirred overnight at room temperature and quenched by water (10 mL), as described in Example 6, Step 3. The crude product was purified by reverse phase HPLC to provide 125.2 mg (57% yield) of 2-((8-((((1,1,1,3,3,3-hexafluoropropan-2-yl)oxy)carbonyl)-1,8-diazaspiro[4.5]decan-1-yl)methyl)-1H-indole-5-carboxylic acid as a white solid. $^1$H NMR (400 MHz, Methanol-d$_4$) δ 8.22 (s, 1H), 8.76 (d, J=8.6 Hz, 1H), 7.33 (d, J=8.6 Hz, 1H), 6.42 (s, 1H), 6.05-6.20 (m, 1H), 4.12-4.28 (m, 2H), 3.80-3.90 (s, 2H), 3.00-3.20 (m, 2H), 2.80-2.90 (m, 2H), 1.90-2.00 (m, 2H), 1.70-1.89 (m, 4H), 1.55-1.65 (m, 2H). LCMS (ESI, m/z): 508 [M+H]$^+$.

Example 16: 1,1,1,3,3,3-Hexafluoropropan-2-yl 1-(5,7-dichloro-1H-indole-2-carbonyl)-1,8-diazaspiro[4.5]decane-8-carboxylate

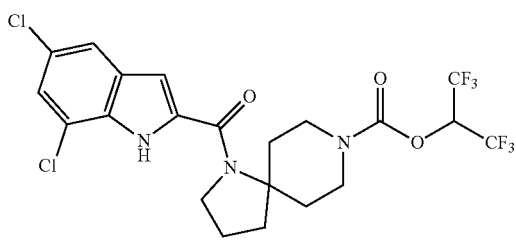 [SMILES: O=C(OC(C(F)(F)F)C(F)(F)F)N1CCC2(CCCN2C(=O)c2cc3cc(Cl)cc(Cl)c3[nH]2)CC1]

Step 1: Synthesis of 1-(t-butyl) 8-(1,1,1,3,3,3-hexafluoropropan-2-yl) 1,8-diazaspiro[4.5]decane-1,8-dicarboxylate

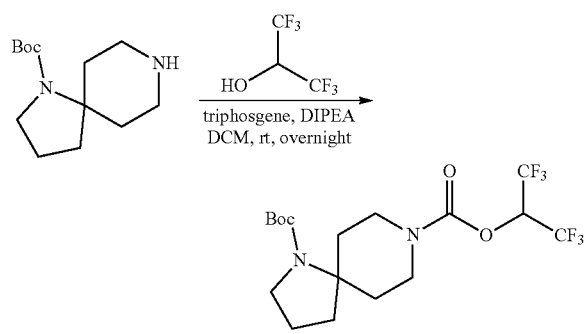

A flask was placed 1,1,1,3,3,3-hexafluoropropan-2-ol (2.00 g, 11.9 mmol, 1.50 equiv), DCM (20 mL), and triphosgene (1.18 g, 3.97 mmol, 0.50 equiv). N,N-diisopropylethylamine (2.55 g, 19.7 mmol, 2.50 equiv) was added dropwise at 0° C. The solution was stirred for 3 h at room temperature. Then t-butyl 1,8-diazaspiro[4.5]decane-1-carboxylate (1.90 g, 7.91 mmol, 1.00 equiv) was added. The resulting solution was stirred overnight at room temperature and quenched by water (20 mL), as described in Example 6, Step 4. The residue was chromatographed on a silica gel column to provide 1.58 g (46% yield) of 1-(t-butyl) 8-(1,1,1,3,3,3-hexafluoropropan-2-yl) 1,8-diazaspiro[4.5]decane-1,8-dicarboxylate as a yellow oil. LCMS (ESI, m/z): 435 [M+H]$^+$.

Step 2: Synthesis of 1,1,1,3,3,3-hexafluoropropan-2-yl 1,8-diazaspiro[4.5]decane-8-carboxylate

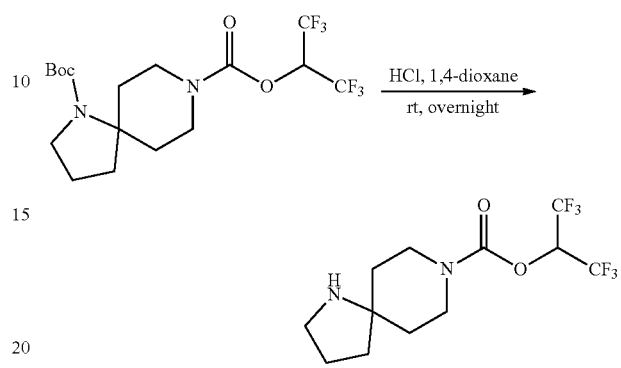

A flask was charged with 1-(t-butyl) 8-(1,1,1,3,3,3-hexafluoropropan-2-yl) 1,8-diazaspiro[4.5]decane-1,8-dicarboxylate (1.58 g, 3.64 mmol, 1.00 equiv), 1,4-dioxane (15 mL) and concentrated hydrochloric acid (5 mL), as described in Example 9, Step 5. The resulting solution was stirred overnight at room temperature and concentrated under reduced pressure to provide 1.15 g (crude) of 1,1,1,3,3,3-hexafluoropropan-2-yl 1,8-diazaspiro[4.5]decane-8-carboxylate as an off-white solid. LCMS (ESI, m/z): 335 [M+H]$^+$.

Step 3: Synthesis of ethyl (E)-2-(2-(2,4-dichlorophenyl)hydrazineylidene)propanoate

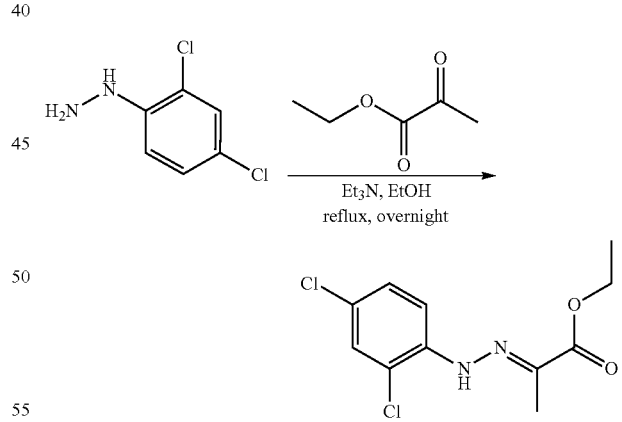

A flask was charged with (2,4-dichlorophenyl)hydrazine (10.0 g, 56.8 mmol, 1.00 equiv), EtOH (50 mL), ethyl 2-oxopropanoate (6.59 g, 56.8 mmol, 1.00 equiv) and triethylamine (5.74 g, 56.8 mmol, 1.50 equiv). The resulting solution was refluxed overnight and concentrated under reduced pressure. The residue was chromatographed on a silica gel column to provide 3.15 g (31% yield) of ethyl (E)-2-(2-(2,4-dichlorophenyl)hydrazineylidene)propanoate as a light yellow solid. LCMS (ESI, m/z): 275 [M+H]$^+$.

Step 4: Synthesis of ethyl 5,7-dichloro-1H-indole-2-carboxylate

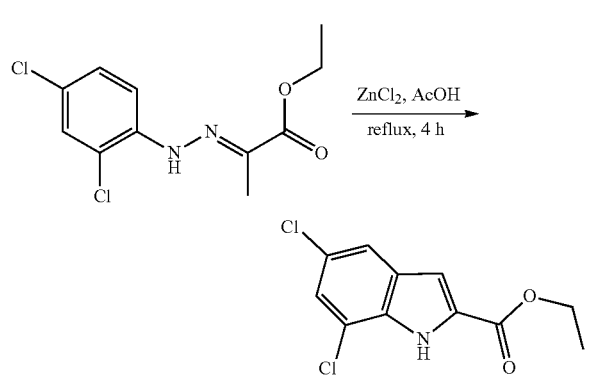

A 100-mL round-bottom flask was charged with ethyl (E)-2-(2-(2,4-dichlorophenyl)hydrazineylidene)propanoate (3.00 g, 10.9 mmol, 1.00 equiv), AcOH (50 mL) and zinc chloride (27.2 g, 200 mmol, 18.3 equiv). The resulting solution was refluxed for 4 h. Then the solution was cooled to room temperature and poured into water (200 mL). The solid was collected by filtration, washed with water (3×10 mL), and dried to provide 2.30 g (82% yield) of ethyl 5,7-dichloro-1H-indole-2-carboxylate as a brown solid. LCMS (ESI, m/z): 258 [M+H]$^+$.

Step 5: Synthesis of 5,7-dichloro-1H-indole-2-carboxylic acid

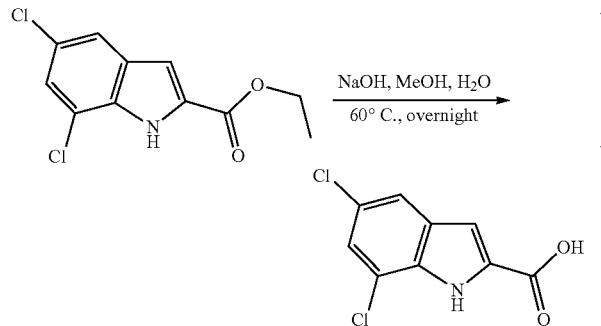

A 40-mL vial was charged with ethyl 5,7-dichloro-1H-indole-2-carboxylate (516 mg, 2.00 mmol, 1.00 equiv), MeOH (1 mL), water (5 mL) and sodium hydroxide (120 mg, 3.00 mmol, 1.50 equiv). The resulting solution was stirred overnight at 60° C. The volume of the solution was concentrated to reduce by half. Then the pH value was adjusted to 4-5 with aqueous hydrochloric acid (1 mol/L), resulting in the precipitation of a solid. The solid was collected by filtration, washed with water (3×10 mL), and dried to provide 294 mg (64% yield) of 5,7-dichloro-1H-indole-2-carboxylic acid as a light brown solid. LCMS (ESI, m/z): 228 [M−H]$^+$.

Step 6: Synthesis of 5,7-dichloro-1H-indole-2-carbonyl chloride

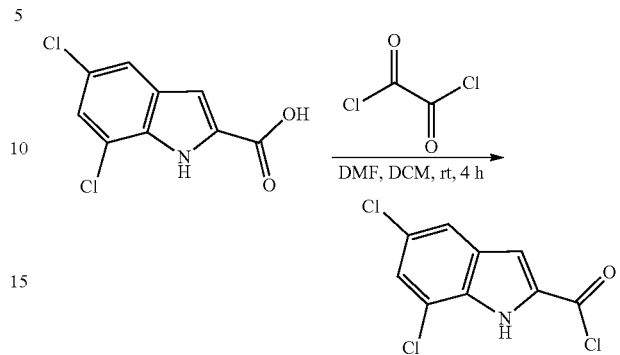

A vial was charged with 5,7-dichloro-1H-indole-2-carboxylic acid (230 mg, 1.00 mmol, 1.00 equiv), DCM (10 mL), and oxalyl chloride (381 mg, 3.00 mmol, 3.00 equiv). N,N-Dimethylformamide (0.05 mL) was added at 0° C., as described in Example 16, Step 3. The resulting solution was stirred for 4 hours at room temperature and concentrated under reduced pressure to provide 248 mg (crude) of 5,7-dichloro-1H-indole-2-carbonyl chloride as a yellow solid.

Step 7: Synthesis of 1,1,1,3,3,3-hexafluoropropan-2-yl 1-(5,7-dichloro-1H-indole-2-carbonyl)-1,8-diazaspiro[4.5]decane-8-carboxylate

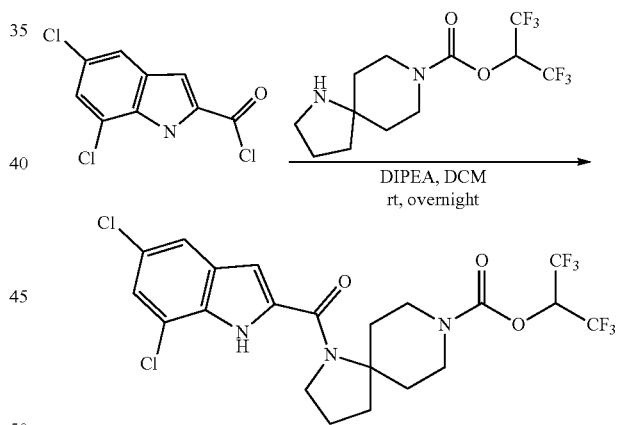

A vial was charged with DCM (10 mL), 1,1,1,3,3,3-hexafluoropropan-2-yl 1,8-diazaspiro[4.5]decane-8-carboxylate (334 mg, 1.00 mmol, 1.00 equiv) and N,N-diisopropylethylamine (258 mg, 2.00 mmol, 2.00 equiv). The resulting solution was stirred overnight at room temperature and quenched by water (10 mL). 5,7-Dichloro-1H-indole-2-carbonyl chloride (248 mg, 1.00 mmol, 1.00 equiv) was added at 0° C., as described in Example 16, Step 4. The crude product was purified by reverse phase HPLC to provide 60.9 mg (11% yield) of 1,1,1,3,3,3-hexafluoropropan-2-yl 1-(5,7-dichloro-1H-indole-2-carbonyl)-1,8-diazaspiro[4.5]decane-8-carboxylate as a light yellow solid. $^1$H NMR (300 MHz, Chloroform-d) δ 9.48 (br, 1H), 7.54 (s, 1H), 7.28 (s, 1H), 6.78 (s, 1H), 5.64-5.89 (m, 1H), 4.12-4.37 (m, 2H), 3.85-4.12 (m, 2H), 2.90-3.18 (m, 4H), 1.96-2.30 (m, 4H), 1.42-1.58 (m, 2H). LCMS (ESI, m/z): 546 [M+H]$^+$.

Example 17: 1,1,1,3,3,3-Hexafluoropropan-2-yl 1-(5-methylbenzo[b]thiophene-2-carbonyl)-1,8-diazaspiro[4.5]decane-8-carboxylate

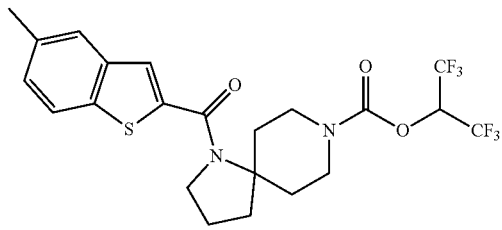 [SMILES: Cc1ccc2sc(C(=O)N3CCCC34CCN(C(=O)OC(C(F)(F)F)C(F)(F)F)CC4)cc2c1]

Step 1: Synthesis of 1-(t-butyl) 8-(1,1,1,3,3,3-hexafluoropropan-2-yl) 1,8-diazaspiro[4.5]decane-1,8-dicarboxylate

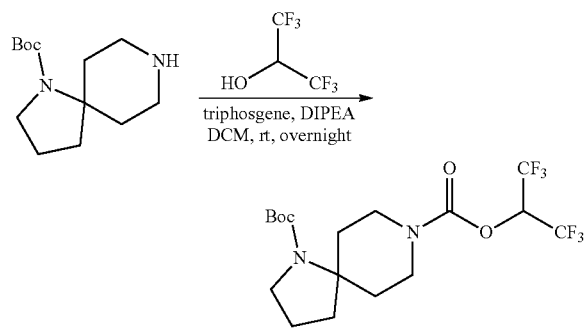

A flask was charged with 1,1,1,3,3,3-hexafluoropropan-2-ol (2.00 g, 11.9 mmol, 1.50 equiv), DCM (20 mL), triphosgene (1.18 g, 3.97 mmol, 0.50 equiv). N,N-diisopropylethylamine (2.55 g, 19.7 mmol, 2.50 equiv) was added dropwise at 0° C. The solution was stirred for 3 h at room temperature. Then t-butyl 1,8-diazaspiro[4.5]decane-1-carboxylate (1.90 g, 7.91 mmol, 1.00 equiv) was added. The resulting solution was stirred overnight at room temperature and quenched by water (20 mL), as described in Example 6, Step 4. The residue was chromatographed on a silica gel column to provide 1.58 g (46% yield) of 1-(t-butyl) 8-(1,1,1,3,3,3-hexafluoropropan-2-yl) 1,8-diazaspiro[4.5]decane-1,8-dicarboxylate as a yellow oil. LCMS (ESI, m/z): 435 [M+H]$^+$.

Step 2: Synthesis of 1,1,1,3,3,3-hexafluoropropan-2-yl 1,8-diazaspiro[4.5]decane-8-carboxylate

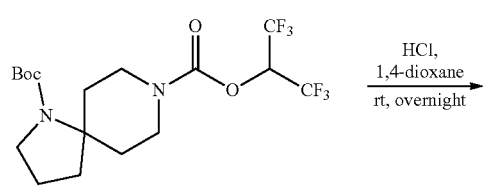

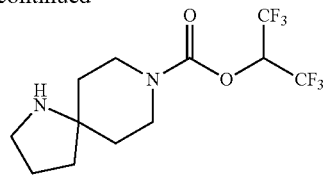

A flask was charged with 1-(t-butyl) 8-(1,1,1,3,3,3-hexafluoropropan-2-yl) 1,8-diazaspiro[4.5]decane-1,8-dicarboxylate (1.58 g, 3.64 mmol, 1.00 equiv), 1,4-dioxane (15 mL) and concentrated hydrochloric acid (5 mL), as described in Example 9, Step 5. The resulting solution was stirred overnight at room temperature and concentrated under reduced pressure to provide 1.15 g (crude) of 1,1,1,3,3,3-hexafluoropropan-2-yl 1,8-diazaspiro[4.5]decane-8-carboxylate as an off-white solid. LCMS (ESI, m/z): 335 [M+H]$^+$.

Step 3: Synthesis of 5-methylbenzo[b]thiophene-2-carboxylic acid

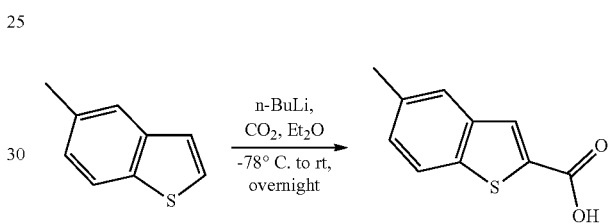

A round-bottom flask was charged with 5-methyl-1-benzothiophene (296 mg, 2.00 mmol, 1.00 equiv) and ether (20 mL). n-Butyllithium (2.0 mL, 5.00 mmol, 2.50 equiv, 2.5M in hexane) was added dropwise at −78° C. The mixture was stirred for 0.5 h at −78° C. and charged with dried carbon dioxide (produced by sodium bicarbonate and concentrated sulfuric acid). The resulting solution was stirred for 15 min at −78° C. and stirred overnight at room temperature. Ice water (20 mL) was added at 0° C. and the pH value was adjusted to 3-4 with hydrochloric acid solution (1 mol/L). The mixture was extracted with ether (3×20 mL) and the organic layers were combined, dried over anhydrous sodium sulfate and concentrated under reduced pressure to provide 91.0 mg (24% yield) of 5-methylbenzo[b]thiophene-2-carboxylic acid as a light yellow solid. LCMS (ESI, m/z): 191 [M−H]$^+$.

Step 4: Synthesis of 1,1,1,3,3,3-hexafluoropropan-2-yl 1-(5-methylbenzo[b]thiophene-2-carbonyl)-1,8-diazaspiro[4.5]decane-8-carboxylate

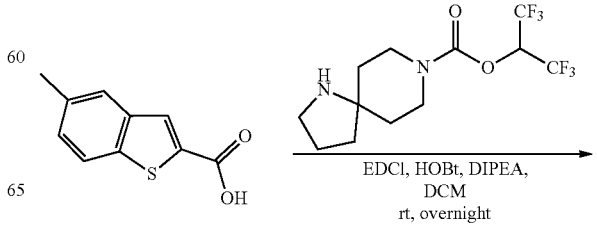

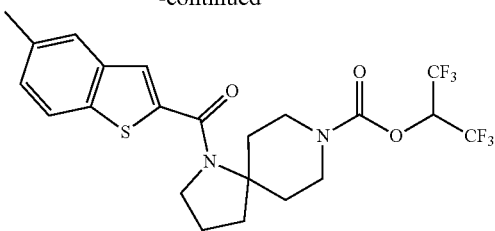

A vial was charged with 5-methylbenzo[b]thiophene-2-carboxylic acid (91.0 mg, 0.470 mmol, 1.00 equiv), DCM (10 mL), N,N-diisopropylethylamine (122 mg, 0.940 mmol, 2.00 equiv), 1-hydroxybenzotrizole (64.0 mg, 0.470 mmol, 1.00 equiv), N-(3-dimethylaminopropyl)-N'-ethylcarbodiimide hydrochloride (91.0 mg, 0.470 mmol, 1.00 equiv) and 1,1,1,3,3,3-hexafluoropropan-2-yl 1,8-diazaspiro[4.5]decane-8-carboxylate (159 mg, 0.480 mmol, 1.00 equiv). The resulting solution was stirred overnight at room temperature and quenched by water (10 mL), as described in Example 15, Step 3. The crude product was purified by reverse phase HPLC to provide 71.8 mg (30% yield) of 1,1,1,3,3,3-hexafluoropropan-2-yl 1-(5-methylbenzo[b]thiophene-2-carbonyl)-1,8-diazaspiro[4.5]decane-8-carboxylate as a white solid. $^1$H NMR (300 MHz, Chloroform-d) δ 7.67-7.82 (m, 1H), 7.50-7.67 (m, 2H), 7.2-7.23 (m, 1H), 5.77-5.89 (m, 1H), 4.08-4.23 (m, 2H), 3.82-3.97 (m, 2H), 2.94-3.30 (m, 4H), 2.46 (s, 3H), 2.03-2.20 (m, 2H), 1.90-2.03 (m, 2H), 1.42-1.55 (m, 2H). LCMS (ESI, m/z): 509 [M+H]$^+$.

Example 18: 1,1,1,3,3,3-Hexafluoropropan-2-yl 4-(7-cyclopropyl-N-methyl-5,6,7,8-tetrahydroimidazo[1,2-a]pyrazine-2-carboxamido)-4-methylpiperidine-1-carboxylate

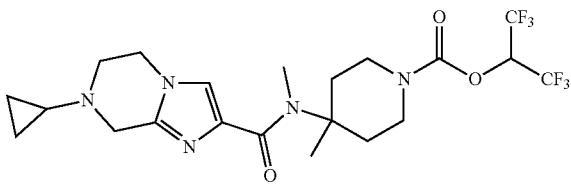 [SMILES: CN(C(=O)c1cn2c(n1)CN(C1CC1)CC2)C1(C)CCN(C(=O)OC(C(F)(F)F)C(F)(F)F)CC1]

Step 1: Synthesis of methyl 5,6,7,8-tetrahydroimidazo[1,2-a]pyrazine-2-carboxylate

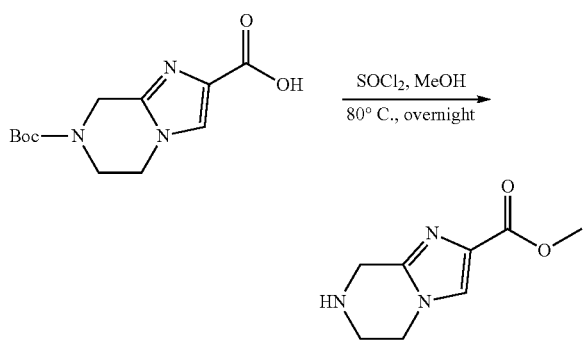

A flask was charged with MeOH (25 mL). Thionyl chloride (5 mL) was added dropwise at room temperature. 7-(t-Butoxycarbonyl)-5,6,7,8-tetrahydroimidazo[1,2-a]pyrazine-2-carboxylic acid (2.50 g, 9.35 mmol, 1.00 equiv) was added, as described in Example 14, Step 3 to provide 2.16 g (crude) of methyl 5H,6H,7H,8H-imidazo[1,2-a]pyrazine-2-carboxylate as a brown solid. LCMS (ESI, m/z): 182 [M+H]$^+$.

Step 2: Synthesis of methyl 7-cyclopropyl-5,6,7,8-tetrahydroimidazo[1,2-a]pyrazine-2-carboxylate

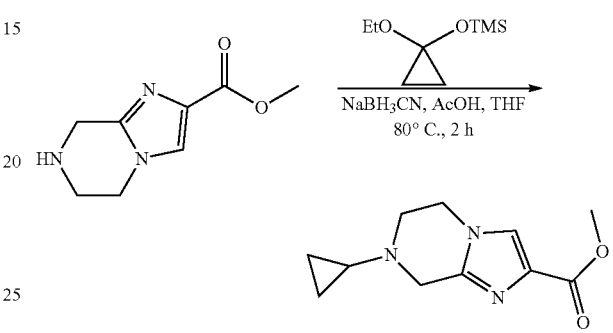

A flask was charged with methyl 5H,6H,7H,8H-imidazo[1,2-a]pyrazine-2-carboxylate (2.16 g, 11.9 mmol, 1.00 equiv), (1-ethoxycyclopropoxy)trimethylsilane (7.27 g, 41.7 mmol, 3.50 equiv), THF (25 mL), AcOH (7.16 g, 119 mmol, 10.0 equiv), and sodium cyanoborohydride (2.26 g, 36.0 mmol, 3.00 equiv). The resulting solution was stirred for 2 h at 80° C. and quenched with water (25 mL), as described in Example 2, Step 1. The residue was chromatographed to provide 2.00 g (97% yield for two steps) of methyl 7-cyclopropyl-5,6,7,8-tetrahydroimidazo[1,2-a]pyrazine-2-carboxylate as a yellow oil. LCMS (ESI, m/z): 222 [M+H]$^+$.

Step 3: Synthesis of 7-cyclopropyl-5,6,7,8-tetrahydroimidazo[1,2-a]pyrazine-2-carboxylic acid

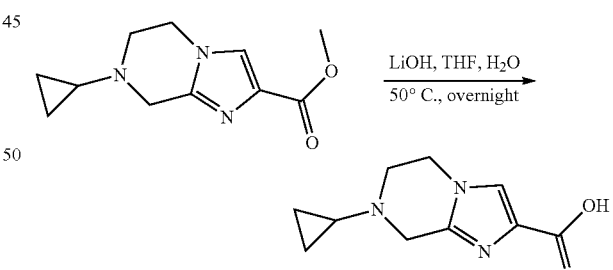

A flask was charged with methyl 7-cyclopropyl-5,6,7,8-tetrahydroimidazo[1,2-a]pyrazine-2-carboxylate (1.90 g, 8.59 mmol, 1.00 equiv), lithium hydroxide (1.03 g, 43.0 mmol, 5.00 equiv), THF (16 mL), and water (4 mL). The resulting solution was stirred overnight at 50° C. The pH value of the solution was adjusted to 5.0 with hydrochloric acid (1 mol/L), as described in Example 3, Step 2. The resulting mixture was concentrated under reduced pressure to provide 2.10 g (crude) of 7-cyclopropyl-5,6,7,8-tetrahydroimidazo[1,2-a]pyrazine-2-carboxylic acid as a yellow oil. LCMS (ESI, m/z): 208 [M+H]$^+$.

Step 4: Synthesis of 1,1,1,3,3,3-hexafluoropropan-2-yl 4-((t-butoxycarbonyl)amino)-4-methylpiperidine-1-carboxylate

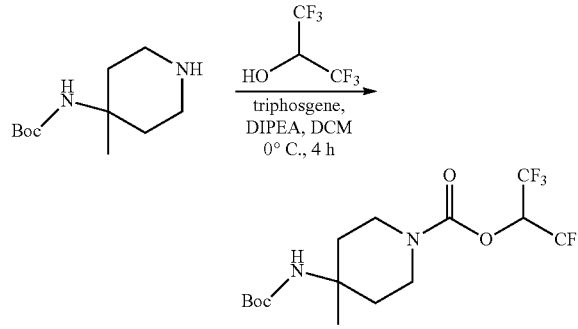

A flask was charged with triphosgene (12.2 g, 41.1 mmol, 1.50 equiv), DCM (50 mL), 1,1,1,3,3,3-hexafluoropropan-2-ol (20.6 g, 122 mmol, 4.50 equiv). N,N-diisopropylethylamine (17.6 g, 136 mmol, 5.00 equiv) was added dropwise at 0° C. The resulting solution was stirred for 2 h at 0° C. t-Butyl N-(4-methylpiperidin-4-yl)carbamate (5.84 g, 27.2 mmol, 1.00 equiv) was added. The resulting solution was stirred for 2 h at 0° C. and quenched with water (100 mL), as described in Example 6, Step 4. The residue was chromatographed on a silica gel column to provide 4.90 g (44% yield) of 1,1,1,3,3,3-hexafluoropropan-2-yl 4-((t-butoxycarbonyl)amino)-4-methylpiperidine-1-carboxylate as a yellow oil. LCMS (ESI, m/z): 409 [M+H]$^+$.

Step 5: Synthesis of 1,1,1,3,3,3-hexafluoropropan-2-yl 4-amino-4-methylpiperidine-1-carboxylate

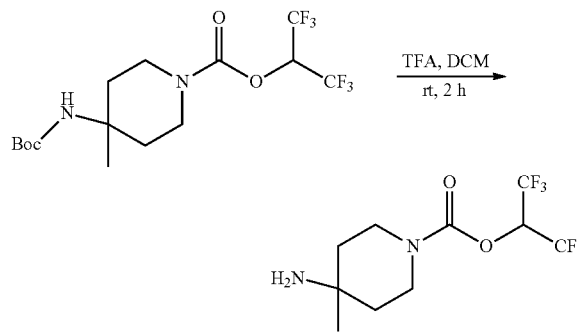

A flask was charged with 1,1,1,3,3,3-hexafluoropropan-2-yl 4-((t-butoxycarbonyl)amino)-4-methylpiperidine-1-carboxylate (5.83 g, 14.3 mmol, 1.00 equiv), DCM (50 mL), and TFA (10 mL), as described in Example 1, Step 1. The resulting solution was stirred for 2 h at room temperature and concentrated under reduced pressure to provide 4.40 g (quantitative) of 1,1,1,3,3,3-hexafluoropropan-2-yl 4-amino-4-methylpiperidine-1-carboxylate as a yellow oil. LCMS (ESI, m/z): 309 [M+H]$^+$.

Step 6: Synthesis of 1,1,1,3,3,3-hexafluoropropan-2-yl 4-((4-methoxybenzyl)amino)-4-methylpiperidine-1-carboxylate

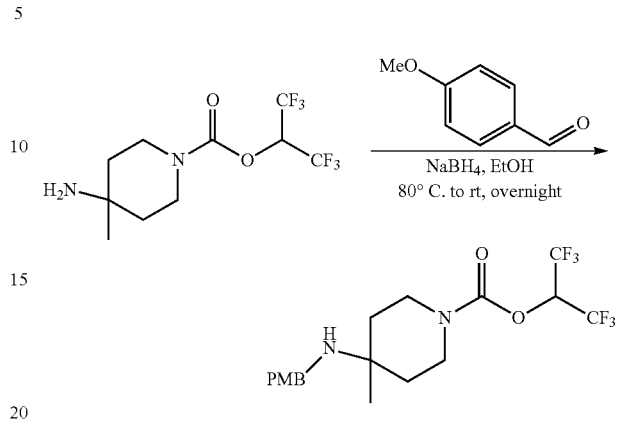

A flask was charged with 1,1,1,3,3,3-hexafluoropropan-2-yl 4-amino-4-methylpiperidine-1-carboxylate (4.40 g, 14.3 mmol, 1.00 equiv), 4-methoxybenzaldehyde (2.04 g, 15.0 mmol, 1.05 equiv), EtOH (20 mL). The resulting solution was stirred for 2 h at 80° C. and cooled to room temperature. Sodium borohydride (1.63 g, 43.1 mmol, 3.00 equiv) was added at room temperature. The resulting solution was stirred overnight at room temperature and quenched with water (20 mL). The resulting solution was extracted with DCM (3×20 mL) and the organic layers were combined, washed with brine (2×20 mL), dried over anhydrous sodium sulfate, filtered and concentrated under reduced pressure. The residue was chromatographed on a silica gel column to provide 3.00 g (49% yield) of 1,1,1,3,3,3-hexafluoropropan-2-yl 4-((4-methoxybenzyl)amino)-4-methylpiperidine-1-carboxylate as a white solid. LCMS (ESI, m/z): 429 [M+H]$^+$.

Step 7: Synthesis of 1,1,1,3,3,3-hexafluoropropan-2-yl 4-((4-methoxybenzyl)(methyl)amino)-4-methylpiperidine-1-carboxylate

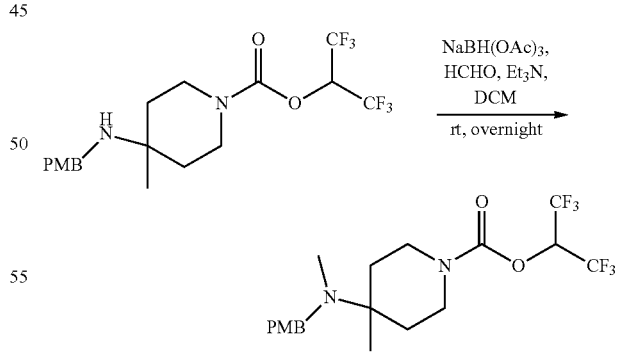

A flask was charged with 1,1,1,3,3,3-hexafluoropropan-2-yl 4-((4-methoxybenzyl)amino)-4-methylpiperidine-1-carboxylate (3.00 g, 7.00 mmol, 1.00 equiv), DCE (20 mL), triethylamine (2.12 g, 21.0 mmol, 3.00 equiv), and paraformaldehyde (2.10 g, 70.0 mmol, 10.0 equiv). The resulting solution was stirred for 1 h at room temperature. Sodium triacetoxyborohydride (4.66 g, 22.0 mmol, 3.00 equiv) was added. The resulting solution was stirred overnight at room temperature and quenched with water (20 mL), as described in Example 12, Step 1. The residue was chromatographed on a silica gel column to provide 2.70 g (87% yield) of 1,1,1,3,3,3-hexafluoropropan-2-yl 4-((4-methoxybenzyl)(methyl)amino)-4-methylpiperidine-1-carboxylate as a white solid. LCMS (ESI, m/z): 443 [M+H]+.

Step 8: Synthesis of 1,1,1,3,3,3-hexafluoropropan-2-yl 4-methyl-4-(methylamino)piperidine-1-carboxylate

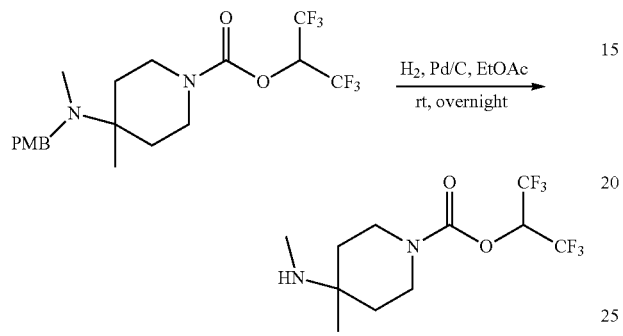

A flask was charged with 1,1,1,3,3,3-hexafluoropropan-2-yl 4-((4-methoxybenzyl)(methyl)amino)-4-methylpiperidine-1-carboxylate (3.30 g, 7.46 mmol, 1.00 equiv), EtOAc (30 mL), and palladium-on-carbon (1.0 g) and hydrogen was introduced in. The resulting solution was stirred overnight at room temperature. The solids were filtered out and the filtrate was concentrated under reduced pressure to provide 2.40 g (quantitative) of 1,1,1,3,3,3-hexafluoropropan-2-yl 4-methyl-4-(methylamino)piperidine-1-carboxylate as a yellow oil. LCMS (ESI, m/z): 323 [M+H]+.

Step 9: Synthesis of 1,1,1,3,3,3-hexafluoropropan-2-yl 4-(7-cyclopropyl-N-methyl-5,6,7,8-tetrahydroimidazo[1,2-a]pyrazine-2-carboxamido)-4-methylpiperidine-1-carboxylate

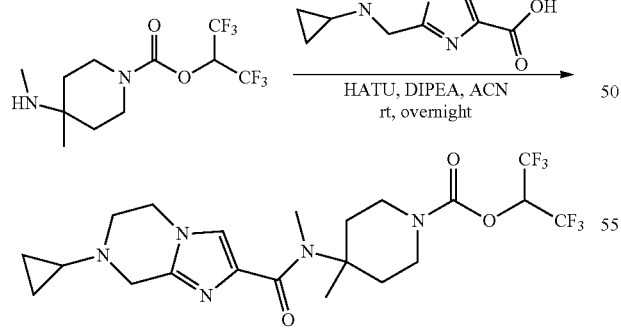

A flask was charged with 1,1,1,3,3,3-hexafluoropropan-2-yl 4-methyl-4-(methylamino)piperidine-1-carboxylate (141 mg, 0.438 mmol, 1.00 equiv), ACN (5 mL), N,N,N',N'-tetramethyl-O-(7-azabenzotriazol-1-yl)uronium hexafluorophospate (175 mg, 0.460 mmol, 1.05 equiv), N,N-diisopropylethylamine (142 mg, 1.10 mmol, 2.50 equiv), and 7-cyclopropyl-5,6,7,8-tetrahydroimidazo[1,2-a]pyrazine-2-carboxylic acid (100 mg, 0.483 mmol, 1.10 equiv). The resulting solution was stirred overnight at room temperature and quenched with water (5 mL), as described in Example 1, Step 2. The crude product (200 mg) was purified by reverse phase HPLC to provide 11.5 mg (5% yield) of 1,1,1,3,3,3-hexafluoropropan-2-yl 4-(7-cyclopropyl-N-methyl-5,6,7,8-tetrahydroimidazo[1,2-a]pyrazine-2-carboxamido)-4-methylpiperidine-1-carboxylate as a light yellow solid. 1H NMR (300 MHz, Chloroform-d) δ 7.32 (s, 1H), 5.70-5.79 (m, 1H), 3.99-4.03 (m, 2H), 3.94 (s, 2H), 3.72-3.78 (m, 2H), 3.32-3.44 (m, 2H), 3.08-3.12 (m, 5H), 2.58-2.63 (m, 2H), 1.90-1.96 (m, 1H), 1.65-1.73 (m, 2H), 1.42 (s, 3H), 0.52-0.62 (m, 4H). LCMS (ESI, m/z): 512 [M+H]+.

Example 19: 1,1,1,3,3,3-hexafluoropropan-2-yl 1-(4-cyano-1,3-dimethyl-1H-pyrazole-5-carbonyl)-1,8-diazaspiro[4.5]decane-8-carboxylate

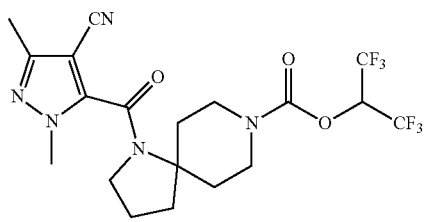 [SMILES: Cc1nn(C)c(C(=O)N2CCCC23CCN(C(=O)OC(C(F)(F)F)C(F)(F)F)CC3)c1C#N]

Step 1: Synthesis of 1-(4-bromo-1,3-dimethyl-1H-pyrazole-5-carbonyl)-1,8-diazaspiro[4.5]decane-8-carboxylic acid

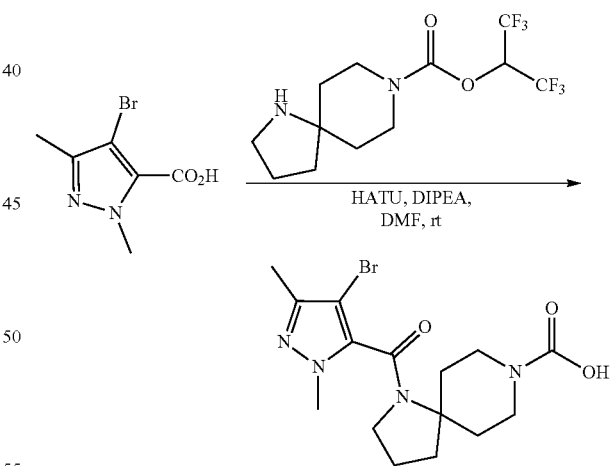

A vial was charged with 1,1,1,3,3,3-hexafluoropropan-2-yl 1,8-diazaspiro[4.5]decane-8-carboxylate (500 mg, 1.50 mmol, 1.00 equiv), ACN (7.5 mL), 4-bromo-1,3-dimethyl-1H-pyrazole-5-carboxylic acid (440 mg, 1.65 mmol, 1.10 equiv), HATU (597 mg, 1.57 mmol, 1.05 equiv), and N,N-diisopropylethylamine (483 mg, 3.74 mmol, 2.50 equiv). The vial was closed with a septum cap and stirred at room temperature overnight. The reaction mixture was concentrated in vacuo to half of the original volume and purified by silica gel chromatography, providing 1,1,1,3,3,3-hexafluoropropan-2-yl 1-(7-(tert-butoxycarbonyl)-5,6,7,8-tetrahydroimidazo[1,2-a]pyrazine-2-carbonyl)-1,8-diazaspiro[4.5]decane-8-carboxylate (804 mg, 92%). LCMS (ESI, m/z): 584 [M+H]+.

Step 2: Synthesis of 1,1,1,3,3,3-hexafluoropropan-2-yl 1-(4-cyano-1,3-dimethyl-1H-pyrazole-5

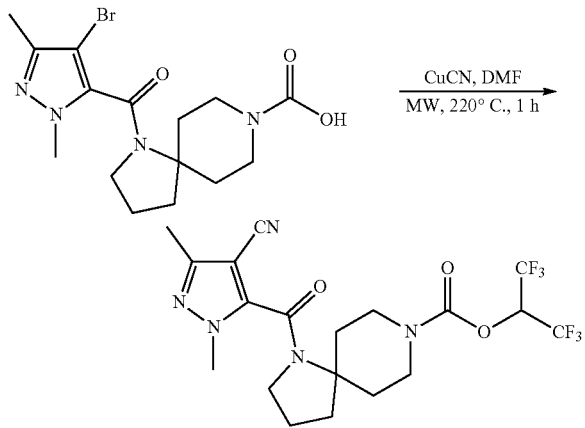

To a microwave vial was added 1-(4-bromo-1,3-dimethyl-1H-pyrazole-5-carbonyl)-1,8-diazaspiro[4.5]decane-8-carboxylic acid (170 mg, 0.32 mmol, 1.0 equiv) and DMF (1.25 mL). Copper cyanide (142 mg, 1.59 mmol, 5.00 equiv) was added in one portion, and the vial was capped and incubated in the microwave at 220° C. for 1 h. The crude product was purified by silica gel chromatography followed by reverse phase HPLC and lyophilization to provide 1,1,1,3,3,3-hexafluoropropan-2-yl 1-(4-cyano-1,3-dimethyl-1H-pyrazole-5-carbonyl)-1,8-diazaspiro[4.5]decane-8-carboxylate (75 mg, 49%). $^1$H NMR (400 MHz, Chloroform-d) δ 5.81-5.70 (m, 1H), 4.32-4.14 (m, 2H), 3.85 (s, 3H), 3.66-3.53 (m, 2H), 3.13-2.91 (m, 4H), 2.36 (s, 3H), 2.20-2.02 (m, 2H), 1.98-1.87 (m, 2H), 1.57-1.49 (m, 2H). LCMS (ESI, m/z): 482 [M+H]+.

Example 20: 1,1,1,3,3,3-hexafluoropropan-2-yl 4-(7-cyclopropyl-N-methyl-5,6,7,8-tetrahydro-[1,2,4]triazolo[4,3-a]pyrazine-3-carboxamido)-4-methylpiperidine-1-carboxylate

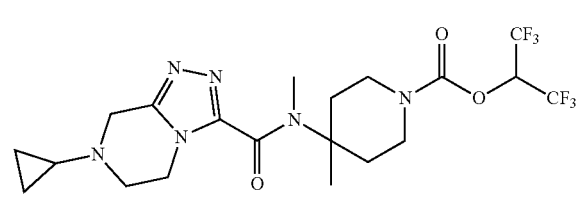 [SMILES: CN(C(=O)c1nnc2n1CCN(C1CC1)C2)C1(C)CCN(C(=O)OC(C(F)(F)F)C(F)(F)F)CC1]

Step 1: Synthesis of benzyl 4-((t-butoxycarbonyl)amino)-4-methylpiperidine-1-carboxylate

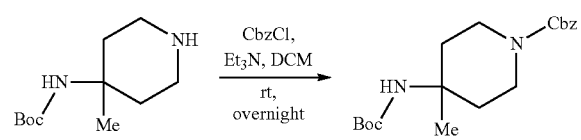

A flask was charged with benzyl chloroformate (3.12 g, 18.3 mmol, 1.30 equiv), t-butyl N-(4-methylpiperidin-4-yl)carbamate (3.00 g, 14.0 mmol, 1.00 equiv), triethylamine (4.25 g, 42.0 mmol, 3.00 equiv) and DCM (30 mL). The resulting solution was stirred overnight at room temperature and quenched by water (30 mL), as described in Example 1, Step 1. The residue was chromatographed on a silica gel column to provide 2.72 g (56% yield) of benzyl 4-((t-butoxycarbonyl)amino)-4-methylpiperidine-1-carboxylate as a white oil. LCMS (ESI, m/z): 349 [M+H]+.

Step 2: Synthesis of benzyl 4-((t-butoxycarbonyl)(methyl)amino)-4-methylpiperidine-1-carboxylate

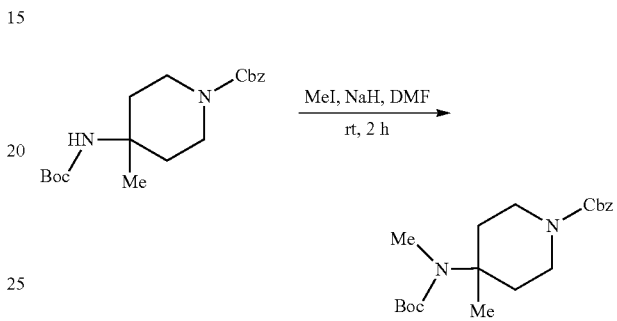

A flask was charged with benzyl 4-((t-butoxycarbonyl)amino)-4-methylpiperidine-1-carboxylate (2.72 g, 7.81 mmol, 1.00 equiv) and DMF (20 mL). Sodium hydride (60% in oil, 1.56 g, 39.1 mmol, 3.00 equiv) was added at 0° C. The resulting solution was stirred for 0.5 hours at room temperature and methyl iodide (1.66 g, 11.7 mmol, 1.50 equiv) was then added. The resulting solution was stirred overnight at room temperature and quenched by water (20 mL). The mixture was extracted with EtOAc (3×50 mL) and the organic layers were combined, washed with water (3×20 mL), dried over anhydrous sodium sulfate, filtered and concentrated under reduced pressure. The residue was chromatographed on a silica gel column to provide 2.00 g (71% yield) of benzyl 4-((t-butoxycarbonyl)(methyl)amino)-4-methylpiperidine-1-carboxylate as a white oil. LCMS (ESI, m/z): 363 [M+H]+.

Step 3: Synthesis of t-butyl methyl(4-methylpiperidin-4-yl)carbamate

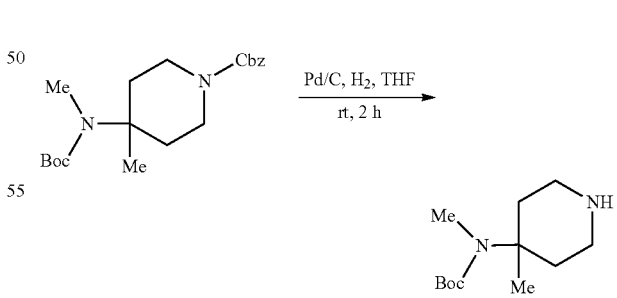

A flask was charged with benzyl 4-((t-butoxycarbonyl)(methyl)amino)-4-methylpiperidine-1-carboxylate (1.00 g, 2.76 mmol, 1.00 equiv), palladium-on-carbon (100 mg) and THF (10 mL) under hydrogen as described in Example 19, Step 8 to provide 0.630 g (crude) of t-butyl methyl(4-methylpiperidin-4-yl)carbamate as a white oil. LCMS (ESI, m/z): 229 [M+H]+.

Step 4: Synthesis of 1,1,1,3,3,3-hexafluoropropan-2-yl 4-((t-butoxycarbonyl)methyl)amino)-4-methylpiperidine-1-carboxylate

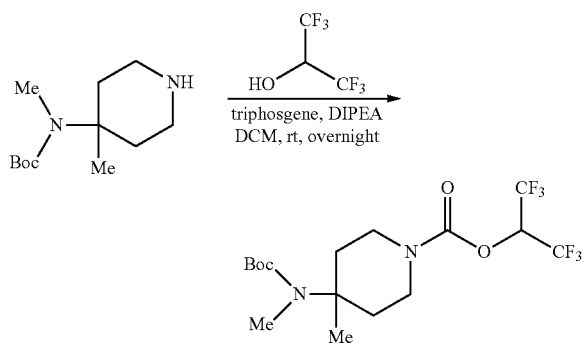

A flask was charged with 1,1,1,3,3,3-hexafluoropropan-2-ol (1.39 g, 8.27 mmol, 3.00 equiv), triphosgene (0.574 g, 1.93 mmol, 0.70 equiv) and DCM (20 mL). Then N,N-diisopropylethylamine (1.07 g, 8.28 mmol, 3.00 equiv) was added dropwise at 0° C. The resulting solution was stirred for 2 hours at room temperature. t-Butyl methyl(4-methylpiperidin-4-yl)carbamate (0.630 g, 2.76 mmol, 1.00 equiv) was then added. The resulting solution was stirred overnight at room temperature and quenched by water (20 mL), as described in Example 6, Step 4. The residue was chromatographed on a silica gel column to provide 0.400 g (34% yield) of 1,1,1,3,3,3-hexafluoropropan-2-yl 4-((t-butoxycarbonyl)(methyl)amino)-4-methylpiperidine-1-carboxylate as a white oil. LCMS (ESI, m/z): 423 [M+H]$^+$.

Step 5: Synthesis of 1,1,1,3,3,3-hexafluoropropan-2-yl 4-methyl-4-(methylamino)piperidine-1-carboxylate

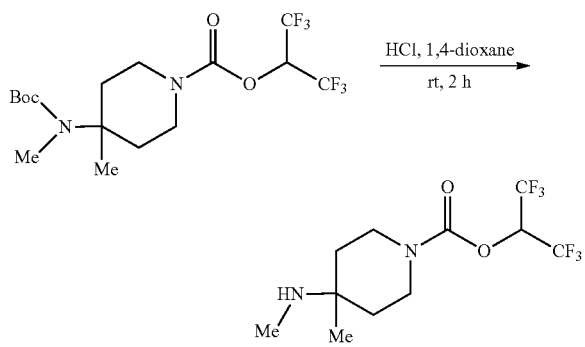

A flask was charged with 1,1,1,3,3,3-hexafluoropropan-2-yl 4-((1-butoxycarbonyl)(methyl)amino)-4-methylpiperidine-1-carboxylate (400 mg, 0.950 mmol, 1.00 equiv), concentrated hydrochloric acid (1 mL) and 1,4-dioxane (3 mL). The resulting solution was stirred for 2 hours at room temperature and then concentrated under reduced pressure as described in Example 8, Step 5 to provide 305 mg (quantitative) of 1,1,1,3,3,3-hexafluoropropan-2-yl 4-methyl-4-(methylamino)piperidine-1-carboxylate as a white solid. LCMS (ESI, m/z): 323 [M+H]$^+$.

Step 6: Synthesis of ethyl 7-cyclopropyl-5,6,7,8-tetrahydro-[1,2,4]triazolo[4,3-a]pyrazine-3-carboxylate

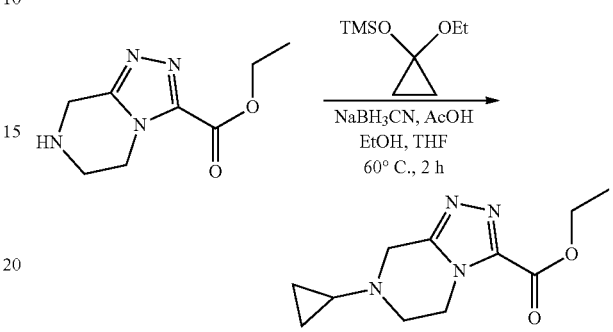

A flask was charged with ethyl 5H,6H,7H,8H-[1,2,4]triazolo[4,3-a]pyrazine-3-carboxylate (300 mg, 1.53 mmol, 1.00 equiv), (1-ethoxycyclopropoxy)trimethylsilane (799 mg, 4.58 mmol, 3.00 equiv), sodium cyanoborohydride (289 mg, 4.60 mmol, 3.00 equiv), acetic acid (918 mg, 15.3 mmol, 10.0 equiv), EtOH (5 mL) and THF (5 mL). The resulting solution was stirred for 2 hours at 60° C. and quenched by water (10 mL), as described in Example 2, Step 1. The residue was chromatographed on a silica gel column to provide 217 mg (60% yield) of ethyl 7-cyclopropyl-5,6,7,8-tetrahydro-[1,2,4]triazolo[4,3-a]pyrazine-3-carboxylate as a yellow solid. LCMS (ESI, m/z): 237 [M+H]$^+$.

Step 7: Synthesis of 7-cyclopropyl-5,6,7,8-tetrahydro-[1,2,4]triazolo[4,3-a]pyrazine-3-carboxylic acid

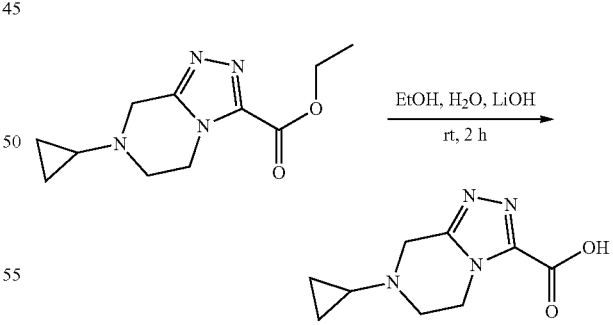

A flask was charged with ethyl 7-cyclopropyl-5,6,7,8-tetrahydro-[1,2,4]triazolo[4,3-a]pyrazine-3-carboxylate (217 mg, 0.920 mmol, 1.00 equiv), lithium hydroxide (66.2 mg, 2.76 mmol, 3.00 equiv), EtOH (5 mL) and water (1 mL), as described in Example 3, Step 2 to provide 191 mg (crude) of 7-cyclopropyl-5,6,7,8-tetrahydro-[1,2,4]triazolo[4,3-a]pyrazine-3-carboxylic acid as a yellow solid. LCMS (ESI, m/z): 209 [M+H]$^+$.

Step 8: Synthesis of 1,1,1,3,3,3-hexafluoropropan-2-yl 4-(7-cyclopropyl-N-methyl-5,6,7,8-tetrahydro-[1,2,4]triazolo[4,3-a]pyrazine-3-carboxamido)-4-methylpiperidine-1-carboxylate

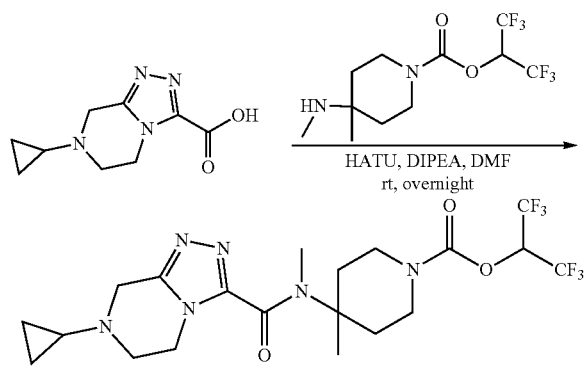

A flask was charged with 7-cyclopropyl-5,6,7,8-tetrahydro-[1,2,4]triazolo[4,3-a]pyrazine-3-carboxylic acid (191 mg, 0.920 mmol, 1.00 equiv), 1,1,1,3,3,3-hexafluoropropan-2-yl 4-methyl-4-(methylamino)piperidine-1-carboxylate (295 mg, 0.920 mmol, 1.00 equiv), o-(7-azabenzotriazol-1-yl)-N,N,N',N'-tetramethyluronium hexafluorophosphate (523 mg, 1.38 mmol, 1.50 equiv), N,N-diisopropylethylamine (356 mg, 2.75 mmol, 3.00 equiv) and DMF (5 mL). The resulting solution was stirred overnight at room temperature and quenched by water (10 mL), as described in Example 1, Step 2. The crude product was purified by reverse phase HPLC to provide 176.1 mg (37% yield) of 1,1,1,3,3,3-hexafluoropropan-2-yl 4-(7-cyclopropyl-N-methyl-5,6,7,8-tetrahydro-[1,2,4]triazolo[4,3-a]pyrazine-3-carboxamido)-4-methylpiperidine-1-carboxylate as a white solid. $^1$H NMR (300 MHz, Methanol-$d_4$) δ 6.05-6.21 (m, 1H), 4.12-4.23 (t, J=5.8 Hz, 2H), 4.00 (s, 2H), 3.70-3.83 (m, 2H), 3.31-3.51 (m, 2H), 3.03-3.21 (m, 5H), 2.54-2.71 (m, 2H), 1.95-2.04 (m, 1H), 1.70-1.86 (m, 2H), 1.46 (s, 3H), 0.58-0.69 (m, 2H), 0.49-0.58 (m, 2H). LCMS (ESI, m/z): 513 [M+H]$^+$.

Example 21: 1,1,1,3,3,3-Hexafluoropropan-2-yl 1-(7-(2-hydroxy-2-methylpropyl)-5,6,7,8-tetrahydro-imidazo[1,2-a]pyrazine-2-carbonyl)-1,8-diazaspiro[4.5]decane-8-carboxylate

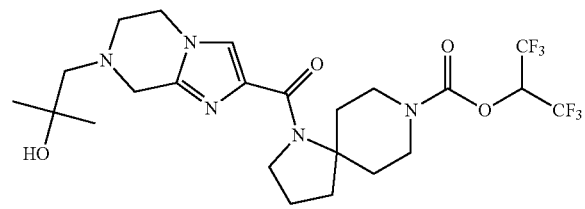 [SMILES: CC(C)(O)CN1CCn2cc(C(=O)N3CCCC34CCN(C(=O)OC(C(F)(F)F)C(F)(F)F)CC4)nc2C1]

Step 1: Synthesis of 7-(t-butoxycarbonyl)-5,6,7,8-tetrahydroimidazo[1,2-a]pyrazine-2-carboxylic acid

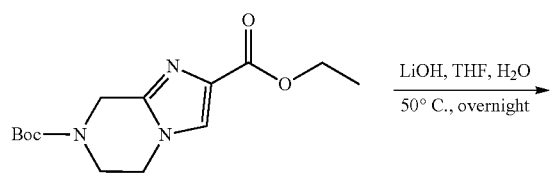

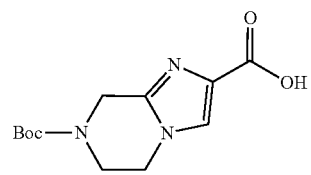

A flask was charged with 7-(t-butyl) 2-ethyl 5,6-dihydroimidazo[1,2-a]pyrazine-2,7(8H)-dicarboxylate (600 mg, 2.03 mmol, 1.00 equiv), lithium hydroxide (244 mg, 10.2 mmol, 5.00 equiv), THF (8.0 mL), and water (2.0 mL). The reaction mixture was stirred overnight at 50° C. The pH value of the solution was adjusted to 5 with hydrochloric acid (1.0 M). The resulting solution was extracted with DCM (5×20 mL) and the organic layers were combined, dried over anhydrous Na$_2$SO$_4$, filtered and concentrated under reduced pressure to provide 450 mg (83% yield) of 7-(t-butoxycarbonyl)-5,6,7,8-tetrahydroimidazo[1,2-a]pyrazine-2-carboxylic acid. LCMS (ESI, m/z): 268 [M+H]$^+$.

Step 2: Synthesis of 1,1,1,3,3,3-hexafluoropropan-2-yl 1-(7-(t-butoxycarbonyl)-5,6,7,8-tetrahydroimidazo[1,2-a]pyrazine-2-carbonyl)-1,8-diazaspiro[4.5]decane-8-carboxylate

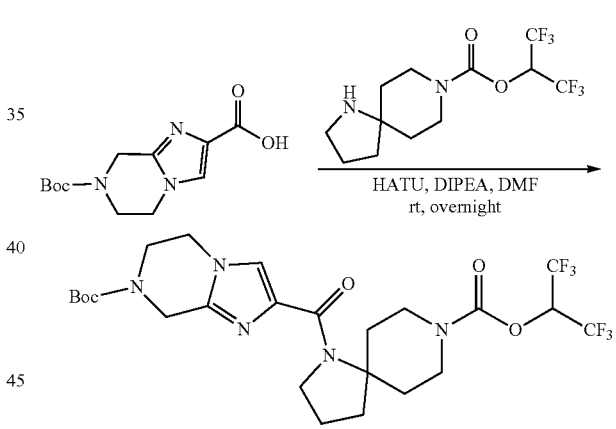

A flask was charged with 7-(t-butoxycarbonyl)-5,6,7,8-tetrahydroimidazo[1,2-a]pyrazine-2-carboxylic acid (140 mg, 0.524 mmol, 1.00 equiv), HATU (299 mg, 0.786 mmol, 1.50 equiv), DIPEA (203 mg, 1.57 mmol, 3.00 equiv), and DMF (10 mL). The mixture was stirred for 30 min at room temperature prior to addition of 1,1,1,3,3,3-hexafluoropropan-2-yl 1,8-diazaspiro[4.5]decane-8-carboxylate (263 mg, 0.786 mmol, 1.50 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The residue was chromatographed on a silica gel column to provide 260 mg (85% yield) of 1,1,1,3,3,3-hexafluoropropan-2-yl 1-(7-(t-butoxycarbonyl)-5,6,7,8-tetrahydroimidazo[1,2-a]pyrazine-2-carbonyl)-1,8-diazaspiro[4.5]decane-8-carboxylate. LCMS (ESI, m/z): 584 [M+H]$^+$.

Step 3: Synthesis of 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate

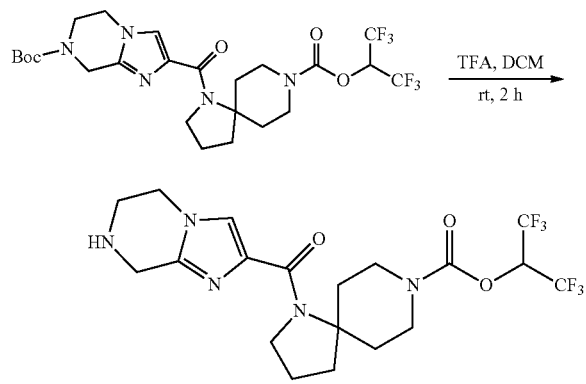

A flask was charged with 1,1,1,3,3,3-hexafluoropropan-2-yl 1-(7-(t-butoxycarbonyl)-5,6,7,8-tetrahydroimidazo[1,2-a]pyrazine-2-carbonyl)-1,8-diazaspiro[4.5]decane-8-carboxylate (260 mg, 0.446 mmol, 1.00 equiv), and DCM (5 mL). Trifluoroacetic acid (1.0 mL) was added dropwise at 0° C. The resulting solution was stirred for 2 h at room temperature and concentrated under reduced pressure to provide 215 mg (quantitative) of 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate. LCMS (ESI, m/z): 484 [M+H]$^+$.

Step 4: Synthesis of 1,1,1,3,3,3-hexafluoropropan-2-yl 1-(7-(2-hydroxy-2-methylpropyl)-5,6,7,8-tetrahydroimidazo[1,2-a]pyrazine-2-carbonyl)-1,8-diazaspiro[4.5]decane-8-carboxylate

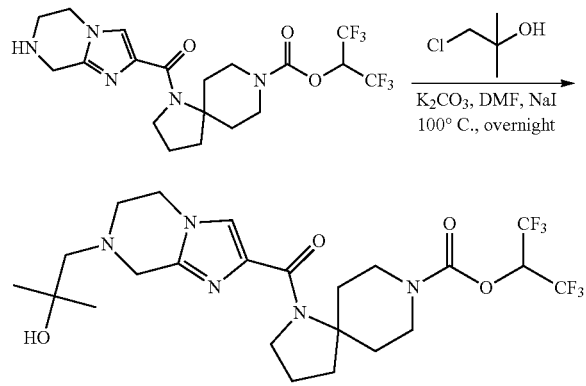

A flask was charged with 1,1,1,3,3,3-hexafluoropropan-2-yl 1-(5,6,7,8-tetrahydroimidazo[1,2-a]pyrazine-2-carbonyl)-1,8-diazaspiro[4.5]decane-8-carboxylate (175 mg, 0.362 mmol, 1.00 equiv), 1-chloro-2-methylpropan-2-ol (156 mg, 1.45 mmol, 4.00 equiv), potassium carbonate (150 mg, 1.09 mmol, 3.00 equiv), sodium iodide (163 mg, 1.09 mmol, 3.00 equiv), and DMF (10 mL). The reaction mixture was stirred overnight at 100° C. and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The crude product (300 mg) was purified by preparative HPLC to afford 26.2 mg (13% yield) of 1,1,1,3,3,3-hexafluoropropan-2-yl 1-(7-(2-hydroxy-2-methylpropyl)-5,6,7,8-tetrahydroimidazo[1,2-a]pyrazine-2-carbonyl)-1,8-diazaspiro[4.5]decane-8-carboxylate. $^1$H NMR (300 MHz, Chloroform-d) δ 7.43 (s, 1H), 5.82-5.73 (m, 1H), 4.23-4.16 (m, 2H), 4.11-4.03 (m, 4H), 3.90 (s, 2H), 3.24-2.96 (m, 6H), 2.57 (s, 2H), 2.42 (s, 1H), 2.04-1.98 (m, 2H), 1.94-1.85 (m, 2H), 1.50-1.44 (m, 2H), 1.25 (s, 6H). LCMS (ESI, m/z): 556 [M+H]$^+$.

Example 22: 1,1,1,3,3,3-Hexafluoropropan-2-yl 4-(7-isopropyl-N-methyl-5,6,7,8-tetrahydroimidazo[1,2-a]pyrazine-2-carboxamido)-4-methylpiperidine-1-carboxylate

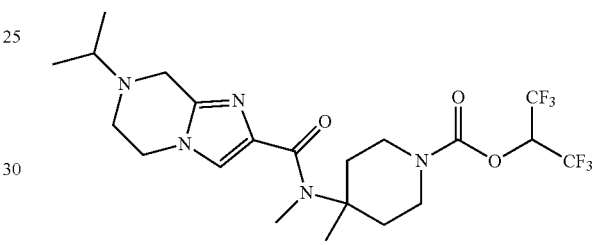

Step 1: Synthesis of benzyl 4-((t-butoxycarbonyl)amino)-4-methylpiperidine-1-carboxylate

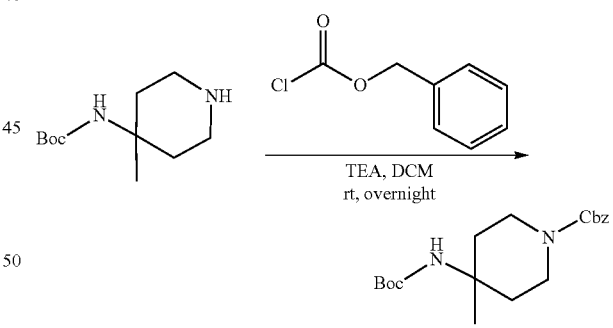

A flask was charged with t-butyl N-(4-methylpiperidin-4-yl)carbamate (3.00 g, 14.0 mmol, 1.00 equiv), benzyl chloroformate (2.88 g, 16.8 mmol, 1.20 equiv), and DCM (30 mL). Triethylamine (4.25 g, 43.0 mmol, 3.00 equiv) was added dropwise at room temperature, and the reaction mixture was stirred overnight at room temperature prior to quenching with water (30 mL). The resulting solution was extracted with DCM (3×50 mL) and the organic layers were combined, washed with brine (2×30 mL), dried over anhydrous Na$_2$SO$_4$, filtered and concentrated under reduced pressure. The residue was chromatographed on a silica gel column to provide 3.24 g (66% yield) of benzyl 4-((t- butoxycarbonyl)amino)-4-methylpiperidine-1-carboxylate. LCMS (ESI, m/z): 349 [M+H]$^+$.

Step 2: Synthesis of benzyl 4-((t-butoxycarbonyl)(methyl)amino)-4-methylpiperidine-1-carboxylate

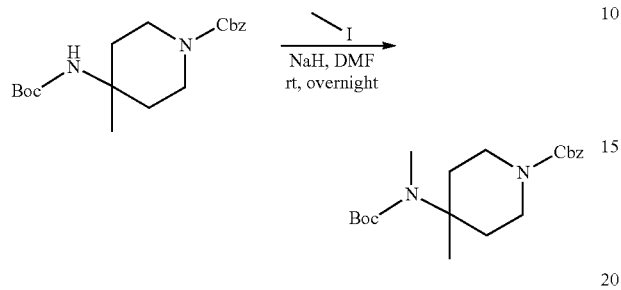

A flask was charged with benzyl 4-((t-butoxycarbonyl)amino)-4-methylpiperidine-1-carboxylate (3.24 g, 4.00 mmol, 1.00 equiv), and DMF (35 mL). Sodium hydride (1.12 g 27.9 mmol, 3.00 equiv, 60% in mineral oil) was added at 0° C., and the mixture was stirred for 30 min at 0° C. prior to addition of iodomethane (1.98 g, 14.0 mmol, 1.50 equiv). The reaction mixture was stirred overnight at room temperature and quenched with water (40 mL). The resulting solution was extracted with EtOAc (3×50 mL) and the organic layers were combined, washed with brine (30 mL), dried over anhydrous Na$_2$SO$_4$, filtered and concentrated under reduced pressure. The residue was chromatographed on a silica gel column to provide 2.00 g (59% yield) of benzyl 4-((t-butoxycarbonyl)(methyl)amino)-4-methylpiperidine-1-carboxylate. LCMS (ESI, m/z): 363 [M+H]$^+$.

Step 3: Synthesis of t-butyl methyl(4-methylpiperidin-4-yl)carbamate

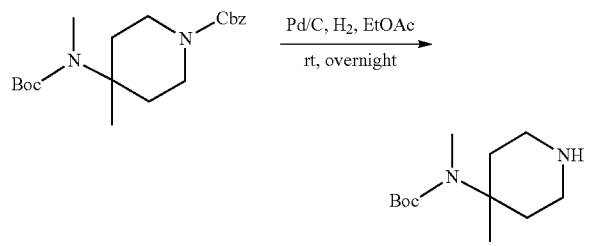

A flask was charged with benzyl 4-((t-butoxycarbonyl)(methyl)amino)-4-methylpiperidine-1-carboxylate (4.00 g, 11.0 mmol, 1.00 equiv), palladium (10% on activated carbon, 1.80 g), and EtOAc (40 mL). The contents of the flask were placed under an atmosphere of hydrogen (3 atm) and allowed to overnight at room temperature. The solids were filtered, and the resulting mixture was concentrated under reduced pressure to provide 2.16 g (86% yield) of t-butyl methyl(4-methylpiperidin-4-yl)carbamate. LCMS (ESI, m/z): 229 [M+H]$^+$.

Step 4: Synthesis of 1,1,1,3,3,3-hexafluoropropan-2-yl 4-((t-butoxycarbonyl)(methyl)amino)-4-methylpiperidine-1-carboxylate

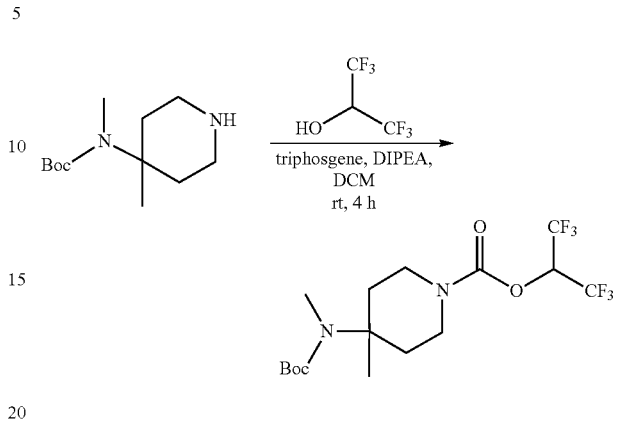

A flask was charged with triphosgene (1.41 g, 4.74 mmol, 0.50 equiv), 1,1,1,3,3,3-hexafluoropropan-2-ol (3.18 g, 18.9 mmol, 2.00 equiv), and DCM (25 mL). DIPEA (4.89 g, 37.9 mmol, 4.00 equiv) was added dropwise at 0° C., and the mixture was stirred for 2 h at room temperature prior to addition of t-butyl methyl(4-methylpiperidin-4-yl)carbamate (2.16 g, 9.47 mmol, 1.00 equiv). The reaction mixture was stirred for 2 h at room temperature and quenched with water (30 mL). The resulting solution was extracted with DCM (3×50 mL) and the organic layers were combined, washed with brine (2×30 mL), dried over anhydrous Na$_2$SO$_4$, filtered and concentrated under reduced pressure. The residue was chromatographed on a silica gel column to provide 2.8 g (70% yield) of 1,1,1,3,3,3-hexafluoropropan-2-yl 4-((t-butoxycarbonyl)(methyl)amino)-4-methylpiperidine-1-carboxylate. LCMS (ESI, m/z): 423 [M+H]$^+$.

Step 5: Synthesis of 1,1,1,3,3,3-hexafluoropropan-2-yl 4-methyl-4-(methylamino)piperidine-1-carboxylate

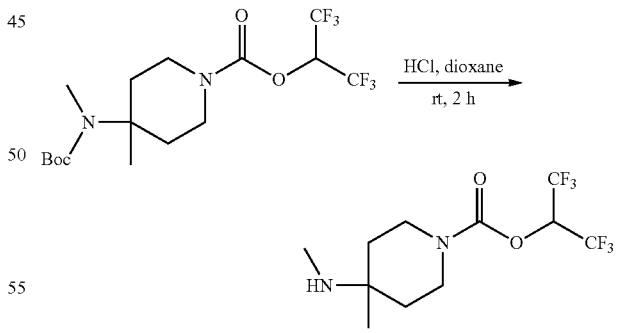

A flask was charged with 1,1,1,3,3,3-hexafluoropropan-2-yl 4-((t-butoxycarbonyl)(methyl)amino)-4-methylpiperidine-1-carboxylate (1.14 g, 0.900 mmol, 1.00 equiv), concentrated aqueous HCl (2.0 mL), and 1,4-dioxane (10 mL). The resulting solution was stirred for 2 h at room temperature and concentrated under reduced pressure to provide 868 mg (quantitative) of 1,1,1,3,3,3-hexafluoropropan-2-yl 4-methyl-4-(methylamino)piperidine-1-carboxylate. LCMS (ESI, m/z): 323 [M+H]$^+$.

Step 6: Synthesis of 7-(t-butoxycarbonyl)-5,6,7,8-tetrahydroimidazo[1,2-a]pyrazine-2-carboxylic acid

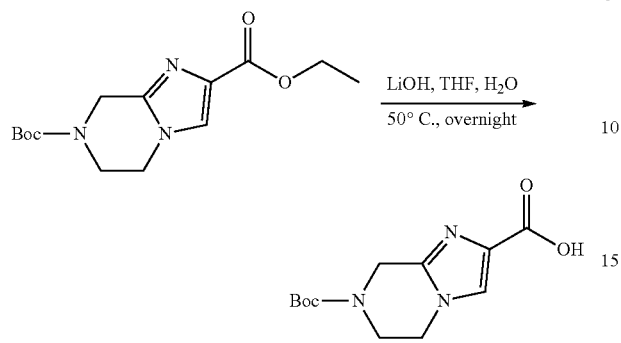

A flask was charged with 7-(t-butyl) 2-ethyl 5,6-dihydroimidazo[1,2-a]pyrazine-2,7(8H)-dicarboxylate (600 mg, 2.03 mmol, 1.00 equiv), LiOH (244 mg, 10.2 mmol, 5.00 equiv), THF (8 mL), and water (2 mL). The reaction mixture was stirred overnight at 50° C. The pH value of the solution was adjusted to 5 with HCl (1.0 M). The resulting solution was extracted with DCM (5×20 mL) and the organic layers were combined, dried over anhydrous Na$_2$SO$_4$, filtered and concentrated under reduced pressure to provide 480 mg (88% yield) of 7-(t-butoxycarbonyl)-5,6,7,8-tetrahydroimidazo[1,2-a]pyrazine-2-carboxylic acid. LCMS (ESI, m/z): 268 [M+H]$^+$.

Step 7: Synthesis of t-butyl 2-((1-(((1,1,1,3,3,3-hexafluoropropan-2-yl)oxy)carbonyl)-4-methylpiperidin-4-yl)(methyl)carbamoyl)-5,6-dihydroimidazo[1,2-a]pyrazine-7(8H)-carboxylate

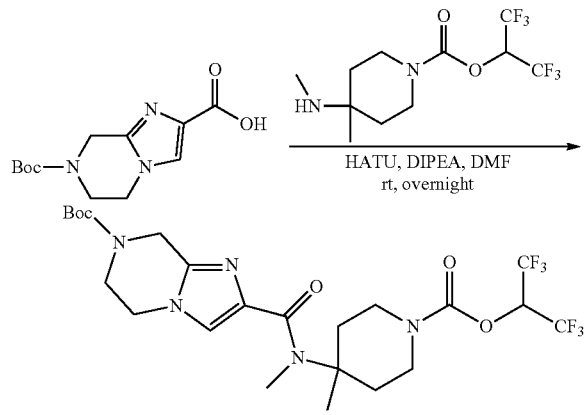

A flask was charged with 7-(t-butoxycarbonyl)-5,6,7,8-tetrahydroimidazo[1,2-a]pyrazine-2-carboxylic acid (480 mg, 1.80 mmol, 1.00 equiv), HATU (1.02 g, 2.70 mmol, 1.50 equiv), DIPEA (696 mg, 5.39 mmol, 3.00 equiv), and DCM (10 mL). The mixture was stirred for 30 min at room temperature prior to addition of 1,1,1,3,3,3-hexafluoropropan-2-yl 4-methyl-4-(methylamino)piperidine-1-carboxylate (868 mg, 2.70 mmol, 1.50 equiv). The reaction mixture was stirred overnight at room temperature and quenched with water (10 mL). The resulting solution was extracted with EtOAc (5×20 mL) and the organic layers were combined, washed with brine (3×10 mL), dried over anhydrous Na$_2$SO$_4$, filtered and concentrated under reduced pressure. The residue was chromatographed on a silica gel column to provide 750 mg (88% yield) of t-butyl 2-((1-(((1,1,1,3,3,3-hexafluoropropan-2-yl)oxy)carbonyl)-4-methylpiperidin-4-yl)(methyl)carbamoyl)-5,6-dihydroimidazo[1,2-a]pyrazine-7(8H)-carboxylate. LCMS (ESI, m/z): 572 [M+H]$^+$.

Step 8: Synthesis of 1,1,1,3,3,3-hexafluoropropan-2-yl 4-methyl-4-(N-methyl-5,6,7,8-tetrahydroimidazo[1,2-a]pyrazine-2-carboxamido)piperidine-1-carboxylate

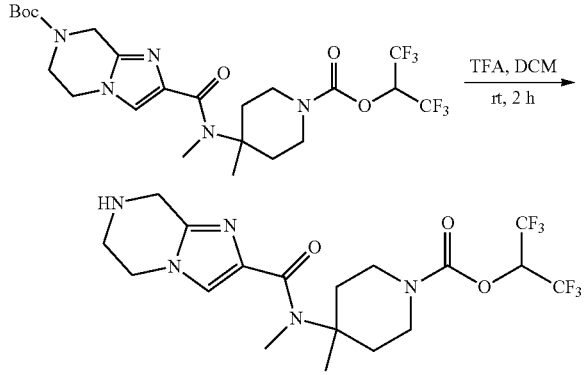

A flask was charged with t-butyl 2-((1-(((1,1,1,3,3,3-hexafluoropropan-2-yl)oxy)carbonyl)-4-methylpiperidin-4-yl)(methyl)carbamoyl)-5,6-dihydroimidazo[1,2-a]pyrazine-7(8H)-carboxylate (750 mg, 0.525 mmol, 1.00 equiv), and DCM (10 mL). TFA (2 mL) was added dropwise at 0° C., and the reaction mixture was stirred for 2 h at room temperature and concentrated under reduced pressure. The crude product was dissolved with DCM (20 mL), and the pH value of the solution was adjusted to 8.0 with saturated NaHCO$_3$. The resulting solution was extracted with DCM (3×20 ml) and the organic layers were combined, washed with brine (2×10 mL), dried over anhydrous Na$_2$SO$_4$, filtered and concentrated under reduced pressure to provide 400 mg (65% yield) of 1,1,1,3,3,3-hexafluoropropan-2-yl 4-methyl-4-(N-methyl-5,6,7,8-tetrahydroimidazo[1,2-a]pyrazine-2-carboxamido)piperidine-1-carboxylate. LCMS (ESI, m/z): 472 [M+H]$^+$.

Step 9: Synthesis of 1,1,1,3,3,3-hexafluoropropan-2-yl 4-(7-isopropyl-N-methyl-5,6,7,8-tetrahydroimidazo[1,2-a]pyrazine-2-carboxamido-4-methylpiperidine-1-carboxylate

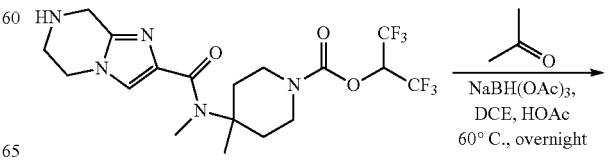

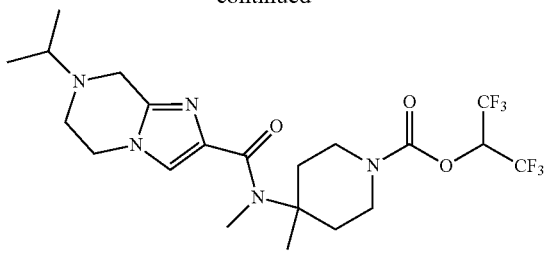

A vial was charged with 1,1,1,3,3,3-hexafluoropropan-2-yl 4-methyl-4-(N-methyl-5,6,7,8-tetrahydroimidazo[1,2-a]pyrazine-2-carboxamido)piperidine-1-carboxylate (80.0 mg, 0.170 mmol, 1.00 equiv), propan-2-one (49.2 mg, 0.849 mmol, 5.00 equiv), DCE (2 mL), and HOAc (163 mg, 2.71 mmol, 1.60 equiv). The mixture was stirred for 90 min at 60° C. and cooled to room temperature prior to addition of sodium triacetoxyborohydride (90.0 mg, 0.425 mmol, 2.50 equiv). The reaction mixture was stirred overnight at 60° C. and quenched with water (5 mL). The resulting solution was extracted with DCM (3×10 mL) and the organic layers were combined, washed with brine (2×5 mL), dried over anhydrous Na$_2$SO$_4$, filtered and concentrated under reduced pressure. The residue was chromatographed on a silica gel column and the crude product (50 mg) was purified by preparative HPLC to afford 6.5 mg (7% yield) of 1,1,1,3,3,3-hexafluoropropan-2-yl 4-(7-isopropyl-N-methyl-5,6,7,8-tetrahydroimidazo[1,2-a]pyrazine-2-carboxamido)-4-methylpiperidine-1-carboxylate. $^1$H NMR (300 MHz, Chloroform-d) δ 7.34 (s, 1H), 5.81-5.72 (m, 1H), 4.02 (t, J=5.4 Hz, 2H), 3.81 (s, 2H), 3.78-3.73 (m, 2H), 3.44-3.34 (m, 2H), 3.18 (s, 3H), 3.00-2.92 (m, 3H), 2.66-2.62 (m, 2H), 1.77-1.70 (m, 2H), 1.44 (s, 3H), 1.16 (d, J=6.6 Hz, 6H). LCMS (ESI, m/z): 514 [M+H]$^+$.

Example 23: 1,1,1,3,3,3-Hexafluoropropan-2-yl 4-(7-cyclobutyl-N-methyl-5,6,7,8-tetrahydroimidazo[1,2-a]pyrazine-2-carboxamido)-4-methylpiperidine-1-carboxylate t-butyl (4-methylpiperidin-4-yl)carbamate

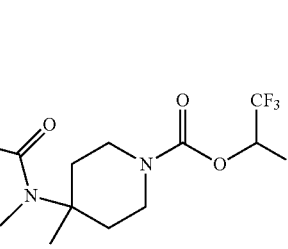

Step 1: Synthesis of 1,1,1,3,3,3-hexafluoropropan-2-yl 4-methyl-4-(methylamino)piperidine-1-carboxylate

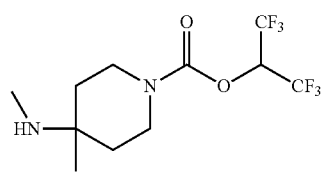 [SMILES: CNC1(C)CCN(C(=O)OC(C(F)(F)F)C(F)(F)F)CC1]

The title compound was prepared using the methods described in Example 22, Steps 1-5, using t-butyl (4-methylpiperidin-4-yl)carbamate in Step 1 to provide 868 mg (quantitative) of 1,1,1,3,3,3-hexafluoropropan-2-yl 4-methyl-4-(methylamino)piperidine-1-carboxylate. LCMS (ESI, m/z): 323 [M+H]$^+$.

Step 2: Synthesis of benzyl 7-cyclobutyl-5,6,7,8-tetrahydroimidazo[1,2-a]pyrazine-2-carboxylate

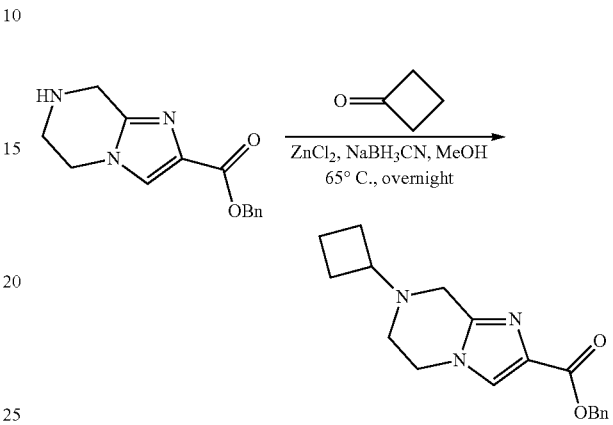

A flask was charged with benzyl 5,6,7,8-tetrahydroimidazo[1,2-a]pyrazine-2-carboxylate (300 mg, 1.17 mmol, 1.00 equiv), cyclobutanone (817 mg, 11.7 mmol, 10.0 equiv), zinc chloride (238 mg, 1.75 mmol, 1.50 equiv), sodium cyanoborohydride (221 mg, 3.52 mmol, 3.00 equiv), and MeOH (10 mL). The reaction mixture was stirred overnight at 65° C. and quenched with water (10 mL). The resulting solution was extracted with DCM (3×20 mL) and the organic layers were combined, washed with brine (2×10 mL), dried over anhydrous Na$_2$SO$_4$, filtered and concentrated under reduced pressure. The residue was chromatographed on a silica gel column to provide 250 mg (69% yield) of benzyl benzyl 7-cyclobutyl-5,6,7,8-tetrahydroimidazo[1,2-a]pyrazine-2-carboxylate. LCMS (ESI, m/z): 312 [M+H]$^+$.

Step 3: Synthesis of 7-cyclobutyl-5,6,7,8-tetrahydroimidazo[1,2-a]pyrazine-2-carboxylic acid

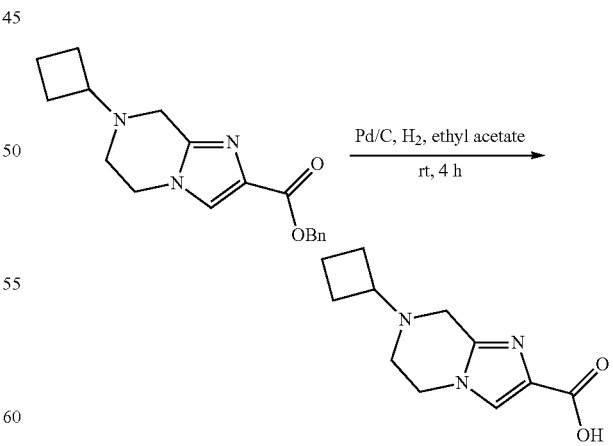

A flask was charged with benzyl 7-cyclobutyl-5,6,7,8-tetrahydroimidazo[1,2-a]pyrazine-2-carboxylate (230 mg, 0.740 mmol, 1.00 equiv), palladium 10% on activated carbon (120 mg). The contents of the flask were placed under an atmosphere of hydrogen (3 atm). The resulting solution was stirred for 4 h at room temperature. The solids were filtered, and the resulting mixture was concentrated under reduced pressure to provide 155 mg (95% yield) of 7-cyclobutyl-5,6,7,8-tetrahydroimidazo[1,2-a]pyrazine-2-carboxylic acid. LCMS (ESI, m/z): 222 [M+H]$^+$.

Step 4: Synthesis of 1,1,1,3,3,3-hexafluoropropan-2-yl 4-(7-cyclobutyl-N-methyl-5,6,7,8-tetrahydroimidazo[1,2-a]pyrazine-2-carboxamido)-4-methylpiperidine-1-carboxylate

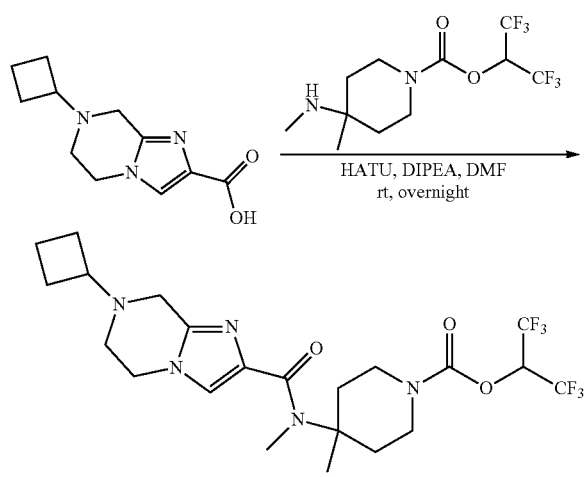

A flask was charged with 7-cyclobutyl-5,6,7,8-tetrahydroimidazo[1,2-a]pyrazine-2-carboxylic acid (155 mg, 0.701 mmol, 1.10 equiv), HATU (266 mg, 0.701 mmol, 1.10 equiv), DIPEA (271 mg, 2.10 mmol, 3.30 equiv), and DMF (5 mL). The mixture was stirred for 30 min at room temperature prior to addition of 1,1,1,3,3,3-hexafluoropropan-2-yl 4-methyl-4-(methylamino)piperidine-1-carboxylate (205 mg, 0.637 mmol, 1.00 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The crude product (300 mg) was purified by preparative HPLC to provide 93.8 mg (28% yield) of 1,1,1,3,3,3-hexafluoropropan-2-yl 4-(7-cyclobutyl-N-methyl-5,6,7,8-tetrahydroimidazo[1,2-a]pyrazine-2-carboxamido)-4-methylpiperidine-1-carboxylate. $^1$H NMR (400 MHz, Chloroform-d) δ 7.34 (s, 1H), 5.77-5.73 (m, 1H), 4.03 (s, 2H), 3.76-3.74 (m, 2H), 3.60 (s, 2H), 3.41-3.33 (m, 2H), 3.16 (s, 3H), 3.01-2.91 (m, 1H), 2.77 (s, 2H), 2.64-2.61 (m, 2H), 2.14 (s, 2H), 1.97-1.92 (m, 2H), 1.81-1.72 (m, 4H), 1.47 (s, 3H). LCMS (ESI, m/z): 526 [M+H]$^+$.

Example 24: 1,1,1,3,3,3-Hexafluoropropan-2-yl 4-(7-(2-hydroxy-2-methylpropyl)-N-methyl-5,6,7,8-tetrahydroimidazo[1,2-a]pyrazine-2-carboxamido)-4-methylpiperidine-1-carboxylate

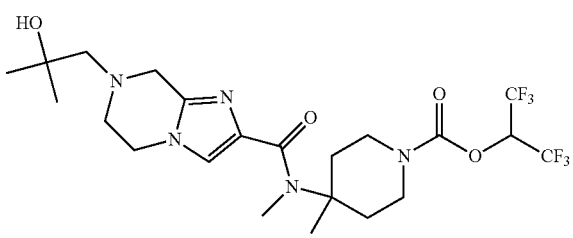 [SMILES: CN(C(=O)c1cn2c(n1)CN(CC(C)(C)O)CC2)C1(C)CCN(C(=O)OC(C(F)(F)F)C(F)(F)F)CC1]

Step 1: Synthesis of benzyl 7-(2-hydroxy-2-methylpropyl)-5,6,7,8-tetrahydroimidazo[1,2-a]pyrazine-2-carboxylate

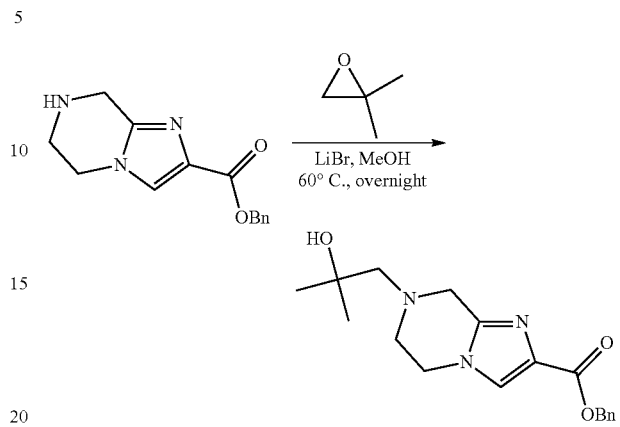

A flask was charged with benzyl 5,6,7,8-tetrahydroimidazo[1,2-a]pyrazine-2-carboxylate (300 mg, 1.17 mmol, 1.00 equiv), 2,2-dimethyloxirane (420 mg, 5.82 mmol, 5.00 equiv), lithium bromide (254 mg, 2.92 mmol, 2.50 equiv), and MeOH (10 mL). The reaction mixture was stirred overnight at 60° C. and quenched with water (10 mL). The resulting solution was extracted with DCM (3×20 mL) and the organic layers were combined, washed with brine (2×10 mL), dried over anhydrous Na$_2$SO$_4$, filtered and concentrated under reduced pressure. The residue was chromatographed on a silica gel column provide 150 mg (39% yield) of benzyl 7-(2-hydroxy-2-methylpropyl)-5,6,7,8-tetrahydroimidazo[1,2-a]pyrazine-2-carboxylate. LCMS (ESI, m/z): 330 [M+H]$^+$.

Step 2: Synthesis of 7-(2-hydroxy-2-methylpropyl)-5,6,7,8-tetrahydroimidazo[1,2-a]pyrazine-2-carboxylic acid

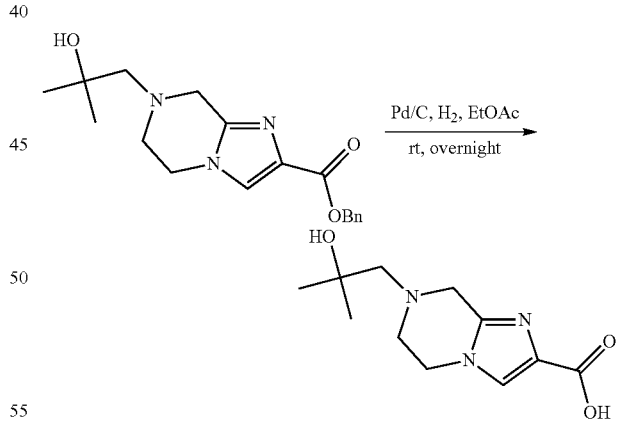

A flask was charged with 7-(2-hydroxy-2-methylpropyl)-5,6,7,8-tetrahydroimidazo[1,2-a]pyrazine-2-carboxylate (130 mg, 0.395 mmol, 1.00 equiv), palladium 10%/a on activated carbon (65 mg), and EtOAc (5 mL). The contents of the flask were placed under an atmosphere of hydrogen (3 atm). The reaction mixture was stirred overnight at room temperature and the solids were filtered. The resulting mixture was concentrated under reduced pressure to provide 90.0 mg (95% yield) of 7-(2-hydroxy-2-methylpropyl)-5,6,7,8-tetrahydroimidazo[1,2-a]pyrazine-2-carboxylic acid. LCMS (ESI, m/z): 240 [M+H]$^+$.

Step 3: Synthesis of 1,1,1,3,3,3-hexafluoropropan-2-yl 4-(7-(2-hydroxy-2-methylpropyl)-N-methyl-5,6,7,8-tetrahydroimidazo[1,2-a]pyrazine-2-carboxamido)-4-methylpiperidine-1-carboxylate

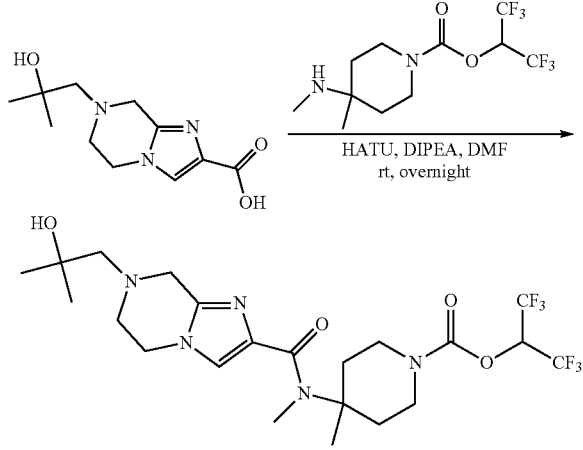

A flask was charged with 7-(2-hydroxy-2-methylpropyl)-5,6,7,8-tetrahydroimidazo[1,2-a]pyrazine-2-carboxylic acid (90.0 mg, 0.376 mmol, 1.00 equiv), HATU (143 mg, 0.376 mmol, 1.00 equiv), DIPEA (146 mg, 1.13 mmol, 3.00 equiv), and DMF (5 mL). The mixture was stirred for 30 min at room temperature prior to addition of 1,1,1,3,3,3-hexafluoropropan-2-yl 4-methyl-4-(methylamino)piperidine-1-carboxylate (prepared as described in Example 23, Step 1; 146 mg, 0.453 mmol, 1.20 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The crude product (200 mg) was purified by preparative HPLC to provide 41.5 mg (20% yield) of 1,1,1,3,3,3-hexafluoropropan-2-yl 4-methyl-4-[N-methyl7-(2-hydroxy-2-methylpropyl)-5H,6H,7H,8H-imidazo[1,2-a]pyrazine-2-amido]piperidine-1-carboxylate. $^1$H NMR (400 MHz, Chloroform-d) δ 7.37 (s, 1H), 5.78-5.73 (m, 1H), 4.05 (s, 2H), 3.92 (s, 2H), 3.76-3.73 (m, 2H), 3.43-3.35 (m, 2H), 3.18 (s, 3H), 3.11 (s, 2H), 2.64-2.60 (m, 2H), 2.57 (s, 2H), 2.43 (s, 1H), 1.74 (s, 2H), 1.44 (s, 3H), 1.25 (s, 6H). LCMS (ESI, m/z): 544 [M+H]$^+$.

Example 25: 1,1,1,3,3,3-Hexafluoropropan-2-yl 4-(7-(cyclopropyl-1-d)-N-methyl-5,6,7,8-tetrahydroimidazo[1,2-a]pyrazine-2-carboxamido-4-methylpiperidine-1-carboxylate

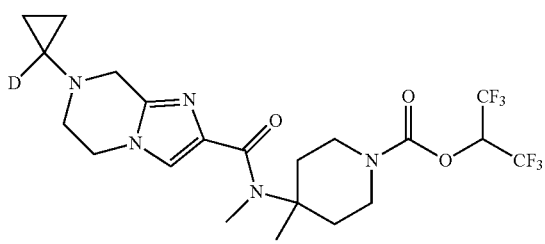 [SMILES: [2H]C1(N2CCn3cc(C(=O)N(C)C4(C)CCN(C(=O)OC(C(F)(F)F)C(F)(F)F)CC4)nc3C2)CC1]

Step 1: Synthesis of benzyl 7-(cyclopropyl-1-d)-5,6,7,8-tetrahydroimidazo[1,2-a]pyrazine-2-carboxylate

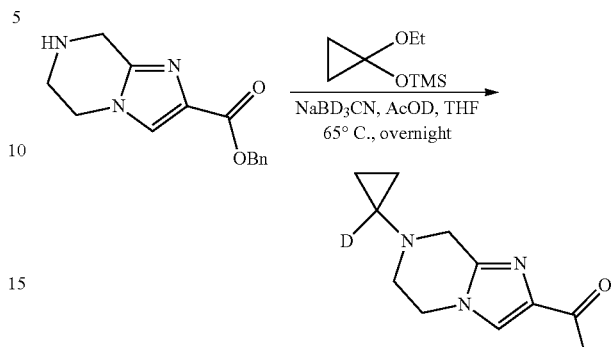

A flask was charged with benzyl 5,6,7,8-tetrahydroimidazo[1,2-a]pyrazine-2-carboxylate (196 mg, 0.763 mmol, 1.00 equiv), (1-ethoxycyclopropoxy)trimethylsilane (398 mg, 2.28 mmol, 3.00 equiv), acetic acid-d$_4$ (465 mg, 7.62 mmol, 10.0 equiv), sodium cyanoborodeuteride (151 mg, 2.29 mmol, 3.00 equiv), and THF (10 mL). The reaction mixture was stirred overnight at 65° C. and quenched with water (10 mL). The resulting solution was extracted with DCM (3×20 mL) and the organic layers were combined, washed with brine (2×10 mL), dried over anhydrous Na$_2$SO$_4$, filtered and concentrated under reduced pressure. The residue was chromatographed on a silica gel column to provide 120 mg (53% yield) of benzyl 7-(cyclopropyl-1-d)-5,6,7,8-tetrahydroimidazo[1,2-a]pyrazine-2-carboxylate. LCMS (ESI, m/z): 299 [M+H]$^+$.

Step 2: Synthesis of 7-(cyclopropyl-1-d)-5,6,7,8-tetrahydroimidazo[1,2-a]pyrazine-2-carboxylic acid

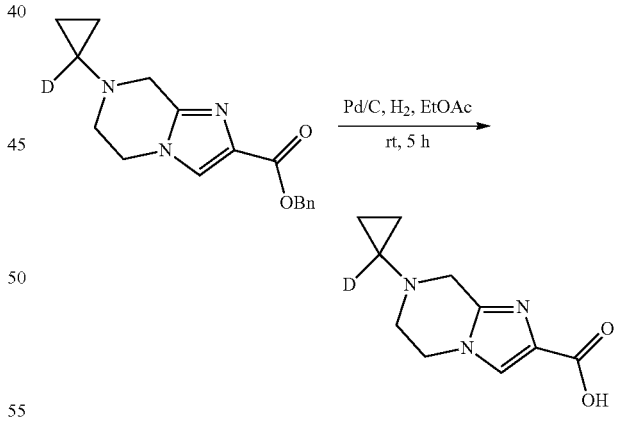

A flask was charged with benzyl 7-(cyclopropyl-1-d)-5,6,7,8-tetrahydroimidazo[1,2-a]pyrazine-2-carboxylate (120 mg, 0.403 mmol, 1.00 equiv), palladium-on-carbon (150 mg), and EtOAc (10 mL). The contents of the flask were placed under an atmosphere of hydrogen (3 atm). The resulting solution was stirred for 5 h at room temperature. Solids were filtered and the resulting mixture was concentrated under reduced pressure to provide 60.0 mg (72% yield) of 7-(cyclopropyl-1-d)-5,6,7,8-tetrahydroimidazo[1,2-a]pyrazine-2-carboxylic acid. LCMS (ESI, m/z): 209 [M+H]$^+$.

Step 3: Synthesis of 1,1,1,3,3,3-hexafluoropropan-2-yl 4-(7-(cyclopropyl-1-d)-N-methyl-5,6,7,8-tetrahydroimidazo[1,2-a]pyrazine-2-carboxamido)-4-methylpiperidine-1-carboxylate

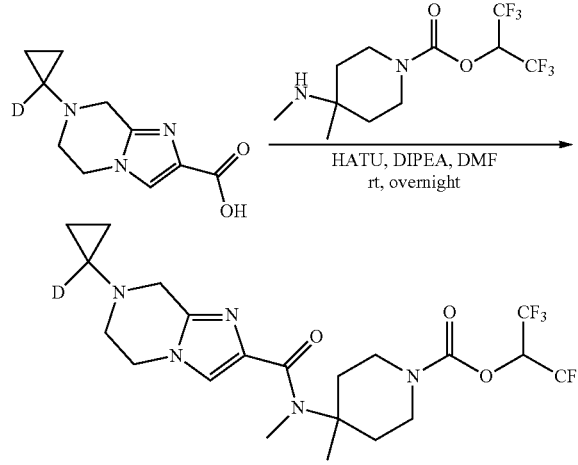

A flask was charged with 7-(cyclopropyl-1-d)-5,6,7,8-tetrahydroimidazo[1,2-a]pyrazine-2-carboxylic acid (90.0 mg, 0.432 mmol, 1.00 equiv), HATU (164 mg, 0.432 mmol, 1.00 equiv), DIPEA (167 mg, 1.29 mmol, 3.00 equiv), and DMF (10 mL). The mixture was stirred for 30 min at room temperature prior to addition of 1,1,1,3,3,3-hexafluoropropan-2-yl 4-methyl-4-(methylamino)piperidine-1-carboxylate (prepared as described in Example 23, Step 1; 153 mg, 0.475 mmol, 1.10 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The crude product (200 mg) was purified by preparative HPLC to provide 51.0 mg (23% yield) of 1,1,1,3,3,3-hexafluoropropan-2-yl 4-(7-(cyclopropyl-1-d)-N-methyl-5,6,7,8-tetrahydroimidazo[1,2-a]pyrazine-2-carboxamido)-4-methylpiperidine-1-carboxylate. $^1$H NMR (400 MHz, Chloroform-d) δ 7.34 (s, 1H), 5.80-5.74 (m, 1H), 4.02-3.99 (m, 2H), 3.88 (s, 2H), 3.79-3.72 (m, 2H), 3.44-3.34 (m, 2H), 3.17 (s, 3H), 3.11-3.08 (m, 2H), 2.65-2.61 (m, 2H), 1.78-1.71 (m, 2H), 1.44 (s, 3H), 0.61-0.58 (m, 2H), 0.55-0.51 (m, 2H). LCMS (ESI, m/z): 513 [M+H]$^+$.

Example 26: 1,1,1,3,3,3-Hexafluoropropan-2-yl 4-(7-acetyl-N-methyl-5,6,7,8-tetrahydroimidazo[1,2-a]pyrazine-2-carboxamido)-4-methylpiperidine-1-carboxylate

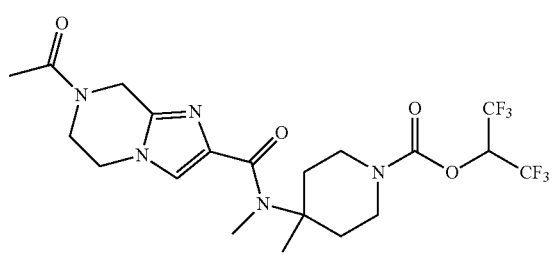 [SMILES: CC(=O)N1CCn2cc(C(=O)N(C)C3(C)CCN(C(=O)OC(C(F)(F)F)C(F)(F)F)CC3)nc2C1]

Step 1: Synthesis of benzyl 7-acetyl-5,6,7,8-tetrahydroimidazo[1,2-a]pyrazine-2-carboxylate

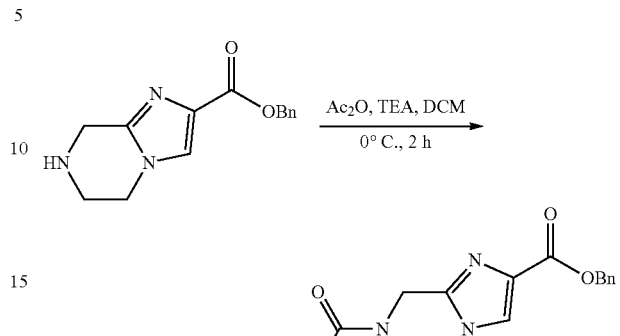

A flask was charged with benzyl 5,6,7,8-tetrahydroimidazo[1,2-a]pyrazine-2-carboxylate (1.50 g, 5.83 mmol, 1.00 equiv), TEA (2.95 g, 29.2 mmol, 5.00 equiv), and DCM (20 mL). Acetic anhydride (893 mg, 8.75 mmol, 1.50 equiv) was added dropwise at 0° C., and the resulting solution was stirred for 2 h at 0° C. before quenching with water (20 mL). The resulting solution was extracted with DCM (3×30 mL) and the organic layers were combined, washed with brine (2×20 mL), dried over anhydrous Na$_2$SO$_4$, filtered and concentrated under reduced pressure. The residue was chromatographed on a silica gel column to provide 1.50 g (85% yield) of benzyl 7-acetyl-5,6,7,8-tetrahydroimidazo[1,2-a]pyrazine-2-carboxylate. LCMS (ESI, m/z): 300 [M+H]$^+$.

Step 2: Synthesis of 7-acetyl-5,6,7,8-tetrahydroimidazo[1,2-a]pyrazine-2-carboxylic acid

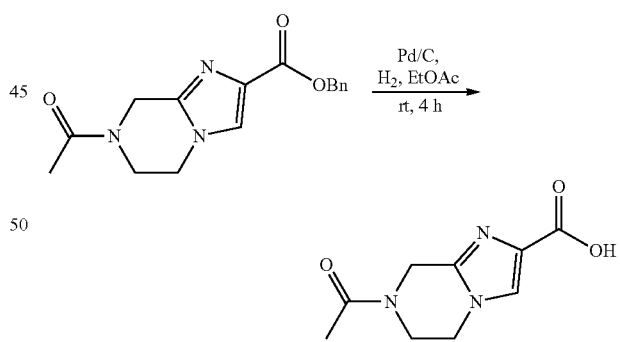

A flask was charged with benzyl 7-acetyl-5,6,7,8-tetrahydroimidazo[1,2-a]pyrazine-2-carboxylate (600 mg, 1.93 mmol, 1.00 equiv), palladium 10% on activated carbon (300 mg), and EtOAc (10 mL). The contents of the flask were placed under an atmosphere of hydrogen (3 atm). The reaction mixture was stirred for 4 h at room temperature prior to filtering of solids. The resulting mixture was concentrated under reduced pressure to provide 200 mg (47% yield) of 7-acetyl-5,6,7,8-tetrahydroimidazo[1,2-a]pyrazine-2-carboxylic acid. LCMS (ESI, m/z): 210 [M+H]$^+$.

Step 3: Synthesis of 1,1,1,3,3,3-hexafluoropropan-2-yl 4-(7-acetyl-N-methyl-5,6,7,8-tetrahydroimidazo[1,2-a]pyrazine-2-carboxamido)-4-methylpiperidine-1-carboxylate

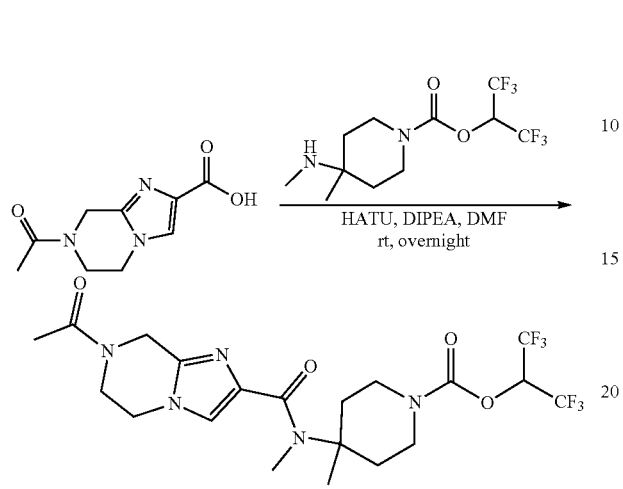

A flask was charged with 7-acetyl-5,6,7,8-tetrahydroimidazo[1,2-a]pyrazine-2-carboxylic acid (100 mg, 0.478 mmol, 1.10 equiv), HATU (182 mg, 0.478 mmol, 1.10 equiv), DIPEA (168 mg, 1.30 mmol, 3.00 equiv), and DMF (5 mL). The mixture was stirred for 30 min at room temperature prior to addition of 1,1,1,3,3,3-hexafluoropropan-2-yl 4-methyl-4-(methylamino)piperidine-1-carboxylate (140 mg, 0.435 mmol, 1.00 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The crude product (250 mg) was purified by preparative HPLC to provide 34.2 mg (15% yield) of 1,1,1,3,3,3-hexafluoropropan-2-yl 4-(7-acetyl-N-methyl-5,6,7,8-tetrahydroimidazo[1,2-a]pyrazine-2-carboxamido)-4-methylpiperidine-1-carboxylate. $^1$H NMR (400 MHz, Chloroform-d) δ 7.40 (s, 1H), 5.78-5.75 (m, 1H), 4.86-4.77 (m, 2H), 4.10-3.90 (m, 4H), 3.77-3.74 (m, 2H), 3.38-3.36 (m, 2H), 3.16 (s, 3H), 2.64-2.60 (m, 2H), 2.24-2.22 (m, 3H), 1.72 (s, 2H), 1.44 (s, 3H). LCMS (ESI, m/z): 514 [M+H]$^+$.

Example 27: 1,1,1,3,3-Hexafluoropropan-2-yl 4-methyl-4-(7-(methylsulfonyl)-5,6,7,8-tetrahydroimidazo[1,2-a]pyrazine-2-carboxamido)piperidine-1-carboxylate

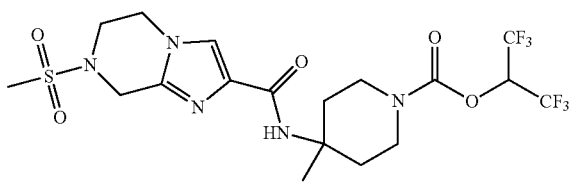 [SMILES: CC1(NC(=O)c2cn3c(n2)CN(S(C)(=O)=O)CC3)CCN(C(=O)OC(C(F)(F)F)C(F)(F)F)CC1]

Step 1: Synthesis of benzyl 7-(methylsulfonyl)-5,6,7,8-tetrahydroimidazo[1,2-a]pyrazine-2-carboxylate

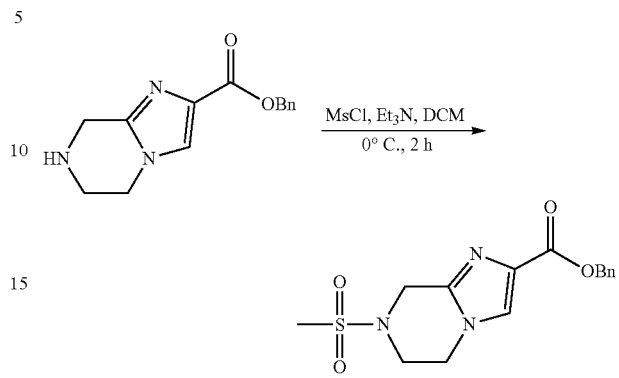

A flask was charged with benzyl 5,6,7,8-tetrahydroimidazo[1,2-a]pyrazine-2-carboxylate (200 mg, 0.778 mmol, 1.00 equiv), TEA (236 mg, 2.33 mmol, 3.00 equiv), and DCM (10 mL). Methanesulfonyl chloride (134 mg, 1.17 mmol, 1.50 equiv) was added dropwise at 0° C., and the reaction mixture was stirred for 2 h at 0° C. and quenched with water (10 mL). The resulting solution was extracted with DCM (3×20 mL) and the organic layers were combined, washed with brine (2×10 mL), dried over anhydrous Na$_2$SO$_4$, filtered and concentrated under reduced pressure. The residue was chromatographed on a silica gel column to provide 200 mg (77% yield) of benzyl 7-(methylsulfonyl)-5,6,7,8-tetrahydroimidazo[1,2-a]pyrazine-2-carboxylate. LCMS (ESI, m/z): 336 [M+H]$^+$.

Step 2: Synthesis of 7-(methylsulfonyl)-5,6,7,8-tetrahydroimidazo[1,2-a]pyrazine-2-carboxylic acid

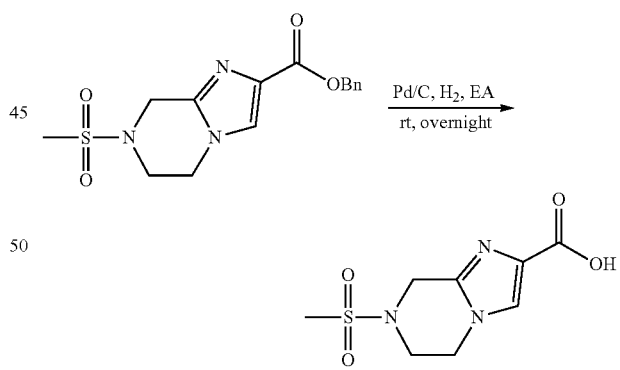

A flask was charged with benzyl 7-(methylsulfonyl)-5,6,7,8-tetrahydroimidazo[1,2-a]pyrazine-2-carboxylate (200 mg, 0.597 mmol, 1.00 equiv), palladium carbon (200 mg), and EtOAc (10 mL). The contents of the flask were placed under an atmosphere of hydrogen (3 atm). The reaction mixture was stirred overnight at room temperature and solids were filtered and discarded. The resulting mixture was concentrated under reduced pressure to provide 100 mg (68% yield) of 7-(methylsulfonyl)-5,6,7,8-tetrahydroimidazo[1,2-a]pyrazine-2-carboxylic acid. LCMS (ESI, m/z): 246 [M+H]$^+$.

Step 3: Synthesis of 1,1,1,3,3,3-hexafluoropropan-2-yl 4-methyl-4-(7-(methylsulfonyl)-5,6,7,8-tetrahydroimidazo[1,2-a]pyrazine-2-carboxamido)piperidine-1-carboxylate

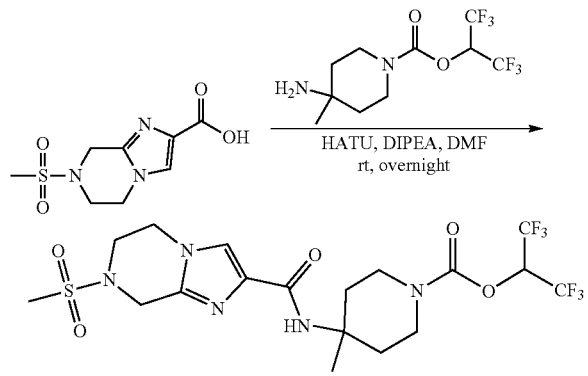

A flask was charged with 7-(methylsulfonyl)-5,6,7,8-tetrahydroimidazo[1,2-a]pyrazine-2-carboxylic acid (100 mg, 0.408 mmol, 1.00 equiv), HATU (155 mg, 0.408 mmol, 1.00 equiv), DIPEA (158 mg, 1.22 mmol, 3.00 equiv), and DMF (5 mL). The mixture was stirred for 30 min at room temperature prior to addition of 1,1,1,3,3,3-hexafluoropropan-2-yl 4-amino-4-methylpiperidine-1-carboxylate (138 mg, 0.449 mmol, 1.10 equiv). The reaction mixture was stirred overnight at room temperature and quenched with water (10 mL). The resulting solution was extracted with EtOAc (3×20 mL) and the organic layers were combined, washed with brine (2×10 mL), dried over anhydrous $Na_2SO_4$, filtered and concentrated under reduced pressure. The crude product (200 mg) was purified by preparative HPLC to provide 135.5 mg (62% yield) of 1,1,1,3,3,3-hexafluoropropan-2-yl 4-methyl-4-(7-(methylsulfonyl)-5,6,7,8-tetrahydroimidazo[1,2-a]pyrazine-2-carboxamido)piperidine-1-carboxylate. $^1$H NMR (400 MHz, Chloroform-d) δ 7.48 (s, 1H), 6.89 (br, 1H), 5.80-5.74 (m, 1H), 4.56 (s, 2H), 4.20-4.17 (m, 2H), 3.91-3.85 (m, 2H), 3.79-3.77 (m, 2H), 3.38-3.29 (m, 2H), 2.97 (s, 3H), 2.38-2.34 (m, 2H), 1.73-1.66 (m, 2H), 1.53 (s, 3H). LCMS (ESI, m/z): 536 [M+H]$^+$.

Example 28: 1,1,1,3,3,3-Hexafluoropropan-2-yl 4-methyl-4-(7-(oxazol-2-yl)-5,6,7,8-tetrahydroimidazo[1,2-a]pyrazine-2-carboxamido)piperidine-1-carboxylate

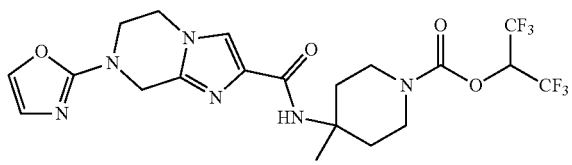 [SMILES: CC1(NC(=O)c2cn3c(n2)CN(c2ncco2)CC3)CCN(C(=O)OC(C(F)(F)F)C(F)(F)F)CC1]

Step 1: Synthesis of t-butyl 2-((1-(((1,1,1,3,3,3-hexafluoropropan-2-yl)oxy)carbonyl)-4-methylpiperidin-4-yl)carbamoyl)-5,6-dihydroimidazo[1,2-a]pyrazine-7(8H)-carboxylate

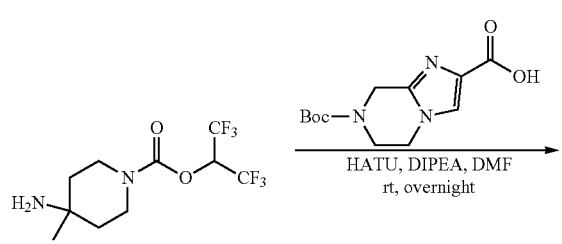

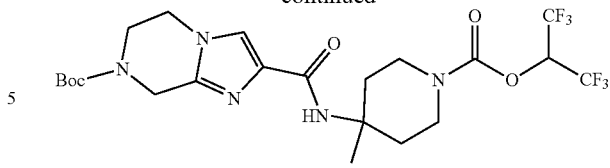

A flask was charged with 7-(t-butoxycarbonyl)-5,6,7,8-tetrahydroimidazo[1,2-a]pyrazine-2-carboxylic acid (500 mg, 1.87 mmol, 1.00 equiv, prepared as described in Example 22, Step 6), HATU (712 mg, 1.87 mmol, 1.00 equiv), DIPEA (725 mg, 5.62 mmol, 3.00 equiv), and DMF (10 mL). The mixture was stirred for 30 min at room temperature prior to addition 1,1,1,3,3,3-hexafluoropropan-2-yl 4-amino-4-methylpiperidine-1-carboxylate (577 mg, 1.87 mmol, 1.00 equiv). The reaction mixture was stirred overnight at room temperature and quenched with water (10 mL). The resulting solution was extracted with DCM (3×20 mL) and the organic layers were combined, washed with brine (2×10 mL), dried over anhydrous $Na_2SO_4$, filtered and concentrated under reduced pressure. The residue was chromatographed on a silica gel column to provide 910 mg (87% yield) of t-butyl 2-((1-(((1,1,1,3,3,3-hexafluoropropan-2-yl)oxy)carbonyl)-4-methylpiperidin-4-yl)carbamoyl)-5,6-dihydroimidazo[1,2-a]pyrazine-7(8H)-carboxylate. LCMS (ESI, m/z): 558 [M+H]$^+$.

Step 2: Synthesis of 1,1,1,3,3,3-hexafluoropropan-2-yl 4-methyl-4-(5,6,7,8-tetrahydroimidazo[1,2-a]pyrazine-2-carboxamido)piperidine-1-carboxylate

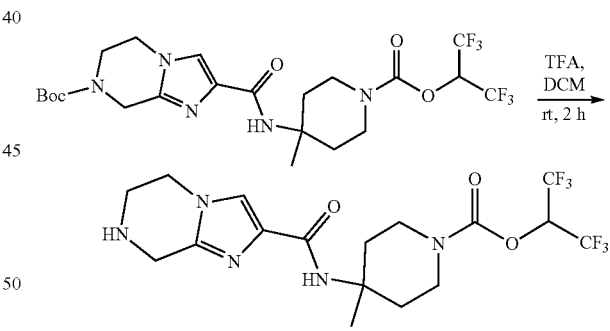

A flask was charged with t-butyl 2-((1-(((1,1,1,3,3,3-hexafluoropropan-2-yl)oxy)carbonyl)-4-methylpiperidin-4-yl)carbamoyl)-5,6-dihydroimidazo[1,2-a]pyrazine-7(8H)-carboxylate (910 mg, 1.63 mmol, 1.00 equiv) and DCM (10 mL). Trifluoroacetic acid (2 mL) was added dropwise at room temperature, and the reaction mixture was stirred for 2 h at room temperature. The resulting solution was concentrated under reduced pressure, and the crude product was dissolved with DCM (20 mL). The pH value of the solution was adjusted to 8.0 with saturated sodium bicarbonate solution. The resulting solution was extracted with DCM (3×20 mL) and the organic layers were combined, washed with brine (2×10 mL), dried over anhydrous Na₂SO₄, filtered and concentrated under reduced pressure to provide 610 mg (82% yield) of 1,1,1,3,3,3-hexafluoropropan-2-yl 4-methyl-4-(5,6,7,8-tetrahydroimidazo[1,2-a]pyrazine-2-carboxamido)piperidine-1-carboxylate. LCMS (ESI, m/z): 458 [M+H]⁺.

Step 3: Synthesis of 1,1,1,3,3,3-hexafluoropropan-2-yl 4-(7-cyano-5,6,7,8-tetrahydroimidazo[1,2-a]pyrazine-2-carboxamido-4-methylpiperidine-1-carboxylate

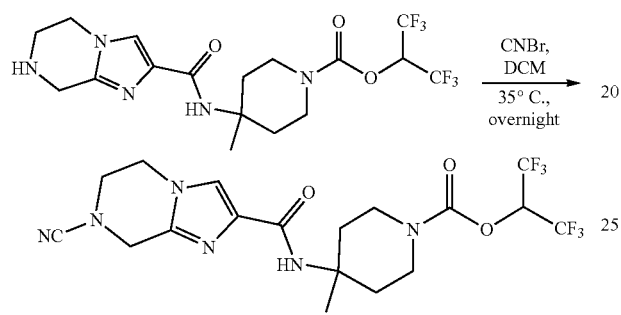

A flask was charged with 1,1,1,3,3,3-hexafluoropropan-2-yl 4-methyl-4-(5,6,7,8-tetrahydroimidazo[1,2-a]pyrazine-2-carboxamido)piperidine-1-carboxylate (610 mg, 1.33 mmol, 1.00 equiv), cyanogen bromide (424 mg, 4.00 mmol, 3.00 equiv), and DCM (10 mL). The reaction mixture was stirred overnight at 35° C. and quenched with water (10 mL). The resulting solution was extracted with DCM (3×20 mL) and the organic layers were combined, washed with brine (2×10 mL), dried over anhydrous Na₂SO₄, filtered and concentrated under reduced pressure. The residue was chromatographed on a silica gel column to provide 500 mg (78% yield) of 1,1,1,3,3,3-hexafluoropropan-2-yl 4-(7-cyano-5,6,7,8-tetrahydroimidazo[1,2-a]pyrazine-2-carboxamido)-4-methylpiperidine-1-carboxylate. LCMS (ESI, m/z): 483 [M+H]⁺.

Step 4: Synthesis of 1,1,1,3,3,3-hexafluoropropan-2-yl 4-methyl-4-(7-(oxazol-2-yl)-5,6,7,8-tetrahydroimidazo[1,2-a]pyrazine-2-carboxamido)piperidine-1-carboxylate

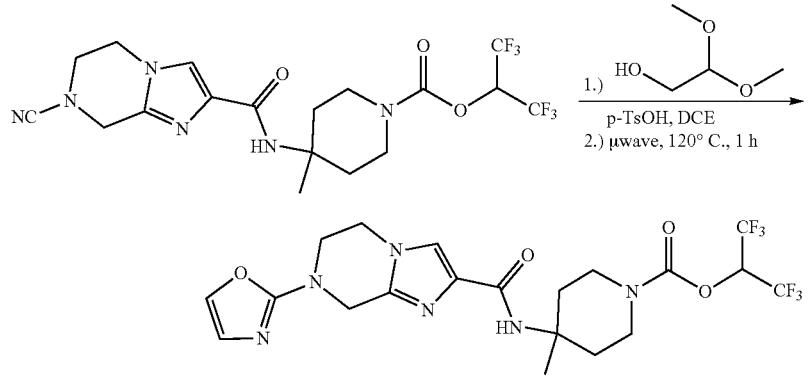

A flask was charged with 1,1,1,3,3,3-hexafluoropropan-2-yl 4-(7-cyano-5,6,7,8-tetrahydroimidazo[1,2-a]pyrazine-2-carboxamido)-4-methylpiperidine-1-carboxylate (160 mg, 0.332 mmol, 1.00 equiv), 4-methylbenzene-1-sulfonic acid (171 mg, 0.996 mmol, 3.00 equiv), and DCE (5 mL). The mixture was stirred for 2 h at room temperature prior to addition of 2,2-dimethoxyethan-1-ol (352 mg, 3.32 mmol, 10.0 equiv). The reaction mixture was stirred for 30 min at room temperature and washed with saturated NaHCO₃ solution (10 mL) and water (10 mL), dried over anhydrous Na₂SO₄, filtered and concentrated under reduced pressure. The solid was dissolved with DCE (5 mL) and the resulting solution was stirred for 1 h at 120° C. (microwave) and quenched with water (10 mL). The mixture was extracted with DCM (3×20 mL) and the organic layers were combined, washed with brine (2×10 mL), dried over anhydrous Na₂SO₄, filtered and concentrated under reduced pressure. The crude product (120 mg) was purified by preparative HPLC to provide 28.0 mg (16% yield) of 1,1,1,3,3,3-hexafluoropropan-2-yl 4-methyl-4-(7-(oxazol-2-yl)-5,6,7,8-tetrahydroimidazo[1,2-a]pyrazine-2-carboxamido)piperidine-1-carboxylate. ¹H NMR (400 MHz, Chloroform-d) δ 7.46 (s, 1H), 7.32 (s, 1H), 6.90-6.89 (m, 2H), 5.80-5.74 (m, 1H), 4.77 (s, 2H), 4.20-4.17 (m, 2H), 4.03-4.00 (m, 2H), 3.92-3.85 (m, 2H), 3.40-3.30 (m, 2H), 2.39-2.36 (m, 2H), 1.73-1.62 (m, 2H), 1.53 (s, 3H). LCMS (ESI, m/z): 525 [M+H]⁺.

Example 29: 1,1,1,3,3,3-Hexafluoropropan-2-yl 4-methyl-4-(7-(pyrazin-2-yl)-5,6,7,8-tetrahydroimidazo[1,2-a]pyrazine-2-carboxamido)piperidine-1-carboxylate

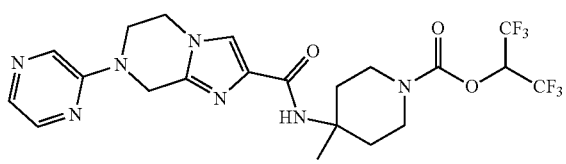 [SMILES: CC1(NC(=O)c2cn3c(n2)CN(c2cnccn2)CC3)CCN(C(=O)OC(C(F)(F)F)C(F)(F)F)CC1]

Step 1: Synthesis of benzyl 7-(pyrazin-2-yl)-5,6,7,8-tetrahydroimidazo[1,2-a]pyrazine-2-carboxylate

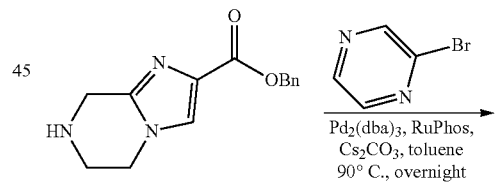

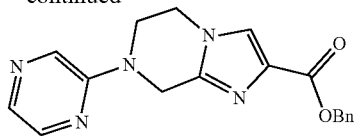

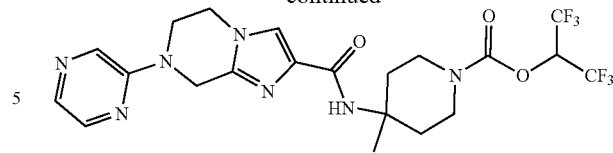

A flask was charged with benzyl 5,6,7,8-tetrahydroimidazo[1,2-a]pyrazine-2-carboxylate (200 mg, 0.778 mmol, 1.00 equiv), 2-bromopyrazine (149 mg, 0.934 mmol, 1.20 equiv), tris(dibenzylideneacetone)dipalladium (35.6 mg, 0.0389 mmol, 0.05 equiv), dicyclohexyl(2',6'-diisopropoxybiphenyl-2-yl)phosphine (72.7 mg, 0.156 mmol, 0.20 equiv), cesium carbonate (761 mg, 2.34 mmol, 3.00 equiv), and toluene (10 mL) under nitrogen. The reaction mixture was stirred overnight at 90° C. and quenched with water (10 mL). The resulting solution was extracted with EtOAc (3×20 mL) and the organic layers were combined, washed with brine (2×10 mL), dried over anhydrous $Na_2SO_4$, filtered and concentrated under reduced pressure. The residue was chromatographed on a silica gel column to provide 180 mg (69% yield) of benzyl 7-(pyrazin-2-yl)-5,6,7,8-tetrahydroimidazo[1,2-a]pyrazine-2-carboxylate. LCMS (ESI, m/z): 336 [M+H]$^+$.

Step 2: Synthesis of 7-(pyrazin-2-yl)-5,6,7,8-tetrahydroimidazo[1,2-a]pyrazine-2-carboxylic acid

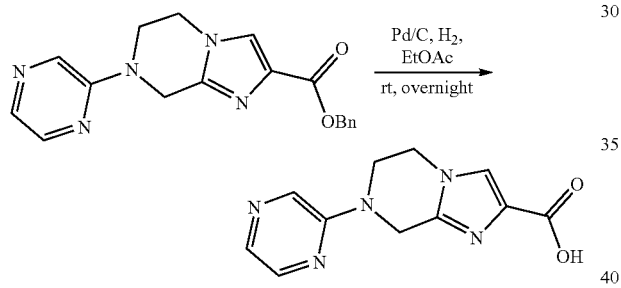

A flask was charged with benzyl 7-(pyrazin-2-yl)-5,6,7,8-tetrahydroimidazo[1,2-a]pyrazine-2-carboxylate (180 mg, 0.537 mmol, 1.00 equiv), palladium 10%0/on activated carbon (180 mL), and EtOAc (10 mL). The contents of the flask were placed under an atmosphere of hydrogen (3 atm). The reaction mixture was stirred overnight at room temperature and solids were filtered and discarded. The resulting solution was concentrated under reduced pressure to provide 105 mg (80% yield) of 7-(pyrazin-2-yl)-5,6,7,8-tetrahydroimidazo[1,2-a]pyrazine-2-carboxylic acid. LCMS (ESI, m/z): 246 [M+H]$^+$.

Step 3: Synthesis of 1,1,1,3,3,3-hexafluoropropan-2-yl 4-methyl-4-(7-(pyrazin-2-yl)-5,6,7,8-tetrahydroimidazo[1,2-a]pyrazine-2-carboxamido)piperidine-1-carboxylate

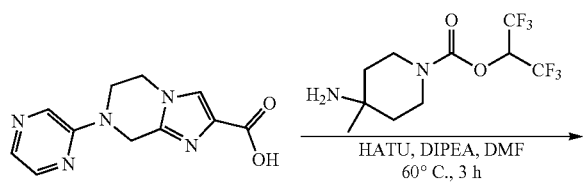

A flask was charged with 7-(pyrazin-2-yl)-5,6,7,8-tetrahydroimidazo[1,2-a]pyrazine-2-carboxylic acid (105 mg, 0.428 mmol, 1.00 equiv), HATU (163 mg, 0.428 mmol, 1.00 equiv), DIPEA (166 mg, 1.28 mmol, 3.00 equiv), and DMF (5 mL). The mixture was stirred for 30 min at room temperature prior to addition of 1,1,1,3,3,3-hexafluoropropan-2-yl 4-amino-4-methylpiperidine-1-carboxylate (158 mg, 0.514 mmol, 1.20 equiv). The reaction mixture was stirred for 3 h at 60° C. and quenched with water (10 mL). The resulting solution was extracted with EtOAc (3×20 mL) and the organic layers were combined, washed with brine (2×10 mL), dried over anhydrous $Na_2SO_4$, filtered and concentrated under reduced pressure. The crude product (200 mg) was purified by preparative HPLC to afford 25.5 mg (11% yield) of 1,1,1,3,3,3-hexafluoropropan-2-yl 4-methyl-4-(7-(pyrazin-2-yl)-5,6,7,8-tetrahydroimidazo[1,2-a]pyrazine-2-carboxamido)piperidine-1-carboxylate. $^1$H NMR (400 MHz, Chloroform-d) δ 8.26 (s, 1H), 8.17 (s, 1H), 8.03 (s, 1H), 7.50 (s, 1H), 6.91 (br, 1H), 5.80-5.75 (m, 1H), 481 (s, 2H), 4.20 (s, 4H), 3.93-3.86 (m, 2H), 3.41-3.31 (m, 2H), 2.40-2.37 (m, 2H), 1.73-1.64 (m, 2H), 1.54 (s, 3H). LCMS (ESI, m/z): 536 [M+H]$^+$.

Example 30: 1,1,1,3,3,3-Hexafluoropropan-2-yl 1-(1-(3-methylpyridin-2-yl)cyclopropane-1-carbonyl)-1,8-diazaspiro[4.5]decane-8-carboxylate

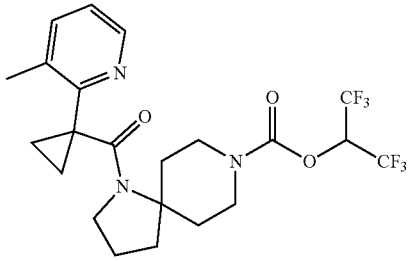 [SMILES: Cc1cccnc1C1(C(=O)N2CCCC23CCN(C(=O)OC(C(F)(F)F)C(F)(F)F)CC3)CC1]

Step 1: Synthesis of 1-(3-methylpyridin-2-yl)cyclopropane-1-carbonitrile

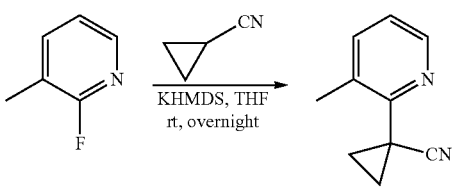

A flask was charged with cyclopropanecarbonitrile (1.00 g, 14.9 mmol, 1.50 equiv) and THF (10 mL) under nitrogen atmosphere. Potassium bis(trimethylsilyl)amide (1 M in THF, 12.0 mL, 12.0 mmol, 1.20 equiv) was added at 0° C., and the reaction mixture was stirred at 0° C. for 1 h prior to addition of 2-fluoro-3-methylpyridine (1.11 g, 9.99 mmol, 1.00 equiv). The resulting solution was stirred overnight at room temperature and quenched with water (10 mL). The mixture was extracted with EtOAc (3×50 mL) and the organic layers were combined, washed with water (3×20 mL), dried over anhydrous Na₂SO₄, filtered and concentrated under reduced pressure. The residue was chromatographed on a silica gel column to provide 0.510 g (32% yield) of 1-(3-methylpyridin-2-yl)cyclopropane-1-carbonitrile. LCMS (ESI, m/z): 159 [M+H]⁺.

Step 2: Synthesis of 1-(3-methylpyridin-2-yl)cyclopropane-1-carboxylic acid

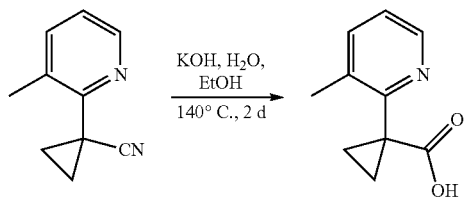

A flask was charged with 1-(3-methylpyridin-2-yl)cyclopropane-1-carbonitrile (0.510 g, 3.22 mmol, 1.00 equiv), EtOH (10 mL), water (5 mL) and KOH (5.42 g, 96.6 mmol, 30.0 equiv). The reaction mixture was stirred for 2 days at 140° C. and concentrated under reduced pressure. The resulting mixture was diluted with ACN (30 mL) and the solids were filtered and discarded. The resulting mixture was concentrated under reduced pressure to provide 0.400 g (crude) of 1-(3-methylpyridin-2-yl)cyclopropane-1-carboxylic acid. LCMS (ESI, m/z): 178 [M+H]⁺.

Step 3: Synthesis of 1,1,1,3,3,3-hexafluoropropan-2-yl 1-(1-(3-methylpyridin-2-yl)cyclopropane-1-carbonyl)-1,8-diazaspiro[4.5]decane-8-carboxylate

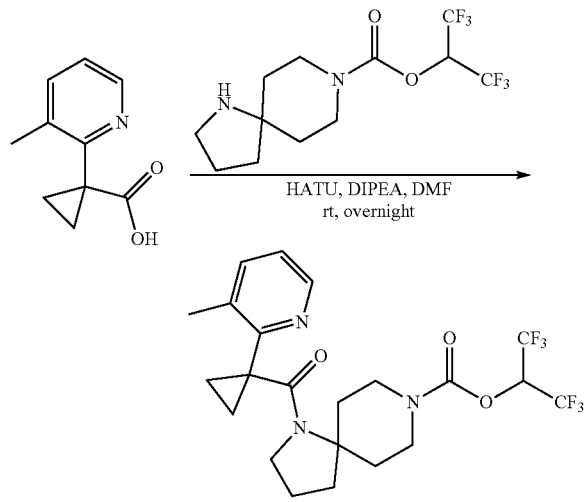

A flask was charged with 1-(3-methylpyridin-2-yl)cyclopropane-1-carboxylic acid (200 mg, 1.13 mmol, 1.00 equiv), HATU (644 mg, 1.69 mmol, 1.50 equiv), DIPEA (437 mg, 3.38 mmol, 3.00 equiv), 1,1,1,3,3,3-hexafluoropropan-2-yl 1,8-diazaspiro[4.5]decane-8-carboxylate (415 mg, 1.24 mmol, 1.10 equiv), and DMF (10 mL). The reaction mixture was stirred overnight at room temperature and quenched with water (10 mL). The resulting solution was extracted with EtOAc (3×50 mL) and the organic layers were combined, washed with water (3×20 mL), dried over anhydrous Na₂SO₄, filtered and concentrated under reduced pressure. The crude product was purified by preparative HPLC to provide 125.8 mg (16% yield) of 1,1,1,3,3,3-hexafluoropropan-2-yl 1-(1-(3-methylpyridin-2-yl)cyclopropane-1-carbonyl)-1,8-diazaspiro[4.5]decane-8-carboxylate. ¹H NMR: (300 MHz, Chloroform-d) δ 8.36 (t, J=4.8 Hz, 1H), 7.53-7.38 (m, 1H), 7.18-7.00 (m, 1H), 5.83-5.65 (m, 1H), 4.26-4.05 (m, 2H), 3.18-2.81 (m, 6H), 2.36 (s, 3H), 1.90-1.76 (m, 2H), 1.76-1.60 (m, 2H), 1.53-1.20 (m, 6H). LCMS (ESI, m/z): 494 [M+H]⁺.

Example 31: 1,1,1,3,3,3-Hexafluoropropan-2-yl 1-(1-(5-chloropyrimidin-2-yl)cyclopropane-1-carbonyl)-1,8-diazaspiro[4.5]decane-8-carboxylate

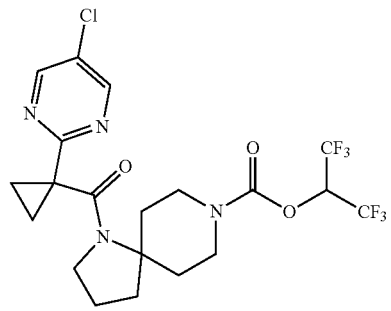 [SMILES: O=C(OC(C(F)(F)F)C(F)(F)F)N1CCC2(CCCN2C(=O)C2(c3ncc(Cl)cn3)CC2)CC1]

Step 1: Synthesis of (1-(methoxycarbonyl)cyclopropyl)zinc(II) bromide

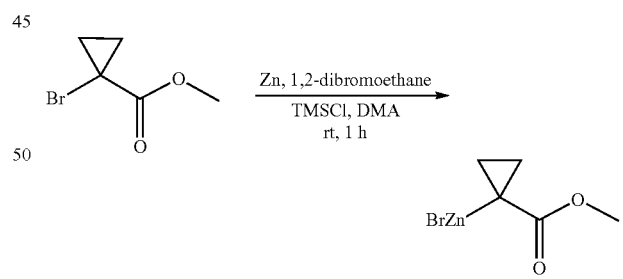

A vial fitted with a magnetic stirrer and flushed with nitrogen was charged with zinc dust (0.813 g, 12.7 mmol, 2.00 equiv) and DMA (10 mL). 1,2-Dibromoethane (0.236 g, 1.27 mmol, 0.20 equiv) was added slowly, followed by chlorotrimethylsilane (0.137 g, 1.27 mmol, 0.20 equiv). The reaction was stirred for 15 min at room temperature prior to dropwise addition of methyl 1-bromocyclopropane-1-carboxylate (1.69 g, 9.44 mmol, 1.50 equiv). The resulting solution was stirred for 1 hour at room temperature yielding 0.80 M solution of (1-(methoxycarbonyl)cyclopropyl)zinc (II) bromide to be used crude.

Step 2: Synthesis of methyl 1-(5-chloropyrimidin-2-yl)cyclopropane-1-carboxylate

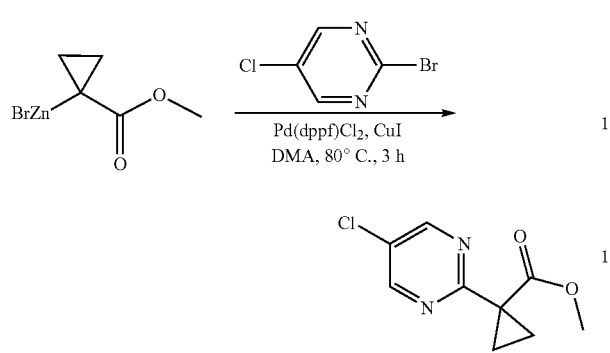

A flask was charged with 2-bromo-5-chloropyrimidine (900 mg, 4.65 mmol, 1.00 equiv), (1-(methoxycarbonyl)cyclopropyl)zinc(II) bromide (8.70 mL, 0.80 M in DMA, 6.96 mmol, 1.50 equiv), 1,1′-bis(diphenylphosphino)ferrocenepalladiumdichloride (335 mg, 0.460 mmol, 0.10 equiv), copper(I) iodide (89.1 mg, 0.470 mmol, 0.10 equiv) and DMA (5 mL) under nitrogen. The resulting solution was stirred for 3 h at 80° C. and quenched with water (20 mL). The mixture was extracted with EtOAc (3×30 mL) and the organic layers were combined, dried over anhydrous $Na_2SO_4$, filtered and concentrated under reduced pressure. The residue was chromatographed on a silica gel column to provide 760 mg (77% yield) of methyl 1-(5-chloropyrimidin-2-yl)cyclopropane-1-carboxylate. LCMS (ESI, m/z): 213 [M+H]$^+$.

Step 3: Synthesis of 1-(5-chloropyrimidin-2-yl)cyclopropane-1-carboxylic acid

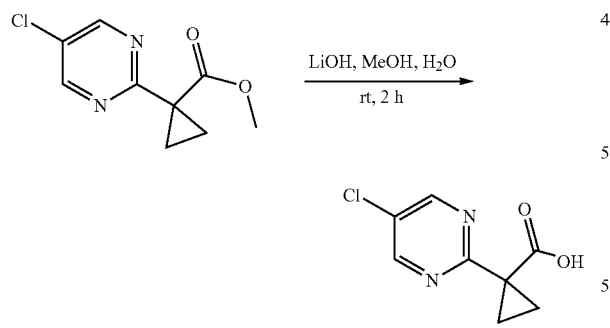

A flask was charged with methyl 1-(5-chloropyrimidin-2-yl)cyclopropane-1-carboxylate (212 mg, 1.00 mmol, 1.00 equiv), LiOH (72.0 mg, 3.00 mmol, 3.00 equiv), MeOH (3 mL) and water (0.5 mL). The resulting solution was stirred for 2 h at room temperature and concentrated under reduced pressure to provide 198 mg (crude) of 1-(5-chloropyrimidin-2-yl)cyclopropane-1-carboxylic acid. LCMS (ESI, m/z): 199 [M+H]$^+$.

Step 4: Synthesis of 1,1,1,3,3,3-hexafluoropropan-2-yl 1-(1-(5-chloropyrimidin-2-yl)cyclopropane-1-carbonyl)-1,8-diazaspiro[4.5]decane-8-carboxylate

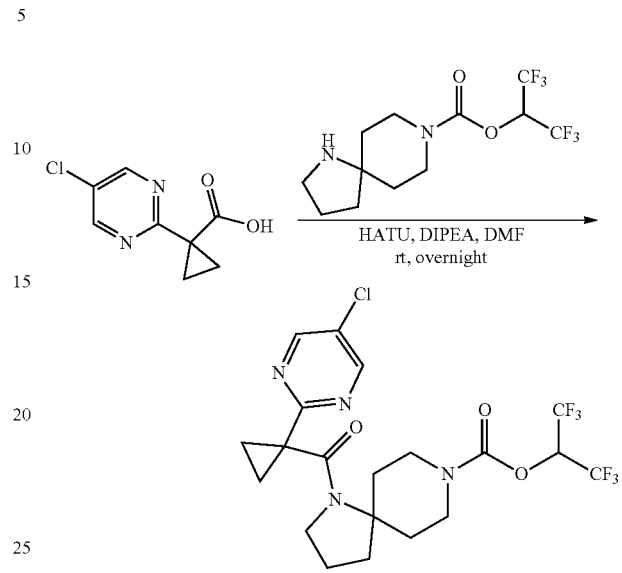

A flask was charged with 1-(5-chloropyrimidin-2-yl)cyclopropane-1-carboxylic acid (59.4 mg, 0.300 mmol, 1.00 equiv), 1,1,1,3,3,3-hexafluoropropan-2-yl 1,8-diazaspiro[4.5]decane-8-carboxylate (100 mg, 0.300 mmol, 1.00 equiv), HATU (171 mg, 0.450 mmol, 1.50 equiv), DIPEA (116 mg, 0.900 mmol, 3.00 equiv) and DMF (5 mL). The reaction mixture was stirred overnight at room temperature and quenched with water (10 mL). The resulting solution was extracted with EtOAc (3×30 mL) and the organic layers were combined, washed with water (3×10 mL), dried over anhydrous $Na_2SO_4$, filtered and concentrated under reduced pressure. The crude product was purified by preparative HPLC to provide 75.7 mg (49% yield) of 1,1,1,3,3,3-hexafluoropropan-2-yl 1-(1-(5-chloropyrimidin-2-yl)cyclopropane-1-carbonyl)-1,8-diazaspiro[4.5]decane-8-carboxylate. $^1$H NMR (300 MHz, Chloroform-d) δ 8.57 (s, 2H), 5.89-5.69 (m, 1H), 4.31-4.11 (m, 2H), 3.46-3.25 (m, 2H), 3.25-2.90 (m, 4H), 2.09-1.86 (m, 2H), 1.86-1.71 (m, 2H), 1.70-1.40 (m, 6H). LCMS (ESI, m/z): 515 [M+H]$^+$.

Example 32: 1,1,1,3,3,3-Hexafluoropropan-2-yl 1-(2,2-difluoro-2-(pyrimidin-2-yl)acetyl)-1,8-diazaspiro[4.5]decane-8-carboxylate

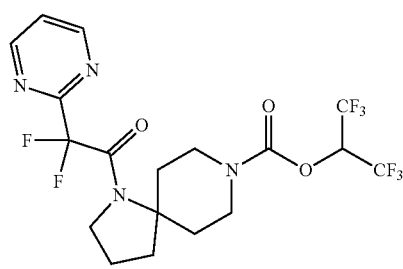 [SMILES: O=C(OC(C(F)(F)F)C(F)(F)F)N1CCC2(CCCN2C(=O)C(F)(F)c2ncccn2)CC1]

Step 1: Synthesis of ethyl 2,2-difluoro-2-(pyrimidin-2-yl)acetate

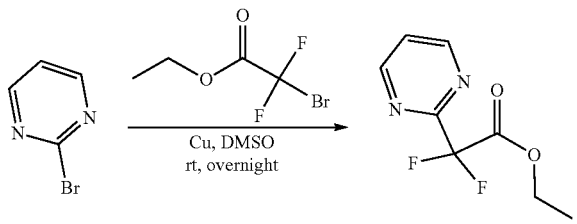

A flask was charged with ethyl 2-bromo-2,2-difluoroacetate (2.6 g, 12.6 mmol, 2.00 equiv), copper (1.62 g, 25.3 mmol, 4.00 equiv) and DMSO (10 mL). The resulting solution was stirred for 1 hour at room temperature prior to addition of 2-bromopyrimidine (1.00 g, 6.29 mmol, 1.00 equiv). The reaction mixture was stirred overnight at room temperature and quenched with water (10 mL). The mixture was extracted with EtOAc (3×30 mL) and the organic layers were combined, washed with water (3×10 mL), dried over anhydrous Na$_2$SO$_4$, filtered and concentrated under reduced pressure. The residue was chromatographed on a silica gel column provide 0.550 g (43% yield) of ethyl 2,2-difluoro-2-(pyrimidin-2-yl)acetate. LCMS (ESI, m/z): 203 [M+H]$^+$.

Step 2: Synthesis of 2,2-difluoro-2-(pyrimidin-2-yl)acetic acid

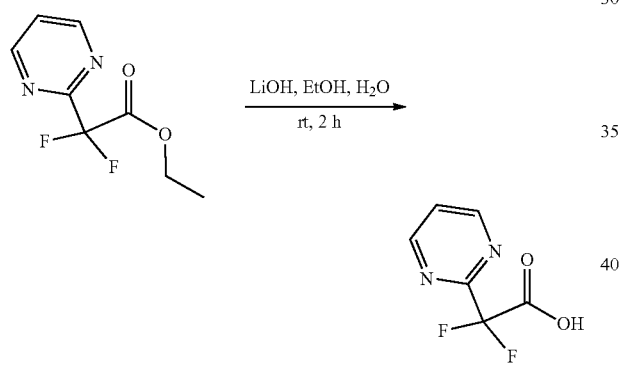

A flask was charged with ethyl 2,2-difluoro-2-(pyrimidin-2-yl)acetate (202 mg, 1.00 mmol, 1.00 equiv), lithium hydroxide (72.0 mg, 3.01 mmol, 3.00 equiv), EtOH (3 mL) and water (0.5 mL). The resulting solution was stirred for 2 h at room temperature and concentrated under reduced pressure to provide 174 mg (crude) of 2,2-difluoro-2-(pyrimidin-2-yl)acetic acid. LCMS (ESI, m/z): 175 [M+H]$^+$.

Step 3: Synthesis of 1,1,1,3,3,3-hexafluoropropan-2-yl 1-(2,2-difluoro-2-(pyrimidin-2-yl)acetyl)-1,8-diazaspiro[4.5]decane-8-carboxylate

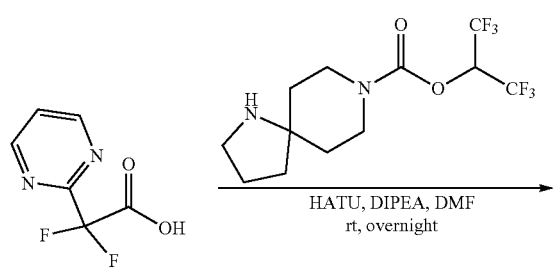

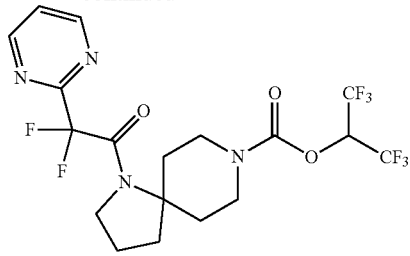

A flask was charged with 2,2-difluoro-2-(pyrimidin-2-yl)acetic acid (45.0 mg, 0.260 mmol, 1.00 equiv), 1,1,1,3,3,3-hexafluoropropan-2-yl 1,8-diazaspiro[4.5]decane-8-carboxylate (86.4 mg, 0.260 mmol, 1.00 equiv), HATU (147 mg, 0.390 mmol, 1.50 equiv), DIPEA (100 mg, 0.770 mmol, 3.00 equiv) and DMF (5 mL). The resulting solution was stirred overnight at room temperature and quenched with water (10 mL). The mixture was extracted with EtOAc (3×30 mL) and the organic layers were combined, washed with water (3×10 mL), dried over anhydrous Na$_2$SO$_4$, filtered and concentrated under reduced pressure. The crude product was purified by preparative HPLC to provide 61.4 mg (48% yield) of 1,1,1,3,3,3-hexafluoropropan-2-yl 1-(2,2-difluoro-2-(pyrimidin-2-yl)acetyl)-1,8-diazaspiro[4.5]decane-8-carboxylate. $^1$H NMR (300 MHz, Chloroform-d) δ 8.89 (d, J=4.9 Hz, 2H), 7.48 (t, J=4.9 Hz, 1H), 5.83-5.65 (m, 1H), 4.31-4.08 (m, 2H), 3.73 (t, J=6.4 Hz, 2H), 3.15-2.90 (m, 4H), 2.15-1.82 (m, 4H), 1.58-1.35 (m, 2H). LCMS (ESI, m/z): 491 [M+H]$^+$.

Example 33: 1,1,1,3,3,3-Hexafluoropropan-2-yl 1-(1-(5-cyclopropylpyrimidin-2-yl)cyclopropane-1-carbonyl)-1,8-diazaspiro[4.5]decane-8-carboxylate

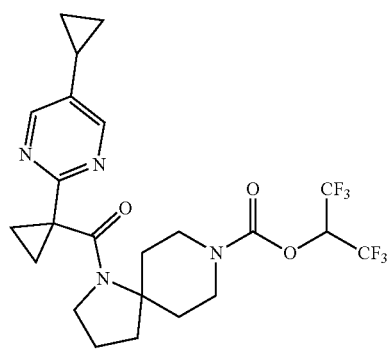 [SMILES: O=C(OC(C(F)(F)F)C(F)(F)F)N1CCC2(CCCN2C(=O)C2(c3ncc(C4CC4)cn3)CC2)CC1]

Step 1: Synthesis of 2-chloro-5-cyclopropylpyrimidine

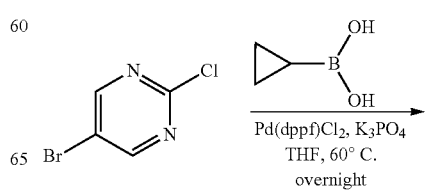

233
-continued

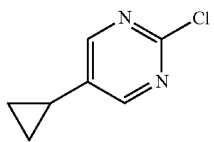

A flask was charged with 5-bromo-2-chloropyrimidine (1.93 g, 9.98 mmol, 1.00 equiv), cyclopropylboronic acid (947 mg, 11.0 mmol, 1.10 equiv), potassium phosphate (6.36 g, 30.0 mmol, 3.00 equiv) and THF (30 mL). 1,1'-Bis(diphenylphosphino)ferrocenepalladiumdichloride (1.46 g, 1.99 mmol, 0.200 equiv) was added under nitrogen atmosphere, and the resulting solution was stirred overnight at 60° C. and quenched with water (30 mL). The mixture was extracted with EtOAc (3×50 mL) and the organic layers were combined, washed with brine (2×40 mL), dried over anhydrous $Na_2SO_4$, filtered and concentrated under reduced pressure. The residue was chromatographed on a silica gel column to provide 500 mg (32% yield) of 2-chloro-5-cyclopropylpyrimidine. LCMS (ESI, m/z): 155 $[M+H]^+$.

Step 2: Synthesis of 1,1,1,3,3,3-hexafluoropropan-2-yl 1-(1-(5-cyclopropylpyrimidin-2-yl)cyclopropane-1-carbonyl)-1,8-diazaspiro[4.5]decane-8-carboxylate

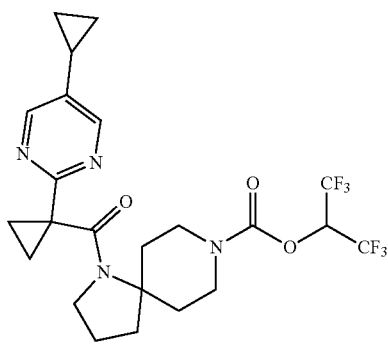 [SMILES: O=C(OC(C(F)(F)F)C(F)(F)F)N1CCC2(CCCN2C(=O)C2(c3ncc(C4CC4)cn3)CC2)CC1]

The title compound was prepared as described in Example 31, Steps 1-4, using methyl 1-bromocyclopropane-1-carboxylate in Step 1 and 2-chloro-5-cyclopropylpyrimidine in Step 2 to provide 61.6 mg (32% yield) of 1,1,1,3,3,3-hexafluoropropan-2-yl 1-(1-(5-cyclopropylpyrimidin-2-yl)cyclopropane-1-carbonyl)-1,8-diazaspiro[4.5]decane-8-carboxylate. $^1$H NMR (400 MHz, Methanol-$d_4$) δ 8.40 (s, 2H), 6.24-6.09 (m, 1H), 4.23-4.10 (m, 2H), 3.41-3.35 (m, 2H), 3.20-2.96 (m, 4H), 2.12-2.00 (m, 2H), 1.99-1.86 (m, 1H), 1.84-1.72 (m, 2H), 1.60-1.47 (m, 4H), 1.46-1.38 (m, 2H), 1.13-1.04 (m, 2H), 0.82-0.76 (m, 2H). LCMS (ESI, m/z): 521 $[M+H]^+$.

Example 34: 1,1,1,3,3,3-Hexafluoropropan-2-yl 1-(1-(5-methyl-1,3,4-oxadiazol-2-yl)cyclopropane-1-carbonyl)-1,8-diazaspiro[4.5]decane-8-carboxylate

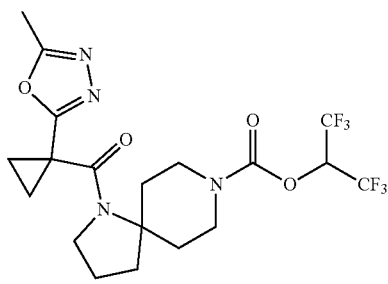 [SMILES: Cc1nnc(C2(C(=O)N3CCCC34CCN(C(=O)OC(C(F)(F)F)C(F)(F)F)CC4)CC2)o1]

234
Step 1: Synthesis of 1-(ethoxycarbonyl)cyclopropane-1-carboxylic acid

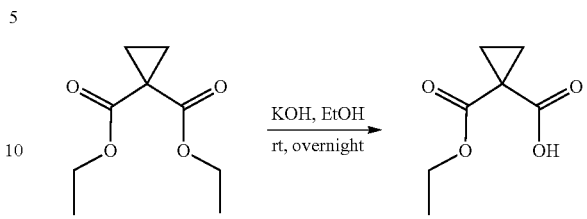

A flask was charged with diethyl cyclopropane-1,1-dicarboxylate (10.0 g, 53.7 mmol, 1.00 equiv), KOH (3.00 g, 53.7 mmol, 1.00 equiv) and EtOH (100 mL). The resulting mixture was stirred overnight at room temperature and concentrated under reduced pressure. The residue was dissolved in water (100 mL) and extracted with diethyl ether (2×50 mL). The pH value of aqueous layer was adjusted to 4 with aqueous HCl (1 M) and extracted with EtOAc (3×100 mL). The organic layers were combined, washed with water (50 mL) and brine (50 mL), dried over anhydrous $Na_2SO_4$, filtered and concentrated under reduced pressure to provide 6.60 g (crude) of 1-(ethoxycarbonyl)cyclopropane-1-carboxylic acid. LCMS (ESI, m/z): 159 $[M+H]^+$.

Step 2: Synthesis of ethyl 1-(2-acetylhydrazine-1-carbonyl)cyclopropane-1-carboxylate

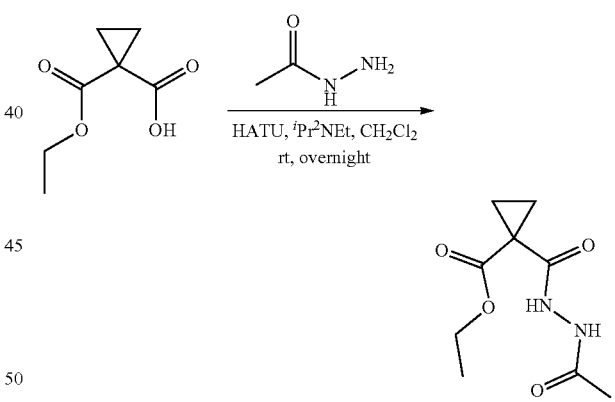

A flask was charged with 1-(ethoxycarbonyl)cyclopropane-1-carboxylic acid (6.60 g, 40.0 mmol, 1.00 equiv), HATU (22.8 g, 60.0 mmol, 1.50 equiv), DIPEA (15.5 g, 120 mmol, 3.00 equiv), acetohydrazide (2.96 g, 40.0 mmol, 1.00 equiv) and DCM (100 mL). The resulting mixture was stirred overnight at room temperature and quenched with water (60 mL). The mixture was extracted with DCM (2×50 mL) and the organic layers were combined, washed with brine (2×30 mL), dried over anhydrous $Na_2SO_4$, filtered and concentrated under reduced pressure. The residue was purified by recrystallization to provide 4.77 g (crude) of ethyl 1-(2-acetylhydrazine-1-carbonyl)cyclopropane-1-carboxylate. LCMS (ESI, m/z): 215 $[M+H]^+$.

Step 3: Synthesis of ethyl 1-(5-methyl-1,3,4-oxadiazol-2-yl)cyclopropane-1-carboxylate

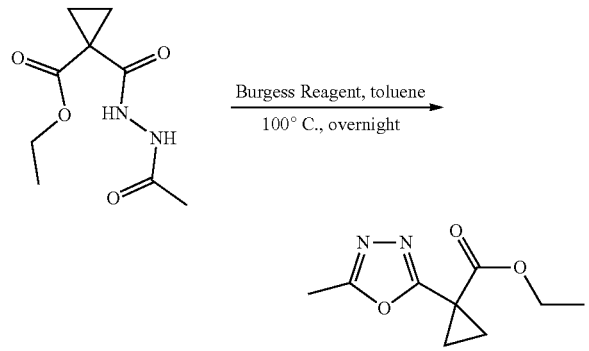

A flask was charged with ethyl 1-(2-acetylhydrazine-1-carbonyl)cyclopropane-1-carboxylate (3.00 g, 14.0 mmol, 1.00 equiv), Burgess reagent (10.0 g, 42.0 mmol, 3.00 equiv) and toluene (100 mL). The resulting mixture was stirred overnight at 100° C. and concentrated under reduced pressure. The residue was quenched with water (50 mL), extracted with EtOAc (3×100 mL) and the organic layers were combined, washed with brine (50 mL), dried over anhydrous $Na_2SO_4$, filtered and concentrated under reduced pressure to provide 2.80 g (crude) of ethyl 1-(5-methyl-1,3,4-oxadiazol-2-yl)cyclopropane-1-carboxylate. LCMS (ESI, m/z): 197 [M+H]$^+$.

Step 4: Synthesis of 1-(5-methyl-1,3,4-oxadiazol-2-yl)cyclopropane-1-carboxylic acid

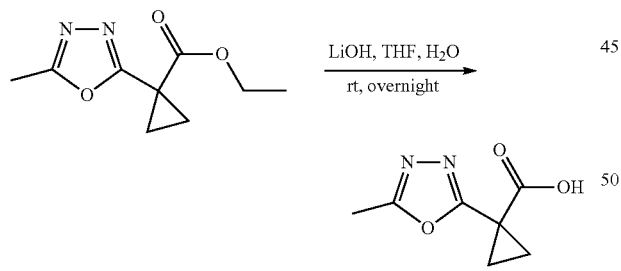

A vial was charged with ethyl 1-(5-methyl-1,3,4-oxadiazol-2-yl)cyclopropane-1-carboxylate (1.20 g, 6.12 mmol, 1.00 equiv), LiOH (0.441 g, 18.4 mmol, 3.00 equiv), THF (10 mL) and water (2 mL). The resulting mixture was stirred overnight at room temperature and concentrated under reduced pressure. The residue was adjusted to pH 5 with aqueous HCl (1 M) and concentrated under reduced pressure to provide 1.40 g (crude) of 1-(5-methyl-1,3,4-oxadiazol-2-yl)cyclopropane-1-carboxylic acid. LCMS (ESI, m/z): 169 [M+H]$^+$.

Step 5: Synthesis of 1,1,1,3,3,3-hexafluoropropan-2-yl 1-(1-(5-methyl-1,3,4-oxadiazol-2-yl)cyclopropane-1-carbonyl)-1,8-diazaspiro[4.5]decane-8-carboxylate

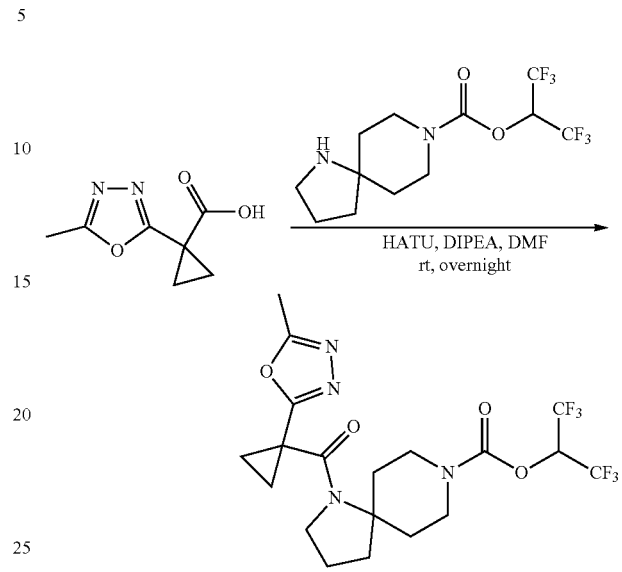

A vial was charged with 1-(5-methyl-1,3,4-oxadiazol-2-yl)cyclopropane-1-carboxylic acid (76.0 mg, 0.450 mmol, 1.00 equiv), 1,1,1,3,3,3-hexafluoropropan-2-yl 1,8-diazaspiro[4.5]decane-8-carboxylate (150 mg, 0.450 mmol, 1.00 equiv), HATU (256 mg, 0.675 mmol, 1.50 equiv), DIPEA (174 mg, 1.35 mmol, 3.00 equiv) and DMF (5 mL). The resulting solution was stirred overnight at room temperature and quenched with water (10 mL). The mixture was extracted with EtOAc (3×30 mL) and the organic layers were combined, washed with brine (2×20 mL), dried over anhydrous $Na_2SO_4$, filtered and concentrated under reduced pressure. The crude product was purified by preparative HPLC to provide 27.5 mg (13% yield) of 1,1,1,3,3,3-hexafluoropropan-2-yl 1-(1-(5-methyl-1,3,4-oxadiazol-2-yl)cyclopropane-1-carbonyl)-1,8-diazaspiro[4.5]decane-8-carboxylate. $^1$H NMR (400 MHz, Chloroform-d) δ 5.80-5.70 (m, 1H), 4.26-4.10 (m, 2H), 3.50-3.40 (m, 2H), 3.08-2.90 (m, 4H), 2.53 (s, 3H), 2.05-1.91 (m, 2H), 1.90-1.80 (m, 2H), 1.68-1.50 (m, 4H), 1.48-1.30 (m, 2H). LCMS (ESI, m/z): 485 [M+H]$^+$.

Example 35: 1,1,1,3,3,3-Hexafluoropropan-2-yl 1-((2-(2-(cyclopropanesulfonamido)-2-oxoethyl)-6-(trifluoromethyl)pyridin-3-yl)methyl)-1,8-diazaspiro[4.5]decane-8-carboxylate

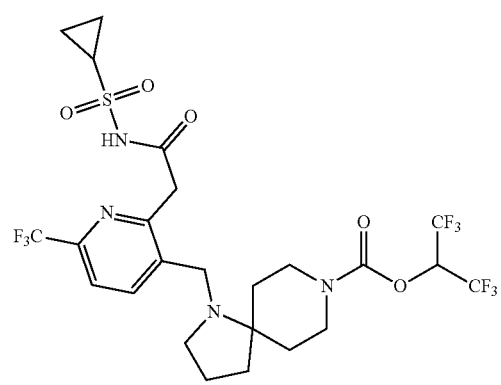 [SMILES: O=C(Cc1nc(C(F)(F)F)ccc1CN1CCCC12CCN(C(=O)OC(C(F)(F)F)C(F)(F)F)CC2)NS(=O)(=O)C1CC1]

Step 1: Synthesis of t-butyl 1-((2-bromo-6-(trifluoromethyl)pyridin-3-yl)methyl)-1,8-diazaspiro[4.5]decane-8-carboxylate

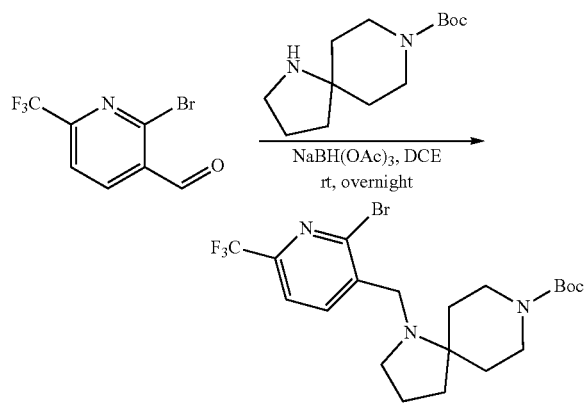

A flask was charged with 2-bromo-6-(trifluoromethyl)pyridine-3-carbaldehyde (1.00 g, 3.94 mmol, 1.00 equiv), t-butyl 1,8-diazaspiro[4.5]decane-8-carboxylate (1.23 g, 5.12 mmol, 1.30 equiv), and DCE (20 mL). The mixture was stirred at room temperature for 30 min prior to addition of sodium triacetoxyborohydride (2.52 g, 11.9 mmol, 3.00 equiv). The reaction mixture was stirred overnight at room temperature and quenched with water (100 mL). The resulting solution was extracted with DCM (3×100 mL) and the organic layers were combined, washed with brine (2×100 mL), dried over anhydrous Na$_2$SO$_4$, filtered and concentrated under reduced pressure. The residue was chromatographed on a silica gel column to provide 1.00 g (53% yield) of t-butyl 1-((2-bromo-6-(trifluoromethyl)pyridin-3-yl)methyl)-1,8-diazaspiro[4.5]decane-8-carboxylate. LCMS (ESI, m/z): 478 [M+H]$^+$.

Step 2: Synthesis of t-butyl 1-((2-(2-ethoxy-2-oxoethyl)-6-(trifluoromethyl)pyridin-3-yl)methyl)-1,8-diazaspiro[4.5]decane-8-carboxylate

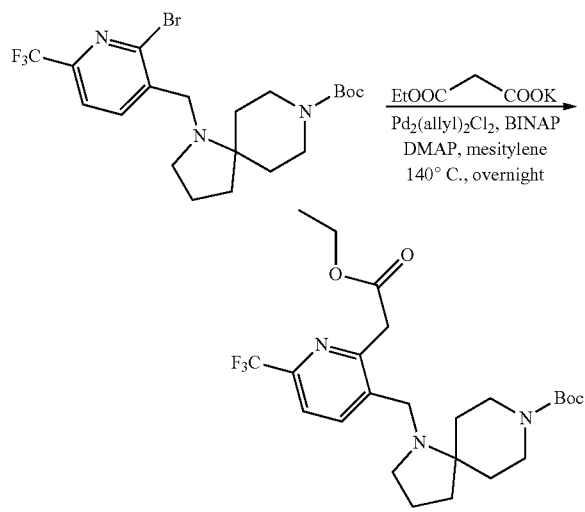

A flask was charged with t-butyl 1-((2-bromo-6-(trifluoromethyl)pyridin-3-yl)methyl)-1,8-diazaspiro[4.5]decane-8-carboxylate (1000 mg, 2.09 mmol, 1.00 equiv), mesitylene (8 mL), 1-ethyl 3-potassium propanedioate (1430 mg, 8.40 mmol, 4.00 equiv), allylpalladium chloride dimer (77.0 mg, 0.0840 mmol, 0.04 equiv), 2,2'-bis(diphenylphosphino)-1,1'-binaphthyl (392 mg, 0.630 mmol, 0.30 equiv), and DMAP (64.0 mg, 0.520 mmol, 0.25 equiv) under nitrogen. The reaction mixture was stirred for 6 h at 140° C. and quenched with water (50 mL). The resulting solution was extracted with EtOAc (2×80 mL) and the organic layers were combined, washed with brine (2×50 mL), dried over anhydrous Na$_2$SO$_4$, filtered and concentrated under reduced pressure. The residue was chromatographed on a silica gel column to provide 240 mg (24% yield) of t-butyl 1-((2-(2-ethoxy-2-oxoethyl)-6-(trifluoromethyl)pyridin-3-yl)methyl)-1,8-diazaspiro[4.5]decane-8-carboxylate. LCMS (ESI, m/z): 486 [M+H]$^+$.

Step 3: Synthesis of 2-(3-((8-(t-butoxycarbonyl)-1,8-diazaspiro[4.5]decan-1-yl)methyl)-6-(trifluoromethyl)pyridin-2-yl)acetic acid

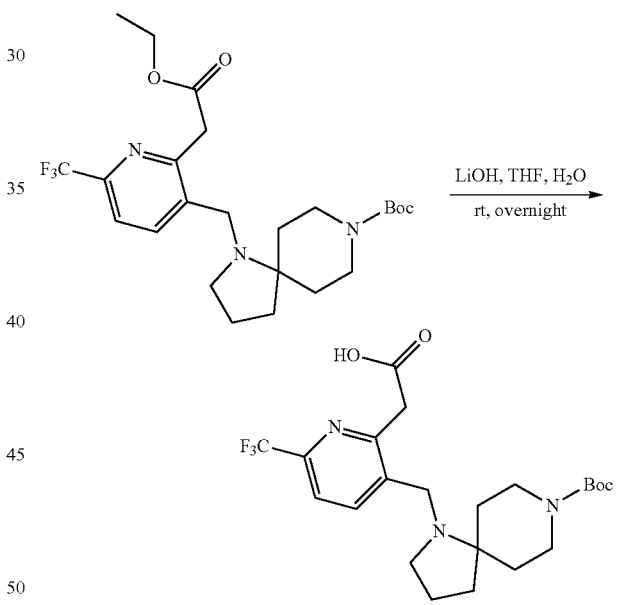

A flask was charged with t-butyl 1-((2-(2-ethoxy-2-oxoethyl)-6-(trifluoromethyl)pyridin-3-yl)methyl)-1,8-diazaspiro[4.5]decane-8-carboxylate (230 mg, 0.470 mmol, 1.00 equiv), LiOH (57.0 mg, 2.38 mmol, 5.00 equiv), THF (5 mL), and water (5 mL). The resulting solution was stirred for 3 h at room temperature. The pH value of the solution was adjusted to 5 with aqueous HCl (1 M). The resulting solution was extracted with DCM (2×50 mL) and the organic layers were combined, washed with brine (2×30 mL), dried over anhydrous Na$_2$SO$_4$, filtered and concentrated under reduced pressure to provide 200 mg (92% yield) of 2-(3-((8-(t-butoxycarbonyl)-1,8-diazaspiro[4.5]decan-1-yl)methyl)-6-(trifluoromethyl)pyridin-2-yl)acetic acid. LCMS (ESI, m/z): 458 [M+H]$^+$.

Step 4: Synthesis of t-butyl 1-((2-(2-(cyclopropane-sulfonamido)-2-oxoethyl)-6-(trifluoromethyl)pyridin-3-yl)methyl)-1,8-diazaspiro[4.5]decane-8-carboxylate

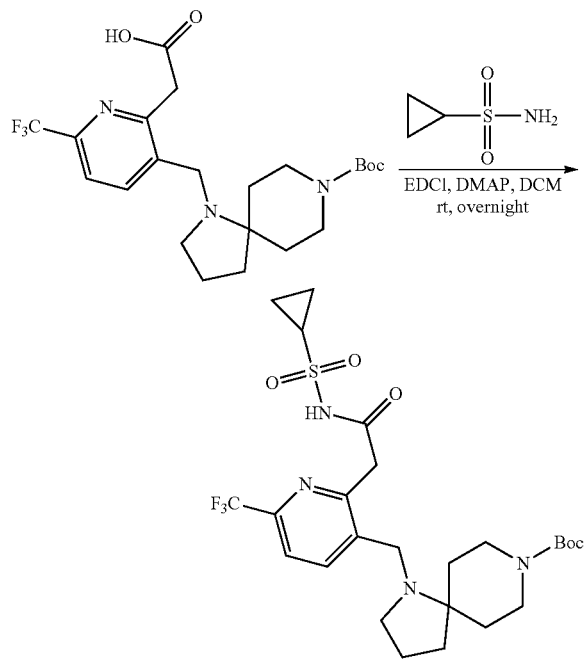

A flask was charged with 2-(3-((8-(t-butoxycarbonyl)-1,8-diazaspiro[4.5]decan-1-yl)methyl)-6-(trifluoromethyl)pyridin-2-yl)acetic acid (200 mg, 0.440 mmol, 1.00 equiv), cyclopropanesulfonamide (106 mg, 0.870 mmol, 2.00 equiv), EDCI (252 mg, 1.31 mmol, 3.00 equiv), DMAP (107 mg, 0.880 mmol, 2.00 equiv), and DCM (10 mL). The reaction mixture was stirred overnight at room temperature and quenched with water (30 mL). The resulting solution was extracted with DCM (2×50 mL) and the organic layers were combined, washed with brine (2×30 mL), dried over anhydrous Na$_2$SO$_4$, filtered and concentrated under reduced pressure. The residue was chromatographed on a silica gel column to provide 50 mg (20% yield) of t-butyl 1-((2-(2-(cyclopropanesulfonamido)-2-oxoethyl)-6-(trifluoromethyl)pyridin-3-yl)methyl)-1,8-diazaspiro[4.5]decane-8-carboxylate. LCMS (ESI, m/z): 561 [M+H]$^+$.

Step 5: Synthesis of 2-(3-((1,8-diazaspiro[4.5]decan-1-yl)methyl)-6-(trifluoromethyl)pyridin-2-yl)-N-(cyclopropylsulfonyl)acetamide

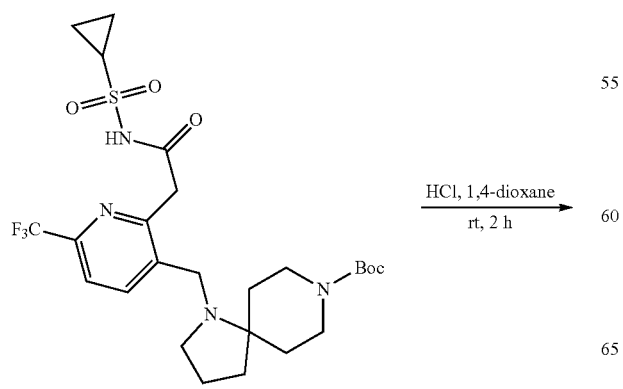

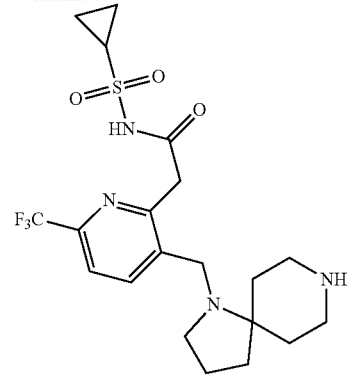

A flask was charged with t-butyl 1-((2-(2-(cyclopropanesulfonamido)-2-oxoethyl)-6-(trifluoromethyl)pyridin-3-yl)methyl)-1,8-diazaspiro[4.5]decane-8-carboxylate (50.0 mg, 0.0900 mmol, 1.00 equiv), concentrated HCl (2 mL), and 1,4-dioxane (10 mL). The resulting solution was stirred for 2 h at room temperature and concentrated under reduced pressure to provide 41.0 mg (quantitative) of 2-(3-((1,8-diazaspiro[4.5]decan-1-yl)methyl)-6-(trifluoromethyl)pyridin-2-yl)-N-(cyclopropylsulfonyl)acetamide. LCMS (ESI, m/z): 461 [M+H]$^+$.

Step 6: Synthesis of 1,1,1,3,3,3-hexafluoropropan-2-yl 1-((2-(2-(cyclopropanesulfonamido)-2-oxoethyl)-6-(trifluoromethyl)pyridin-3-yl)methyl)-1,8-diazaspiro[4.5]decane-8-carboxylate

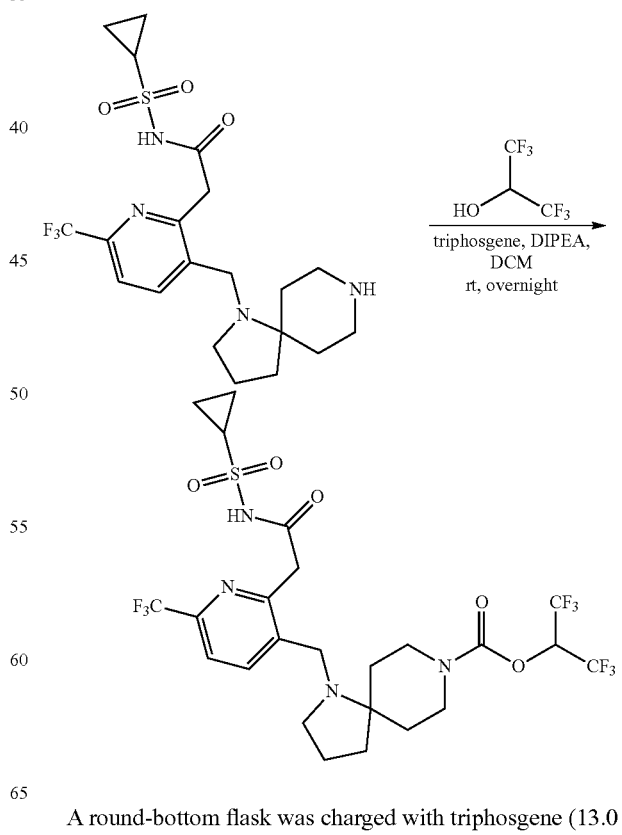

A round-bottom flask was charged with triphosgene (13.0 mg, 0.040 mmol, 0.50 equiv), 1,1,1,3,3,3-hexafluoropropan- 2-ol (30.0 mg, 0.180 mmol, 2.00 equiv), and DCM (10 mL). DIPEA (34.0 mg, 0.260 mmol, 3.00 equiv) was added dropwise at 0° C., and the resulting solution was stirred for 1 h at room temperature prior to addition of 2-(3-((1,8-diazaspiro[4.5]decan-1-yl)methyl)-6-(trifluoromethyl)pyridin-2-yl)-N-(cyclopropylsulfonyl)acetamide (41.0 mg, 0.090 mmol, 1.00 equiv). The reaction mixture was stirred overnight at room temperature and quenched with water (20 mL). The resulting solution was extracted with DCM (3×20 mL) and the organic layers were combined, washed with brine (2×20 mL), dried over anhydrous $Na_2SO_4$, filtered and concentrated under reduced pressure. The crude product (100 mg) was purified by preparative HPLC to provide 4.7 mg (8% yield) of 1,1,1,3,3,3-hexafluoropropan-2-yl 1-((2-(2-(cyclopropanesulfonamido)-2-oxoethyl)-6-(trifluoromethyl)pyridin-3-yl)methyl)-1,8-diazaspiro[4.5]decane-8-carboxylate. $^1$H NMR (400 MHz, Methanol-$d_4$) δ 8.72 (s, 1H), 8.10-8.05 (m, 1H), 7.78-7.76 (m, 1H), 6.13-6.12 (m, 1H), 4.24-4.68 (m, 3H), 3.82-3.76 (m, 1H), 3.45-3.40 (m, 1H), 3.28-3.02 (m, 2H), 2.99-2.87 (m, 1H), 2.31-2.05 (m, 4H), 1.77-1.31 (m, 6H), 1.16-1.04 (m, 2H), 1.02-1.95 (m, 2H). LCMS (ESI, m/z): 655 [M+H]$^+$.

Example 36: 1,1,1,3,3,3-Hexafluoropropan-2-yl 4-(7-isopropyl-5,6,7,8-tetrahydro-[1,2,4]triazolo[4,3-a]pyrazine-3-carboxamido)-4-methylpiperidine-1-carboxylate

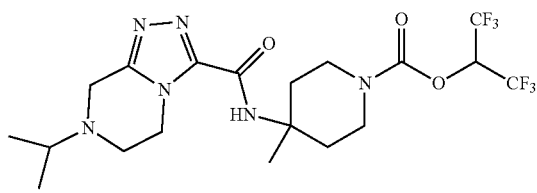 [SMILES: CC(C)N1CCn2c(nnc2C(=O)NC2(C)CCN(C(=O)OC(C(F)(F)F)C(F)(F)F)CC2)C1]

Step 1: Synthesis of 1,1,1,3,3,3-hexafluoropropan-2-yl 4-((t-butoxycarbonyl)amino)-4-methylpiperidine-1-carboxylate

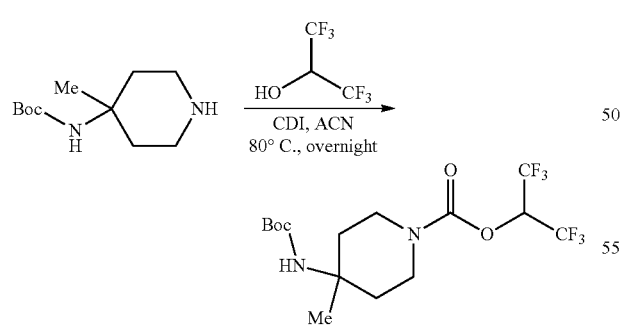

A flask was charged with t-butyl N-(4-methylpiperidin-4-yl)carbamate (8.00 g, 37.3 mmol, 1.00 equiv), 1,1,1,3,3,3-hexafluoropropan-2-ol (75.4 g, 449 mmol, 12.0 equiv), N,N-carbonyldiimidazole (9.08 g, 56.0 mmol, 1.50 equiv) and ACN (100 mL). The resulting solution was stirred for 48 hours at 80° C. and quenched with water (50 mL). The mixture was extracted with DCM (3×150 mL) and the organic layers were combined, washed with water (3×50 mL), dried over anhydrous $Na_2SO_4$, filtered and concentrated under reduced pressure. The residue was chromatographed on a silica gel column to provide 11.4 g (75% yield) of 1,1,1,3,3,3-hexafluoropropan-2-yl 4-((t-butoxycarbonyl)amino)-4-methylpiperidine-1-carboxylate. LCMS (ESI, m/z): 409 [M+H]$^+$.

Step 2: Synthesis of 1,1,1,3,3,3-hexafluoropropan-2-yl 4-amino-4-methylpiperidine-1-carboxylate

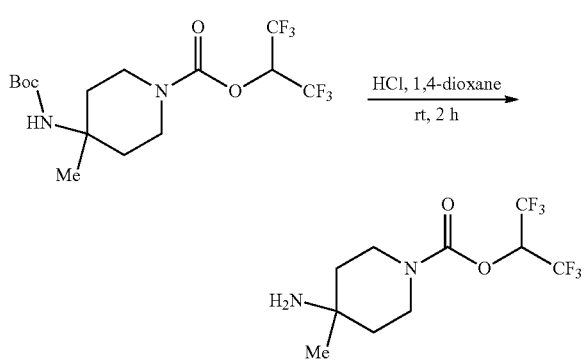

A flask was charged with 1,1,1,3,3,3-hexafluoropropan-2-yl 4-((t-butoxycarbonyl)amino)-4-methylpiperidine-1-carboxylate (4.12 g, 10.1 mmol, 1.00 equiv), concentrated HCl (4 mL) and 1,4-dioxane (15 mL). The resulting solution was stirred for 2 hours at room temperature and concentrated under pressure to provide 3.11 g (quantitative) of 1,1,1,3,3,3-hexafluoropropan-2-yl 4-amino-4-methylpiperidine-1-carboxylate. LCMS (ESI, m/z): 309 [M+H]$^+$.

Step 3: Synthesis of 7-(t-butoxycarbonyl)-5,6,7,8-tetrahydro-[1,2,4]triazolo[4,3-a]pyrazine-3-carboxylic acid

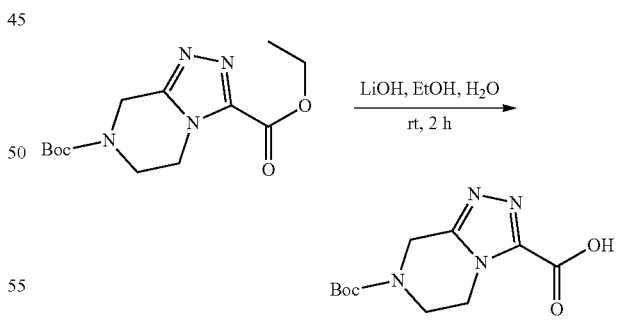

A flask was charged with 7-(t-butyl) 3-ethyl 5,6-dihydro-[1,2,4]triazolo[4,3-a]pyrazine-3,7(8H)-dicarboxylate (3.00 g, 10.1 mmol, 1.00 equiv), LiOH (1.21 g, 30.3 mmol, 3.00 equiv), EtOH (20 mL) and water (2 mL). The resulting solution was stirred for 2 h at room temperature and concentrated under reduced pressure to provide 2.70 g (crude) of 7-(t-butoxycarbonyl)-5,6,7,8-tetrahydro-[1,2,4]triazolo[4,3-a]pyrazine-3-carboxylic acid. LCMS (ESI, m/z): 269 [M+H]$^+$.

Step 4: Synthesis of t-butyl 3-((1-(((1,1,1,3,3,3-hexafluoropropan-2-yl)oxy)carbonyl)-4-methyl piperidin-4-yl)carbamoyl)-5,6-dihydro-[1,2,4]triazolo[4,3-a]pyrazine-7(8H)-carboxylate

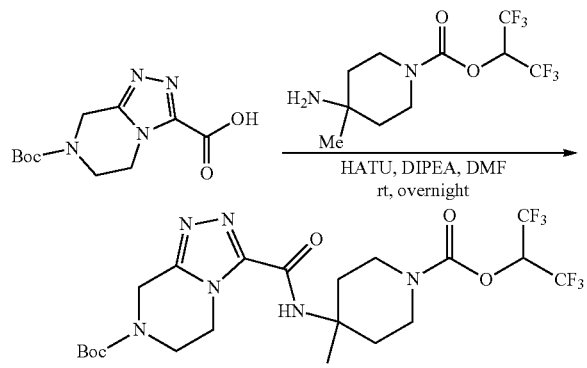

A flask was charged with 7-(t-butoxycarbonyl)-5,6,7,8-tetrahydro-1,2,4]triazolo[4,3-a]pyrazine-3-carboxylic acid (2.70 g, 10.1 mmol, 1.00 equiv), 1,1,1,3,3,3-hexafluoropropan-2-yl 4-amino-4-methylpiperidine-1-carboxylate (3.11 g, 10.1 mmol, 1.00 equiv), HATU (5.76 g 15.2 mmol, 1.50 equiv), DIPEA (5.21 g, 40.4 mmol, 4.00 equiv) and DMF (50 mL). The resulting solution was stirred overnight at room temperature and quenched with water (20 mL). The mixture was extracted with EtOAc (3×50 mL) and the organic layers were combined, washed with brine (2×50 mL), dried over anhydrous Na$_2$SO$_4$, filtered and concentrated under reduced pressure. The residue was chromatographed on a silica gel column to provide 4.33 g (77% yield) of t-butyl 3-((1-(((1,1,1,3,3,3-hexafluoropropan-2-yl)oxy)carbonyl)-4-methylpiperidin-4-yl)carbamoyl)-5,6-dihydro-[1,2,4]triazolo[4,3-a]pyrazine-7(8H)-carboxylate. LCMS (ESI, m/z): 559 [M+H]$^+$.

Step 5: Synthesis of 1,1,1,3,3,3-hexafluoropropan-2-yl 4-methyl-4-(5,6,7,8-tetrahydro-[1,2,4]triazolo[4,3-a]pyrazine-3-carboxamido)piperidine-1-carboxylate

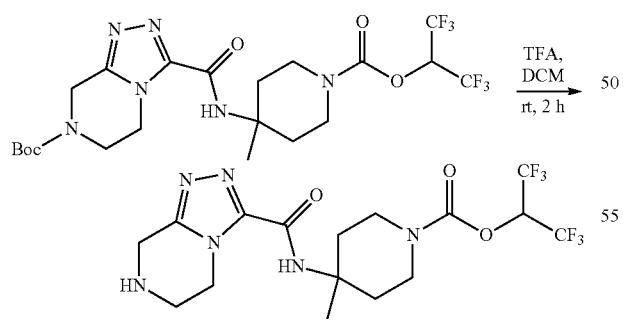

A vial was charged with t-butyl 3-((1-(((1,1,1,3,3,3-hexafluoropropan-2-yl)oxy)carbonyl)-4-methylpiperidin-4-yl)carbamoyl)-5,6-dihydro-[1,2,4]triazolo[4,3-a]pyrazine-7 (8H)-carboxylate (1.00 g, 1.79 mmol, 1.00 equiv), TFA (3 mL) and DCM (15 mL). The resulting solution was stirred for 2 h at room temperature and concentrated under reduced pressure to provide 0.553 g (crude) of 1,1,1,3,3,3-hexafluoropropan-2-yl 4-methyl-4-(5,6,7,8-tetrahydro-[1,2,4]triazolo[4,3-a]pyrazine-3-carboxamido)piperidine-1-carboxylate. LCMS (ESI, m/z): 459 [M+H]$^+$.

Step 6: Synthesis of 1,1,1,3,3,3-hexafluoropropan-2-yl 4-(7-isopropyl-5,6,7,8-tetrahydro-[1,2,4]triazolo[4,3-a]pyrazine-3-carboxamido)-4-methylpiperidine-1-carboxylate

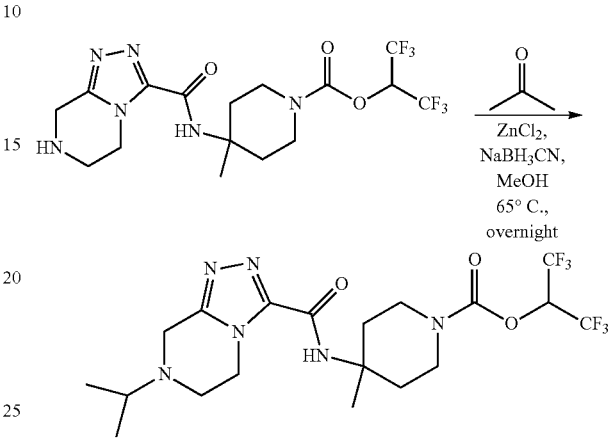

A vial was charged with 1,1,1,3,3,3-hexafluoropropan-2-yl 4-methyl-4-(5,6,7,8-tetrahydro-[1,2,4]triazolo[4,3-a] pyrazine-3-carboxamido)piperidine-1-carboxylate (100 mg, 0.218 mmol, 1.00 equiv), propan-2-one (126 mg, 2.18 mmol, 10.00 equiv), chlorozinc (44.5 mg, 0.327 mmol, 1.50 equiv), MeOH (15 mL) and sodium cyanoborohydride (41.2 mg, 0.654 mmol, 3.00 equiv). The resulting solution was stirred overnight at 65° C., quenched with water (10 mL), extracted with DCM (3×20 mL). The organic layers were combined, washed with brine (2×20 mL), dried over anhydrous Na$_2$SO$_4$, filtered and concentrated under reduced pressure. The crude product was purified by preparative HPLC to provide 75.6 mg (69% yield) of 1,1,1,3,3,3-hexafluoropropan-2-yl 4-(7-isopropyl-5,6,7,8-tetrahydro-[1, 2,4]triazolo[4,3-a]pyrazine-3-carboxamido)-4-methylpiperidine-1-carboxylate. $^1$H NMR (300 MHz, MeOH-d$_4$) δ 6.22-6.01 (m, 1H), 4.35 (t, J=5.5 Hz, 2H), 3.93 (s, 2H), 3.91-3.72 (m, 2H), 3.51-3.32 (m, 2H), 3.09-2.90 (m, 3H), 2.47-2.30 (m, 2H), 1.77-1.55 (m, 2H), 1.49 (s, 3H), 1.15 (t, J=6.5 Hz, 6H). LCMS (ESI, m/z): 501 [M+H]$^+$.

Example 37: 1,1,1,3,3,3-Hexafluoropropan-2-yl 4-(7-isobutyryl-5,6,7,8-tetrahydroimidazo[1,2-a]pyrazine-2-carboxamido)-4-methylpiperidine-1-carboxylate

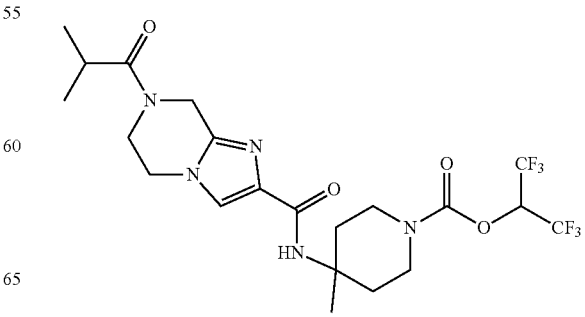

Step 1: Synthesis of 1,1,1,3,3,3-hexafluoropropan-2-yl 4-(7-isobutyryl-5,6,7,8-tetrahydroimidazo[1,2-a]pyrazine-2-carboxamido)-4-methylpiperidine-1-carboxylate

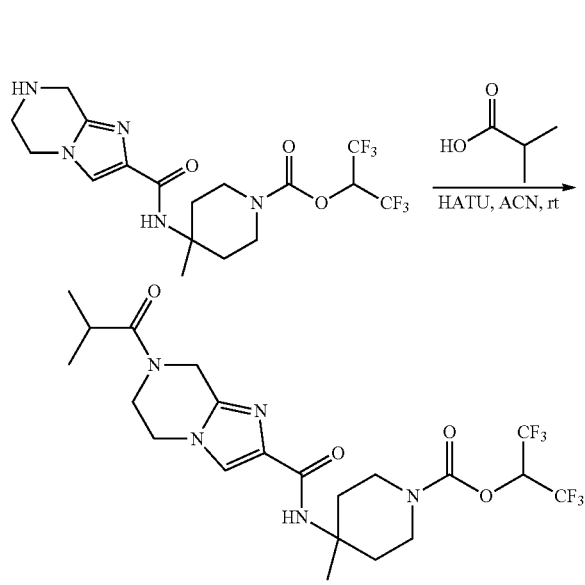

A vial was charged with [2,2,2-trifluoro-1-(trifluoromethyl)ethyl] 4-methyl-4-(5,6,7,8-tetrahydroimidazo[1,2-a]pyrazine-2-carbonylamino)piperidine-1-carboxylate (75 mg, 0.16 mmol, Example 28), ACN (0.75 mL) and HATU (71.7 mg, 0.19 mmol), prior to addition of 2-methylpropanoic acid (22.8 uL, 0.25 mmol) and DIPEA (0.10 mL, 0.58 mmol) respectively. The reaction mixture was stirred at room temperature for 24 h and purified by column chromatography to afford 79 mg (91% yield) of 1,1,1,3,3,3-hexafluoropropan-2-yl 4-(7-isobutyryl-5,6,7,8-tetrahydroimidazo[1,2-a]pyrazine-2-carboxamido)-4-methylpiperidine-1-carboxylate. $^1$H NMR (400 MHz, Chloroform-d) δ 7.46 (s, 1H), 6.87 (s, 1H), 5.74 (hept, J=6.2 Hz, 1H), 4.78 (s, 2H), 3.79-4.20 (m, 6H), 3.25-3.40 (m, 2H), 2.84 (hept, J=6.9 Hz, 1H), 2.34 (d, J=13.8 Hz, 2H), 1.57-1.77 (m, 2H), 1.51 (s, 3H), 1.17 (d, J=6.6 Hz, 6H). LCMS (ESI, m/z): 528 [M+H]$^+$.

Example 38: 1,1,1,3,3,3-Hexafluoropropan-2-yl 1-(1-(2-cyclopropylpyrimidin-5-yl)cyclopropane-1-carbonyl)-1,8-diazaspiro[4.5]decane-8-carboxylate Step 1: Synthesis of methyl 1-(2-cyclopropylpyrimidin-5-yl)cyclopropane-1-carboxylate

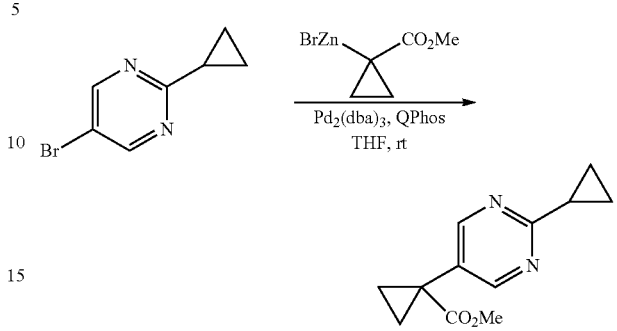

A flask was charged with zinc dust (50 g) and HCl (100 mL, 0.1M). The suspension was stirred for 2-3 minutes, and solids were filtered and washed with water (100 mL), EtOH (100 mL), and diethyl ether (100 mL). The zinc dust was dried under high vacuum at 110° C. for 18 h. To a flame-dried flask with stir bar was added activated zinc (380 mg, 5.90 mmol), followed by THF (10.5 mL). Bromine (0.040 mL, 0.78 mmol) was added by syringe in one portion. To the resulting solution was added 1-bromocyclopropane carboxylate (2.1 mL, 19.5 mmol) by dropwise addition. The mixture was heated to 55-62° C. (internal) for 3.5 h. The resulting solution was cooled to rt and the solids were allowed to settle. To an oven-dried vial was added Pd$_2$(dba)$_3$ (45.9 mg, 0.050 mmol), QPhos (35.6 mg, 0.050 mmol) and 5-bromo-2-cyclopropylpyrimidine (68.0 µL, 2.51 mmol). Under an nitrogen atmosphere, THF (11.5 mL) was added, followed by dropwise addition of bromo-(1-methoxycarbonylcyclopropyl)zinc (18.5 mL, 3.7 mmol) over 5 minutes. The subsequent solution was allowed to stir at room temperature for 1.5 h. The reaction was quenched with saturated aq. NH$_4$Cl (5 mL), and further diluted with aq. NH$_4$Cl (30 mL) and EtOAc (60 mL). The organics were extracted (2×60 ml EtOAc), dried over Na$_2$SO$_4$, decanted and concentrated. The crude material was purified by column chromatography to afford 511 mg (94% yield) of methyl 1-(2-cyclopropylpyrimidin-5-yl)cyclopropane-1-carboxylate. $^1$H NMR [400 MHz, Chloroform-d] δ 8.51 (d, J=1.8 Hz, 2H), 3.64 (d, J=1.8 Hz, 3H), 2.20-2.35 (m, 1H), 1.68 (t, J=2.5 Hz, 3H), 0.82-1.39 (m, 6H). LCMS (ESI, m/z): 219 [M+H]$^+$.

Step 2: Synthesis of 1-(2-cyclopropylpyrimidin-5-yl)cyclopropane-1-carboxylic acid

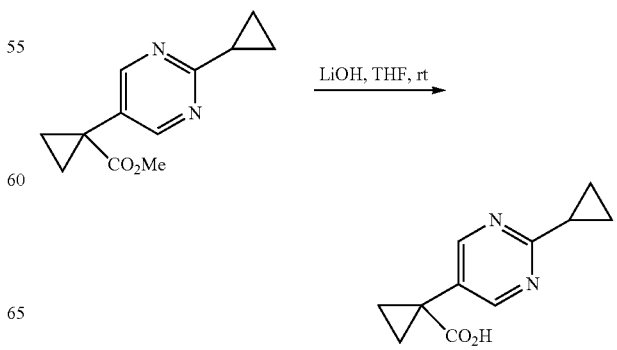

A vial containing methyl 1-(2-cyclopropylpyrimidin-5-yl)cyclopropane-1-carboxylate (511 mg, 2.34 mmol) was charged with THF (7.0 mL) and 5M aqueous LiOH (2.4 mL, 12 mmol). The reaction mixture was stirred at room temperature for 2 h, at which point the reaction mixture was diluted with water (3.0 mL) and EtOAc (3.0 mL). The pH of the organic layer was adjusted to 2 with aqueous HCl (1M). The aqueous layer was extracted with DCM (3×20 mL) and the organics were dried over $Na_2SO_4$, decanted, and concentrated to afford 345 mg (crude) 1-(2-cyclopropylpyrimidin-5-yl)cyclopropane-1-carboxylic acid. LCMS (ESI, m/z): 205 $[M+H]^+$.

Step 3: Synthesis of 1,1,1,3,3,3-hexafluoropropan-2-yl 1-(1-(2-cyclopropylpyrimidin-5-yl)cyclopropane-1-carbonyl)-1,8-diazaspiro[4.5]decane-8-carboxylate

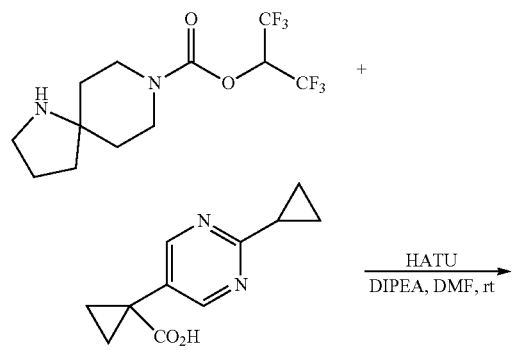

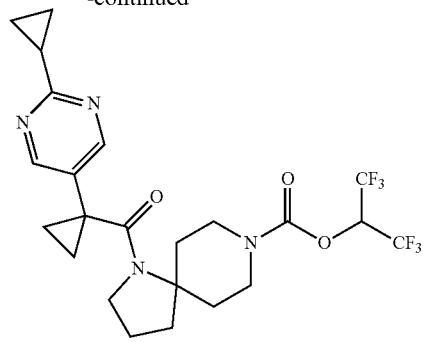

A vial was charged with 1,1,1,3,3,3-hexafluoropropan-2-yl 1,8-diazaspiro[4.5]decane-8-carboxylate (75 mg, 0.22 mmol), 1-(2-cyclopropylpyrimidin-5-yl)cyclopropanecarboxylic acid (50.4 mg, 0.25 mmol), HATU (102.3 mg, 0.27 mmol), DIPEA (0.10 mL, 0.57 mmol), and DMF (1.0 mL). The reaction mixture was stirred at room temperature for 1.5 h. The resulting solution was diluted with DMF (2.0 mL) and purified by preparative HPLC to provide 71 mg (62% yield) of 1,1,1,3,3,3-hexafluoropropan-2-yl 1-(1-(2-cyclopropylpyrimidin-5-yl)cyclopropane-1-carbonyl)-1,8-diazaspiro[4.5]decane-8-carboxylate. $^1$H NMR (400 MHz, Chloroform-d) δ 8.37 (s, 2H), 5.82-5.67 (m, 1H), 4.25-4.07 (m, 2H), 3.38-3.24 (m, 2H), 3.12-2.84 (m, 4H), 2.29-2.17 (m, 1H), 1.98-1.70 (m, 4H), 1.52-1.42 (m, 2H), 1.33 (t, J=10.7 Hz, 2H), 1.23-1.00 (m, 6H). LCMS (ESI, m/z): 521 $[M+H]^+$.

Examples 39-229

Examples 39-229 were prepared by similar procedures as described in Examples 1-38.

| Ex | Name | Structure | NMR ($^1$H NMR, 300 MHz or 400 MHz, chloroform-d) | MS $[M+H]^+$ |
|---|---|---|---|---|
| 39 | 1,1,1,3,3,3-Hexafluoropropan-2-yl 1-((5-(4-fluorophenyl)isoxazol-3-yl)methyl)-1,8-diazaspiro[4.5]decane-8-carboxylate | | δ 7.74-7.64 (m, 2H), 7.13-7.02 (m, 2H), 6.38 (s, 1H), 5.76-5.62 (m, 1H), 4.23-4.07 (m, 2H), 3.62 (s, 2H), 3.01-2.81 (m, 2H), 2.78-2.65 (m, 2H), 1.82-1.60 (m, 6H), 1.47-1.35 (m, 2H) | 510 |
| 40 | 1,1,1,3,3,3-Hexafluoropropan-2-yl 1-((5-chlorobenzo[b]thiophen-2-yl)methyl)-1,8-diazaspiro[4.5]decane-8-carboxylate | | δ 7.63-7.51 (m, 2H), 7.17 (s, 1H), 7.17-7.11 (m, 1H), 6.98 (s, 1H), 5.75-5.61 (m, 1H), 4.24-4.07 (m, 2H), 3.79 (s, 2H), 3.03-2.82 (m, 2H), 2.82-2.63 (m, 2H), 1.83-1.70 (m, 4H), 1.53-1.39 (m, 4H) | 515 |

-continued

| Ex | Name | Structure | NMR (¹H NMR, 300 MHz or 400 MHz, chloroform-d) | MS [M + H]⁺ |
|---|---|---|---|---|
| 41 | 1,1,1,3,3,3-Hexafluoropropan-2-yl 1-((5-(trifluoromethyl)benzo[b]thiophen-2-yl)methyl)-1,8-diazaspiro[4.5]decane-8-carboxylate | | δ 7.92 (d, J = 3.6 Hz, 1H), 7.89-7.82 (m, 1H), 7.81-7.74 (m, 1H), 7.49-7.33 (m, 1H), 7.26-7.15 (m, 1H), 7.16-7.03 (m, 1H), 5.75-5.62 (m, 1H), 4.89 (d, J = 4.0 Hz, 1H), 4.14 (t, J = 15.9 Hz, 2H), 3.83 (d, J = 3.8 Hz, 2H), 3.01-2.82 (m, 2H), 2.80-2.65 (m, 2H), 1.87-1.68 (m, 4H), 1.71-1.55 (m, 2H) | 549 |
| 42 | 1,1,1,3,3,3-Hexafluoropropan-2-yl 1-((3-chlorobenzo[b]thiophen-2-yl)methyl)-1,8-diazaspiro[4.5]decane-8-carboxylate | | δ 7.71-7.62 (m, 2H), 7.38-7.24 (m, 2H), 5.75-5.62 (m, 1H), 4.26-4.06 (m, 2H), 3.90-3.78 (m, 2H), 3.01-2.70 (m, 4H), 1.85-1.58 (m, 6H), 1.50-1.40 (m, 2H) | 515 |
| 43 | 1,1,1,3,3,3-Hexafluoropropan-2-yl 1-((3-methylbenzo[b]thiophen-2-yl)methyl)-1,8-diazaspiro[4.5]decane-8-carboxylate | | δ 7.80-7.75 (m, 1H), 7.67-7.61 (m, 1H), 7.41-7.34 (m, 1H), 7.32-7.29 (m, 1H), 5.84-5.75 (m, 1H), 4.33-4.19 (m, 2H), 3.88 (s, 2H), 3.11-2.94 (m, 2H), 2.92-2.77 (m, 2H), 2.37 (s, 3H), 1.93-1.70 (m, 6H), 1.70-1.46 (m, 2H) | 495 |
| 44 | 1,1,1,3,3,3-Hexafluoropropan-2-yl 1-((4-chlorobenzo[b]thiophen-2-yl)methyl)-1,8-diazaspiro[4.5]decane-8-carboxylate | | δ 7.56 (s, 1H), 7.24-7.20 (m, 2H), 7.13-7.07 (m, 1H), 5.75-5.62 (m, 1H), 4.22-4.07 (m, 2H), 3.86-3.75 (m, 2H), 2.99-2.83 (m, 2H), 2.80-2.68 (m, 2H), 1.83-1.68 (m, 4H), 1.66-1.53 (m, 2H), 1.49-1.39 (m, 2H) | 515 |
| 45 | 1,1,1,3,3,3-Hexafluoropropan-2-yl 1-((4-chloro-1H-indol-3-yl)methyl)-1,8-diazaspiro[4.5]decane-8-carboxylate | | δ 8.06 (s, 1H), 7.17-7.13 (m, 1H), 7.10-7.06 (m, 1H), 6.98-6.96 (m, 2H), 5.77-5.61 (m, 1H), 4.24-4.05 (m, 2H), 3.98 (s, 2H), 3.01-2.65 (m, 4H), 1.91-1.64 (m, 6H), 1.53-1.32 (m, 2H) | 498 |
| 46 | 1,1,1,3,3,3-Hexafluoropropan-2-yl 1-((5-(4-methoxyphenyl)isoxazol-3-yl)methyl)-1,8-diazaspiro[4.5]decane-8-carboxylate | | δ 7.80-7.69 (m, 2H), 7.05-6.93 (m, 2H), 6.45 (s, 1H), 5.88-5.69 (m, 1H), 4.35-4.20 (m, 2H), 3.92-3.85 (m, 3H), 3.81-3.65 (m, 2H), 3.11-2.93 (m, 2H), 2.92-2.75 (m, 2H), 2.00-1.80 (m, 4H), 1.81-1.67 (m, 2H), 1.54 (s, 2H) | 522 |

-continued

| Ex | Name | Structure | NMR (¹H NMR, 300 MHz or 400 MHz, chloroform-d) | MS [M + H]⁺ |
|---|---|---|---|---|
| 47 | 1,1,1,3,3,3-Hexafluoropropan-2-yl 1-((5-(4-chlorophenyl)isoxazol-3-yl)methyl)-1,8-diazaspiro[4.5]decane-8-carboxylate | | δ 7.78-7.67 (m, 2H), 7.50-7.38 (m, 2H), 6.52 (s, 1H), 5.84-5.70 (m, 1H), 4.33-4.16 (m, 2H), 3.71 (s, 2H), 3.08-2.88 (m, 2H), 2.81 (dt, J = 6.8, 3.4 Hz, 2H), 1.94-1.66 (m, 6H), 1.57-1.43 (m, 2H) | 526 |
| 48 | 1,1,1,3,3,3-Hexafluoropropan-2-yl 1-((5-chloro-3-methyl-1H-indol-2-yl)methyl)-1,8-diazaspiro[4.5]decane-8-carboxylate | | δ 8.20 (s, 1H), 7.37 (s, 1H), 7.14-7.09 (m, 1H), 7.02-6.96 (m, 1H), 5.74-5.61 (m, 1H), 4.24-4.03 (m, 2H), 3.66 (s, 2H), 3.03-2.84 (m, 2H), 2.68-2.49 (m, 2H), 2.13 (s, 3H), 1.83-1.60 (m, 6H), 1.50-1.39 (m, 2H) | 511 |
| 49 | 1,1,1,3,3,3-Hexafluoropropan-2-yl 1-((2-chloro-6-methylquinolin-3-yl)methyl)-1,8-diazaspiro[4.5]decane-8-carboxylate | | δ 8.03 (s, 1H), 7.82 (d, J = 8.6 Hz, 1H), 7.51 (s, 1H), 7.47-7.38 (m, 1H), 5.70 (hept, J = 6.3 Hz, 1H), 4.25-4.10 (m, 2H), 3.75 (s, 2H), 3.03-2.85 (m, 2H), 2.77-2.64 (m, 2H), 2.45 (s, 3H), 1.87-1.76 (m, 4H), 1.76-1.65 (m, 2H), 1.55-1.41 (m, 2H) | 524 |
| 50 | 1,1,1,3,3,3-Hexafluoropropan-2-yl 4-methyl-4-(methyl((3-methylbenzo[b]thiophen-2-yl)methyl)amino)piperidine-1-carboxylate | | δ 7.74-7.67 (m, 1H), 7.58-7.50 (m, 1H), 7.31-7.24 (m, 1H), 7.24-7.18 (m, 1H), 5.79-5.65 (m, 1H), 3.80-3.62 (m, 4H), 3.57-3.42 (m, 2H), 2.31-2.23 (m, 3H), 2.16-2.06 (m, 3H), 1.99-1.84 (m, 2H), 1.46-1.29 (m, 2H), 1.02-0.92 (m, 3H) | 483 |
| 51 | 1,1,1,3,3,3-Hexafluoropropan-2-yl 2-((5-chlorobenzo[b]thiophen-2-yl)methyl)-2,8-diazaspiro[4.5]decane-8-carboxylate | | δ 7.74-7.64 (m, 2H), 7.28-7.24 (m, 1H), 7.08 (s, 1H), 5.82-5.70 (m, 1H), 3.93-3.82 (m, 2H), 3.57-3.41 (m, 4H), 2.81-2.67 (m, 2H), 2.56-2.42 (m, 2H), 1.75-1.70 (m, 2H), 1.68-1.54 (m, 4H) | 515 |
| 52 | 1,1,1,3,3,3-Hexafluoropropan-2-yl 1-((5-fluoro-1H-indol-2-yl)methyl)-1,8-diazaspiro[4.5]decane-8-carboxylate | | δ 8.45 (s, 1H), 7.27-7.17 (m, 2H), 6.95-6.84 (m, 1H), 6.31 (s, 1H), 5.87-5.72 (m, 1H), 4.35-4.15 (m, 2H), 3.83-3.74 (m, 2H), 3.12-2.93 (m, 2H), 2.80-2.69 (m, 2H), 1.95-1.80 (m, 4H), 1.78-1.69 (m, 2H), 1.59-1.44 (m, 2H) | 482 |

-continued

| Ex | Name | Structure | NMR (¹H NMR, 300 MHz or 400 MHz, chloroform-d) | MS [M + H]⁺ |
|---|---|---|---|---|
| 53 | 1,1,1,3,3,3-Hexafluoropropan-2-yl 1-((7-methoxy-1H-indol-2-yl)methyl)-1,8-diazaspiro[4.5]decane-8-carboxylate | | δ 8.59 (s, 1H), 7.23-7.15 (m, 1H), 7.07-6.94 (m, 1H), 6.69-6.57 (m, 1H), 6.37-6.25 (m, 1H), 5.84-5.71 (m, 1H), 4.33-4.16 (m, 2H), 4.00 (s, 3H), 3.79 (s, 2H), 3.10-2.91 (m, 2H), 2.79-2.66 (m, 2H), 1.92-1.68 (m, 6H), 1.58-1.42 (m, 2H) | 493 |
| 54 | 1,1,1,3,3,3-Hexafluoropropan-2-yl 1-(quinolin-2-ylmethyl)-1,8-diazaspiro[4.5]decane-8-carboxylate | | δ 8.07-7.92 (m, 2H), 7.78-7.68 (m, 1H), 7.65-7.52 (m, 2H), 7.50-7.39 (m, 1H), 5.76-5.61 (m, 1H), 4.24-4.06 (m, 2H), 3.87 (s, 2H), 3.03-2.82 (m, 2H), 2.76-2.61 (m, 2H), 1.87-1.54 (m, 6H), 1.54-1.42 (m, 2H) | 476 |
| 55 | 1,1,1,3,3,3-Hexafluoropropan-2-yl 1-((6-chloroquinolin-2-yl)methyl)-1,8-diazaspiro[4.5]decane-8-carboxylate | | δ 7.98-7.92 (m, 1H), 7.93-7.86 (m, 1H), 7.71 (s, 1H), 7.61-7.51 (m, 2H), 5.74-5.61 (m, 1H), 4.24-4.08 (m, 2H), 3.84 (s, 2H), 3.03-2.82 (m, 2H), 2.71-2.63 (m, 2H), 1.86-1.63 (m, 6H), 1.52-1.38 (m, 2H) | 510 |
| 56 | 1,1,1,3,3,3-Hexafluoropropan-2-yl 1-((6-fluoroquinolin-2-yl)methyl)-1,8-diazaspiro[4.5]decane-8-carboxylate | | δ 8.10-7.98 (m, 2H), 7.71-7.61 (m, 1H), 7.53-7.39 (m, 2H), 5.84-5.70 (m, 1H), 4.32-4.18 (m, 2H), 3.93 (s, 2H), 3.13-2.93 (m, 2H), 2.87-2.68 (m, 2H), 1.98-1.71 (m, 6H), 1.64-1.47 (m, 2H) | 494 |
| 57 | 1,1,1,3,3,3-Hexafluoropropan-2-yl 1-((8-chloroquinolin-2-yl)methyl)-1,8-diazaspiro[4.5]decane-8-carboxylate | | δ 8.18-8.08 (m, 1H), 7.87-7.79 (m, 1H), 7.78-7.71 (m, 2H), 7.47-7.35 (m, 1H), 5.83-5.72 (m, 1H), 4.30-4.16 (m, 2H), 4.04 (s, 2H), 3.12-2.92 (m, 2H), 2.86-2.74 (m, 2H), 1.96-1.74 (m, 6H), 1.60-1.49 (m, 2H) | 510 |
| 58 | 1,1,1,3,3,3-Hexafluoropropan-2-yl 1-((5-fluoro-3-methyl-1H-indol-2-yl)methyl)-1,8-diazaspiro[4.5]decane-8-carboxylate | | δ 8.15 (s, 1H), 7.15-7.07 (m, 1H), 7.07-7.00 (m, 1H), 6.82-6.73 (m, 1H), 5.69 (pd, J = 6.2, 1.3 Hz, 1H), 4.23-4.04 (m, 2H), 3.65 (s, 2H), 3.01-2.80 (m, 2H), 2.70-2.53 (m, 2H), 2.12 (s, 3H), 1.84-1.58 (m, 6H), 1.49-1.34 (m, 2H) | |
| 59 | 1,1,1,3,3,3-Hexafluoropropan-2-yl 1-(6-methylbenzo[b]thiophene-2-carbonyl)-1,8-diazaspiro[4.5]decane-8-carboxylate | | δ 7.66-7.55 (m, 2H), 7.49 (s, 1H), 7.17-7.08 (m, 1H), 5.75-5.60 (m, 1H), 4.21-4.05 (m, 2H), 3.90-3.77 (m, 2H), 3.19-3.06 (m, 2H), 3.04-2.88 (m, 2H), 2.41 (s, 3H), 2.10-1.94 (m, 2H), 1.92-1.82 (m, 2H), 1.47-1.34 (m, 2H) | 508 |

-continued

| Ex | Name | Structure | NMR (¹H NMR, 300 MHz or 400 MHz, chloroform-d) | MS [M + H]⁺ |
|---|---|---|---|---|
| 60 | 1,1,1,3,3,3-Hexafluoropropan-2-yl 1-(6-chlorobenzo[b]thiophene-2-carbonyl)-1,8-diazaspiro[4.5]decane-8-carboxylate | | δ 7.90-7.81 (m, 1H), 7.78-7.67 (m, 1H), 7.63-7.53 (m, 1H), 7.41-7.31 (m, 1H), 5.85-5.70 (m, J = 6.7 Hz, 1H), 4.33-4.12 (m, 2H), 4.00-3.82 (m, 2H), 3.26-2.93 (m, 4H), 2.22-1.90 (m, 4H), 1.57-1.38 (m, 2H) | 529 |
| 61 | 1,1,1,3,3,3-Hexafluoropropan-2-yl 1-((5-methylbenzo[b]thiophen-2-yl)methyl)-1,8-diazaspiro[4.5]decane-8-carboxylate | | δ 7.70-7.62 (m, 1H), 7.48 (s, 1H), 7.15-7.09 (m, 1H), 7.07 (s, 1H), 5.85-5.72 (m, 1H), 4.31-4.16 (m, 2H), 3.91-3.85 (m, 2H), 3.10-2.92 (m, 2H), 2.89-2.76 (m, 2H), 2.46 (s, 3H), 1.91-1.77 (m, 4H), 1.77-1.67 (m, 2H), 1.58-1.48 (m, 2H) | 495 |
| 62 | 1,1,1,3,3,3-Hexafluoropropan-2-yl 4-(((5-chlorobenzo[b]thiophen-2-yl)methyl)(methyl)amino)-4-methylpiperidine-1-carboxylate | | δ 7.63-7.52 (m, 2H), 7.22-7.12 (m, 1H), 7.00 (s, 1H), 5.72 (hept, J = 6.6 Hz, 1H), 3.82-3.68 (m, 4H), 3.56-3.40 (m, 2H), 2.12 (s, 3H), 1.97-1.86 (m, 2H), 1.49-1.32 (m, 2H), 0.95 (s, 3H) | 503 |
| 63 | 1,1,1,3,3,3-Hexafluoropropan-2-yl 1-(3,5,7-trimethyl-1H-indole-2-carbonyl)-1,8-diazaspiro[4.5]decane-8-carboxylate | | δ 8.27 (s, 1H), 7.21 (s, 1H), 6.90 (s, 1H), 5.87-5.69 (m, 1H), 4.33-4.18 (m, 2H), 3.64 (t, J = 6.6 Hz, 2H), 3.30-3.14 (m, 2H), 3.15-2.98 (m, 2H), 2.46-2.40 (m, 6H), 2.34 (s, 3H), 2.19-2.00 (m, 2H), 1.97-1.84 (m, 2H), 1.58-1.47 (m, 2H) | 520 |
| 64 | 1,1,1,3,3,3-Hexafluoropropan-2-yl 2-(pyridin-3-ylmethyl)-2,8-diazaspiro[4.5]decane-8-carboxylate | | δ 8.30-8.72 (m, 2H), 7.55-7.80 (m, 1H), 7.20-7.30 (m, 1H), 5.65-5.89 (m, 1H), 3.30-3.75 (m, 6H), 2.50-2.80 (m, 2H), 2.25-2.50 (m, 2H), 1.50-1.80 (m, 6H) | 426 |
| 65 | 1,1,1,3,3,3-Hexafluoropropan-2-yl 2-(pyrimidin-2-ylmethyl)-2,8-diazaspiro[4.5]decane-8-carboxylate | | δ 8.65-8.82 (m, 2H), 7.12-7.28 (m, 1H), 5.65-5.89 (m, 1H), 3.88-4.02 (s, 2H), 3.38-3.62 (m, 4H), 2.74-2.90 (m, 2H), 2.50-2.72 (m, 2H), 1.72-1.90 (m, 2H), 1.65-1.72 (m, 4H) | 427 |
| 66 | 1,1,1,3,3,3-Hexafluoropropan-2-yl 2-(thiazol-2-ylmethyl)-2,8-diazaspiro[4.5]decane-8-carboxylate | | δ 7.70 (d, J = 3.3 Hz, 1H), 7.31 (d, J = 3.3 Hz, 1H), 5.65-5.90 (m, 1H), 3.95 (s, 2H), 3.40-3.62 (m, 4H), 2.74-3.00 (m, 2H), 2.46-2.70 (m, 2H), 1.50-1.85 (m, 6H) | 432 |

| Ex | Name | Structure | NMR (¹H NMR, 300 MHz or 400 MHz, chloroform-d) | MS [M + H]⁺ |
|---|---|---|---|---|
| 67 | 1,1,1,3,3,3-Hexafluoropropan-2-yl 2-(pyrimidin-5-ylmethyl)-2,8-diazaspiro[4.5]decane-8-carboxylate | | δ 9.12 (s, 1H), 8.72 (s, 2H), 5.58-5.89 (m, 1H), 3.40-3.70 (m, 6H), 2.50-2.72 (m, 2H), 2.38-2.46 (m, 2H), 1.70-1.80 (m, 2H), 1.55-1.65 (m, 4H) | 427 |
| 68 | 1,1,1,3,3,3-Hexafluoropropan-2-yl 1-(pyrimidine-5-carbonyl)-1,8-diazaspiro[4.5]decane-8-carboxylate | | δ 9.25 (s, 1H), 8.83 (s, 2H), 5.73-5.80 (m, 1H), 4.20-4.28 (m, 2H), 3.51 (t, J = 6.8 Hz, 2H), 2.95-3.17 (m, 4H), 2.04-2.15 (m, 2H), 1.88-1.95 (m, 2H), 1.45-1.55 (m, 2H) | 441 |
| 69 | 1,1,1,3,3,3-Hexafluoropropan-2-yl 1-(imidazo[1,2-a]pyridine-2-carbonyl)-1,8-diazaspiro[4.5]decane-8-carboxylate | | δ 8.15 (d, J = 6.8 Hz, 1H), 8.05 (s, 1H), 7.64 (d, J = 9.2 Hz, 1H), 7.23-7.27 (m, 1H), 6.86-6.89 (m, 1H), 5.73-5.80 (m, 1H), 4.12-4.24 (m, 4H), 3.16-3.23 (m, 2H), 2.97-3.09 (m, 2H), 1.95-2.11 (m, 2H), 1.89-1.94 (m, 2H), 1.45-1.55 (m, 2H) | 479 |
| 70 | 1,1,1,3,3,3-Hexafluoropropan-2-yl 1-(1-methyl-1H-pyrazole-4-carbonyl)-1,8-diazaspiro[4.5]decane-8-carboxylate | | δ 7.77 (s, 1H), 7.71 (s, 1H), 5.72-5.80 (m, 1H), 4.14-4.23 (m, 2H), 3.91 (s, 3H), 3.79 (t, J = 6.4 Hz, 2H), 2.94-3.21 (m, 4H), 1.89-2.09 (m, 4H), 1.37-1.43 (m, 2H) | 443 |
| 71 | 1,1,1,3,3,3-Hexafluoropropan-2-yl 1-(1-isopropyl-1H-pyrazole-4-carbonyl)-1,8-diazaspiro[4.5]decane-8-carboxylate | | δ 7.89 (s, 1H), 7.72 (s, 1H), 5.72-5.80 (m, 1H), 4.44-4.53 (m, 1H), 4.14-4.23 (m, 2H), 3.80-3.84 (m, 2H), 2.94-3.22 (m, 4H), 1.92-2.09 (m, 4H), 1.51 (d, J = 6.6 Hz, 6H), 1.42-1.48 (m, 2H) | 471 |
| 72 | 1,1,1,3,3,3-Hexafluoropropan-2-yl 1-(1-phenyl-1H-pyrazole-4-carbonyl)-1,8-diazaspiro[4.5]decane-8-carboxylate | | δ 8.32 (s, 1H), 7.94 (s, 1H), 7.69 (d, J = 8.4 Hz, 2H), 7.45-7.50 (m, 2H), 7.32-7.37 (m, 1H), 5.73-5.81 (m, 1H), 4.16-4.25 (m, 2H), 3.84-3.88 (m, 2H), 2.95-3.22 (m, 4H), 1.93-2.15 (m, 4H), 1.44-1.50 (m, 2H) | 505 |
| 73 | 1,1,1,3,3,3-Hexafluoropropan-2-yl 2-(pyridin-2-ylmethyl)-2,8-diazaspiro[4.5]decane-8-carboxylate | | δ 8.43-8.60 (m, 1H), 7.60-7.75 (m, 1H), 7.35-7.48 (m, 1H), 7.00-7.22 (m, 1H), 5.60-5.85 (m, 1H), 3.60-3.89 (m, 2H), 3.30-3.68 (m, 4H), 2.55-2.80 (m, 2H), 2.30-2.55 (m, 2H), 1.50-1.80 (m, 6H) | 426 |

| Ex | Name | Structure | NMR (¹H NMR, 300 MHz or 400 MHz, chloroform-d) | MS [M + H]⁺ |
|---|---|---|---|---|
| 74 | 1,1,1,3,3,3-Hexafluoropropan-2-yl 2-(pyrimidin-4-ylmethyl)-2,8-diazaspiro[4.5]decane-8-carboxylate | | δ 9.15 (s, 1H), 8.72 (d, J = 5.1 Hz, 1H), 7.48 (d, J = 5.1 Hz, 1H), 5.65-5.88 (m, 1H), 3.65-3.95 (m, 2H), 3.35-3.65 (m, 4H), 2.65-2.96 (m, 2H), 2.38-2.65 (m, 2H), 1.50-1.92 (m, 6H) | 427 |
| 75 | 1,1,1,3,3,3-Hexafluoropropan-2-yl 1-(benzo[d]thiazole-2-carbonyl)-1,8-diazaspiro[4.5]decane-8-carboxylate | | δ 8.07 (d, J = 8.0 Hz, 1H), 7.95 (d, J = 7.6 Hz, 1H), 7.45-7.54 (m, 2H), 5.72-5.80 (m, 1H), 4.19-4.23 (m, 4H), 2.97-3.21 (m, 4H), 1.95-2.14 (m, 4H), 1.45-1.55 (m, 2H) | 496 |
| 76 | 1,1,1,3,3,3-Hexafluoropropan-2-yl 1-(1H-indole-2-carbonyl)-1,8-diazaspiro[4.5]decane-8-carboxylate | | δ 9.26 (s, 1H), 7.65 (d, J = 8.0 Hz, 1H), 7.41 (d, J = 8.4 Hz, 1H), 7.26-7.31 (m, 1H), 7.13 (t, J = 7.2 Hz, 1H), 6.85 (s, 1H), 5.73-5.83 (m, 1H), 4.18-4.26 (m, 2H), 4.01-4.05 (m, 2H), 3.15-3.23 (m, 2H), 2.97-3.10 (m, 2H), 1.99-2.14 (m, 4H), 1.45-1.55 (m, 2H) | 478 |
| 77 | 1,1,1,3,3,3-Hexafluoropropan-2-yl 1-(benzofuran-5-carbonyl)-1,8-diazaspiro[4.5]decane-8-carboxylate | | δ 7.67 (s, 2H), 7.51 (d, J = 8.4 Hz, 1H), 7.34-7.36 (m, 1H), 6.79 (s, 1H), 5.74-5.80 (m, 1H), 4.19-4.27 (m, 2H), 3.46-3.50 (m, 2H), 3.18-3.23 (m, 2H), 2.97-3.09 (m, 2H), 2.02-2.12 (m, 2H), 1.80-1.87 (m, 2H), 1.50-1.55 (m, 2H) | 479 |
| 78 | 1,1,1,3,3,3-Hexafluoropropan-2-yl 1-(1-(4-chlorophenyl)-1H-pyrazole-4-carbonyl)-1,8-diazaspiro[4.5]decane-8-carboxylate | | δ 8.29 (s, 1H), 7.92 (s, 1H), 7.41-7.66 (m, 2H), 7.42-7.47 (m, 2H), 5.70-5.83 (m, 1H), 4.16-4.25 (m, 2H), 3.83-3.87 (m, 2H), 2.95-3.21 (m, 4H), 1.93-2.12 (m, 4H), 1.44-1.50 (m, 2H) | 539 |
| 79 | 1,1,1,3,3,3-Hexafluoropropan-2-yl 1-(1-methyl-1H-pyrazole-3-carbonyl)-1,8-diazaspiro[4.5]decane-8-carboxylate | | δ 7.32 (d, J = 2.1 Hz, 1H), 6.69 (d, J = 2.1 Hz, 1H), 5.72-5.80 (m, 1H), 4.15-4.22 (m, 2H), 3.96-4.01 (m, 2H), 3.91 (s, 3H), 3.15-3.23 (m, 2H), 2.95-3.09 (m, 2H), 1.84-2.06 (m, 4H), 1.41-1.55 (m, 2H) | 443 |
| 80 | 1,1,1,3,3,3-Hexafluoropropan-2-yl 1-(benzo[b]thiophene-2-carbonyl)-1,8-diazaspiro[4.5]decane-8-carboxylate | | δ 7.79-7.86 (m, 2H), 7.60 (s, 1H), 7.36-7.42 (m, 2H), 5.73-5.79 (m, 1H), 4.17-4.25 (m, 2H), 3.92 (t, J = 6.8 Hz, 2H), 3.14-3.23 (m, 2H), 2.97-3.09 (m, 2H), 1.99-2.13 (m, 2H), 1.93-1.98 (m, 2H), 1.45-1.55 (m, 2H) | 495 |

-continued

| Ex | Name | Structure | NMR (¹H NMR, 300 MHz or 400 MHz, chloroform-d) | MS [M + H]⁺ |
|---|---|---|---|---|
| 81 | | | 1,1,1,3,3,3-Hexafluoropropan-2-yl 1-(1-isopropyl-1H-pyrazole-3-carbonyl)-1,8-diazaspiro[4.5]decane-8-carboxylate | δ 7.37 (d, J = 2.4 Hz, 1H), 6.70 (d, J = 2.1 Hz, 1H), 5.72-5.80 (m, 1H), 4.44-4.53 (m, 1H), 4.14-4.22 (m, 2H), 4.00-4.04 (m, 2H), 3.16-3.25 (m, 2H), 2.95-3.09 (m, 2H), 2.00-2.06 (m, 2H), 1.84-1.98 (m, 2H), 1.61 (d, J = 6.0 Hz, 6H), 1.48-1.59 (m, 2H) | 471 |
| 82 | | | 1,1,1,3,3,3-Hexafluoropropan-2-yl 1-(1-phenyl-1H-pyrazole-3-carbonyl)-1,8-diazaspiro[4.5]decane-8-carboxylate | δ 7.89 (d, J = 2.4 Hz, 1H), 7.68-7.70 (m, 2H), 7.44-7.50 (m, 2H), 7.30-7.35 (m, 1H), 6.94 (d, J = 2.4 Hz, 1H), 5.73-5.81 (m, 1H), 4.13-4.25 (m, 4H), 3.16-3.28 (m, 2H), 2.97-3.11 (m, 2H), 2.00-2.10 (m, 2H), 1.88-1.97 (m, 2H), 1.47-1.53 (m, 2H) | 505 |
| 83 | | | 1,1,1,3,3,3-Hexafluoropropan-2-yl 1-(benzofuran-2-carbonyl)-1,8-diazaspiro[4.5]decane-8-carboxylate | δ 7.65 (d, J = 7.6 Hz, 1H), 7.50 (d, J = 7.6 Hz, 1H), 7.37-7.41 (m, 1H), 7.31-7.33 (m, 1H), 7.26-7.30 (m, 1H), 5.74-5.80 (m, 1H), 4.17-4.25 (m, 2H), 4.02 (t, J = 6.4 Hz, 2H), 3.15-3.21 (m, 2H), 2.97-3.10 (m, 2H), 1.94-2.13 (m, 4H), 1.46-1.53 (m, 2H) | 479 |
| 84 | | | 1,1,1,3,3,3-Hexafluoropropan-2-yl 1-(benzo[d]oxazole-2-carbonyl)-1,8-diazaspiro[4.5]decane-8-carboxylate | δ 7.80 (d, J = 7.6 Hz, 1H), 7.63 (d, J = 8.0 Hz, 1H), 7.38-7.49 (m, 2H), 5.74-5.81 (m, 1H), 4.23-4.28 (m, 2H), 4.15-4.19 (m, 2H), 3.12-3.20 (m, 2H), 2.97-3.10 (m, 2H), 2.04-2.14 (m, 2H), 1.94-2.01 (m, 2H), 1.46-1.53 (m, 2H) | 480 |
| 85 | | | 1,1,1,3,3,3-Hexafluoropropan-2-yl 1-(imidazo[1,2-a]pyridine-6-carbonyl)-1,8-diazaspiro[4.5]decane-8-carboxylate | δ 8.36 (s, 1H), 7.70 (s, 1H), 7.61-7.64 (m, 2H), 7.23-7.26 (m, 1H), 5.74-5.80 (m, 1H), 4.19-4.27 (m, 2H), 3.56 (t, J = 6.8 Hz, 2H), 2.96-3.20 (m, 4H), 2.02-2.14 (m, 2H), 1.80-1.92 (m, 2H), 1.46-1.53 (m, 2H) | 479 |
| 86 | | | 1,1,1,3,3,3-Hexafluoropropan-2-yl 1-(benzo[d]thiazole-5-carbonyl)-1,8-diazaspiro[4.5]decane-8-carboxylate | δ 9.06 (s, 1H), 8.16 (s, 1H), 7.99 (d, J = 8.4 Hz, 1H), 7.51-7.54 (m, 1H), 5.74-5.80 (m, 1H), 4.19-4.28 (m, 2H), 4.47-4.51 (m, 2H), 3.19-3.26 (m, 2H), 2.97-3.10 (m, 2H), 2.02-2.14 (m, 2H), 1.80-1.87 (m, 2H), 1.51-1.55 (m, 2H) | 496 |
| 87 | | | 1,1,1,3,3,3-Hexafluoropropan-2-yl 1-(benzo[d]oxazole-5-carbonyl)-1,8-diazaspiro[4.5]decane-8-carboxylate | δ 8.17 (s, 1H), 7.85 (s, 1H), 7.62 (d, J = 4.5 Hz, 1H), 7.48-7.52 (m, 1H), 5.74-5.82 (m, 1H), 4.19-4.28 (m, 2H), 3.45-3.49 (m, 2H), 3.18-3.26 (m, 2H), 2.97-3.12 (m, 2H), 2.01-2.16 (m, 2H), 1.80-1.89 (m, 2H), 1.50-1.56 (m, 2H) | 480 |

| Ex | Name | Structure | NMR (¹H NMR, 300 MHz or 400 MHz, chloroform-d) | MS [M + H]⁺ |
|---|---|---|---|---|
| 88 | 1,1,1,3,3,3-Hexafluoropropan-2-yl 1-(1-benzyl-1H-pyrazole-4-carbonyl)-1,8-diazaspiro[4.5]decane-8-carboxylate | | δ 7.78 (s, 1H), 7.79 (s, 1H), 7.32-7.40 (m, 3H), 7.24-7.26 (m, 2H), 5.72-5.80 (m, 1H), 5.30 (s, 2H), 4.14-4.22 (m, 2H), 3.76-3.80 (m, 2H), 2.94-3.20 (m, 4H), 2.00-2.07 (m, 2H), 1.91-1.97 (m, 2H), 1.40-1.46 (m, 2H) | 519 |
| 89 | 1,1,1,3,3,3-Hexafluoropropan-2-yl 1-(1H-indole-5-carbonyl)-1,8-diazaspiro[4.5]decane-8-carboxylate | | δ 7.87-7.89 (m, 2H), 7.50 (d, J = 5.6 Hz, 1H), 7.34-7.39 (m, 2H), 5.74-5.80 (m, 1H), 4.18-4.27 (m, 2H), 3.47 (d, J = 8.4 Hz, 2H), 3.19-3.26 (m, 2H), 2.97-3.09 (m, 2H), 2.00-2.12 (m, 2H), 1.81-1.85 (m, 2H), 1.51-1.55 (m, 2H) | 478 |
| 90 | 1,1,1,3,3,3-Hexafluoropropan-2-yl 1-(benzo[b]thiophene-5-carbonyl)-1,8-diazaspiro[4.5]decane-8-carboxylate | | δ 8.55 (s, 1H), 7.69 (s, 1H), 7.33 (s, 1H), 6.99-7.26 (m, 1H), 6.55 (s, 1H), 5.73-5.82 (m, 1H), 4.17-4.25 (m, 2H), 3.50 (d, J = 6.0 Hz, 2H), 3.20 (s, 2H), 2.96-3.08 (m, 2H), 1.98-2.10 (m, 2H), 1.81-1.93 (m, 2H), 1.63-1.79 (m, 2H) | 495 |
| 91 | 1,1,1,3,3,3-Hexafluoropropan-2-yl 1-(1-benzyl-1H-pyrazole-3-carbonyl)-1,8-diazaspiro[4.5]decane-8-carboxylate | | δ 7.32-7.38 (m, 4H), 7.18-7.22 (m, 2H), 6.75 (d, J = 2.4 Hz, 1H), 5.73-5.81 (m, 1H), 5.32 (s, 2H), 4.16-4.24 (m, 2H), 3.99-4.04 (m, 2H), 3.15-3.20 (m, 2H), 2.96-3.11 (m, 2H), 1.99-2.06 (m, 2H), 1.84-1.93 (m, 2H), 1.47-1.51 (m, 2H) | 519 |
| 92 | 1,1,1,3,3,3-Hexafluoropropan-2-yl 1-(1-(4-chlorophenyl)-1H-pyrazole-3-carbonyl)-1,8-diazaspiro[4.5]decane-8-carboxylate | | δ 7.87 (d, J = 2.4 Hz, 1H), 7.62-7.66 (m, 2H), 7.42-7.47 (m, 2H), 6.95 (d, J = 2.4 Hz, 1H), 5.74-5.82 (m, 1H), 4.15-4.26 (m, 2H), 4.11-4.13 (m, 2H), 3.16-3.26 (m, 2H), 2.98-3.12 (m, 2H), 2.03-2.09 (m, 2H), 1.90-1.98 (m, 2H), 1.47-1.54 (m, 2H) | 539 |
| 93 | 1,1,1,3,3,3-Hexafluoropropan-2-yl 1-(5-chloro-1H-indole-2-carbonyl)-1,8-diazaspiro[4.5]decane-8-carboxylate | | δ 9.50 (s, 1H), 7.62 (s, 1H), 7.30-7.39 (m, 1H), 7.15-7.30 (m, 1H), 6.69 (s, 1H), 5.62-5.90 (m, 1H), 4.15-4.21 (m, 2H), 3.85-4.12 (m, 2H), 2.92-3.30 (m, 4H), 1.90-2.20 (m, 4H), 1.42-1.52 (m, 2H) | 512 |
| 94 | 1,1,1,3,3,3-Hexafluoropropan-2-yl 1-(3-methylbenzo[b]thiophene-2-carbonyl)-1,8-diazaspiro[4.5]decane-8-carboxylate | | δ 7.80-7.90 (m, 1H), 7.65-7.78 (m, 1H), 7.35-7.45 (m, 2H), 5.70-5.86 (m, 1H), 4.18 (t, J = 8.0 Hz, 2H), 3.40-3.52 (m, 2H), 3.12-3.28 (m, 2H), 2.92-3.12 (m, 2H), 2.35-2.45 (s, 3H), 2.00-2.18 (m, 2H), 1.80-1.92 (m, 2H), 1.40-1.62 (m, 2H) | 509 |

| Ex | Name | Structure | NMR (¹H NMR, 300 MHz or 400 MHz, chloroform-d) | MS [M + H]⁺ |
|---|---|---|---|---|
| 95 | 1,1,1,3,3,3-Hexafluoropropan-2-yl 1-(5-chlorobenzo[b]thiophene-2-carbonyl)-1,8-diazaspiro[4.5]decane-8-carboxylate | | δ 7.70-7.80 (m, 2H), 7.60 (s, 1H), 7.30-7.39 (m, 1H), 5.70-5.85 (m, 1H), 4.10-4.40 (m, 2H), 3.85-3.95 (m, 2H), 3.11-3.25 (m, 2H), 2.95-3.10 (m, 2H), 2.02-2.20 (m, 2H), 1.88-2.01 (m, 2H), 1.42-1.58 (m, 2H) | 529 |
| 96 | 1,1,1,3,3,3-Hexafluoropropan-2-yl 1-(7-fluorobenzo[b]thiophene-2-carbonyl)-1,8-diazaspiro[4.5]decane-8-carboxylate | | δ 7.55-7.65 (m, 2H), 7.30-7.40 (m, 1H), 7.00-7.15 (m, 1H), 5.68-5.85 (m, 1H), 4.12-4.30 (m, 2H), 3.85-3.95 (m, 2H), 3.10-3.18 (m, 2H), 2.92-3.10 (m, 2H), 2.05-2.20 (m, 2H), 1.90-2.05 (m, 2H), 1.42-1.58 (m, 2H) | 513 |
| 97 | 1,1,1,3,3,3-Hexafluoropropan-2-yl 1-(3-chlorobenzo[b]thiophene-2-carbonyl)-1,8-diazaspiro[4.5]decane-8-carboxylate | | δ 7.72-8.00 (m, 2H), 7.40-7.65 (m, 2H), 5.60-6.00 (m, 1H), 4.00-4.38 (m, 2H), 3.40-3.70 (m, 2H), 2.82-3.35 (m, 4H), 2.00-2.20 (m, 2H), 1.80-2.00 (m, 2H), 1.50-1.65 (m, 2H) | 529 |
| 98 | 1,1,1,3,3,3-Hexafluoropropan-2-yl 1-(7-(trifluoromethyl)benzo[b]thiophene-2-carbonyl)-1,8-diazaspiro[4.5]decane-8-carboxylate | | δ 7.85-8.10 (m, 1H), 7.58-7.85 (m, 2H), 7.35-7.55 (m, 1H), 5.60-5.92 (m, 1H), 4.10-4.32 (m, 2H), 3.80-4.05 (m, 2H), 2.85-3.40 (m, 4H), 1.90-2.30 (m, 4H), 1.45-1.58 (m, 2H) | 563 |
| 99 | 1,1,1,3,3,3-Hexafluoropropan-2-yl 1-(5-fluorobenzo[b]thiophene-2-carbonyl)-1,8-diazaspiro[4.5]decane-8-carboxylate | | δ 7.70-7.90 (m, 1H), 7.55 (s, 1H), 7.40-7.50 (m, 1H), 7.05-7.22 (m, 1H), 5.50-6.00 (m, 1H), 4.05-4.40 (m, 2H), 3.70-4.05 (m, 2H), 2.82-3.38 (m, 4H), 2.05-2.20 (m, 2H), 1.90-2.05 (m, 2H), 1.40-1.58 (m, 2H) | 513 |
| 100 | 1,1,1,3,3,3-Hexafluoropropan-2-yl 1-(5-(trifluoromethyl)-1H-indole-2-carbonyl)-1,8-diazaspiro[4.5]decane-8-carboxylate | | δ 9.70 (s, 1H), 8.95 (s, 1H), 7.40-7.59 (m, 2H), 6.80-7.00 (m, 1H), 5.65-5.95 (m, 1H), 4.10-4.40 (m, 2H), 3.90-4.10 (m, 2H), 2.95-3.35 (m, 4H), 1.90-2.22 (m, 4H), 1.40-1.60 (m, 2H) | 546 |

| Ex | Name | Structure | NMR (¹H NMR, 300 MHz or 400 MHz, chloroform-d) | MS [M + H]⁺ |
|---|---|---|---|---|
| 101 | 1,1,1,3,3,3-Hexafluoropropan-2-yl 1-(6-(trifluoromethyl)benzo[b]thiophene-2-carbonyl)-1,8-diazaspiro[4.5]decane-8-carboxylate | | δ 8.15 (s, 1H), 7.90-8.00 (m, 1H), 7.52-7.70 (m, 2H), 5.65-5.88 (m, 1H), 4.13-4.30 (m, 2H), 3.85-3.98 (m, 2H), 2.92-3.25 (m, 4H), 2.05-2.20 (m, 2H), 1.90-2.05 (m, 2H), 1.40-1.52 (m, 2H) | 563 |
| 102 | 1,1,1,3,3,3-Hexafluoropropan-2-yl 1-(5-(trifluoromethyl)benzo[b]thiophene-2-carbonyl)-1,8-diazaspiro[4.5]decane-8-carboxylate | | δ 8.10 (s, 1H), 7.80-8.00 (m, 1H), 7.55-7.70 (m, 2H), 5.70-5.85 (m, 1H), 4.10-4.33 (m, 2H), 3.85-4.00 (m, 2H), 2.90-3.30 (m, 4H), 2.05-2.20 (m, 2H), 1.90-2.05 (m, 2H), 1.42-1.58 (m, 2H) | 563 |
| 103 | 1,1,1,3,3,3-Hexafluoropropan-2-yl 1-(6-fluorobenzo[b]thiophene-2-carbonyl)-1,8-diazaspiro[4.5]decane-8-carboxylate | | δ 7.70-7.80 (m, 1H), 7.48-7.60 (m, 2H), 7.05-7.20 (m, 1H), 5.62-5.90 (m, 1H), 4.10-4.30 (m, 2H), 3.80-4.00 (m, 2H), 2.88-3.30 (m, 4H), 2.03-2.20 (m, 2H), 1.88-2.03 (m, 2H), 1.42-1.58 (m, 2H) | 512 |
| 104 | 1,1,1,3,3,3-Hexafluoropropan-2-yl 1-(5-fluoro-3-methyl-1H-indole-2-carbonyl)-1,8-diazaspiro[4.5]decane-8-carboxylate | | δ 8.60 (s, 1H), 7.12-7.22 (m, 2H), 6.85-7.00 (m, 1H), 5.65-5.90 (m, 1H), 4.08-4.30 (m, 2H), 3.45-3.68 (m, 2H), 2.90-3.30 (m, 4H), 2.30 (s, 3H), 2.00-2.20 (m, 2H), 1.80-2.00 (m, 2H), 1.42-1.58 (m, 2H) | 510 |
| 105 | 1,1,1,3,3,3-Hexafluoropropan-2-yl 1-(7-chlorobenzo[b]thiophene-2-carbonyl)-1,8-diazaspiro[4.5]decane-8-carboxylate | | δ 7.70-7.75 (s, 1H), 7.66 (s, 1H), 7.30-7.45 (m, 2H), 5.70-5.85 (m, 1H), 4.12-4.30 (m, 2H), 3.85-3.98 (m, 2H), 2.92-3.28 (m, 4H), 2.03-2.20 (m, 2H), 1.90-2.03 (m, 2H), 1.45-1.57 (m, 2H). | 529 |
| 106 | 1,1,1,3,3,3-Hexafluoropropan-2-yl 2-(pyridazin-4-ylmethyl)-2,8-diazaspiro[4.5]decane-8-carboxylate | | δ 9.12-9.58 (m, 2H), 7.46 (s, 1H), 5.68-5.81 (m, 1H), 3.75 (s, 2H), 3.50-3.60 (m, 2H), 3.38-3.49 (m, 2H), 2.57-2.82 (m, 2H), 2.45 (s, 2H), 1.63-1.80 (m, 6H). | 427 |

| Ex | Name | Structure | NMR (¹H NMR, 300 MHz or 400 MHz, chloroform-d) | MS [M + H]⁺ |
|---|---|---|---|---|
| 107 | 1,1,1,3,3,3-Hexafluoropropan-2-yl 1-(5-fluoro-1H-indole-2-carbonyl)-1,8-diazaspiro[4.5]decane-8-carboxylate | | δ 9.48 (s, 1H), 7.28-7.39 (m, 2H), 6.94-7.12 (m, 1H), 6.78 (s, 1H), 5.68-5.90 (m, 1H), 4.13-4.31 (m, 2H), 3.89-4.12 (m, 2H), 2.90-3.24 (m, 4H), 1.90-2.24 (m, 4H), 1.40-1.52 (m, 2H) | 496 |
| 108 | 1,1,1,3,3,3-Hexafluoropropan-2-yl 1-(7-methyl-1H-indole-2-carbonyl)-1,8-diazaspiro[4.5]decane-8-carboxylate | | δ 9.22 (s, 1H), 7.38-7.60 (m, 1H), 6.94-7.18 (m, 2H), 6.78-6.94 (m, 1H), 5.61-5.92 (m, 1H), 4.15-4.28 (m, 2H), 3.80-4.12 (m, 2H), 2.89-3.35 (m, 4H), 2.52 (s, 3H), 1.86-2.20 (m, 4H), 1.43-1.58 (m, 2H) | 492 |
| 109 | 1,1,1,3,3,3-Hexafluoropropan-2-yl 1-(5-chloro-3-methyl-1H-indole-2-carbonyl)-1,8-diazaspiro[4.5]decane-8-carboxylate | | δ 8.55 (s, 1H), 7.54 (s, 1H), 7.22-7.24 (m, 1H), 7.15-7.22 (m, 1H), 5.68-5.89 (m, 1H), 4.00-4.42 (m, 2H), 3.50-3.72 (m, 2H), 2.90-3.25 (m, 4H), 2.32 (s, 3H), 1.98-2.18 (m, 2H), 1.85-1.98 (m, 2H), 1.42-1.58 (m, 2H) | 526 |
| 110 | 1,1,1,3,3,3-Hexafluoropropan-2-yl 1-((5,7-dichloro-1H-indol-2-yl)methyl)-1,8-diazaspiro[4.5]decane-8-carboxylate | | δ 8.54 (s, 1H), 7.40 (s, 1H), 7.15 (s, 1H), 6.32 (s, 1H), 5.64-5.88 (m, 1H), 4.13-4.39 (m, 2H), 3.52-4.02 (m, 2H), 2.89-3.13 (m, 2H), 2.53-2.87 (m, 2H), 1.50-1.89 (m, 8H) | 532 |
| 111 | 1,1,1,3,3,3-Hexafluoropropan-2-yl 1-(5,6-dichloro-1H-indole-2-carbonyl)-1,8-diazaspiro[4.5]decane-8-carboxylate | | δ 9.37 (s, 1H), 7.73 (s, 1H), 7.52 (s, 1H), 6.73 (s, 1H), 5.65-5.90 (m, 1H), 4.10-4.41 (m, 2H), 3.90-4.10 (m, 2H), 2.92-3.21 (m, 4H), 1.95-2.20 (m, 4H), 1.40-1.550 (m, 2H) | 546 |
| 112 | 1,1,1,3,3,3-Hexafluoropropan-2-yl 1-((5,6-dichloro-1H-indol-2-yl)methyl)-1,8-diazaspiro[4.5]decane-8-carboxylate | | δ 8.55 (s, 1H), 7.58 (s, 1H), 7.42 (s, 1H), 6.25 (s, 1H), 5.60-5.78 (m, 1H), 4.10-4.38 (m, 2H), 3.60-3.98 (m, 2H), 2.90-3.20 (m, 2H), 2.70-2.85 (m, 2H), 1.80-2.00 (m, 4H), 1.69-1.79 (m, 2H), 1.42-1.60 (m, 2H) | 531 |

-continued

| Ex | Name | Structure | NMR (¹H NMR, 300 MHz or 400 MHz, chloroform-d) | MS [M + H]⁺ |
|---|---|---|---|---|
| 113 | 3-(4-((8-(((1,1,1,3,3,3-Hexafluoropropan-2-yl)oxy)carbonyl)-2,8-diazaspiro[4.5]decan-2-yl)methyl)-1-isopropyl-1H-pyrazol-3-yl)benzoic acid | | δ 8.30 (s, 1H), 7.98 (d, J = 7.6 Hz, 1H), 7.80 (d, J = 7.6 Hz, 1H), 7.60 (s, 1H), 7.47 (t, J = 7.6 Hz, 1H), 5.68-5.76 (m, 1H), 4.49-4.60 (m, 1H), 4.02 (s, 2H), 3.43-3.44 (m, 4H), 2.90-2.93 (m, 2H), 2.75-2.78 (m, 2H), 1.74 (t, J = 6.8 Hz, 2H), 1.52-1.54 (m, 10H) | 577 |
| 114 | 3-(4-((8-(((1,1,1,3,3,3-Hexafluoropropan-2-yl)oxy)carbonyl)-1,8-diazaspiro[4.5]decan-1-yl)methyl)-1-isopropyl-1H-pyrazol-3-yl)benzoic acid | | (Methanol-d₄) δ 8.23 (s, 1H), 8.04 (d, J = 7.8 Hz, 1H), 7.87 (s, 1H), 7.79 (d, J = 7.8 Hz, 1H), 7.52 (t, J = 7.8 Hz, 1H), 6.12-6.21 (m, 1H), 4.53-4.71 (m, 1H), 4.18-4.20 (m, 2H), 4.04 (s, 2H), 3.00-3.17 (m, 4H), 2.03-2.08 (m, 2H), 1.84-1.97 (m, 4H), 1.64-1.68 (m, 2H), 1.55 (d, J = 6.6 Hz, 6H) | 577 |
| 115 | 1,1,1,3,3,3-Hexafluoropropan-2-yl 1-((8-chloro-6-methylimidazo[1,2-a]pyridin-2-yl)methyl)-1,8-diazaspiro[4.5]decane-8-carboxylate | | δ 7.77 (s, 1H), 7.49 (s, 1H), 7.08 (s, 1H), 5.81-5.69 (m, 1H), 4.29-4.12 (m, 2H), 4.03-3.69 (m, 2H), 3.10-2.79 (m, 4H), 2.29 (s, 3H), 1.97-1.64 (m, 6H), 1.58-1.40 (m, 2H) | 513 |
| 116 | 1,1,1,3,3,3-Hexafluoropropan-2-yl 1-(8-chloro-6-(trifluoromethyl)imidazo[1,2-a]pyridine-2-carbonyl)-1,8-diazaspiro[4.5]decane-8-carboxylate | | δ 8.5-8.45 (m, 1H), 8.26-8.20 (m, 1H), 7.46-7.42 (m, 1H), 5.82-5.71 (m, 1H), 4.29-4.12 (m, 4H), 3.24-3.11 (m, 2H), 3.11-2.95 (m, 2H), 2.12-1.89 (m, 4H), 1.56-1.46 (m, 2H). | 581 |
| 117 | 1,1,1,3,3,3-Hexafluoropropan-2-yl 1-(2-chloro-4-(pyrrolidin-1-yl)pyrimidine-5-carbonyl)-1,8-diazaspiro[4.5]decane-8-carboxylate | | δ 6.45 (s, 1H), 5.74-5.67 (m, 1H), 4.33-4.06 (m, 2H), 3.77-3.52 (m, 4H), 3.41-3.32 (m, 2H), 3.14-2.90 (m, 4H), 2.11-1.91 (m, 6H), 1.91-1.79 (m, 2H), 1.54-1.43 (m, 2H) | 544 |

| Ex | Name | Structure | NMR ($^1$H NMR, 300 MHz or 400 MHz, chloroform-d) | MS [M + H]$^+$ |
|---|---|---|---|---|
| 118 | 2-(3-(3-Chlorophenyl)-4-((8-(((1,1,1,3,3,3-hexafluoropropan-2-yl)oxy)carbonyl)-1,8-diazaspiro[4.5]decan-1-yl)methyl)-1H-pyrazol-1-yl)acetic acid | | (Methanol-d$_4$) δ 7.84 (s, 1H), 7.69 (s, 1H), 7.50-7.54 (m, 1H), 7.38-7.44 (m, 2H), 6.11-6.20 (m, 1H), 4.75 (s, 2H), 4.18-4.23 (m, 2H), 4.09 (s, 2H), 3.02-3.17 (m, 4H), 2.10-2.12 (m, 2H), 1.93-1.95 (m, 4H), 1.71-1.74 (m, 2H) | 583 |
| 119 | 1,1,1,3,3,3-Hexafluoropropan-2-yl 1-(2-chloro-6-(pyrrolidin-1-yl)pyrimidine-4-carbonyl)-1,8-diazaspiro[4.5]decane-8-carboxylate | | δ 6.47 (s, 1H), 5.82-5.69 (m, 1H), 4.29-4.12 (m, 2H), 3.77-3.58 (m, 4H), 3.44-3.31 (m, 2H), 3.18-2.85 (m, 4H), 2.18-1.77 (m, 8H), 1.58-1.46 (m, 2H) | 544 |
| 120 | 1,1,1,3,3,3-Hexafluoropropan-2-yl 1-(4-chloro-1-methyl-1H-pyrazole-3-carbonyl)-1,8-diazaspiro[4.5]decane-8-carboxylate | | δ 7.29 (s, 1H), 5.75-5.61 (m, 1H), 4.21-4.05 (m, 2H), 3.80 (s, 3H), 3.66-3.56 (m, 2H), 3.18-3.05 (m, 2H), 3.03-2.85 (m, 2H), 2.06-1.87 (m, 2H), 1.84-1.72 (m, 2H), 1.48-1.37 (m, 2H) | 477 |
| 121 | 1,1,1,3,3,3-Hexafluoropropan-2-yl 1-(3-chloro-5-methyl-7-(trifluoromethyl)pyrazolo[1,5-a]pyrimidine-2-carbonyl)-1,8-diazaspiro[4.5]decane-8-carboxylate | | δ 7.13 (s, 1H), 5.85-5.69 m, 1H), 4.38-4.09 (m, 2H), 3.73-3.54 (m, 2H), 3.31-2.93 (m, 4H), 2.75 (s, 3H), 2.23-2.01 (m, 2H), 1.97-1.81 (m, 2H), 1.65-1.48 (m, 2H) | 596 |
| 122 | 1,1,1,3,3,3-Hexafluoropropan-2-yl 1-(4-(trifluoromethyl)pyrimidine-5-carbonyl)-1,8-diazaspiro[4.5]decane-8-carboxylate | | δ 9.38 (s, 1H), 8.85 (s, 1H), 5.84-5.68 (m, 1H), 4.34-4.15 (m, 2H), 3.30-2.87 (m, 6H), 2.20-2.01 (m, 2H), 1.97-1.83 (m, 2H), 1.62-1.46 (m, 2H) | 509 |

| Ex | Name | Structure | NMR (¹H NMR, 300 MHz or 400 MHz, chloroform-d) | MS [M + H]⁺ |
|---|---|---|---|---|
| 123 | 1-(3-((8-(((1,1,1,3,3,3-Hexafluoropropan-2-yl)oxy)carbonyl)-1,8-diazaspiro[4.5]decan-1-yl)methyl)-6-(trifluoromethyl)pyridin-2-yl)piperidine-4-carboxylic acid | | (Methanol-d₄) δ 8.06 (d, J = 6.6 Hz, 1H), 7.35 (d, J = 6.6 Hz, 1H), 6.12-6.18 (m, 1H), 4.21 (s, 2H), 3.75 (s, 2H), 3.48-3.52 (m, 2H), 3.03-3.32 (m, 2H), 2.89-2.93 (m, 2H), 2.70-2.73 (m, 2H), 2.48-2.55 (m, 1H), 1.74-2.05 (m, 10H), 1.57-1.61 (m, 2H) | 621 |
| 124 | 1-(3-((8-(((1,1,1,3,3,3-Hexafluoropropan-2-yl)oxy)carbonyl)-1,8-diazaspiro[4.5]decan-1-yl)methyl)pyridin-2-yl)piperidine-4-carboxylic acid | | (Methanol-d₄) δ 8.18-8.20 (m, 1H), 7.90-7.94 (m, 1H), 7.07-7.11 (m, 1H), 6.12-6.21 (m, 1H), 4.20-4.24 (m, 2H), 3.85 (s, 2H), 3.34-3.37 (m, 2H), 3.08-3.32 (m, 2H), 2.84-2.92 (m, 4H), 2.42-2.49 (m, 1H), 2.01-2.06 (m, 4H), 1.80-2.00 (m, 6H), 1.62-1.67 (m, 2H) | 553 |
| 125 | 1,1,1,3,3,3-Hexafluoropropan-2-yl 1-(3-chloro-1,5-dimethyl-1H-pyrazole-4-carbonyl)-1,8-diazaspiro[4.5]decane-8-carboxylate | | δ 5.85-5.66 (m, 1H), 4.31-4.11 (m, 2H), 3.76 (s, 3H), 3.49-3.41 (m, 2H), 3.21-2.92 (m, 4H), 2.23 (s, 3H), 2.14-2.97 (m, 2H), 1.91-1.80 (m, 2H), 1.52-1.42 (m, 2H) | 491 |
| 126 | 1,1,1,3,3,3-Hexafluoropropan-2-yl 1-(3-chloro-1-methyl-1H-pyrazole-4-carbonyl)-1,8-diazaspiro[4.5]decane-8-carboxylate | | δ 7.60 (s, 1H), 5.81-5.69 (m, 1H), 4.29-4.11 (m, 2H), 3.85 (s, 3H), 3.69-3.58 (m, 2H), 3.26-2.89 (m, 4H), 2.17-1.79 (m, 4H), 1.54-1.38 (m, 2H) | 477 |
| 127 | 1,1,1,3,3,3-Hexafluoropropan-2-yl 1-(4-methylpyrimidine-5-carbonyl)-1,8-diazaspiro[4.5]decane-8-carboxylate | | δ 9.10 (s, 1H), 8.51 (s, 1H), 5.84-5.70 (m, 1H), 4.33-4.17 (m, 2H), 3.35-2.91 (m, 6H), 2.53 (s, 3H), 2.20-1.99 (m, 2H), 1.89 (p, J = 6.8 Hz, 2H), 1.62-1.46 (m, 2H) | 455 |

-continued

| Ex | Name | Structure | NMR ($^1$H NMR, 300 MHz or 400 MHz, chloroform-d) | MS [M + H]$^+$ |
|---|---|---|---|---|
| 128 | 1,1,1,3,3,3-Hexafluoropropan-2-yl 1-(2,4-dimethyloxazole-5-carbonyl)-1,8-diazaspiro[4.5]decane-8-carboxylate | | δ 5.83-5.66 (m, 1H), 4.28-4.09 (m, 2H), 3.87-3.75 (m, 2H), 3.21-2.90 (m, 4H), 2.46 (s, 3H), 2.39 (s, 3H), 2.15-1.83 (m, 4H), 1.54-1.37 (m, 2H) | 458 |
| 129 | 1,1,1,3,3,3-Hexafluoropropan-2-yl 1-(2,5-dimethyloxazole-4-carbonyl)-1,8-diazaspiro[4.5]decane-8-carboxylate | | δ 5.81-5.69 (m, 1H), 4.25-4.11 (m, 2H), 3.96-3.82 (m, 2H), 3.20-2.92 (m, 4H), 2.49 (s, 3H), 2.39 (s, 3H), 2.24-1.78 (m, 4H), 1.50-1.39 (m, 2H) | 458 |
| 130 | 1,1,1,3,3,3-Hexafluoropropan-2-yl 1-(4-methyl-oxazole-5-carbonyl)-1,8-diazaspiro[4.5]decane-8-carboxylate | | δ 7.77 (s, 1H), 5.86-5.66 (m, 1H), 4.31-4.07 (m, 2H), 3.89-3.76 (m, 2H), 3.23-2.84 (m, 4H), 2.46 (s, 3H), 2.18-1.84 (m, 4H), 1.56-1.39 (m, 2H) | 444 |
| 131 | 1,1,1,3,3,3-Hexafluoropropan-2-yl 1-(4-chloro-1,5-dimethyl-1H-pyrazole-3-carbonyl)-1,8-diazaspiro[4.5]decane-8-carboxylate | | δ 5.82-5.68 (m, 1H), 4.27-4.12 (m, 2H), 3.78 (s, 3H), 3.72-3.63 (m, 2H), 3.25-3.11 (m, 2H), 3.09-2.92 (m, 2H), 2.25 (s, 3H), 2.15-1.93 (m, 2H), 1.89-1.79 (m, 2H), 1.54-1.43 (m, 2H) | 491 |
| 132 | 1,1,1,3,3,3-Hexafluoropropan-2-yl 1-((2-(4-cyclopropylpiperazin-1-yl)thiazol-5-yl)methyl)-1,8-diazaspiro[4.5]decane-8-carboxylate | | δ 6.94 (s, 1H), 5.81-5.68 (m, 1H), 4.26-4.10 (m, 2H), 3.63 (s, 2H), 3.51-3.31 (m, 4H), 3.05-2.87 (m, 2H), 2.83-2.63 (m, 6H), 1.91-1.56 (m, 7H), 1.53-1.33 (m, 2H), 0.56-0.36 (m, 4H) | 556 |
| 133 | 1,1,1,3,3,3-Hexafluoropropan-2-yl 1-((4-chloro-1-methyl-1H-pyrazol-3-yl)methyl)-1,8-diazaspiro[4.5]decane-8-carboxylate | | δ 7.28 (s, 1H), 5.82-5.69 (m, 1H), 4.32-4.09 (m, 2H), 3.82 (s, 3H), 3.57 (bs, 2H), 3.09-2.74 (m, 4H), 1.88-1.72 (m, 6H), 1.55-1.42 (m, 2H) | 463 |
| 134 | 1,1,1,3,3,3-Hexafluoropropan-2-yl 1-(2-methyl-imidazo[1,2-a]pyridine-3-carbonyl)-1,8-diazaspiro[4.5]decane-8-carboxylate | | δ 8.34-8.26 (m, 1H), 7.56-7.48 (m, 1H), 7.25-7.20 (m, 1H), 6.87-6.77 (m, 1H), 5.84-5.68 (m, 1H), 4.33-4.14 (m, 2H), 3.62-3.50 (m, 2H), 3.33-2.95 (m, 5H), 2.47 (s, 3H), 2.20-2.01 (m, 2H), 2.00-1.84 (m, 3H), 1.59-1.48 (m, 3H) | 493 |

| Ex | Name | Structure | NMR (¹H NMR, 300 MHz or 400 MHz, chloroform-d) | MS [M + H]⁺ |
|---|---|---|---|---|
| 135 | 1,1,1,3,3,3-Hexafluoropropan-2-yl 1-(4-morpholino-pyrimidine-5-carbonyl)-1,8-diazaspiro[4.5]decane-8-carboxylate | | (Methanol-d₄) δ 8.55 (s, 1H), 8.16 (s, 1H), 6.12-6.22 (m, 1H), 4.16-4.22 (m, 2H), 3.75-3.78 (m, 4H), 3.69 (s, 4H), 3.48-3.59 (m, 2H), 3.05-3.20 (m, 2H), 2.98 (s, 2H), 2.11-2.22 (m, 2H), 1.91-1.96 (m, 2H), 1.60 (s, 2H) | 526 |
| 136 | 1,1,1,3,3,3-Hexafluoropropan-2-yl 1-(4-(4-methylpiperazin-1-yl)pyrimidine-5-carbonyl)-1,8-diazaspiro[4.5]decane-8-carboxylate | | Methanol-d₄) δ ][ 8.54 (s, 1H), 8.15 (s, 1H), 6.14-6.21 (m, 1H), 4.16-4.22 (m, 2H), 3.60-3.85 (m, 4H), 3.47 (s, 2H), 2.90-3.20 (m, 4H), 2.54 (s, 4H), 2.35 (s, 3H), 2.10-2.30 (m, 2H), 1.90-1.96 (m, 2H), 1.60 (s, 2H) | 539 |
| 137 | 1,1,1,3,3,3-Hexafluoropropan-2-yl 1-(5,6,7,8-tetrahydroimidazo[1,2-a]pyrazine-3-carbonyl)-1,8-diazaspiro[4.5]decane-8-carboxylate | | δ 7.23 (s, 1H), 5.77-5.65 (m, 1H), 4.30-4.08 (m, 5H), 3.81-3.74 (m, 2H), 3.25-3.16 (m, 2H), 3.14-2.89 (m, 4H), 2.36-2.11 (m, 2H), 2.10-1.82 (m, 4H), 1.47-1.35 (m, 2H) | 484 |
| 138 | 1,1,1,3,3,3-Hexafluoropropan-2-yl 1-((2-methoxythiazol-5-yl)methyl)-1,8-diazaspiro[4.5]decane-8-carboxylate | | δ 6.89 (s, 1H), 5.81-5.69 (m, 1H), 4.26-4.11 (m, 2H), 4.02 (s, 3H), 3.63 (s, 2H), 3.08-2.84 (m, 2H), 2.83-2.69 (m, 2H), 1.87-1.54 (m, 6H), 1.50-1.38 (m, 2H) | 462 |
| 139 | 1,1,1,3,3,3-Hexafluoropropan-2-yl 1-(2-(trifluoromethyl)-5,6,7,8-tetrahydroimidazo[1,2-a]pyridine-3-carbonyl)-1,8-diazaspiro[4.5]decane-8-carboxylate | | δ 5.84-5.67 (m, 1H), 4.33-4.03 (m, 3H), 3.75-3.61 (m, 1H), 3.58-3.46 (m, 1H), 3.33-3.22 (m, 1H), 3.14-2.81 (m, 6H), 2.26 -2.12 (m, 1H), 2.10-1.75 (m, 7H), 1.56-1.39 (m, 2H) | 551 |
| 140 | 1,1,1,3,3,3-Hexafluoropropan-2-yl 1-(imidazo[1,2-a]pyridine-3-carbonyl)-1,8-diazaspiro[4.5]decane-8-carboxylate | | δ 9.33 (d, J = 7.0 Hz, 1H), 8.00 (s, 1H), 7.68 (d, J = 8.9 Hz, 1H), 7.40-7.33 (m, 1H), 6.99-6.92 (m, 1H), 5.85-5.70 (m, 1H), 4.32-4.15 (m, 2H), 4.00-3.87 (m, 2H), 3.31-3.16 (m, 2H), 3.13-2.95 (m, 2H), 2.19-1.92 (m, 4H), 1.58-1.45 (m, 2H) | 479 |

| Ex | Name | Structure | NMR (¹H NMR, 300 MHz or 400 MHz, chloroform-d) | MS [M + H]⁺ |
|---|---|---|---|---|
| 141 | | 1,1,1,3,3,3-Hexafluoropropan-2-yl 1-(imidazo[1,2-a]pyrimidine-3-carbonyl)-1,8-diazaspiro[4.5]decane-8-carboxylate | δ 9.77-9.69 (m, 1H), 8.74-8.66 (m, 1H), 8.18 (s, 1H), 7.08-6.99 (m, 1H), 5.85-5.70 (m, 1H), 4.38-4.12 (m, 2H), 3.96 (t, J = 6.5 Hz, 2H), 3.30-2.91 (m, 4H), 2.24-1.91 (m, 5H), 1.63-1.38 (m, 3H) | 480 |
| 142 | | 1,1,1,3,3,3-Hexafluoropropan-2-yl 1-(6-chloro-2-methylimidazo[1,2-b]pyridazine-3-carbonyl)-1,8-diazaspiro[4.5]decane-8-carboxylate | δ 7.91 (d, J = 9.4 Hz, 1H), 7.12 (d, J = 9.4 Hz, 1H), 5.82-5.70 (m, 1H), 4.34-4.18 (m, 2H), 3.41 (bs, 2H), 3.27-2.94 (m, 4H), 2.55 (s, 3H), 2.23-2.02 (m, 2H), 1.96-1.83 (m, 2H), 1.68-1.52 (m, 2H) | 528 |
| 143 | | 1,1,1,3,3,3-Hexafluoropropan-2-yl 1-(2-methyl-imidazo[1,2-b]pyridazine-3-carbonyl)-1,8-diazaspiro[4.5]decane-8-carboxylate | δ 8.47-8.36 (m, 1H), 8.09-7.99 (m, 1H), 7.22-7.12 (m, 1H), 5.83-5.70 (m, 1H), 4.34-4.16 (m, 2H), 3.43 (bs, 2H), 3.30-3.14 (m, 2H), 3.14-2.93 (m, 2H), 2.58 (s, 3H), 2.22-2.02 (m, 2H), 1.95-1.81 (m, 2H), 1.68-1.53 (m, 2H) | 494 |
| 144 | | 1,1,1,3,3,3-Hexafluoropropan-2-yl 1-(pyrazolo[1,5-a]pyrimidine-3-carbonyl)-1,8-diazaspiro[4.5]decane-8-carboxylate | δ 8.79-8.55 (m, 2H), 8.36 (s, 1H), 6.97-6.88 (m, 1H), 5.84-5.69 (m, 1H), 4.31-4.13 (m, 2H), 3.90-3.73 (m, 2H), 3.34-3.17 (m, 2H), 3.15-3.04 (m, 2H), 2.19-1.99 (m, 2H), 1.96-1.82 (m, 2H), 1.68-1.48 (m, 4H) | 480 |
| 145 | | 1,1,1,3,3,3-Hexafluoropropan-2-yl 1-(5-chloropyrazolo[1,5-a]pyrimidine-3-carbonyl)-1,8-diazaspiro[4.5]decane-8-carboxylate | δ 8.58 (d, J = 7.2 Hz, 1H), 8.36 (s, 1H), 6.88 (d, J = 7.2 Hz, 1H), 5.84-5.69 (m, 1H), 4.29-4.13 (m, 2H), 3.85-3.71 (m, 2H), 3.28-2.94 (m, 4H), 2.18-2.01 (m, 2H), 1.95-1.82 (m, 2H), 1.60-1.49 (m, 2H) | 514 |

| Ex | Name | Structure | NMR (¹H NMR, 300 MHz or 400 MHz, chloroform-d) | MS [M + H]⁺ |
|---|---|---|---|---|
| 146 | 1,1,1,3,3,3-Hexafluoropropan-2-yl 1-(pyrazolo[1,5-a]pyridine-3-carbonyl)-1,8-diazaspiro[4.5]decane-8-carboxylate | | δ 8.51-8.44 (m, 1H), 8.29-8.23 (m 1H), 8.14 (s, 1H), 7.37-7.28 (m, 1H), 6.95-6.88 (m, 1H), 5.83-5.71 (m, 1H), 4.29-4.14 (m, 2H), 3.97-3.86 (m, 2H), 3.35-3.18 (m, 2H), 3.14-2.95 (m, 2H), 2.18-1.87 (m, 4H), 1.57-1.43 (m, 2H) | 479 |
| 147 | 1,1,1,3,3,3-Hexafluoropropan-2-yl 1-(4,5,6,7-tetrahydropyrazolo[1,5-a]pyrimidine-3-carbonyl)-1,8-diazaspiro[4.5]decane-8-carboxylate | | δ 7.46 (s, 1H), 6.72 (bs, 1H), 5.81-5.69 (m, 1H), 4.23-4.04 (m, 4H), 3.84-3.74 (m, 2H), 3.42-3.33 (m, 2H), 3.20-2.92 (m, 4H), 2.19-2.09 (m, 2H), 2.07-1.89 (m, 4H), 1.49-1.36 (m, 2H) | 484 |
| 148 | 1,1,1,3,3,3-Hexafluoropropan-2-yl 1-(4,5,6,7-tetrahydropyrazolo[1,5-a]pyridine-3-carbonyl)-1,8-diazaspiro[4.5]decane-8-carboxylate | | δ 7.59 (s, 1H), 5.81-5.68 (m, 1H), 4.25-4.07 (m, 4H), 3.76-3.71 (m, 2H), 3.24-2.92 (m, 6H), 2.12-1.79 (m, 8H), 1.52-1.36 (m, 2H) | 483 |
| 149 | 1,1,1,3,3,3-Hexafluoropropan-2-yl 1-(6,7-dihydro-5H-pyrazolo[5,1-b][1,3]oxazine-3-carbonyl)-1,8-diazaspiro[4.5]decane-8-carboxylate | | δ 7.52 (s, 1H), 5.81-5.67 (m, 1H), 4.51-4.30 (m, 2H), 4.27-4.05 (m, 4H), 3.84-3.61 (m, 2H), 3.25-3.10 (m, 2H), 3.08-2.90 (m, 2H), 2.32-2.20 (m, 2H), 2.10-1.82 (m, 4H), 1.49-1.35 (m, 2H) | 485 |
| 150 | 1,1,1,3,3,3-Hexafluoropropan-2-yl 1-(pyrazolo[1,5-a]pyrimidine-2-carbonyl)-1,8-diazaspiro[4.5]decane-8-carboxylate | | δ 8.72-8.68 (m, 1H), 8.65-8.60 (m, 1H), 8.36 (s, 1H), 6.95-6.91 (m, 1H), 5.85-5.70 (m, 1H), 4.30-4.12 (m, 2H), 3.88-3.76 (m, 2H), 3.33-3.18 (m, 2H), 3.14-2.94 (m, 2H), 2.18-2.00 (m, 2H), 1.96-1.82 (m, 2H), 1.62-1.48 (m, 2H) | 480 |
| 151 | 1,1,1,3,3,3-Hexafluoropropan-2-yl 1-(5-chloropyrazolo[1,5-a]pyrimidine-2-carbonyl)-1,8-diazaspiro[4.5]decane-8-carboxylate | | δ 8.58 (d, J = 7.2 Hz, 1H), 8.36 (s, 1H), 6.89 (d, J = 7.2 Hz, 1H), 5.86-5.69 (m, 1H), 4.32-4.10 (m, 2H), 3.86-3.69 (m, 2H), 3.27-3.14 (m, 2H), 3.12-2.95 (m, 2H), 2.18-2.02 (m, 2H), 1.94-1.83 (m 2H), 1.66-1.48 (m, 2H) | 514 |

| Ex | Name | Structure | NMR (¹H NMR, 300 MHz or 400 MHz, chloroform-d) | MS [M + H]⁺ |
|---|---|---|---|---|
| 152 | 1,1,1,3,3,3-Hexafluoropropan-2-yl 1-(4,5,6,7-tetrahydrothieno[3,2-c]pyridine-2-carbonyl)-1,8-diazaspiro[4.5]decane-8-carboxylate | | δ 7.11 (s, 1H), 5.83-5.68 (m, 1H), 4.27-4.10 (m, 2H), 4.02 (s, 2H), 3.88-3.77 (m, 2H), 3.32-3.23 (m, 2H), 3.20-2.91 (m, 7H), 2.13-1.88 (m, 4H), 1.51-1.38 (m, 2H) | 500 |
| 153 | 1,1,1,3,3,3-Hexafluoropropan-2-yl 1-(4,5,6,7-tetrahydro-[1,2,4]triazolo[1,5-a]pyrimidine-2-carbonyl)-1,8-diazaspiro[4.5]decane-8-carboxylate | | δ 5.82-5.68 (m, 1H), 4.25-4.06 (m, 4H), 3.99-3.89 (m, 2H), 3.57-3.46 (m, 2H), 3.41-3.15 (m, 2H), 3.14-2.89 (m, 4H), 2.24-2.14 (m, 2H), 2.12-1.78 (m, 4H), 1.50-1.40 (m, 2H) | 485 |
| 154 | 1,1,1,3,3,3-Hexafluoropropan-2-yl 1-(7-(cyclopropylmethyl)-5,6,7,8-tetrahydroimidazo[1,2-a]pyrazine-2-carbonyl)-1,8-diazaspiro[4.5]decane-8-carboxylate | | δ 7.40 (s, 1H), 5.82-5.69 (m, 1H), 4.27-3.81 (m, 8H), 3.23-2.91 (m, 6H), 2.73-2.45 (m, 2H), 2.07-1.79 (m, 5H), 1.51-1.38 (m, 2H), 1.11-0.92 (m, 1H), 0.73-0.54 (m, 2H), 0.33-0.16 (m, 2H) | 538 |
| 155 | 1,1,1,3,3,3-Hexafluoropropan-2-yl 1-(5-cyclopropyl-4,5,6,7-tetrahydropyrazolo[1,5-a]pyrazine-2-carbonyl)-1,8-diazaspiro[4.5]decane-8-carboxylate | | δ 6.42 (s, 1H), 5.85-5.65 (m, 1H), 4.30-3.80 (m, 6H), 3.27-2.88 (m, 5H), 2.12-1.77 (m, 5H), 1.69-1.35 (m, 5H), 0.60 (s, 4H) | 524 |
| 156 | 1,1,1,3,3,3-Hexafluoropropan-2-yl 1-(5-(cyclopropylmethyl)-4,5,6,7-tetrahydropyrazolo[1,5-a]pyrazine-2-carbonyl)-1,8-diazaspiro[4.5]decane-8-carboxylate | | δ 6.41 (s, 1H), 5.81-5.75 (m, 1H), 4.30-4.09 (m, 4H), 3.99-3.89 (m, 2H), 3.80 (s, 2H), 3.27-2.88 (m, 6H), 2.50 (d, J = 6.6 Hz, 2H), 2.10-1.80 (m, 4H), 1.51-1.39 (m, 2H), 1.02-0.87 (m, 1H), 0.67-0.56 (m, 2H), 0.25-0.15 (m, 2H) | 538 |
| 157 | 1,1,1,3,3,3-Hexafluoropropan-2-yl 1-(3-chloropyrazolo[1,5-a]pyrimidine-2-carbonyl)-1,8-diazaspiro[4.5]decane-8-carboxylate | | δ 8.72-8.45 (m, 2H), 7.06-6.84 (m, 1H), 5.84-5.69 (m, 1H), 4.37-4.10 (m, 2H), 3.65-3.54 (m, 2H), 3.29-3.14 (m, 2H), 3.13-2.94 (m, 2H), 2.22-2.00 (m, 2H), 1.96-1.82 (m, 2H), 1.65-1.49 (m, 2H) | 514 |

| Ex | Name | Structure | NMR (¹H NMR, 300 MHz or 400 MHz, chloroform-d) | MS [M + H]⁺ |
|---|---|---|---|---|
| 158 | 2-(2-(8-(((1,1,1,3,3,3-Hexafluoropropan-2-yl)oxy)carbonyl)-1,8-diazaspiro[4.5]decane-1-carbonyl)-5,6-dihydroimidazo[1,2-a]pyrazin-7(8H)-yl)acetic acid | | (Methanol-d₄) δ 7.44 (s, 1H), 6.10-6.15 (m, 1H), 4.09-4.16 (m, 4H), 3.85-3.89 (m, 4H), 3.43 (s, 2H), 3.00-3.14 (m, 6H), 2.08-2.13 (m, 2H), 1.88-1.94 (m, 2H), 1.49-1.52 (m, 2H) | 542 |
| 159 | 1,1,1,3,3,3-Hexafluoropropan-2-yl 1-(imidazo[1,2-a]pyrazine-2-carbonyl)-1,8-diazaspiro[4.5]decane-8-carboxylate | | δ 9.11 (s, 1H), 8.20 (s, 1H), 8.14-8.09 (m, 1H), 7.97-7.91 (m, 1H), 5.84-5.70 (m, 1H), 4.28-4.13 (m, 2H), 3.26-2.95 (m, 4H), 2.14-1.89 (m, 4H), 1.57-1.46 (m, 2H) | 480 |
| 160 | 1,1,1,3,3,3-Hexafluoropropan-2-yl 1-([1,2,4]triazolo[1,5-a]pyrimidine-2-carbonyl)-1,8-diazaspiro[4.5]decane-8-carboxylate | | δ 8.96-8.79 (m, 2H), 7.24-7.19 (m, 1H), 5.82-5.70 (m, 1H), 4.34-4.13 (m, 2H), 3.98-3.88 (m, 2H), 3.26-3.14 (m, 2H), 3.12-2.94 (m, 2H), 2.15-2.01 (m, 2H), 1.96-1.87 (m, 2H), 1.59-1.48 (m, 2H) | 481 |
| 161 | 1,1,1,3,3,3-Hexafluoropropan-2-yl 1-(7-(oxetan-3-yl)-5,6,7,8-tetrahydroimidazo[1,2-a]pyrazine-2-carbonyl)-1,8-diazaspiro[4.5]decane-8-carboxylate | | δ 7.41 (s, 1H), 5.81-5.69 (m, 1H), 4.77-4.70 (m, 2H), 4.68-4.61 (m, 2H), 4.23-3.99 (m, 6H), 3.82-3.70 (m, 1H), 3.60 (s, 2H), 3.23-2.92 (m, 4H), 2.81-2.75 (m, 2H), 2.06-1.81 (m, 4H), 1.50-1.38 (m, 2H) | 540 |
| 162 | 1,1,1,3,3,3-Hexafluoropropan-2-yl 1-(7-(tetrahydro-2H-pyran-4-yl)-5,6,7,8-tetrahydroimidazo[1,2-a]pyrazine-2-carbonyl)-1,8-diazaspiro[4.5]decane-8-carboxylate | | δ 7.39 (s, 1H), 5.81-5.69 (m, 1H), 4.24-3.92 (m, 10H), 3.81-3.64 (m, 2H), 3.46-3.36 (m, 2H), 3.19-2.92 (m, 5H), 2.86-2.73 (m, 1H), 2.07-1.79 (m, 5H), 1.74-1.60 (m, 2H), 1.50-1.40 (m, 2H) | 568 |
| 163 | 1,1,1,3,3,3-Hexafluoropropan-2-yl 1-(6-chloroimidazo[1,2-b]pyridazine-2-carbonyl)-1,8-diazaspiro[4.5]decane-8-carboxylate | | δ 8.37 (s, 1H), 7.92-7.84 (m, 1H), 7.17-7.07 (m, 1H), 5.85-5.68 (m, 1H), 4.31-3.97 (m, 4H), 3.31-2.85 (m, 4H), 2.14-1.86 (m, 4H), 1.58-1.43 (m, 2H) | 514 |

| Ex | Name | Structure | NMR (¹H NMR, 300 MHz or 400 MHz, chloroform-d) | MS [M + H]⁺ |
|---|---|---|---|---|
| 164 | 1,1,1,3,3,3-Hexafluoropropan-2-yl 1-(7-(trifluoromethyl)pyrazolo[1,5-a]pyrimidine-2-carbonyl)-1,8-diazaspiro[4.5]decane-8-carboxylate | | δ 8.65 (d, J = 4.1 Hz, 1H), 7.31 (s, 1H), 5.83-5.71 (m, 1H), 4.32-4.14 (m, 2H), 4.09-3.99 (m, 2H), 3.28-3.14 (m, 2H), 3.13-2.95 (m, 2H), 2.16-1.88 (m, 4H), 1.59-1.47 (m, 2H) | 548 |
| 165 | 1,1,1,3,3,3-Hexafluoropropan-2-yl 1-(7-cyclopropylpyrazolo[1,5-a]pyrimidine-2-carbonyl)-1,8-diazaspiro[4.5]decane-8-carboxylate | | δ 8.38 (d, J = 4.4 Hz, 1H), 7.04 (s, 1H), 6.38 (d, J = 4.4 Hz, 1H), 5.84-5.71 (m, 1H), 4.31-4.13 (m, 2H), 4.06-3.94 (m, 2H), 3.32-3.16 (m, 2H), 3.16-2.95 (m, 2H), 2.95-2.83 (m, 1H), 2.15-2.00 (m, 2H), 1.98-1.86 (m, 2H), 1.60-1.46 (m, 2H), 1.42-1.30 (m, 2H), 1.18-1.06 (m, 2H) | 520 |
| 166 | 1,1,1,3,3,3-Hexafluoropropan-2-yl 1-(5,7-bis(difluoromethyl)pyrazolo[1,5-a]pyrimidine-2-carbonyl)-1,8-diazaspiro[4.5]decane-8-carboxylate | | δ 7.48 (s, 1H), 7.47-7.17 (m, 2H), 6.79-6.48 (m, 1H), 5.86-5.69 (m, 1H), 4.32-4.14 (m, 2H), 4.01-3.91 (m, 2H), 3.29-2.92 (m, 4H), 2.17-1.88 (m, 4H), 1.59-1.47 (m, 2H) | 580 |
| 167 | 1.1,1,3,3,3-Hexafluoropropan-2-yl 1-(5-cyclopropyl-7-(difluoromethyl)pyrazolo[1,5-a]pyrimidine-2-carbonyl)-1,8-diazaspiro[4.5]decane-8-carboxylate | | δ 7.42-7.10 (m, 1H), 7.00 (s, 1H), 6.92 (s, 1H), 5.83-5.71 (m, 1H), 4.33-4.11 (m, 2H), 3.99-3.90 (m, 2H), 3.29-3.13 (m, 2H), 3.13-2.94 (m, 2H), 2.23-1.99 (m, 3H), 1.96-1.85 (m, 2H), 1.59-1.44 (m, 2H), 1.31-1.12 (m, 4H) | 570 |
| 168 | 1,1,1,3,3,3-Hexafluoropropan-2-yl 4-methyl-4-(N-methylimidazo[1,2-b]pyridazine-3-carboxamido)piperidine-1-carboxylate | | δ 8.46-8.48 (m, 1H), 8.03-8.11 (m, 2H), 7.15-7.19 (m, 1H), 5.74-5.82 (m, 1H), 3.85-3.92 (m, 2H), 3.35-3.45 (m, 2H), 2.92 (s, 3H), 2.68-2.79 (m, 2H), 1.66-1.76 (m, 2H), 1.50 (s, 3H) | 468 |

| Ex | Name | Structure | NMR (¹H NMR, 300 MHz or 400 MHz, chloroform-d) | MS [M + H]⁺ |
|---|---|---|---|---|
| 169 | 1,1,1,3,3,3-Hexafluoropropan-2-yl 1-(7-(1-methoxypropan-2-yl)-5,6,7,8-tetrahydroimidazo[1,2-a]pyrazine-2-carbonyl)-1,8-diazaspiro[4.5]decane-8-carboxylate | | δ 7.37 (d, J = 1.1 Hz, 1H), 5.85-5.65 (m, 1H), 4.29-3.88 (m, 8H), 3.59-3.39 (m, 2H), 3.35 (s, 3H), 3.22-2.91 (m, 7H), 2.07-1.81 (m, 4H), 1.52-1.38 (m, 2H), 1.25-1.09 (bs, 3H) | 556 |
| 170 | 1,1,1,3,3,3-Hexafluoropropan-2-yl 1-(7-((3-methyloxetan-3-yl)methyl)-5,6,7,8-tetrahydroimidazo[1,2-a]pyrazine-2-carbonyl)-1,8-diazaspiro[4.5]decane-8-carboxylate | | δ 7.41 (s, 1H), 5.83-5.68 (m, 1H), 4.55-4.48 (m, 2H), 4.43-4.35 (m, 2H), 4.25-4.10 (m, 2H), 4.10-3.99 (m, 4H), 3.71 (s, 2H), 3.21-2.92 (m, 4H), 2.91-2.76 (m, 4H), 2.07-1.82 (m, 4H), 1.53-1.37 (m, 5H) | 568 |
| 171 | 1,1,1,3,3,3-Hexafluoropropan-2-yl 1-(2-methylpyrazolo[1,5-a]pyrimidine-3-carbonyl)-1,8-diazaspiro[4.5]decane-8-carboxylate | | δ 8.62-8.55 (m, 1H), 8.54-8.47 (m, 1H), 6.85-6.78 (m, 1H), 5.85-5.69 (m, 1H), 4.30-4.09 (m, 2H), 3.81-3.58 (m, 4H), 3.32-3.17 (m, 2H), 3.14-2.96 (m, 2H), 2.58 (s, 3H), 2.18-2.01 (m, 2H), 1.90-1.78 (m, 2H), 1.63-1.51 (m, 2H) | 494 |
| 172 | 1,1,1,3,3,3-Hexafluoropropan-2-yl 1-(2,5,7-trimethylpyrazolo[1,5-a]pyrimidine-3-carbonyl)-1,8-diazaspiro[4.5]decane-8-carboxylate | | δ 6.55 (s, 1H), 5.83-5.69 (m, 1H), 4.29-4.14 (m, 2H), 3.83-3.54 (m, 2H), 3.32-3.18 (m, 2H), 3.16-2.95 (m, 2H), 2.72 (s, 3H), 2.60-2.53 (m, 6H), 2.2.17-2.01 (m, 2H), 1.95-1.77 (m, 2H), 1.64-1.54 (m, 2H) | 522 |
| 173 | 2-(4-Chloro-3-(8-(((1,1,1,3,3,3-hexafluoropropan-2-yl)oxy)carbonyl)-1,8-diazaspiro[4.5]decane-1-carbonyl)-1H-pyrazol-1-yl)acetic acid | | δ 7.51 (s, 1H), 5.82-4.70 (m, 1H), 4.75 (s, 2H), 4.26-4.10 (m, 2H), 3.64-3.54 (m, 2H), 3.19-2.88 (m, 4H), 2.11-1.96 (m, 2H), 1.90-1.80 (m, 2H), 1.54-1.43 (m, 2H) | 521 |
| 174 | 1,1,1,3,3,3-Hexafluoropropan-2-yl 4-(7-cyclopropyl-5,6,7,8-tetrahydroimidazo[1,2-a]pyrazine-2-carboxamido)-4-methylpiperidine-1-carboxylate | | δ 7.38 (s, 1H), 6.86 (s, 1H), 5.72-5.78 (m, 1H), 4.00 (t, J = 5.6 Hz, 2H), 3.82-3.88 (m, 4H), 3.27-3.37 (m, 2H), 3.08 (t, J = 5.6 Hz, 2H), 2.35 (d, J = 13.6 Hz, 2H), 1.89-1.94 (m, 1H), 1.58-1.69 (m, 2H), 1.50 (s, 3H), 0.40-0.66 (m, 4H) | 498 |

-continued

| Ex | Name | Structure | NMR (¹H NMR, 300 MHz or 400 MHz, chloroform-d) | MS [M + H]⁺ |
|---|---|---|---|---|
| 175 | 1,1,1,3,3,3-Hexafluoropropan-2-yl 1-((1-methyl-1H-pyrazol-4-yl)methyl)-1,8-diazaspiro[4.5]decane-8-carboxylate | | δ 7.37 (s, 1H), 7.26 (s, 1H), 5.72-5.84 (m, 1H), 4.16-4.24 (m, 2H), 3.85 (s, 3H), 3.47 (s, 2H), 2.90-3.04 (m, 2H), 2.76-2.77 (m, 2H), 1.68-1.80 (m, 6H), 1.42-1.46 (m, 2H) | 429 |
| 176 | 1,1,1,3,3,3-Hexafluoropropan-2-yl 4-methyl-4-(N-methyl-1-(pyrazin-2-yl)cyclopropane-1-carboxamido)piperidine-1-carboxylate | | δ 8.47-8.61 (m, 1H), 8.35-8.47 (m, 2H), 5.68-5.95 (m, 1H), 3.56-3.71 (m, 2H), 3.32-3.56 (m, 2H), 2.80 (s, 3H), 2.32-2.52 (m, 2H), 1.79-1.95 (m, 2H), 1.46-1.78 (m, 4H), 1.41 (s, 3H) | 469 |
| 177 | 1,1,1,3,3,3-Hexafluoropropan-2-yl 4-methyl-4-(N-methyl-1-(pyrimidin-2-yl)cyclopropane-1-carboxamido)piperidine-1-carboxylate | | δ 8.51-8.62 (d, J = 4.9 Hz, 2H), 7.03-7.12 (t, J = 4.9 Hz, 1H), 5.71-5.88 (m, 1H), 3.76-3.89 (m, 2H), 3.29-3.52 (m, 2H), 2.71-2.87 (m, 4H), 2.57-2.71 (m, 1H), 1.47-1.82 (m, 6H), 1.35 (s, 3H) | 469 |
| 178 | 1,1,1,3,3,3-Hexafluoropropan-2-yl 4-(7-cyclopropyl-N-ethyl-5,6,7,8-tetrahydroimidazo[1,2-a]pyrazine-2-carboxamido)-4-methylpiperidine-1-carboxylate | | δ 7.28 (s, 1H), 5.71-5.79 (m, 1H), 3.97-4.04 (m, 4H), 3.86 (s, 2H), 3.50-3.64 (m, 4H), 3.08 (t, J = 5.6 Hz, 2H), 2.37-2.45 (m, 2H), 1.89-1.98 (m, 3H), 1.60 (s, 3H), 1.13 (t, J = 7.0 Hz, 3H), 0.50-0.62 (m, 4H) | 526 |
| 179 | 1,1,1,3,3,3-Hexafluoropropan-2-yl 1-(1-(pyridazin-3-yl)cyclopropane-1-carbonyl)-1,8-diazaspiro[4.5]decane-8-carboxylate | | δ 9.13-8.99 (m, 1H), 7.60-7.32 (m, 2H), 5.90-5.64 (m, 1H), 4.28-4.10 (m, 2H), 3.39-3.25 (m, 2H), 3.21-2.83 (m, 4H), 2.00-1.85 (m, 2H), 1.79-1.65 (m, 4H), 1.56-1.49 (m, 2H), 1.42-1.31 (m, 2H) | 481 |
| 180 | 1,1,1,3,3,3-Hexafluoropropan-2-yl 1-(1-(5-fluoropyrimidin-2-yl)cyclopropane-1-carbonyl)-1,8-diazaspiro[4.5]decane-8-carboxylate | | δ 8.45 (s, 2H), 5.81-5.69 (m, 1H), 4.26-4.11 (m, 2H), 3.41-3.20 (m, 2H), 3.20-2.89 (m, 4H), 2.05-1.86 (m, 2H), 1.80-1.70 (m, 2H), 1.64-1.35 (m, 6H) | 499 |

| Ex | Name | NMR (¹H NMR, 300 MHz or 400 MHz, chloroform-d) | MS [M + H]⁺ |
|---|---|---|---|
| 181 | 1,1,1,3,3,3-Hexafluoropropan-2-yl 4-methyl-4-(5,6,7,8-tetrahydroimidazo[1,2-a]pyrazine-2-carboxamido)piperidine-1-carboxylate | δ 7.40 (s, 1H), 6.85 (s, 1H), 5.84-5.66 (m, 1H), 4.15-3.97 (m, 4H), 3.93-3.77 (m, 2H), 3.42-3.21 (m, 4H), 2.42-2.26 (m, 2H), 2.02 (bs, 1H), 1.73-1.56 (m, 2H), 1.53-1.47 (m, 3H) | 458 |
| 182 | 1,1,1,3,3,3-Hexafluoropropan-2-yl 4-(7-isopropyl-5,6,7,8-tetrahydroimidazo[1,2-a]pyrazine-2-carboxamido)-4-methylpiperidine-1-carboxylate | δ 7.39 (s, 1H), 6.87 (s, 1H), 5.89-5.64 (m, 1H), 4.02 (d, J = 5.9 Hz, 2H), 3.95-3.71 (m, 4H), 3.45-3.18 (m, 2H), 3.11-2.79 (m, 3H), 2.35 (d, J = 13.9 Hz, 2H), 1.73-1.54 (m, 3H), 1.50 (s, 3H), 1.29-0.99 (m, 6H) | 500 |
| 183 | 1,1,1,3,3,3-Hexafluoropropan-2-yl 4-(7-cyclobutyl-5,6,7,8-tetrahydroimidazo[1,2-a]pyrazine-2-carboxamido)-4-methylpiperidine-1-carboxylate | δ 7.40 (s, 1H), 6.86 (s, 1H), 5.84-5.62 (m, 1H), 4.04 (s, 2H), 3.92-3.72 (m, 2H), 3.58 (s, 2H), 3.31 (q, J = 13.4, 12.7 Hz, 2H), 2.99 (d, J = 7.7 Hz, 1H), 2.78 (s, 2H), 2.35 (d, J = 14.0 Hz, 2H), 2.23-2.04 (m, 2H), 1.95 (s, 2H), 1.86-1.53 (m, 6H), 1.50 (s, 3H) | 512 |
| 184 | 1,1,1,3,3,3-Hexafluoropropan-2-yl 4-methyl-4-(7-(oxetan-3-yl)-5,6,7,8-tetrahydroimidazo[1,2-a]pyrazine-2-carboxamido)piperidine-1-carboxylate | δ 7.42 (s, 1H), 6.88 (s, 1H), 5.74 (hept, J = 6.3 Hz, 1H), 4.82-4.59 (m, 4H), 4.17-4.01 (m, 2H), 3.97-3.71 (m, 3H), 3.59 (s, 2H), 3.45-3.22 (m, 2H), 2.80 (t, J = 5.4 Hz, 2H), 2.34 (d, J = 13.8 Hz, 2H), 1.80 (s, 2H), 1.74-1.56 (m, 2H), 1.50 (s, 3H) | 514 |
| 185 | [2,2,2-Trifluoro-1-(trifluoromethyl)ethyl] 4-methyl-4-[methyl-[7-(oxetan-3-yl)-6,8-dihydro-5H-imidazo[1,2-a]pyrazine-2-carbonyl]amino]piperidine-1-carboxylate | δ 7.37 (s, 1H), 5.74 (hept, J = 6.3 Hz, 1H), 4.75 (t, J = 6.6 Hz, 2H), 4.64 (t, J = 6.2 Hz, 2H), 4.09 (t, J = 5.5 Hz, 2H), 3.88-3.64 (m, 5H), 3.54-3.27 (m, 2H), 3.15 (s, 3H), 2.82 (t, J = 5.5 Hz, 2H), 1.83-1.61 (m, 3H), 1.41 (s, 3H) | 528 |
| 186 | 1,1,1,3,3,3-Hexafluoropropan-2-yl 4-methyl-4-(N-methyl-5,6,7,8-tetrahydroimidazo[1,2-a]pyrazine-2-carboxamido)piperidine-1-carboxylate | (Methanol-d₄) δ 7.47 (s, 1H), 6.20-6.11 (m, 1H), 4.10-4.06 (m, 2H), 4.02 (s, 2H), 3.86-3.79 (m, 2H), 3.45-3.37 (m, 1H), 3.33-3.30 (m, 1H), 3.24 (t, J = 5.6 Hz, 2H), 3.09 (s, 3H), 2.70-2.67 (m, 2H), 1.75-1.62 (m, 2H), 1.43 (s, 3H) | 472 |

-continued

| Ex | Name | Structure | NMR (¹H NMR, 300 MHz or 400 MHz, chloroform-d) | MS [M + H]⁺ |
|---|---|---|---|---|
| 187 | 1,1,1,3,3,3-Hexafluoropropan-2-yl 4-(7-isobutyryl-N-methyl-5,6,7,8-tetrahydroimidazo[1,2-a]pyrazine-2-carboxamido)-4-methylpiperidine-1-carboxylate | | δ 7.40 (s, 1H), 5.81-5.72 (m, 1H), 4.83 (s, 2H), 4.06 (s, 4H), 3.78-3.73 (m, 2H), 3.43-3.34 (m, 2H), 3.17 (s, 3H), 2.91-2.82 (m, 1H), 2.65-2.60 (m, 2H), 1.79-1.71 (m, 2H), 1.45 (s, 3H), 1.18 (d, J = 6.3 Hz, 6H) | 542 |
| 188 | 1,1,1,3,3,3-Hexafluoropropan-2-yl 4-(7-(cyclopropane-carbonyl)-N-methyl-5,6,7,8-tetrahydroimidazo[1,2-a]pyrazine-2-carboxamido)-4-methylpiperidine-1-carboxylate | | δ 7.40 (s, 1H), 5.81-5.72 (m, 1H), 4.98 (s, 2H), 4.80 (s, 2H), 3.80-3.73 (m, 2H), 3.43-3.34 (m, 2H), 3.18 (s, 3H), 2.65-2.60 (m, 2H), 1.85-1.71 (m, 3H), 1.45 (s, 3H), 1.08-1.06 (m, 2H), 0.92-0.86 (m, 2H) | 540 |
| 189 | 1,1,1,3,3,3-Hexafluoropropan-2-yl 1-(1-(5-methyl-1,3,4-oxadiazol-2-yl)cyclopropane-1-carbonyl)-1,8-diazaspiro[4.5]decane-8-carboxylate | | δ 7.46-7.45 (m, 1H), 6.93-6.90 (m, 1H), 5.78-5.75 (m, 1H), 4.82-4.73 (m, 2H), 4.12-4.06 (m, 3H), 3.91-3.84 (m, 3H), 3.38-3.28 (m, 2H), 2.34 (s, 2H), 2.24-2.22 (m, 3H), 1.72-1.66 (m, 2H), 1.52 (s, 3H) | 500 |
| 190 | 1,1,1,3,3,3-Hexafluoropropan-2-yl 4-methyl-4-(7-(1-methylcyclopropane-1-carbonyl)-5,6,7,8-tetrahydroimidazo[1,2-a]pyrazine-2-carboxamido) piperidine-1-carboxylate | | δ 7.45 (s, 1H), 6.86 (s, 1H), 5.80-5.73 (m, 1H), 4.90 (s, 2H), 4.08 (s, 4H), 3.91-3.84 (m, 2H), 3.39-3.30 (m, 2H), 2.38-2.35 (m, 2H), 1.72-1.69 (m, 2H), 1.53 (s, 3H), 1.38 (s, 3H), 1.01-0.99 (m, 2H), 0.72-0.69 (m, 2H) | 540 |
| 191 | 1,1,1,3,3,3-Hexafluoropropan-2-yl 4-methyl-4-(7-pivaloyl-5,6,7,8-tetrahydroimidazo[1,2-a]pyrazine-2-carboxamido) piperidine-1-carboxylate | | δ 7.45 (s, 1H), 6.86 (s, 1H), 5.78-5.73 (m, 1H), 4.87 (s, 2H), 4.07 (s, 4H), 3.91-3.84 (m, 2H), 3.38-3.29 (m, 2H), 2.38-2.35 (m, 2H), 1.72-1.62 (m, 2H), 1.52 (s, 3H), 1.34 (s, 9H) | 542 |
| 192 | 1,1,1,3,3,3-Hexafluoropropan-2-yl 4-(7-(1-fluorocyclopropane-1-carbonyl)-5,6,7,8-tetrahydroimidazo[1,2-a]pyrazine-2-carboxamido)-4-methylpiperidine-1-carboxylate | | δ 7.47 (s, 1H), 6.87 (s, 1H), 5.80-5.74 (m, 1H), 5.07-4.81 (m, 2H), 4.14 (s, 4H), 3.92-3.85 (m, 2H), 3.39-3.30 (m, 2H), 2.39-2.35 (m, 2H), 1.73-1.69 (m, 2H), 1.53 (s, 3H), 1.44-1.30 (m, 4H) | 544 |
| 193 | 1,1,1,3,3,3-Hexafluoropropan-2-yl 4-(7-(2,2-dimethylbutanoyl)-5,6,7,8-tetrahydroimidazo[1,2-a]pyrazine-2-carboxamido)-4-methylpiperidine-1-carboxylate | | δ 7.45 (s, 1H), 6.86 (s, 1H), 5.79-5.73 (m, 1H), 4.86 (s, 2H), 4.06 (s, 4H), 3.91-3.84 (m, 2H), 3.38-3.29 (m, 2H), 2.37-2.34 (m, 2H), 1.72-1.62 (m, 4H), 1.52 (s, 3H), 1.30 (s, 6H), 0.86 (t, J = 5.6 Hz, 3H) | 556 |

| Ex | Name | Structure | NMR (¹H NMR, 300 MHz or 400 MHz, chloroform-d) | MS [M + H]⁺ |
|---|---|---|---|---|
| 194 | 1,1,1,3,3,3-Hexafluoropropan-2-yl 1-(1-(5-isopropoxypyrimidin-2-yl)cyclopropane-1-carbonyl)-1,8-diazaspiro[4.5]decane-8-carboxylate | | δ 8.27 (s, 2H), 5.88-5.69 (m, 1H), 4.69-4.50 (m, 1H), 4.40-4.21 (m, 2H), 3.47-3.25 (m, 2H), 3.25-2.90 (m, 4H), 2.10-1.87 (m, 2H), 1.87-1.69 (m, 2H), 1.64-1.31 (m, 12H) | 539 |
| 195 | 1,1,1,3,3,3-Hexafluoropropan-2-yl 1-(2-(pyrimidin-2-yl)acetyl)-1,8-diazaspiro[4.5]decane-8-carboxylate | | δ 8.72 (d, J= 5.0 Hz, 2H), 7.18 (t, J = 4.9 Hz, 1H), 5.80-5.61 (m, 1H), 4.22-4.05 (m, 2H), 4.00 (s, 2H), 3.70-3.52 (m, 2H), 3.12-2.84 (m, 4H), 2.10-1.85 (m, 4H), 1.49-1.31 (m, 2H) | 455 |
| 196 | 1,1,1,3,3,3-Hexafluoropropan-2-yl 1-(2,2-difluoro-2-(5-fluoropyrimidin-2-yl)acetyl)-1,8-diazaspiro[4.5]decane-8-carboxylate | | (Methanol-d₄) δ 8.91 (s, 2H), 6.21-6.06 (m, 1H), 4.25-4.09 (m, 2H), 3.57-3.42 (m, 2H), 3.21-3.00 (m, 2H), 3.00-2.83 (m, 2H), 2.08 (d, J = 6.9 Hz, 2H), 1.93-1.79 (m, 2H), 1.60-1.47 (m, 2H) | 509 |
| 197 | 1,1,1,3,3,3-Hexafluoropropan-2-yl 1-(2,2-difluoro-2-(pyrazin-2-yl)acetyl)-1,8-diazaspiro[4.5]decane-8-carboxylate | | δ 8.99 (s, 1H), 8.85-8.58 (s, 2H), 5.84-5.63 (m, 1H), 4.31-4.05 (m, 2H), 3.80 (t, J = 6.5 Hz, 2H), 3.11-2.86 (m, 4H), 2.13-1.85 (m, 4H), 1.54-1.36 (m, 2H) | 491 |
| 198 | 1,1,1,3,3,3-Hexafluoropropan-2-yl 4-(2,2-difluoro-N-methyl-2-(pyrazin-2-yl)acetamido)-4-methylpiperidine-1-carboxylate | | δ 9.00 (d, J = 1.4 Hz, 1H), 8.75 (d, J = 2.4 Hz, 1H), 8.65 (d, J = 1.7 Hz, 1H), 5.90-5.69 (m, 1H), 3.82-3.66 (m, 2H), 3.49-3.25 (m, 2H), 3.05 (t, J = 2.0 Hz, 3H), 2.60-2.40 (m, 2H), 1.86-1.70 (m, 2H), 1.42 (s, 3H) | 479 |

| Ex | Name | Structure | NMR (¹H NMR, 300 MHz or 400 MHz, chloroform-d) | MS [M + H]⁺ |
|---|---|---|---|---|
| 199 | 1,1,1,3,3,3-Hexafluoropropan-2-yl 4-(2,2-difluoro-2-(5-methoxypyrazin-2-yl)-N-methylacetamido)-4-methylpiperidine-1-carboxylate | | δ 8.48 (s, 1H), 8.19 (s, 1H), 5.85-5.65 (m, 1H), 4.02 (s, 3H), 3.80-3.65 (m, 2H), 3.39-3.20 (m, 2H), 2.98 (s, 3H), 2.60-2.40 (m, 2H), 1.79-1.69 (m, 2H), 1.40 (s, 3H) | 531 [M + Na]⁺ |
| 200 | 1,1,1,3,3,3-Hexafluoropropan-2-yl 1-(1-(2-methoxypyrimidin-4-yl)cyclopropane-1-carbonyl)-1,8-diazaspiro[4.5]decane-8-carboxylate | | δ 8.36 (d, J = 5.2 Hz, 1H), 6.84 (d, J = 5.2 Hz, 1H), 5.83-5.68 (m, 1H), 4.30-4.11 (m, 2H), 3.98 (s, 3H), 3.42-3.28 (m, 2H), 3.20-2.89 (m, 4H), 2.08-1.87 (m, 2H), 1.85-1.70 (m, 2H), 1.70-1.55 (m, 2H), 1.51-1.32 (m, 4H) | 511 |
| 201 | 1,1,1,3,3,3-Hexafluoropropan-2-yl 1-(1-(2-cyclopropylpyrimidin-4-yl)cyclopropane-1-carbonyl)-1,8-diazaspiro[4.5]decane-8-carboxylate | | δ 8.40 (d, J = 5.3 Hz, 1H), 6.87 (d, J = 5.3 Hz, 1H), 5.84-5.69 (m, 1H), 4.31-4.11 (m, 2H), 3.40-3.22 (m, 2H), 3.20-2.87 (m, 4H), 2.25-2.10 (m, 1H), 2.08-1.85 (m, 2H), 1.83-1.69 (m, 2H), 1.60-1.32 (m, 6H), 1.17-0.95 (m, 4H) | 521 |
| 202 | 1,1,1,3,3,3-Hexafluoropropan-2-yl 1-(1-(4-(trifluoromethyl)pyrimidin-2-yl)cyclopropane-1-carbonyl)-1,8-diazaspiro[4.5]decane-8-carboxylate | | δ 8.85 (d, J = 5.1 Hz, 1H), 7.45 (d, J = 5.1 Hz, 1H), 5.85-5.67 (m, 1H), 4.30-4.10 (m, 2H), 3.45-3.25 (m, 2H), 3.25-2.90 (m, 4H), 2.10-1.85 (m, 2H), 1.80-1.40 (m, 8H) | 549 |

| Ex | Name | Structure | NMR (¹H NMR, 300 MHz or 400 MHz, chloroform-d) | MS [M + H]⁺ |
|---|---|---|---|---|
| 203 | 1,1,1,3,3,3-Hexafluoropropan-2-yl 1-(1-(4-methoxypyrimidin-2-yl)cyclopropane-1-carbonyl)-1,8-diazaspiro[4.5]decane-8-carboxylate | | δ 8.25 (d, J = 6.0 Hz, 1H), 7.50 (d, J = 6.0 Hz, 1H), 5.85-5.67 (m, 1H), 4.30-4.10 (m, 2H), 3.95 (s, 3H), 3.45-3.25 (m, 2H), 3.25-2.90 (m, 4H), 2.10-1.85 (m, 2H), 1.80-1.40 (m, 8H) | 511 |
| 204 | 1,1,1,3,3,3-Hexafluoropropan-2-yl 4-(7-cyclopropyl-5,6,7,8-tetrahydro-[1,2,4]triazolo[4,3-a]pyrazine-3-carboxamido)-4-methylpiperidine-1-carboxylate | | (Methanol-d₄) δ 6.28-6.06 (m, 1H), 4.35 (t, J = 5.6 Hz, 2H), 3.99 (s, 2H), 3.93-3.74 (m, 2H), 3.53-3.34 (m, 2H), 3.10 (t, J = 5.7 Hz, 2H), 2.48-2.27 (m, 2H), 2.05-1.89 (m, 1H), 1.76-1.55 (m, 2H), 1.49 (s, 3H), 0.69-0.58 (m, 2H), 0.58-0.43 (m, 2H) | 499 |
| 205 | 1,1,1,3,3,3-Hexafluoropropan-2-yl 4-(7-cyclobutyl-5,6,7,8-tetrahydro-[1,2,4]triazolo[4,3-a]pyrazine-3-carboxamido)-4-methylpiperidine-1-carboxylate | | (Methanol-d₄) δ 6.31-6.04 (m, 1H), 4.37 (t, J = 5.6 Hz, 2H), 3.96-3.79 (m, 2H), 3.73 (s, 2H), 3.50-3.32 (m, 2H), 3.17-3.02 (m, 1H), 2.82 (t, J = 5.6 Hz, 2H), 2.47-2.28 (m, 2H), 2.25-2.08 (m, 2H), 2.06-1.88 (m, 2H), 1.88-1.73 (m, 2H), 1.73-1.56 (m, 2H), 1.50 (s, 3H) | 513 |
| 206 | 1,1,1,3,3-Hexafluoropropan-2-yl 4-(7-(2-hydroxy-2-methylpropyl)-5,6,7,8-tetrahydro-[1,2,4]triazolo[4,3-a]pyrazine-3-carboxamido)-4-methylpiperidine-1-carboxylate | | (Methanol-d₄) δ 6.22-6.02 (m, 1H), 4.40 (t, J = 5.5 Hz, 2H), 4.01 (s, 2H), 3.95-3.78 (m, 2H), 3.51-3.33 (m, 2H), 3.08 (t, J = 5.6 Hz, 2H), 2.56 (s, 2H), 2.49-2.29 (m, 2H), 1.80-1.59 (m, 2H), 1.50 (s, 3H), 1.23 (s, 6H) | 531 |
| 207 | 1,1,1,3,3,3-Hexafluoropropan-2-yl 4-methyl-4-(7-(oxetan-3-yl)-5,6,7,8-tetrahydro-[1,2,4]triazolo[4,3-a]pyrazine-3-carboxamido)piperidine-1-carboxylate | | (Methanol-d₄) δ 6.23-6.01 (m, 1H), 4.79 (t, J = 6.7 Hz, 2H), 4.65 (t, J = 6.0 Hz, 2H), 4.38 (t, J = 5.5 Hz, 2H), 3.98-3.71 (m, 5H), 3.48-3.32 (m, 2H), 2.86 (t, J = 5.6 Hz, 2H), 2.45-2.27 (m, 2H), 1.77-1.55 (m, 2H), 1.50 (s, 3H) | 515 |
| 208 | 1,1,1,3,3,3-Hexafluoropropan-2-yl 4-methyl-4-(7-(THF-3-yl)-5,6,7,8-tetrahydro-[1,2,4]triazolo[4,3-a]pyrazine-3-carboxamido)piperidine-1-carboxylate | | (Methanol-d₄) δ 6.28-6.03 (m, 1H), 4.37 (t, J = 5.5 Hz, 2H), 4.08-3.65 (m, 8H), 3.49-3.32 (m, 3H), 3.09-2.87 (m, 2H), 2.49-2.27 (m, 2H), 2.27-2.10 (m, 1H), 2.08-1.89 (m, 1H), 1.78-1.57 (m, 2H), 1.49 (s, 3H) | 529 |

-continued

| Ex | Name | Structure | NMR (¹H NMR, 300 MHz or 400 MHz, chloroform-d) | MS [M + H]⁺ |
|---|---|---|---|---|
| 209 | 1,1,1,3,3,3-Hexafluoropropan-2-yl 4-methyl-4-(7-(tetrahydro-2H-pyran-4-yl)-5,6,7,8-tetrahydro-[1,2,4]triazolo[4,3-a]pyrazine-3-carboxamido)piperidine-1-carboxylate | | (Methanol-d₄) δ 6.27-6.08 (m, 1H), 4.35 (t, J = 5.4 Hz, 2H), 4.18-3.95 (m, 4H), 3.92-3.72 (m, 2H), 3.54-3.34 (m, 4H), 3.01 (t, J = 5.6 Hz, 2H), 2.90-2.68 (m, 1H), 2.48-2.30 (m, 2H), 2.00-1.81 (m, 2H), 1.75-1.55 (m, 4H), 1.50 (s, 3H) | 543 |
| 210 | 1,1,1,3,3,3-Hexafluoropropan-2-yl 4-methyl-4-(N-methyl-5,6,7,8-tetrahydro-[1,2,4]triazolo[4,3-a]pyrazine-3-carboxamido)piperidine-1-carboxylate | | (Methanol-d₄) δ 6.30-6.12 (m, 1H), 4.31-4.10 (m, 4H), 3.90-3.70 (m, 2H), 3.53-3.38 (m, 2H), 3.27-3.18 (m, 2H), 3.11 (s, 3H), 2.83-2.55 (m, 2H), 1.95-1.69 (m, 2H), 1.49 (s, 3H) | 473 |
| 211 | 1,1,1,3,3,3-Hexafluoropropan-2-yl 4-methyl-4-(5,6,7,8-tetrahydro-[1,2,4]triazolo[4,3-a]pyrazine-3-carboxamido)piperidine-1-carboxylate | | (Methanol-d₄) 6.24-6.08 (m, 1H), 4.33 (t, J = 5.6 Hz, 2H), 4.15 (s, 2H), 3.96-3.73 (m, 2H), 3.49-3.34 (m, 2H), 3.20 (t, J = 5.7 Hz, 2H), 2.49-2.25 (m, 2H), 1.78-1.56 (m, 2H), 1.50 (s, 3H) | 459 |
| 212 | 1,1,1,3,3,3-hexafluoropropan-2-yl 4-(N-(2-methoxyethyl)-1-(pyrimidin-2-yl)cyclopropane-1-carboxamido)-4-methylpiperidine-1-carboxylate | | δ 8.51-8.62 (d, J = 4.8 Hz, 2H), 7.03-7.13 (t, J = 9.7 Hz, 1H), 5.70-5.87 (m, 1H), 3.37-3.73 (m, 8H), 3.27 (s, 3H), 2.46-2.68 (m, 2H), 1.75-1.91 (m, 2H), 1.57-1.70 (m, 4H), 1.49 (s, 3H) | 535 |
| 213 | 1,1,1,3,3,3-Hexafluoropropan-2-yl 2-((3-(t-butyl)-1-(tetrahydro-2H-pyran-4-yl)-1H-pyrazol-5-yl)methyl)-2,8-diazaspiro[4.5]decane-8-carboxylate | | δ 5.88 (s, 1H), 5.72-5.80 (m, 1H), 4.35-4.43 (m, 1H), 4.09-4.14 (m, 2H), 3.42-3.56 (m, 8H), 2.66-2.70 (m, 2H), 2.35-2.48 (m, 4H), 1.75-1.80 (m, 2H), 1.52-1.70 (m, 6H), 1.38 (s, 9H) | 555 |

| Ex | Name | Structure | NMR (¹H NMR, 300 MHz or 400 MHz, chloroform-d) | MS [M + H]⁺ |
|---|---|---|---|---|
| 214 | 1,1,1,3,3,3-Hexafluoropropan-2-yl 2-((3-isopropyl-1-(tetrahydro-2H-pyran-4-yl)-1H-pyrazol-5-yl)methyl)-2,8-diazaspiro[4.5]decane-8-carboxylate | | δ 5.88 (s, 1H), 5.71-5.79 (m, 1H), 4.34-4.44 (m, 1H), 4.08-4.13 (m, 2H), 3.34-3.61 (m, 8H), 2.90-2.99 (m, 1H), 2.55-2.60 (m, 2H), 2.26-2.38 (m, 4H), 1.76-1.80 (m, 2H), 1.50-1.69 (m, 6H), 1.22 (d, J = 6.8 Hz, 6H) | 541 |
| 215 | 1,1,1,3,3,3-Hexafluoropropan-2-yl 2-((1-(2-chlorophenyl)-3-ethyl-1H-pyrazol-5-yl)methyl)-2,8-diazaspiro[4.5]decane-8-carboxylate | | δ 7.46-7.51 (m, 1H), 7.31-7.42 (m, 3H), 6.16 (s, 1H), 5.70-5.81 (m, 1H), 3.35-3.46 (m, 6H), 2.67-2.74 (m, 2H), 2.48-2.52 (m, 2H), 2.29 (s, 2H), 1.46-1.58 (m, 6H), 1.27-1.32 (m, 3H) | 553 |
| 216 | 1,1,1,3,3,3-Hexafluoropropan-2-yl 2-((1-(2-chlorophenyl)-3-isopropyl-1H-pyrazol-5-yl)methyl)-2,8-diazaspiro[4.5]decane-8-carboxylate | | δ 7.47-7.50 (m, 1H), 7.30-7.43 (m, 3H), 6.16 (s, 1H), 5.70-5.78 (m, 1H), 3.35-3.46 (m, 6H), 2.98-3.08 (m, 1H), 2.49-2.53 (m, 2H), 2.29 (s, 2H), 1.47-1.59 (m, 6H), 1.30 (d, J = 6.9 Hz, 6H) | 567 |
| 217 | 1,1,1,3,3,3-Hexafluoropropan-2-yl 2-((3-(t-butyl)-1-(2-chlorophenyl)-1H-pyrazol-5-yl)methyl)-2,8-diazaspiro[4.5]decane-8-carboxylate | | δ 7.32-7.49 (m, 4H), 6.18 (s, 1H), 5.72-5.76 (m, 1H), 3.42-3.44 (m, 6H), 2.48-2.52 (m, 2H), 2.28 (s, 2H), 1.54-1.58 (m, 2H), 1.44-1.50 (m, 4H), 1.33 (s, 9H) | 581 |
| 218 | 1,1,1,3,3,3-Hexafluoropropan-2-yl 2-((3-(3-chlorophenyl)-1-isopropyl-1H-pyrazol-4-yl)methyl)-2,8-diazaspiro[4.5]decane-8-carboxylate | | δ 8.05 (s, 1H), 7.73-7.76 (m, 1H), 7.26-7.36 (m, 3H), 5.70-5.79 (m, 1H), 4.46-4.55 (m, 1H), 3.40-3.56 (m, 6H), 2.61 (t, J = 6.9 Hz, 2H), 2.44 (s, 2H), 1.60-1.69 (m, 6H), 1.53 (d, J = 6.9 Hz, 6H) | 567 |

-continued

| Ex | Name | Structure | NMR (¹H NMR, 300 MHz or 400 MHz, chloroform-d) | MS [M + H]⁺ |
|---|---|---|---|---|
| 219 | | | 1,1,1,3,3,3-Hexafluoropropan-2-yl 1-((3-(3-chlorophenyl)-1-isopropyl-1H-pyrazol-4-yl)methyl)-1,8-diazaspiro[4.5]decane-8-carboxylate | δ 7.96 (s, 1H), 7.65-7.70 (m, 1H), 7.25-7.33 (m, 2H), 5.71-5.79 (m, 1H), 4.45-4.54 (m, 1H), 4.14-4.24 (m, 2H), 3.54 (s, 2H), 2.91-3.05 (m, 2H), 2.70 (t, J = 6.8 Hz, 2H), 1.71-1.88 (m, 6H), 1.51-1.59 (m, 8H) | 567 |
| 220 | | | 1,1,1,3,3,3-Hexafluoropropan-2-yl 1-((3-(3,5-dichlorophenyl)-1-isopropyl-1H-pyrazol-4-yl)methyl)-1,8-diazaspiro[4.5]decane-8-carboxylate | δ 7.89 (d, J = 2.1 Hz, 2H), 7.27-7.41 (m, 2H), 5.70-5.79 (m, 1H), 4.44-4.54 (m, 1H), 4.15-4.30 (m, 2H), 3.53 (s, 2H), 2.92-3.06 (m, 2H), 2.67-2.72 (m, 2H), 1.72-1.90 (m, 6H), 1.55-1.57 (m, 2H), 1.52 (d, J = 6.6 Hz, 6H) | 601 |
| 221 | | | 1,1,1,3,3,3-Hexafluoropropan-2-yl 1-((3-(2-fluorophenyl)-1-isopropyl-1H-pyrazol-4-yl)methyl)-1,8-diazaspiro[4.5]decane-8-carboxylate | δ 7.51-7.54 (m, 1H), 7.49 (s, 1H), 7.28-7.40 (m, 1H), 7.07-7.18 (m, 2H), 5.71-5.79 (m, 1H), 4.47-4.56 (m, 1H), 4.08-4.17 (m, 2H), 3.42-3.52 (m, 2H), 2.84-2.98 (m, 2H), 2.59-2.63 (m, 2H), 1.58-1.75 (m, 6H), 1.53 (d, J = 6.6 Hz, 6H), 1.21-1.38 (m, 2H) | 551 |
| 222 | | | 1,1,1,3,3,3-Hexafluoropropan-2-yl 1-((3-(2-chlorophenyl)-1-isopropyl-1H-pyrazol-4-yl)methyl)-1,8-diazaspiro[4.5]decane-8-carboxylate | δ 7.35-7.44 (m, 3H), 7.28-7.31 (m, 1H), 7.23-7.25 (m, 1H), 5.70-5.78 (m, 1H), 4.46-4.54 (m, 1H), 4.04-4.13 (m, 2H), 3.35-3.44 (m, 2H), 2.81-2.95 (m, 2H), 2.57-2.61 (m, 2H), 1.59-1.72 (m, 6H), 1.54 (d, J = 6.9 Hz, 6H), 1.12-1.30 (m, 2H) | 567 |
| 223 | | | 1,1,1,3,3,3-Hexafluoropropan-2-yl 1-(benzo[b]thiophen-2-ylmethyl)-1,8-diazaspiro[4.5]decane-8-carboxylate | δ 7.86-7.76 (m, 1H), 7.72-7.67 (m, 1H), 7.36-7.26 (m, 2H), 7.16 (s, 1H), 5.86-5.74 (m, 1H), 4.34-4.18 (m, 2H), 3.97-3.85 (m, 2H), 3.01 (dtd, J = 22.8, 13.1, 2.8 Hz, 2H), 2.84 (dq, J = 10.2, 4.4, 4.0 Hz, 2H), 1.97-1.79 (m, 4H), 1.79-1.70 (m, 2H), 1.61-1.49 (m, 2H) | 481 |

-continued

| Ex | Name | Structure | NMR (¹H NMR, 300 MHz or 400 MHz, chloroform-d) | MS [M + H]⁺ |
|---|---|---|---|---|
| 224 | 1,1,1,3,3,3-Hexafluoropropan-2-yl 1-((5-chloro-1H-indol-2-yl)methyl)-1,8-diazaspiro[4.5]decane-8-carboxylate | | δ 8.47 (s, 1H), 7.42 (s, 1H), 7.20-7.16 (m, 1H), 7.05-6.97 (m, 1H), 6.19 (s, 1H), 5.73-5.63 (m, 1H), 4.25-4.07 (m, 2H), 3.71 (s, 2H), 3.00-2.84 (m, 2H), 2.72-2.58 (m, 2H), 1.84-1.72 (m, 4H), 1.69-1.61 (m, 2H), 1.49-1.40 (m, 2H) | 498 |
| 225 | 1,1,1,3,3,3-Hexafluoropropan-2-yl 1-(thiazol-5-ylmethyl)-1,8-diazaspiro[4.5]decane-8-carboxylate | | δ 8.73 (s, 1H), 7.71 (s, 1H), 5.85-5.72 (m, 1H), 4.30-4.16 (m, 2H), 3.84 (s, 2H), 3.07-2.90 (m, 2H), 2.80-2.69 (m, 2H), 1.92-1.76 (m, 4H), 1.74-1.65 (m, 2H), 1.55-1.45 (m, 2H) | 432 |
| 226 | 1,1,1,3,3,3-Hexafluoropropan-2-yl 1-((2-(pyrrolidin-1-yl)thiazol-5-yl)methyl)-1,8-diazaspiro[4.5]decane-8-carboxylate | | δ 6.96 (s, 1H), 5.82-5.71 (m, 1H), 4.26-4.13 (m, 2H), 3.64 (s, 2H), 3.48-3.38 (m, 4H), 3.05-2.89 (m, 2H), 2.83-2.73 (m, 2H), 2.08-2.00 (m, 4H), 1.84-1.75 (m, 4H), 1.75-1.64 (m, 2H), 1.49-1.41 (m, 2H) | 501 |
| 227 | 1,1,1,3,3,3-Hexafluoropropan-2-yl 1-((2-phenylthiazol-4-yl)methyl)-1,8-diazaspiro[4.5]decane-8-carboxylate | | δ 7.84 (dt, J = 7.3, 1.8 Hz, 2H), 7.33 (ddt, J = 6.8, 4.8, 2.6 Hz, 3H), 7.06 (s, 1H), 5.69 (dtt, J = 12.6, 6.3, 3.1 Hz, 1H), 4.22-4.04 (m, 2H), 3.76 (s, 2H), 3.02-2.80 (m, 4H), 1.85-1.59 (m, 6H), 1.43 (dd, J = 11.6, 5.4 Hz, 2H) | 508 |
| 228 | 1,1,1,3,3,3-Hexafluoropropan-2-yl 1-(imidazo[1,2-a]pyridin-3-ylmethyl)-1,8-diazaspiro[4.5]decane-8-carboxylate | | δ 8.24-8.16 (m, 1H), 7.64-7.55 (m, 1H), 7.43 (s, 1H), 7.18-7.11 (m, 1H), 6.78-6.69 (m, 1H), 5.77-5.64 (m, 1H), 4.28-4.12 (m, 2H), 3.87 (s, 2H), 3.03-2.84 (m, 2H), 2.56-2.47 (m, 2H), 2.03 (s, 1H), 1.85-1.72 (m, 3H), 1.70-1.60 (m, 2H), 1.54-1.42 (m, 2H) | 465 |
| 229 | 1,1,1,3,3,3-Hexafluoropropan-2-yl 1-((6-chloroimidazo[1,2-a]pyridin-3-yl)methyl)-1,8-diazaspiro[4.5]decane-8-carboxylate | | δ 8.40-8.31 (m, 1H), 7.61-7.45 (m, 2H), 7.15 (s, 1H), 5.89-5.72 (m, 1H), 4.37-4.21 (m, 2H), 4.00-3.89 (m, 2H), 3.14-2.95 (m, 2H), 2.65-2.54 (m, 2H), 1.97-1.81 (m, 4H), 1.80-1.69 (m, 2H), 1.64-1.50 (m, 2H) | 499 |

II. Biological Evaluation

Compounds were tested to assess their MAGL activity using the following in vitro and in vivo assays.

In Vitro Competitive Activity-Based Protein Profiling.

Proteomes (human prefrontal cortex or cell membrane fractions) (50 μL, 1.0 mg/mL total protein concentration) were preincubated with varying concentrations of inhibitors at 37° C. After 30 min, FP-Rh or HT-01 (1.0 μL, 50 μM in DMSO) was added and the mixture was incubated for another 30 min at room temperature. Reactions were quenched with SDS loading buffer (15 μL—4×) and run on SDS-PAGE. Following gel imaging, serine hydrolase activity was determined by measuring fluorescent intensity of gel bands corresponding to MAGL using ImageJ 1.49 k software. $IC_{50}$ data from this assay is shown in Table 1.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | MAGL % Inhibition at 1 μM (human PC3) | MAGL % Inhibition at 1 μM (human PFC) | MAGL Human PC3 ($IC_{50}$, uM) | MAGL Human PFC ($IC_{50}$, uM) | MAGL % Inhibition at 5 mg/kg (Mouse) | MAGL % Inhibition at 1 uM (Mouse) | MAGL Mouse Brain ($IC_{50}$, uM) |
|---|---|---|---|---|---|---|---|
| 1 | ### | ### | ** | | ### | ### | |
| 2 | ### | ### | *** | *** | ### | ### | *** |
| 3 | ### | ### | *** | | | ### | |
| 4 | | ### | *** | | | ### | |
| 5 | | ### | *** | *** | ### | ### | |
| 6 | | | | | ## | ### | *** |
| 7 | | | | | ### | ### | *** |
| 8 | | | | | | ### | ** |
| 9 | | ### | | | | | |
| 10 | ### | | *** | | | ### | |
| 11 | | | | | ### | ### | *** |
| 12 | | # | | | | # | |
| 13 | | | | | | ### | |
| 14 | | | | | | ### | *** |
| 15 | | | | | | ## | |
| 16 | | | | | ### | ### | *** |
| 17 | | ### | | *** | | ### | |
| 18 | ### | ### | *** | | ### | ### | *** |
| 19 | | ### | | | | ### | |
| 20 | ### | ### | *** | | ### | ### | |
| 21 | ### | ### | *** | | # | ### | |
| 22 | ### | ### | *** | | | ### | |
| 23 | ### | ### | *** | | | ### | |
| 24 | ### | ### | ** | | | ### | |
| 25 | ### | | *** | | | ### | |
| 26 | ### | ### | | | | ## | |
| 27 | ### | | *** | | # | | |
| 28 | ### | | | | | ### | |
| 29 | ### | | | | | ### | |
| 30 | ### | ### | | | | ### | |
| 31 | ### | ### | *** | | ### | ### | |
| 32 | ### | ### | *** | | | | |
| 33 | ### | | | *** | | ### | |
| 34 | ### | ### | | | | ### | |
| 35 | ### | | | | | | |
| 36 | ### | ### | *** | | | ### | |
| 37 | ### | ### | *** | | # | ### | |
| 38 | ### | ### | *** | | ### | ### | |
| 39 | | | *** | | ### | ### | *** |
| 40 | | | *** | | ### | ### | *** |
| 41 | | | | | ### | ### | *** |
| 42 | | | | | ### | ### | *** |
| 43 | | | | | ### | | *** |
| 44 | | | | | | ### | ** |
| 45 | | | | | | | ** |
| 46 | | | | | ## | | *** |
| 47 | | | | | | ### | *** |
| 48 | | | *** | | ### | ### | *** |
| 49 | | | *** | | ### | ### | *** |
| 50 | | | | | | ### | ** |
| 51 | | | | | ### | ### | *** |
| 52 | | | | | ### | ### | *** |
| 53 | | | *** | | ### | ### | *** |
| 54 | | | | | ### | ### | *** |
| 55 | | | | | | ### | *** |
| 56 | | | *** | | ### | ### | *** |
| 57 | | | *** | | | ### | *** |

TABLE 1-continued

| Ex | MAGL % Inhibition at 1 μM (human PC3) | MAGL % Inhibition at 1 μM (human PFC) | MAGL Human PC3 (IC$_{50}$, uM) | MAGL Human PFC (IC$_{50}$, uM) | MAGL % Inhibition at 5 mg/kg (Mouse) | MAGL % Inhibition at 1 uM (Mouse) | MAGL Mouse Brain (IC$_{50}$, uM) |
|---|---|---|---|---|---|---|---|
| 58 | | | *** | | ### | ### | *** |
| 59 | | | | | ### | ### | *** |
| 60 | | | *** | | ### | ### | *** |
| 61 | | | | | ### | ### | *** |
| 62 | | | *** | | ### | ### | *** |
| 63 | | | *** | | ### | ### | *** |
| 64 | | | | | | ### | ** |
| 65 | | | | | | ### | |
| 66 | | | | | | ### | *** |
| 67 | | | | | | ### | ** |
| 68 | | ## | | | | # | |
| 69 | | | *** | | | ### | *** |
| 70 | | | | | | ### | ** |
| 71 | | | *** | | | ### | *** |
| 72 | | | | | | ### | *** |
| 73 | | | | | | ### | ** |
| 74 | | | | | | ### | *** |
| 75 | | | *** | | | ### | *** |
| 76 | | | | | | ### | *** |
| 77 | | | | | ### | ### | *** |
| 78 | | | | | | ### | *** |
| 79 | | | *** | | | ### | ** |
| 80 | | | | | | ### | *** |
| 81 | | | | | | ### | *** |
| 82 | | | | | | ### | *** |
| 83 | | | | | | ### | *** |
| 84 | | | | | | ### | *** |
| 85 | | | *** | | | ### | ** |
| 86 | | | *** | | | ### | *** |
| 87 | | | *** | | | ### | *** |
| 88 | | | *** | | | ### | *** |
| 89 | | | | | | ### | *** |
| 90 | | | | | | ### | *** |
| 91 | | | *** | | | ### | *** |
| 92 | | | *** | | | ### | *** |
| 93 | | | | | ### | ### | *** |
| 94 | | | | | | ### | *** |
| 95 | | | | | | ### | *** |
| 96 | | | *** | *** | | ### | *** |
| 97 | | | | | | ### | |
| 98 | | | | | | ### | *** |
| 99 | | | | | | ### | *** |
| 100 | | | | | | ### | |
| 101 | | | | | ### | ### | *** |
| 102 | | | | | ### | ### | *** |
| 103 | | | | | ### | ### | *** |
| 104 | | | *** | | | ### | *** |
| 105 | | | | | ### | ### | *** |
| 106 | | ### | | | | | |
| 107 | | | | | | ### | *** |
| 108 | | | | | | ### | *** |
| 109 | | | | | ### | ### | *** |
| 110 | | | | *** | | ### | *** |
| 111 | | | | | | ### | *** |
| 112 | | ### | | *** | | ### | |
| 113 | | ## | | | | ## | |
| 114 | | ### | ** | | | ### | |
| 115 | | ### | *** | | | ### | |
| 116 | | ### | | | | ### | |
| 117 | | ### | *** | | | ### | |
| 118 | | ### | *** | | | ### | |
| 119 | | ### | *** | *** | | ### | |
| 120 | | ### | *** | | ### | ### | |
| 121 | | ### | | *** | | ### | |
| 122 | | ### | ** | | | ### | |
| 123 | | ### | *** | | ### | ### | |
| 124 | | ## | | | | ### | |
| 125 | | ### | *** | | | ### | |
| 126 | | ### | ** | | | ### | |
| 127 | | ## | | | | # | |
| 128 | | ### | *** | | | ### | |
| 129 | | ### | ** | | | ### | |
| 130 | | ### | ** | | | ## | |
| 131 | | ### | *** | | | ### | |

TABLE 1-continued

| Ex | MAGL % Inhibition at 1 μM (human PC3) | MAGL % Inhibition at 1 μM (human PFC) | MAGL Human PC3 (IC$_{50}$, uM) | MAGL Human PFC (IC$_{50}$, uM) | MAGL % Inhibition at 5 mg/kg (Mouse) | MAGL % Inhibition at 1 uM (Mouse) | MAGL Mouse Brain (IC$_{50}$, uM) |
|---|---|---|---|---|---|---|---|
| 132 |  | ### | *** |  |  | ### |  |
| 133 |  | ### | *** |  |  | ### |  |
| 134 |  | ### | *** |  |  | ### |  |
| 135 | ## | ### | ** |  |  | ## |  |
| 136 |  | ## |  |  |  | # |  |
| 137 |  | ### | ** |  |  | # |  |
| 138 |  | ### | *** |  |  | ### |  |
| 139 |  | ### | *** |  |  | ### |  |
| 140 |  | ### | ** |  |  | ### |  |
| 141 |  | ### | ** |  |  | ### |  |
| 142 | ### | ### | *** |  | ### | ### |  |
| 143 | ### | ### | *** |  | ### | ### |  |
| 144 | ### | ### | ** |  |  | ### |  |
| 145 | ### | ### | *** |  |  | ### |  |
| 146 | ### | ### |  |  |  | ### |  |
| 147 | ### | ### | *** |  |  | ### |  |
| 148 | ### | ### | *** |  | ### | ### |  |
| 149 | ### | ### | *** |  |  | ### |  |
| 150 | ### | ### | ** |  | ### | ### |  |
| 151 | ### | ### |  |  | ## | ### |  |
| 152 |  |  | *** |  |  |  |  |
| 153 |  |  | *** |  |  |  |  |
| 154 | ### | ### | *** |  | ### | ### |  |
| 155 | ### | ### | *** |  | ### | ### |  |
| 156 | ### | ### | *** |  |  | ### |  |
| 157 | ### | ### |  |  |  | ### |  |
| 158 | ### | ### |  |  |  | ## |  |
| 159 |  | ### | *** |  |  | ### |  |
| 160 |  | ### | ** |  |  | # |  |
| 161 | ### |  | *** |  | ## | ### |  |
| 162 | ### |  | *** |  |  | ### |  |
| 163 | ### |  |  |  |  | ### |  |
| 164 | ### | ### |  |  |  | ### |  |
| 165 | ### | ### |  |  |  | ### |  |
| 166 | ### | ### |  |  |  | ### |  |
| 167 | ### | ### |  |  |  | ### |  |
| 168 | ### | ### | *** |  |  | ### |  |
| 169 | ### | ### | *** |  | # | ### |  |
| 170 | ### | ### | *** |  | # | ### |  |
| 171 | ### | ### | *** |  |  | ### |  |
| 172 | ### | ### | *** |  |  | ### |  |
| 173 |  | ### |  |  |  | # |  |
| 174 | ### | ### | *** |  | ### | ### |  |
| 175 | ### | ### |  |  |  | ## |  |
| 176 | ### | ### | *** |  | # | ### |  |
| 177 | ### | ### |  |  |  | ### |  |
| 178 | ### | ### |  |  |  | ### |  |
| 179 | ### | ### | *** |  | ## | ### |  |
| 180 | ### | ### | *** |  | ### | ### |  |
| 181 | ### |  | ** |  | ### | ### | ** |
| 182 | ### | ### | *** |  | ### |  |  |
| 183 | ### | ### | *** |  |  |  |  |
| 184 | ### |  | ** |  |  | ### |  |
| 185 | ### |  | ** |  |  | ### |  |
| 186 | ### | ### | ** |  | ### | ### | ** |
| 187 | ### | ### | ** |  |  | ### |  |
| 188 | ### | ### | ** |  |  | ### |  |
| 189 | ### | ### | ** |  |  | ### |  |
| 190 | ### |  | *** |  | # | ### |  |
| 191 | ### |  | *** |  | # | ### |  |
| 192 | ### |  | *** |  |  | ### |  |
| 193 | ### |  | *** |  |  | ### |  |
| 194 | ### | ### | *** |  | ### | ### |  |
| 195 | ### | ### |  |  |  | # |  |
| 196 | ### | ### |  |  |  | ### |  |
| 197 | ### | ### |  |  |  |  |  |
| 198 | ### | ### |  |  |  | ### |  |
| 199 | ### | ### |  | *** |  | ### |  |
| 200 | ### | ### | *** |  | ### | ### |  |
| 201 | ### | ### | *** |  |  | ### |  |
| 202 | ### | ### | *** |  |  | ### |  |
| 203 | ### | ### | *** |  |  | ### |  |
| 204 | ### | ### | *** |  | ### | ### |  |
| 205 | ### | ### | *** |  |  | ### |  |

TABLE 1-continued

| Ex | MAGL % Inhibition at 1 µM (human PC3) | MAGL % Inhibition at 1 µM (human PFC) | MAGL Human PC3 (IC$_{50}$, uM) | MAGL Human PFC (IC$_{50}$, uM) | MAGL % Inhibition at 5 mg/kg (Mouse) | MAGL % Inhibition at 1 uM (Mouse) | MAGL Mouse Brain (IC$_{50}$, uM) |
|---|---|---|---|---|---|---|---|
| 206 | ### | ### | *** | | ### | ### | |
| 207 | ### | ### | *** | | ### | ### | |
| 208 | ### | ### | *** | | ### | ### | |
| 209 | ### | ### | *** | | ### | ### | |
| 210 | ## | ### | | | | ## | |
| 211 | ### | ### | ** | | | ## | |
| 212 | ### | ### | *** | | | ### | |
| 213 | | | | | ### | ### | *** |
| 214 | | | | | ### | ### | *** |
| 215 | | | | | ### | ### | *** |
| 216 | | | | | ### | ### | *** |
| 217 | | | | | | ### | *** |
| 218 | | | | | ### | ### | *** |
| 219 | | | | | ### | ### | *** |
| 220 | | | | | | ### | |
| 221 | | | *** | | ### | ### | *** |
| 222 | | | | | ### | ### | *** |
| 223 | | | | | ### | ### | *** |
| 224 | | | | | | ### | *** |
| 225 | | | | | | ### | |
| 226 | | | *** | | ### | ### | *** |
| 227 | | | | | ### | ### | *** |
| 228 | | | *** | | ### | ### | *** |
| 229 | | | *** | | ### | ### | *** |

* IC$_{50}$ is less than or equal to 100 nM;  IC$_{50}$ is greater than 100 nM and less than 1 µM; * IC$_{50}$ is greater than or equal to 1 µM and less or equal to 10 µM.
### is % inhibition is greater than or equal to 75%; ## is % inhibition is less than 75% and greater than 25%; # is % inhibition less or equal to 25%.

What is claimed is:

1. A compound having the structure of Formula (II):

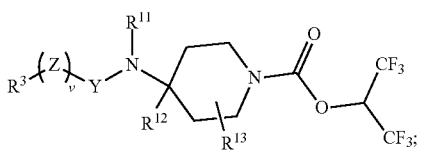

Formula (II)

wherein:
Y is —CH$_2$— or —C(O)—;
Z is C$_{3-6}$cycloalkyl;
R$^3$ is a 5- to 6-membered heteroaryl ring or a 9- to 10-membered bicyclic heteroaryl ring; wherein the 5- to 6-membered heteroaryl ring and the 9- to 10-membered bicyclic heteroaryl ring are optionally substituted with one, two, or three R$^4$;
each R$^4$ is independently selected from C$_{1-6}$alkyl, halogen, —CN, C$_{1-6}$haloalkyl, C$_{3-8}$cycloalkyl, C$_{2-9}$heterocycloalkyl, —C$_{1-6}$alkyl-(C$_{2-9}$heterocycloalkyl), phenyl, —CH$_2$-phenyl, C$_{1-9}$heteroaryl, —OR$^7$, —CO$_2$R$^6$, and —CH$_2$CO$_2$R$^6$; wherein C$_{2-9}$heterocycloalkyl, —C$_{1-6}$alkyl(C$_{2-9}$heterocycloalkyl), phenyl, and C$_{1-9}$heteroaryl are optionally substituted with one or two R$^5$; or two adjacent R$^4$ form a 6-membered cycloalkyl or 6-membered heterocycloalkyl ring, wherein the cycloalkyl and heterocycloalkyl ring are optionally substituted with one or two R$^5$;
each R$^5$ is independently selected from halogen, C$_{1-6}$alkyl, C$_{1-6}$haloalkyl, C$_{1-6}$heteroalkyl, C$_{1-6}$alkoxy, C$_{3-8}$cycloalkyl, —C$_{1-6}$alkyl(C$_{3-8}$cycloalkyl), C$_{2-9}$heterocycloalkyl, —CO$_2$R$^6$, —CH$_2$CO$_2$R$^6$, and —C$_{1-6}$alkyl(C$_{2-9}$heterocycloalkyl) optionally substituted with C$_{1-6}$alkyl;

each R$^6$ is independently selected from H and C$_{1-6}$alkyl;
each R$^7$ is independently selected from H, C$_{1-6}$alkyl, C$_{1-6}$haloalkyl, and C$_{3-8}$cycloalkyl;
R$^{11}$ is H, C$_{1-6}$alkyl, or —C$_{1-6}$alkyl-O—C$_{1-6}$alkyl;
R$^{12}$ is C$_{1-6}$ alkyl;
R$^{13}$ is H or C$_{1-6}$alkyl; and
v is 0 or 1;
or a solvate, hydrate, tautomer, N-oxide, stereoisomer, or pharmaceutically acceptable salt thereof.

2. The compound of claim 1, or a solvate, hydrate, tautomer, N-oxide, stereoisomer, or pharmaceutically acceptable salt thereof, wherein R$^{13}$ is H.

3. The compound of claim 1, or a solvate, hydrate, tautomer, N-oxide, stereoisomer, or pharmaceutically acceptable salt thereof, wherein v is 0.

4. The compound of claim 1, wherein Y is —C(O)—.

5. The compound of claim 1, wherein R$^{11}$ is C$_{1-6}$alkyl.

6. The compound of claim 1, wherein R$^{12}$ is —CH$_3$.

7. The compound of claim 1, or a solvate, hydrate, tautomer, N-oxide, stereoisomer, or pharmaceutically acceptable salt thereof, wherein R$^3$ is selected from:

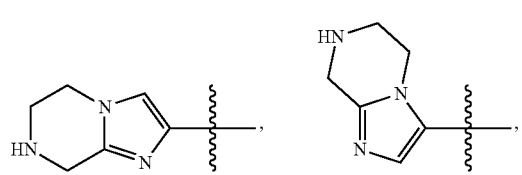

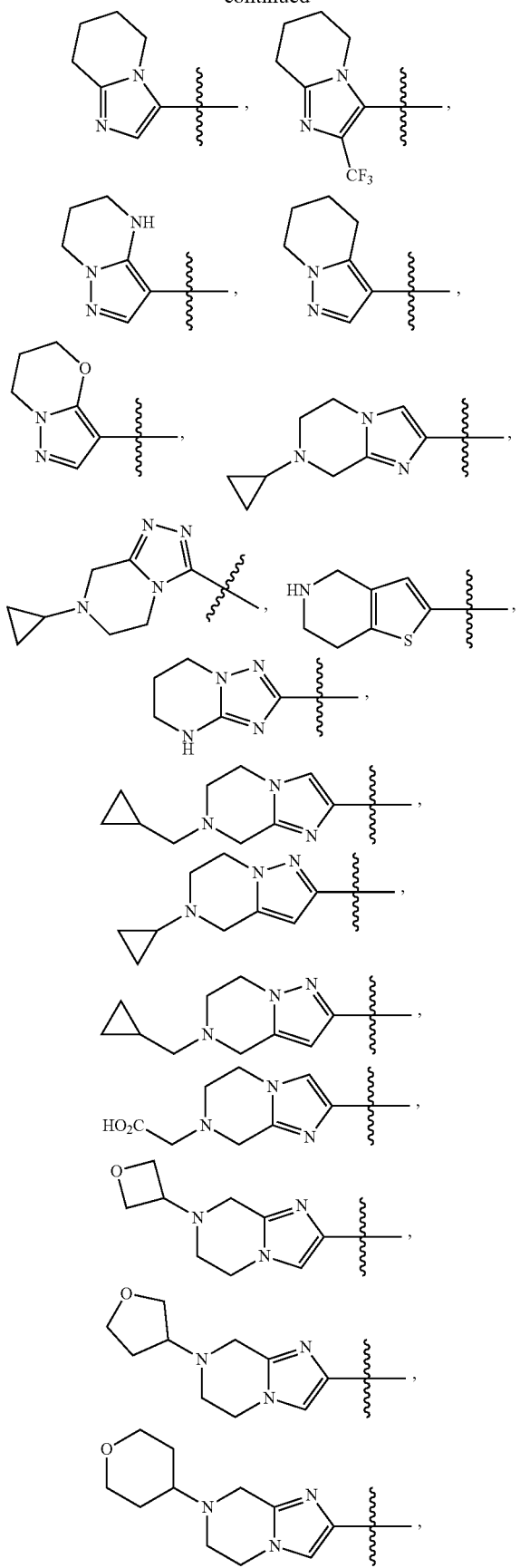

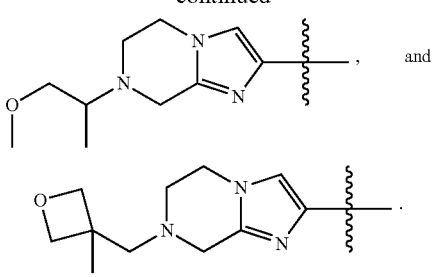

8. The compound of claim 1, or a solvate, hydrate, tautomer, N-oxide, stereoisomer, or pharmaceutically acceptable salt thereof, wherein $R^3$ is a 9- to 10-membered bicyclic heteroaryl ring optionally substituted with one, two, or three $R^4$.

9. The compound of claim 8, or a solvate, hydrate, tautomer, N-oxide, stereoisomer, or pharmaceutically acceptable salt thereof, wherein $R^3$ is a 9-membered bicyclic heteroaryl ring substituted with one, two, or three $R^4$.

10. The compound of claim 8, or a solvate, hydrate, tautomer, N-oxide, stereoisomer, or pharmaceutically acceptable salt thereof, wherein $R^3$ is a 9-membered bicyclic heteroaryl ring substituted with one or two $R^4$, wherein each $R^4$ is independently selected from halogen, $C_{1-6}$alkyl, and $C_{1-6}$haloalkyl.

11. The compound of claim 8, or a solvate, hydrate, tautomer, N-oxide, stereoisomer, or pharmaceutically acceptable salt thereof, wherein $R^3$ is an unsubstituted 9-membered bicyclic heteroaryl ring.

12. The compound of claim 8, or a solvate, hydrate, tautomer, N-oxide, stereoisomer, or pharmaceutically acceptable salt thereof, wherein $R^3$ is selected from:

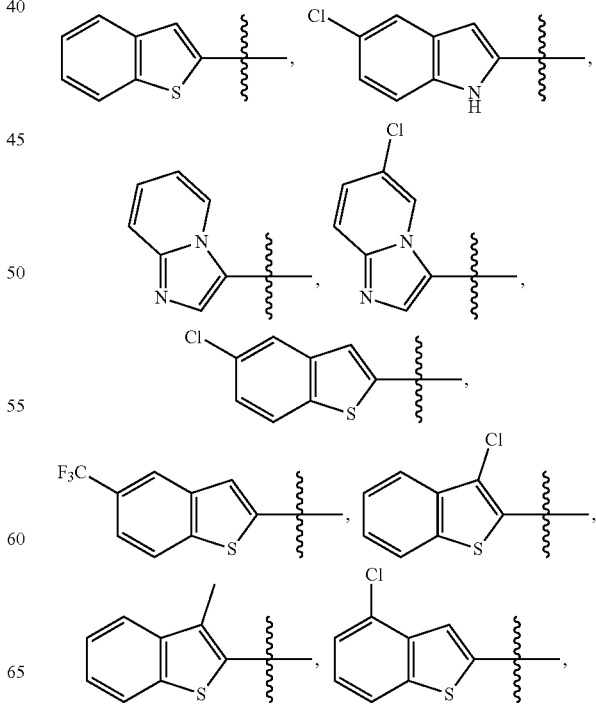

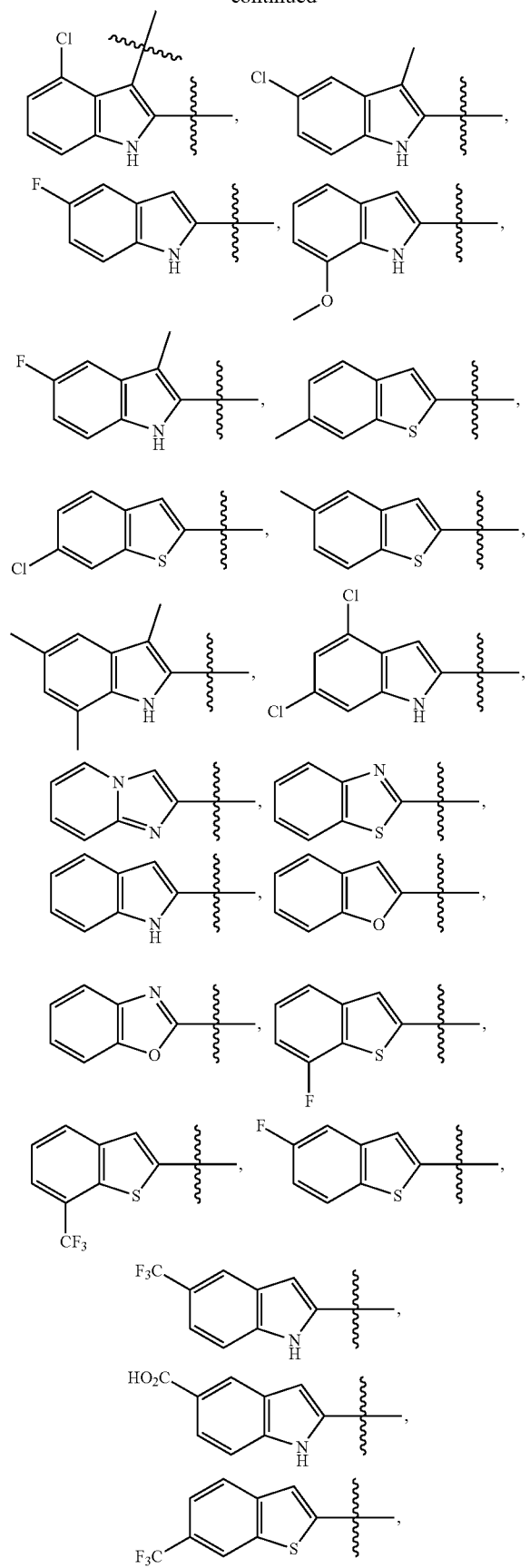
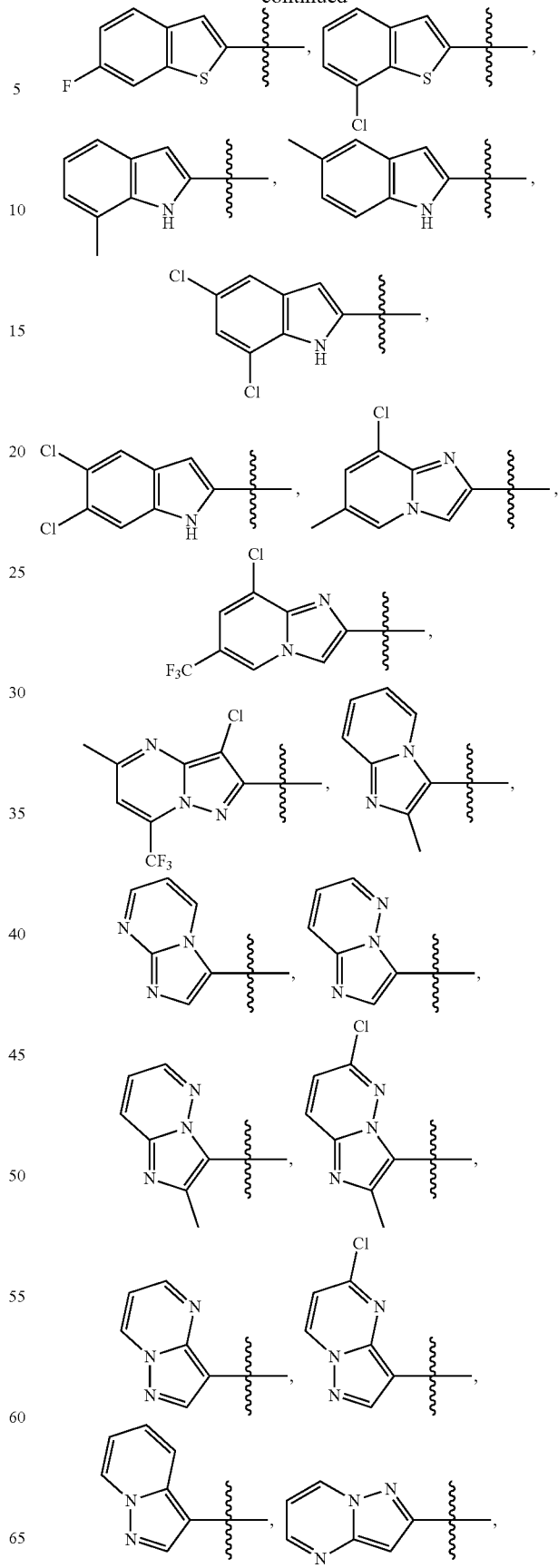

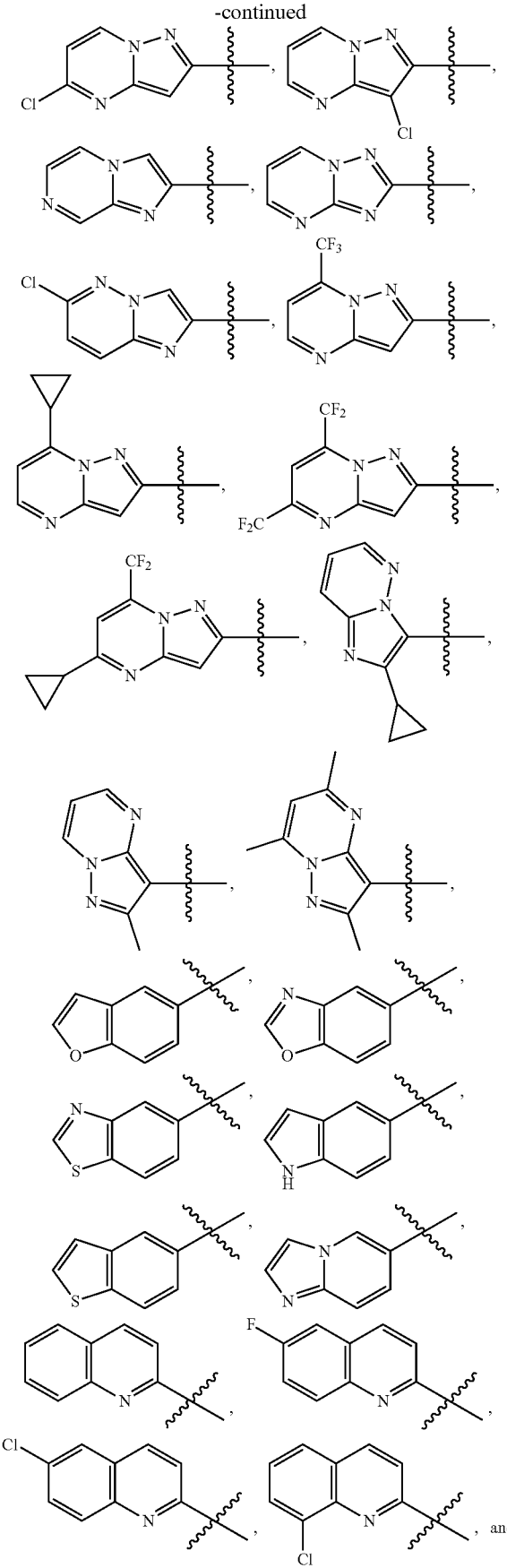
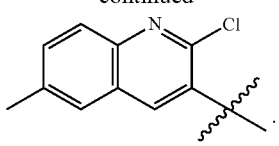
13. The compound of claim 1 selected from:
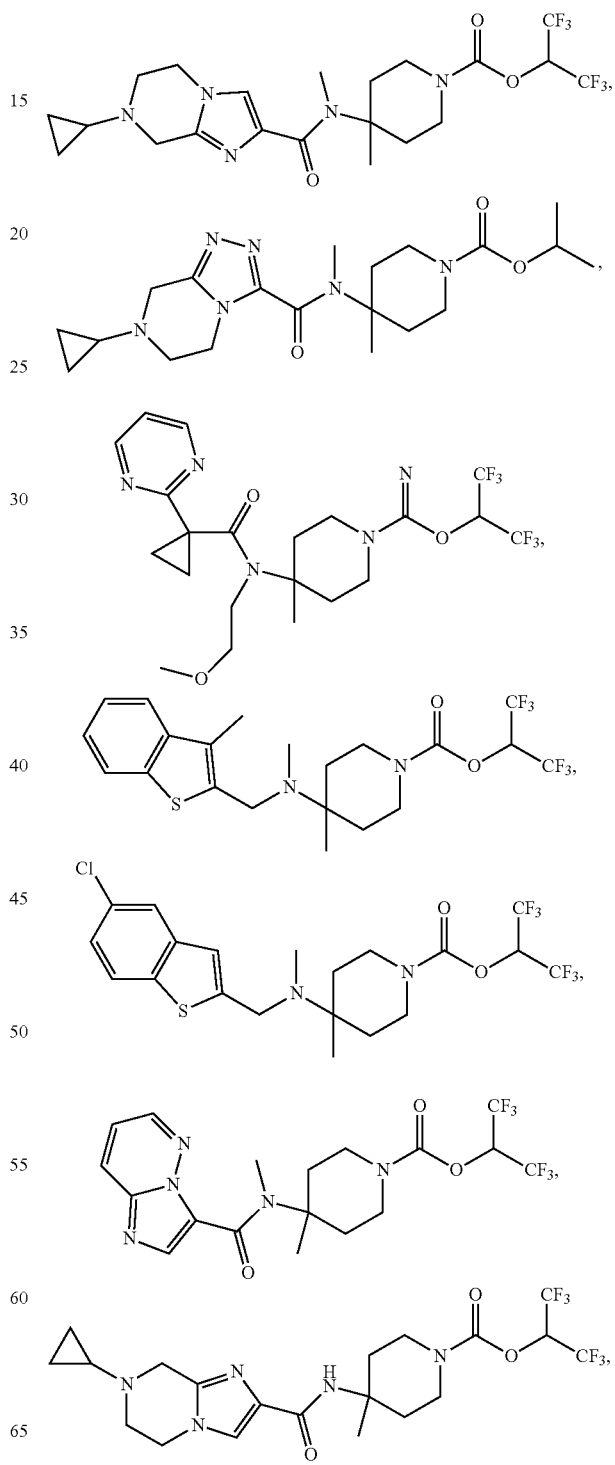

327
-continued
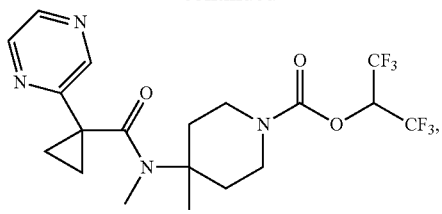 [SMILES: CN(C(=O)C1(c2cnccn2)CC1)C1(C)CCN(C(=O)OC(C(F)(F)F)C(F)(F)F)CC1]
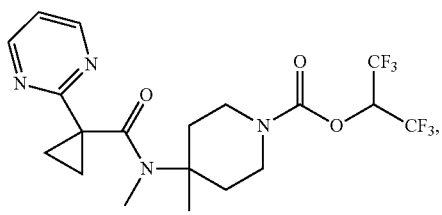
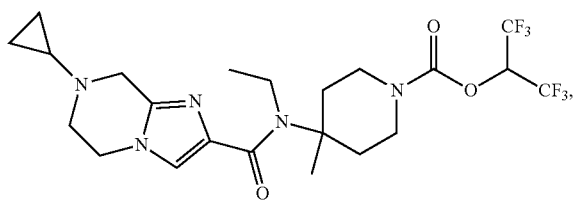
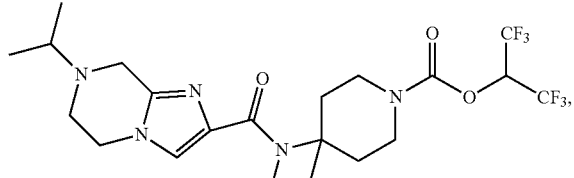
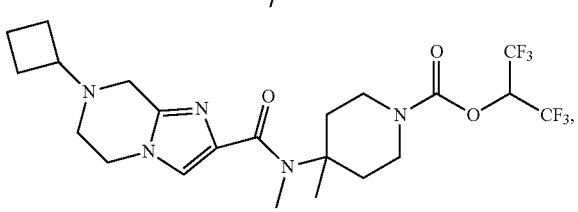
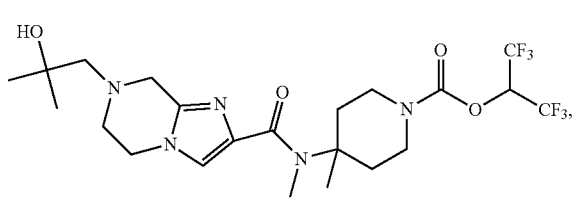
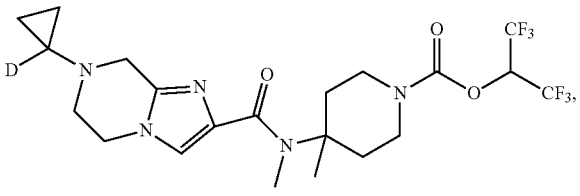
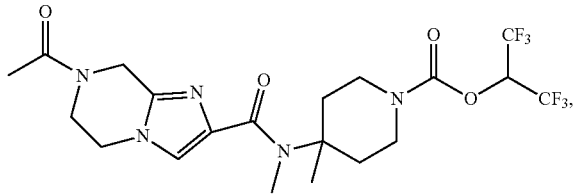
328
-continued
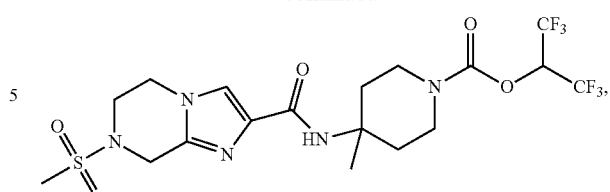
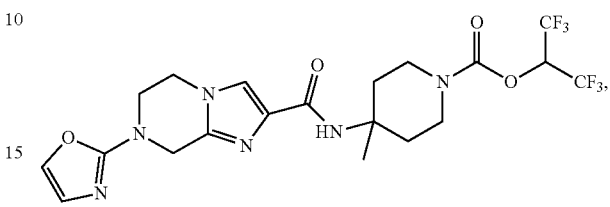
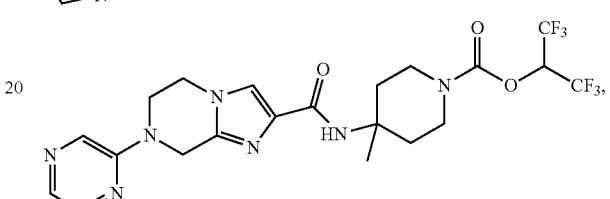
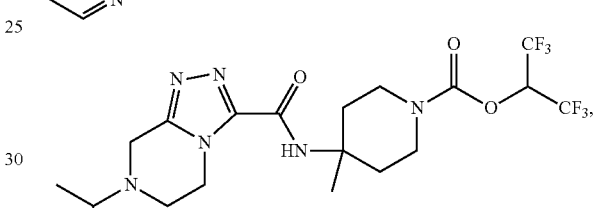
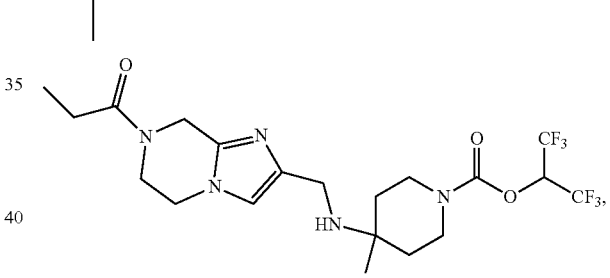
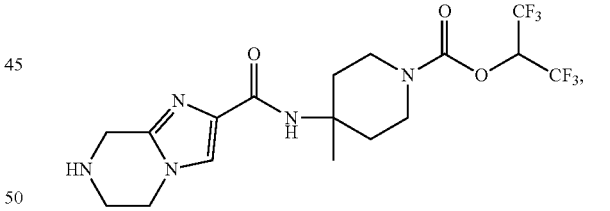
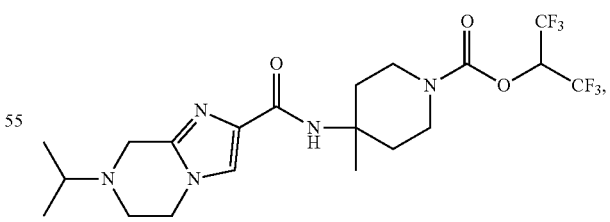
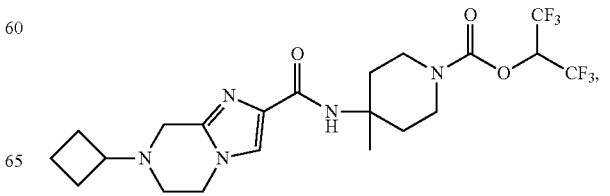

329
-continued
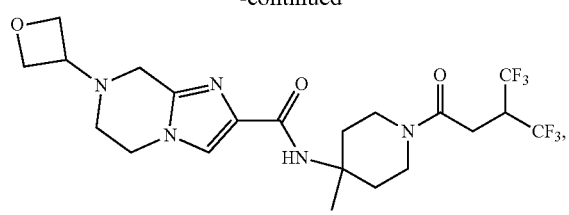
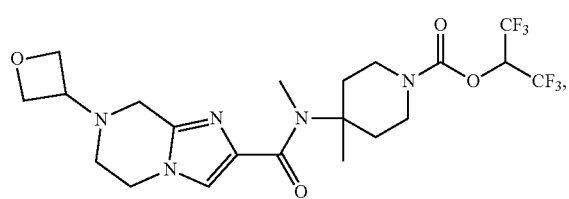
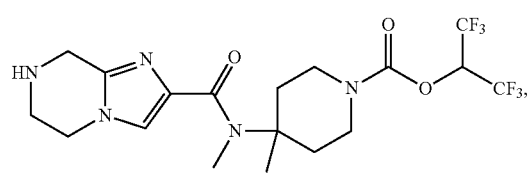
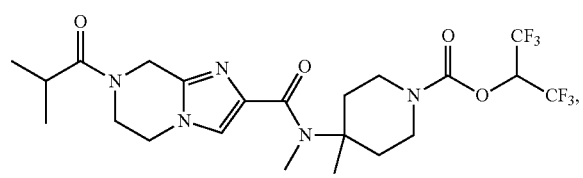
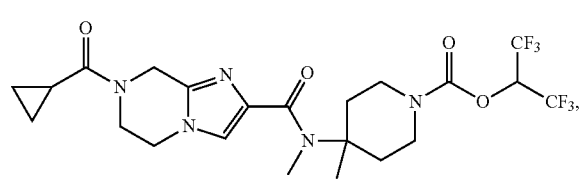
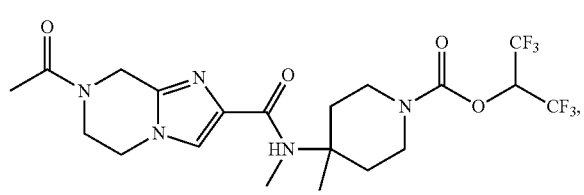
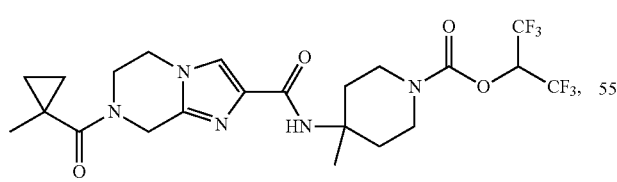
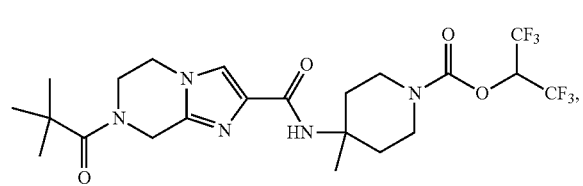
330
-continued
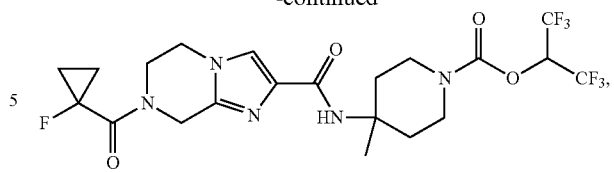
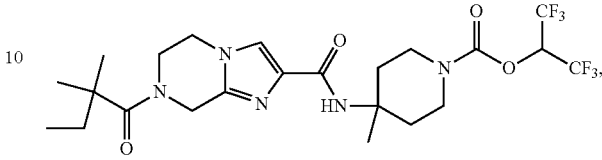
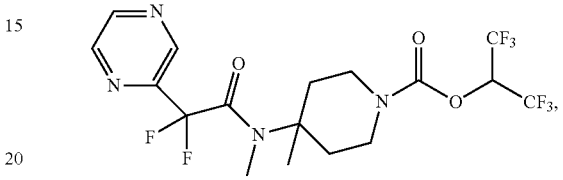
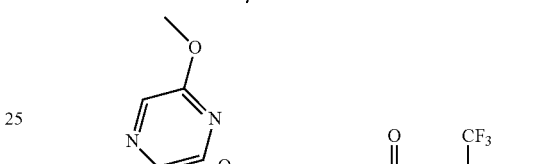
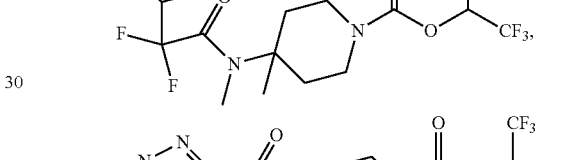
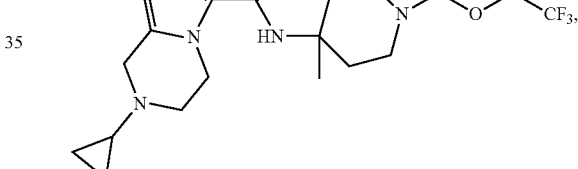
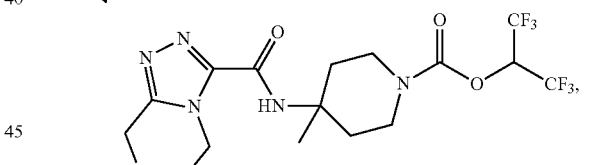
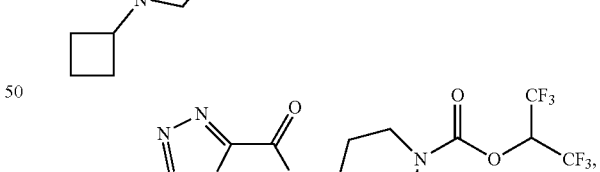
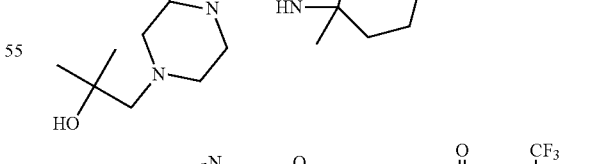
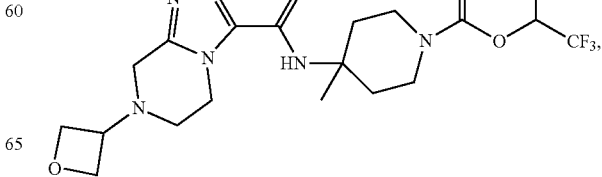

331
-continued

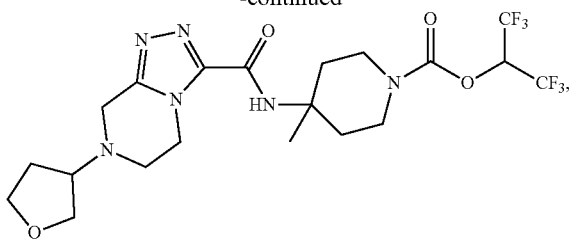

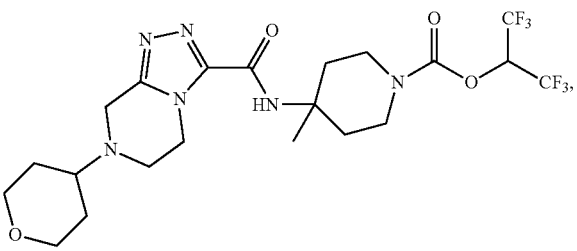

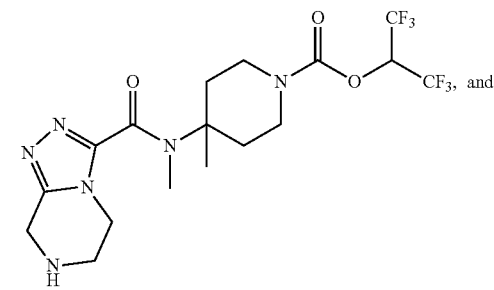

332
-continued

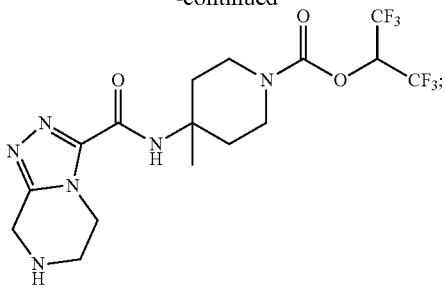

or a solvate, hydrate, tautomer, N-oxide, stereoisomer, or a pharmaceutically acceptable salt thereof.

14. A pharmaceutical composition comprising a compound of claim 1, or a solvate, hydrate, tautomer, N-oxide, stereoisomer, or a pharmaceutically acceptable salt thereof, and at least one pharmaceutically acceptable excipient.

15. A method of treating pain in a patient in need thereof, comprising administering to the patient a therapeutically effective amount of a compound of claim 1, or a solvate, hydrate, tautomer, N-oxide, stereoisomer, or a pharmaceutically acceptable salt thereof.

16. A method of treating a disease or disorder in a patient in need thereof, comprising administering to the patient a therapeutically effective amount of a compound of claim 1, or a pharmaceutically acceptable salt or solvate thereof, wherein the disease or disorder is selected from migraine, epilepsy/seizure disorder, neuromyelitis optica (NMO), Tourette syndrome, persistent motor tic disorder, persistent vocal tic disorder, and abdominal pain associated with irritable bowel syndrome.

* * * * *